(12) United States Patent
Hachiya et al.

(10) Patent No.: US 7,585,886 B2
(45) Date of Patent: Sep. 8, 2009

(54) PYRROLIDINE DERIVATIVE OR SALT THEREOF

(75) Inventors: Shunichiro Hachiya, Tokyo (JP); Makoto Oku, Chuo-ku (JP); Hana Mukai, Chuo-ku (JP); Takashi Shin, Chuo-ku (JP); Keisuke Matsuura, Chuo-ku (JP); Ryushi Seo, Chuo-ku (JP); Takashi Kamikubo, Chuo-ku (JP); Yoh Terada, Chuo-ku (JP); Masanao Sanagi, Chuo-ku (JP); Kousei Yoshihara, Chuo-ku (JP); Taisuke Takahashi, Chuo-ku (JP)

(73) Assignee: Astellas Pharma Inc., Tokyo (JP)

( * ) Notice: Subject to any disclaimer, the term of this patent is extended or adjusted under 35 U.S.C. 154(b) by 297 days.

(21) Appl. No.: 11/662,539

(22) PCT Filed: May 18, 2006

(86) PCT No.: PCT/JP2006/309891

§ 371 (c)(1),
(2), (4) Date: Mar. 12, 2007

(87) PCT Pub. No.: WO2006/123725

PCT Pub. Date: Nov. 23, 2006

(65) Prior Publication Data

US 2009/0062366 A1 Mar. 5, 2009

(30) Foreign Application Priority Data

May 19, 2005 (JP) .............................. 2005-146457

(51) Int. Cl.
C07D 207/00 (2006.01)
A61K 31/40 (2006.01)
(52) U.S. Cl. ...................................... 514/423; 548/531
(58) Field of Classification Search .................. 514/423; 548/531
See application file for complete search history.

(56) References Cited

U.S. PATENT DOCUMENTS

2006/0247238 A1* 11/2006 Zbinden et al. .......... 514/235.2

FOREIGN PATENT DOCUMENTS

| JP | 10-503768 A1 | 4/1998 |
| WO | WO 94/18959 A1 | 9/1994 |
| WO | WO 96/04274 A1 | 2/1996 |
| WO | WO 03/099776 A1 | 12/2003 |
| WO | WO 2005/115975 A1 | 12/2005 |

OTHER PUBLICATIONS

Brown et al, Cloning and characterization of an extracellular . . . , Nature, Dec. 9, 1993, p. 575-580, vol. 366, Nature Publishing Group, U.S.
Cohen et al., Calcimimetics: therapeutic potential in hyperparathyroidism, Cur. Opi. Pharmacol, 2002, 734-739, 2, U.S.
Joy et al., Calcimimetics and the treatment of primary and secondary hyperparathyroidism, The annals of Pharacotherapy, Nov. 2004, 1871-1880, vol. 38, U.S.
Sensipar TM (Cinaclcet HCl) Tablet http://www.fda.gov/cder/foi/label/2004/21688_Sensipar_lbl.pdf.
Ray et al., Expression of the Calcium-sensing Receptor on Human Antral Gastrin Cells in Culture, J. Clin. Invest, May 1997, 2328-2333, vol. 99, The American Society of Clinical Investigation, Inc. U.S.
Cheng et al., Expression of calcium-sensing receptor in rat colonic epithelium: evidence for modulation of fluid secretion, Am J Physiol Gastrointest Liver Physiol, Mar. 2002, G240-G250, The American Physiological Society, U.S.
Bruce et al., Molecular and functional identification of a Ca2 (polyvalent cation)-sensing receptor in rat pancreas, Jul. 1999, 20561-20568, The American Society for Biochemistry and Molecular Biology, Inc., U.S.
Straub et al., The calcimimetic R-467 potentiates insulin secretion in pancreatic B cells by activation of a nonspecific cation channel, Jun. 2000, 18777-18784, The Journal of Biological Chemistry, U.S.A.
Emanuel et al., Calcium-sensing receptor expression and regulation by extracellular calcium in the AtT-20 pituitary cell line, 1996, 555-565, vol. 10, Mol Endocrinol, Astellas Pharm Inc., U.S.A.

* cited by examiner

*Primary Examiner*—Kamal A Saeed
*Assistant Examiner*—Samantha L Shterengarts
(74) *Attorney, Agent, or Firm*—Sughrue Mion, PLLC

(57) ABSTRACT

[Problem] To provide a compound which may be used in treating diseases in which a calcium sensing receptor (CaSR) is concerned, particularly hyperparathyroidism. [Means for Resolution] It was found that novel pyrrolidine derivatives which are characterized by the possession of aminomethyl group substituted with arylalkyl group or the like, or salts thereof, have excellent CaSR agonistic regulatory activity and also have excellent selectivity with CYP2D6 inhibitory activity having a possibility of causing drug interaction. Based on the above, these novel pyrrolidine derivatives are useful as therapeutic agents for treating diseases in which CaSR is concerned (hyperparathyroidism, renal osteodystrophy, hypercalcemia and the like).

15 Claims, No Drawings

PYRROLIDINE DERIVATIVE OR SALT THEREOF

This is a notational stage application under 35 U.S.C. § 371 of PCT/JP2006/309891 filed on May 18, 2006, which claims priority from Japanese patent application JP 2005-146457 filed on May 19, 2005, all of which are incorporated herein by reference.

TECHNICAL FIELD

This invention relates to medicines, particularly a therapeutic agent for diseases in which calcium sensing receptor (CaSR) is concerned, such as hyperparathyroidism.

BACKGROUND OF THE INVENTION

Extracellular $Ca^{2+}$ concentration takes a very important role in various living body functions including maintenance of life. Thus, serum $Ca^{2+}$ concentration is strictly controlled within a very narrow range by many regulatory mechanisms.

Parathyroid hormone (PTH) is a polypeptide hormone produced in and secreted from the parathyroid glands and mainly regulates serum $Ca^{2+}$ concentration. This PTH increases serum $Ca^{2+}$ concentration by accelerating bone resorption and accelerating reabsorption of calcium in renal trouble. Increase of the serum $Ca^{2+}$ concentration inhibits secretion of PTH, but on the contrary, decrease of the $Ca^{2+}$ concentration accelerates secretion of PTH, so that it is considered that the serum $Ca^{2+}$ concentration is controlled, in a sense, by a negative feedback mechanism.

Included in the hyperparathyroidism in which excessive secretion of PTH continuously occurs are primary hyperparathyroidism considered to be due to adenoma, hyperplasia, cancer which arises in the parathyroid gland itself and secondary hyperparathyroidism caused by chronic kidney disease and the like.

It has been reported that many patients with chronic kidney disease were simultaneously suffering from secondary hyperparathyroidism. Secondary hyperparathyroidism is one of the causative diseases of renal osteodystrophy including ectopic calcification, and considered to be a cause of the reduction of QOL of patients with chronic kidney disease due to bone fracture, bone pain and the like and of the death of patients with chronic kidney disease caused by a cardiovascular disease considered to be due to calcification in the cardiovascular system. Thus, the secondary hyperparathyroidism is a big problem in the clinical field, too.

In the secondary hyperparathyroidism caused by chronic kidney disease, excessive secretion of PTH is occurred from the reduction of serum $Ca^{2+}$ concentration caused by the lowering of phosphorus excretion in the kidney and the reduction of active vitamin D. It is considered that this excessive secretion of PTH is continued and exacerbated due to further reduction of renal function, parathyroid hyperplasia, resistance of the PTH target organ and the like.

At present, vitamin D replacement therapy is mainly carried out as an internal therapy for the secondary hyperparathyroidism. However, since vitamin D preparations increase the serum $Ca^{2+}$ concentration, they have an administration limit, so that it is not the state of being able to carry out sufficient treatment. Based on the above, concern has been directed toward the development of a secondary hyperparathyroidism treating agent which has high efficacy and does not increase serum $Ca^{2+}$ concentration.

Calcium sensing receptor (CaSR) has been cloned initially as a G-protein coupled receptor (GPCR) which can sense extracellular $Ca^{2+}$ in the bovine parathyroid (Non-patent Reference 1). CaSR has a function to change intracellular $Ca^{2+}$ concentration by sensing extracellular $Ca^{2+}$ concentration, and thereby to regulate production of molecules related to $Ca^{2+}$ metabolism regulation, typified by PTH. As a fact to support this, many reports have been published stating that activation mutation or inactivation mutation of human CaSR is a cause of familial hypercalcemia or hypocalcemia. In addition, reduction of sensitivity of the parathyroid gland for $Ca^{2+}$ has been observed in both primary and secondary hyperparathyroidism.

It is considered that an agonistic regulatory agent of CaSR reduces PTH without increasing serum $Ca^{2+}$ concentration, by increasing $Ca^{2+}$ sensitivity through its direct action upon CaSR of the parathyroid gland. Recently, it has been reported that an agonistic regulatory agent of CaSR, cinacalcet, has an activity to inhibit PTH secretion by increasing $Ca^{2+}$ sensitivity of CaSR through its direct action upon CaSR of the parathyroid gland (Non-patent References 2 and 3). Cinacalcet is expected as a new hyperparathyroidism treating agent which may be used jointly with a vitamin D preparation as an already known therapeutic means, a $Ca^{2+}$-containing phosphate binder which has been used for the purpose of treating hyperphosphatemia and the like.

However, it has been reported that cinacalcet has a strong activity to inhibit CYP2D6 which is one of the subtypes of cytochrome p450 (CYP). This CYP2D6 also has an important role in the metabolism of various drugs used in the clinical field. Since cinacalcet inhibits CYP2D6, there is a danger of causing drug-drug interaction (DDI) by changing pharmacokinetics of a drug through the delay of metabolism of a drug metabolized by CYP2D6 (Non-patent Reference 4). Based on the above, concern has been directed toward the development of a strong CaSR regulatory agent free from CYP2D6 inhibitory activity.

It is considered that mRNA of CaSR is expressed in various tissues including the kidney and parathyroid gland, in addition to the parathyroid gland which is a main PTH secreting tissue and takes various physiological roles.

It is expected that an agent which regulates CaSR antagonistically or agonistically (CaSR regulator) could become a therapeutic agent of various diseases including bone disease and diseases of upper and lower digestive organs (Non-patent References 5 and 6), diabetes mellitus (Non-patent References 7 and 8), hypo-/hyper-function of pituitary (Non-patent Reference 9) and the like, in addition to the aforementioned hyperparathyroidism.

Regarding the CaSR regulator, there are two reports of the following Patent References 1 and 2.

In the Patent Reference 1, compounds represented by the following formula (A) and formula (B) comprising a broad range of compounds are disclosed. However, as Ar, R and $R_3$, there is no disclosure on pyrrolidine which is a characteristic of the invention.

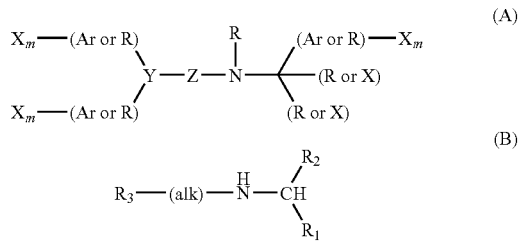

(In the formula, Ar, R and $R_3$ represent the following meanings.

Ar: a hydrophobic substance.

R: hydrogen, methyl, ethyl, propyl, isopropyl, butyl, isobutyl, cyclopentyl, cyclohexyl, cycloheptyl, cyclooctyl, indenyl, indanyl or 2-, 3- or 4-piperidyl.

$R_3$: a monocyclic or bicyclic aryl or cycloalkyl having 5 or 6 ring constituting atoms, which may be substituted.

See said reference for other signs.)

A compound represented by the following formula (C) is disclosed in the Patent Reference 2 published after the priority date of the instant application. However, in the compound represented by formula (C), amino group is directly linked to a nitrogen-containing ring.

$$R^1-X-N\underset{(CH_2)_n}{\overset{}{\diagdown}}\overset{H}{N}\diagdown\underset{CH_3}{\overset{}{\diagup}}Ar \quad (C)$$

(See Said Reference for the Signs.)

In addition, Patent Reference 3 describes that compounds represented by the following formula (D) including pyrrolidine derivatives are effective for migraine, as an agonist of $5HT_1$-like receptor. However, there are no descriptions on their efficacy for CaSR regulatory activity and hyperparathyroidism.

$$Z-E\diagup\diagdown\overset{Q-N}{\underset{T}{\diagdown}}\diagup\underset{R^a}{\overset{R}{\diagdown M}} \quad (D)$$

(The M in the formula represents a residual part of azetidine, pyrrolidine or piperidine ring. See said reference for other signs.)

Non-patent reference 1: Brown et al., *Nature*, (England), 1993, vol. 366, p. 575-580

Non-patent reference 2: Cohen et al., *Current Opinion in Pharmacology*, (Holland), 2002, vol. 2, p/734-739

Non-patent reference 3: Joy et al., *The Annals of Pharmacotherapy*, (USE), 2004, vol. 38, p. 1871-1880

Non-patent reference 4: Sensipar™ (cinacalcet HCl) Tablets), [online], 2004, FDA [retrieved date [Mar. 28, 2005], internet, (URL:http://www.fda.gov./cfer/foi/label/2004/21688-Sensipar-1bl.pdf).

Non-patent reference 5: Jeannine et al., *The Journal of Clinical Investigation*, (USA), 1997, vol. 99, p. 2328-2333

Non-patent reference 6: Cheng et al., *The American Journal of Physiology-Gastrointestinal and Liver Physiology*, (USA), 2002, vol. 383, p. G240-G250

Non-patent reference 7: Bruce et al., *The Journal of Biological Chemistry*, (USA), 1999, vol. 274, p. 20561-20568

Non-patent reference 8: Straub et al., *The Journal of Biological Chemistry*, (USA), 2000, vol. 275, p. 18777-18784

Non-patent reference 9: Emanuel et al., *Molecular Endocrinology*, (USA), 1996, vol. 10, p. 555-565

Patent Reference 1: International Publication No. 94/18959

Patent Reference 2: International Publication No. 2005/115975

Patent Reference 3: International Publication No. 96/04274

DISCLOSURE OF THE INVENTION

Problems that the Invention is to Solve

Since the already existing CaSR regulators are not satisfactory in terms of either efficacy or safety, great concern has been directed toward the provision of a CaSR regulator having superior efficacy and safety.

Means for Solving the Invention

Under such a situation, we have conducted intensive studies with the aim of developing a CaSR regulator having superior efficacy and safety. As a result, it was found that novel pyrrolidine derivatives having specific groups such as substituted aminomethyl group and the like can show strong CaSR agonistic regulatory activity. In addition, it was found also that these novel pyrrolidine derivatives have high selectivity with CYP2D6 inhibitory activity having a possibility of causing drug interaction, thus accomplishing the invention.

That is, the invention relates to a pyrrolidine derivative represented by a general formula (I) or a pharmaceutically acceptable salt thereof $$R^1\diagdown\underset{B}{\overset{X}{\diagdown N}}\diagup\underset{}{\overset{A}{\diagdown}}\underset{R^3}{\overset{R^2}{\diagdown}}\diagup\underset{R^5\ R^6}{\overset{H}{N}}\diagdown R^4 \quad (I)$$

[signs in the formula have the following meanings;

A and B: each independently —$C(R^7)(R^{7a})$— or —C(O)—, $R^7$ and $R^{7a}$: each independently —H, lower alkyl, aryl or —C(O)$OR^0$, $R^0$: —H or lower alkyl, X: single bond, *—C(O)—, *—OC(O)—, *—$N(R^8)C(O)$— or *—$S(O)_n$—, wherein * represents bonding to $R^1$, $R^8$: —H, lower alkyl or lower alkylene-aryl, n: 0, 1 or 2, $R^1$: —H, or $C_{1-12}$ alkyl, lower alkenyl, aryl, hetero ring group or cycloalkyl, which may respectively be substituted, $R^2$ and $R^3$: each independently —H, lower alkyl, halogeno lower alkyl, —OC(O)—$R^0$, cycloalkyl, lower alkylene-cycloalkyl, aryl, lower alkylene-aryl, hetero ring group or lower alkylene-hetero ring group, wherein the aryl and hetero ring group in $R^2$ and $R^3$ may be substituted respectively, or $R^2$ and $R^3$ in combination may form cycloalkyl ring or hetero ring, which may respectively be substituted, together with the carbon atom to which they are bonded, $R^4$: aryl or hetero ring group, which may respectively be substituted, $R^5$: lower alkyl or halogeno lower alkyl, and $R^6$: —H, lower alkyl or halogeno lower alkyl, with the proviso that when $R^4$ is unsubstituted phenyl, at least one of $R^2$ and $R^3$ is not —H, the same shall apply hereinafter].

In addition, the invention also relates to a pharmaceutical composition which comprises the aforementioned pyrrolidine derivative or a pharmaceutically acceptable salt thereof and a pharmaceutically acceptable carrier, particularly a pharmaceutical composition which is a calcium sensing receptor regulator, a hyperparathyroidism treating agent, a renal osteodystrophy treating agent or a hypercalcemia treating agent.

That is, (1) a pharmaceutical composition which comprises the compound described in the formula (I) or a pharmaceutically acceptable salt thereof and a pharmaceutically acceptable carrier, (2) the pharmaceutical composition described in (1), which is a calcium sensing receptor regulator, (3) the pharmaceutical composition described in (1), which is a hyperparathyroidism treating agent, (4) the pharmaceutical composition described in (1), which is a renal osteodystrophy treating agent, (5) the pharmaceutical composition described in (1), which is a hypercalcemia treating agent, (6) use of the compound described in the formula (I) or a pharmaceutically acceptable salt thereof for producing a calcium sensing receptor regulator, a hyperparathyroidism treating agent, a renal osteodystrophy treating agent or a hypercalcemia treating agent, and (7) a method for treating a hyperparathyroidism treating agent, a renal osteodystrophy treating agent or a hypercalcemia treating agent, which comprises administering a therapeutically effective amount of the compound described in the formula (I) or a salt thereof to a patient.

Effects of the Invention

The excellent CaSR agonistic activity of the compound (I) or the invention was confirmed by the following tests.

Test 1. Human Calcium Sensing Receptor (CaSR) Agonistic Activity Test

1) Preparation of Human CaSR Expression Vector

A DNA fragment coding for human CaSR was cloned in the standard method. Illustratively, using 203 to 2387 of NM_000388 as a DNA fragment D4, and 2210 to 3633 as a DNA fragment B2, they were amplified using a human kidney cDNA (mfd. by Invitrogen) as the template and using a DNA polymerase (a registered trade name: Pyrobest, mfd. by Takara Bio), and respectively cloned into a pCR2.1 vector using a pCR2.1-Topo vector (mfd. by Invitrogen). Next, DNA fragments prepared by digesting pCR2.1-D4 with SpeI and XbaI were inserted into the same sites of pcDNA3.1/Zeo(+) vector. Successively, the fragments prepared by digesting pCR2.1-B2 with SacI and XbaI were inserted into the SacI and XbaI sites of previously prepared pcDNA3.1/Zeo(+)-D4 (SpeI-XbaI), thereby obtaining a human CaSR expression vector pcDNA3.1/Zeo(+)-hCaSR in which human CaSR open reading frame (ORF) was contained in the pcDNA3.1/Zeo(+) vector.

2) Preparation of Human CaSR Expression Cell

The human CaSR expression vector was transferred into HEK 293 cell using a transfection reagent (registered trademark: FuGene 6, mfd. by Roche Diagnostics). After the gene transfer, this was cultured in DMEM (mfd. by Invitrogen) medium containing 40 μg/ml Zeocin (registered trademark) (mfd. by Invitrogen) and 10% fetal bovine serum at 37° C. for 2 weeks in the presence of 5% $CO_2$, thereby obtaining Zeocin-resistant clones. An human CaSR stably expressing HEK 293 clone was obtained from these clones by selection using the responsiveness to extracellular $Ca^{2+}$ as the index.

3) Human CaSR Agonistic Activity Test

The HEK 293 cell stably expressing human CaSR was inoculated into a poly-D-lysine-coated black clear bottom 96 well plate (mfd. by BD Bioscience). Hanks' balanced salt solution (HBSS) ($Ca^{2+}$ (−), $Mg^{2+}$ (−), mfd. by Invitrogen) containing 20 mM HEPES (2-[4-(2-hydroxyethyl)-1-piperazinyl]ethanesulfonic acid) buffer (pH 7.4), 2.5 mM probenecid (mfd. by Sigma) and 0.1% bovine serum albumin was prepared as a washing buffer. After the inoculation and subsequent overnight culturing, the medium was discarded, the washing buffer supplemented with 1 mM $CaCl_2$ and 10 μM Fluo-3 AM (trade name, mfd by DOJINDO) was added thereto in 100 μl per well portions, and then the incubation was carried out at 37° C. for 1 Hour in the presence of 5% $CO_2$. This was washed twice with 200 μl of the washing buffer, replaced by 100 μl of the washing buffer supplemented with 0.5 mM $CaCl_2$ and allowed to stand still for 10 minutes, and then the responsiveness to each compound to be evaluated was detected using a plate reader for fluorometry image analysis use (registered trademark: FLIPR, mfd. by Molecular Devices). In this connection, the compound to be evaluated was used by optionally diluting with the washing buffer supplemented with 0.5 mM $Ca^{2+}$.

The human CaSR agonistic activity strength of each compound to be evaluated was calculated by defining the solvent group as 0% and the 2 mM $Ca^{2+}$ in final concentration group as 100%, and the compound concentration showing 50% activity ($EC_{50}$) was calculated from a concentration-activity curve by the method of least squares.

As a result, it was revealed that the compounds of the invention have strong human CaSR agonistic activity. Activity strengths of typical compounds of the invention are shown in Table 1.

TABLE 1

| Example No. | $EC_{50}$ (nM) |
|---|---|
| 31 | 3.6 |
| 33 | 2.3 |
| 41 | 4.9 |
| 45 | 3.1 |
| 48 | 4.0 |
| 53 | 5.2 |
| 98 | 5.2 |
| 109 | 28 |
| 116 | 17 |
| 130 | 15 |
| 133 | 6.9 |
| 171 | 16 |
| 174 | 3.4 |
| 179 | 0.77 |
| 183 | 3.5 |

Test 2. Measurement of Rat Plasma Calcium Concentration and Plasma PTH Concentration The compounds of the invention were administered to rats, and their influences upon the plasma calcium concentration and plasma PTH concentration were examined. The test was carried out by single oral administration of the compounds 5 or 6 normal male rats.

As a vehicle group, an MC solution prepared by adding 0.5% methyl cellulose (MC) solution or ethanol to a final concentration of 5% was administered at a dose of 5 ml/kg. As the comparative control, cinacalcet was dissolved in the MC solution and administered at a dose of 3 mg/kg. Each of the compounds, of the invention was dissolved or suspended the MC solution, or dissolved in ethanol and then diluted with the MC solution as occasion demands, and administered at a dose of 1, 3 or 10 mg/kg.

Blood samples were collected from the orbital venous plexus under ether anesthesia before the administration and 2Hours, 4Hours, or 8Hours in some cases, after the administration, and the plasma calcium concentration was measured using Calcium E-Test Wako (mfd. by Wako Pure Chemical Industries), and the plasma PTH concentration using Rat Intact PTH ELISA Kit (mfd. by Immutopics) or Rat Bioactive Intact PTH ELISA Kit (mfd. by Immutopics).

As a result, it was able to confirm that the compounds of the invention have the action to reduce plasma calcium and plasma PTH levels by the in vivo test. Results of typical compounds of the invention are shown in Table 2.

TABLE 2

| Example No. | Rat plasma calcium concentration reducing ratio (%) 4 hours after administration |
|---|---|
| 33 | 21 |
| 109 | 17 |
| 116 | 18 |
| 133 | 20* |
| 171 | 20 |
| 183 | 20 |

*Example 133 alone 1 mg/kg oral administration, other compounds are 3 mg/kg oral administration Test 3. Human CYP2D6 Inhibition Test Inhibitory activity evaluation for CYP2D6 was carried out by measuring it in accordance, roughly, with a reference ("Drug Metabolism and Disposition", 2001, vol. 29, p. 1196-1200).

Final concentrations of the reagents in the enzyme reaction solution were respectively ser to CYP2D6=7.5 µmol/ml (mfd. by BD Gentest, Cat. No.: 456217), reduced type nicotinamide adenine dinucleotide phosphate (NADPH) regeneration system (0.0081 mM nicotinamide adenine dinucleotide phosphate (NADP+), 0.41 mM glucose-6-phosphate, 0.41 mM $MgCl_2$, 0.41 mM/ml glucose-6-phosphate dehydrogenase), and a fluorescence substrate AMMC=1.5 µM, 100 mM potassium phosphate buffer (pH 7.4). Each compound was made into a 50% acetonitrile solution and added to the enzyme reaction solution (acetonitrile final concentration 2.5%). The enzyme reaction was carried out at 37° C. for 30 minutes, the reaction was stopped using a stopping liquid (0.1 M tris(hydroxymethyl)aminomethane (Tris-base):acetonitrile=20:80), and then fluorescence intensity was measured. The concentration showing 50% inhibition ($IC_{50}$) was calculated from the thus obtained fluorescence intensity, by defining the enzyme activity at the time of no compound addition as 100%.

As a result, it was revealed that the compounds of the invention have weak human CYP2D6 inhibitory activity. CYP2D6 inhibitory strengths of typical compounds of the invention are shown in Table 3.

TABLE 3

| Example No. | $IC_{50}$ (µM) |
|---|---|
| 31 | ≧6 |
| 41 | ≧6 |
| 45 | ≧6 |
| 98 | ≧6 |
| 109 | ≧6 |
| 116 | ≧6 |
| 179 | ≧6 |
| 183 | ≧6 |

BEST MODE FOR CARRYING OUT THE INVENTION

The following describes the invention in detail.

In this description, the "alkyl" means a straight or branched saturated aliphatic hydrocarbon chain.

The "lower alkyl" means a $C_{1-6}$ alkyl. For example, methyl, ethyl, propyl, butyl, pentyl, hexyl, isopropyl, tert-butyl and the like may be cited. Preferred are methyl, ethyl, propyl and isopropyl.

The "lower alkenyl" means a $C_{2-6}$ alkenyl. Its double bond may be at an optional position, and it may have two or more double bonds. For example, vinyl, 1-propenyl, allyl, butenyl, pentenyl, hexenyl, isopropenyl and the like may be cited. Preferred are vinyl and allyl.

The "lower alkylene" means a divalent group resulting from the removal of optional one hydrogen atom from the aforementioned "lower alkyl". For example, methylene, ethylene, propylene, butylene, methylmethylene, dimethylmethylene and the like may be cited. Preferred are methylene, ethylene and propylene.

The "lower alkenylene" means a divalent group resulting from the removal of optional one hydrogen atom from the aforementioned "lower alkenyl". For example, vinylene, propenylene, butenylene and the like may be cited. Preferred are vinylene and propenylene.

The "halogen" means F, Cl, Br and I.

The "halogeno lower alkyl" means a lower alkyl substituted with one or more halogen. For example, fluoromethyl, difluoromethyl, trifluoromethyl, fluoroethyl, difluoroethyl and trifluoroethyl may be cited. Preferred are difluoromethyl, trifluoromethyl and difluoroethyl.

The "cycloalkyl" is a $C_{3-12}$ cycloalkyl which may form a bridge ring or spiro ring and may have one or two double bond. For example, cyclopropyl, cyclobutyl, cyclopentyl, cyclohexyl, cycloheptyl, adamantyl, norbornyl, cyclohexenyl, norbornenyl and the like may be cited. Preferred are cyclopropyl, cyclopentyl, cyclohexyl and adamantyl.

The "aryl" means a $C_{6-14}$ monocyclic to tricyclic aryl. In addition, a $C_{5-8}$ cycloalkyl ring may be ring-condensed with phenyl. For example, phenyl, naphthyl, indanyl, tetrahydronaphthyl, azulenyl and the like may be cited. Preferred are phenyl and naphthyl.

The "hetero ring" means a saturated, unsaturated or partially unsaturated 4- to 8-membered monocyclic hereto ring, 8- to 14-membered bicyclic hetero ring or 11- to 20-membered tricyclic hetero ring, which has 1 to 4Hetero atoms selected from O, S and N. Also, a part of the rings of the aforementioned bicyclic and tricyclic hetero rings may be a $C_{5-8}$ cycloalkyl ring. In addition, it may form an oxide or dioxide in which the ring atom S or N is oxidized, and may form a bridge ring or spiro ring. Illustrative examples of the monocyclic hetero ring include pyridyl, pyridazinyl, pyrimidinyl, pyrazinyl, furyl, thienyl, pyrrolyl, oxazolyl, isoxazolyl, oxadiazolyl, thiazolyl, thiadiazolyl, imidazolyl, triazolyl, tetrazolyl, pyrrolidinyl, dihydropyridyl, dihydropyrrolyl, dihydrooxazolyl, dihydrothiazolyl, dihydroimidazolyl, piperidyl, morpholinyl, thiomorpholinyl, piperazinyl, pyrazolinyl, imidazolidinyl, oxazolidinyl, thiazolidinyl, homopiperazinyl, tetrahydrofuranyl, tetrahydropyranyl, tetrahydrothiopyranyl tetrahydropyrimidinyl, chromanyl, dioxolanyl, diazepinyl, homomorpholinyl and the like. Illustrative examples of the bicyclic hetero ring include benzofuranyl, indolyl, benzothienyl, benzoxazolyl, benzoimidazolyl, benzothiazolyl, quinolinyl, quinazolinyl, quinoxalinyl, cinnolinyl, dihydrobenzodioxinyl and the like. Illustrative examples of the tricyclic hetero ring include carbazolyl, acridinyl and the like. As the bridgeed hetero ring, 1-azabicyclo[2.2.2]octyl, 2,5-diazabicyclo[2.2.1]heptyl and the like may be exemplified. Preferred are pyrrolyl, furyl, thienyl, thiazolyl, pyridyl, pyrimidinyl, pyrazinyl, piperidyl, morpholinyl, thiomorpholinyl, piperazinyl, pyrrolidinyl, tetrahydrofuranyl, tetrahydropyranyl, tetrahydrothiopyranyl, diazepinyl, 1-azabicyclo[2.2.2]octyl, indolyl, benzothienyl and quinolinyl.

The term "may be substituted" means "not substituted" or "substituted with 1 to 5 substituent groups which may be the same or different".

As the substituent group acceptable by the term "may be substituted" according to this description, it may be any group which is generally used in said technical field as a substituent group of respective group. In addition, when two or more groups are present like the case of the $R^O$ of —C(O)N(R)$_2$, respective groups may be the same or different from each other.

Preferably, the substituent group of "aryl" and "heteroaryl" which may be respectively substituted according to $R^1$ is a group selected from the following group P. Group P: halogen, nitro, cyano, lower alkyl, halogeno lower alkyl, —C(OH)(halogeno lower alkyl)$_2$, lower alkylene-C(O)OR$^O$, lower alkenylene-C(O)OR$^O$, lower alkylene-C(O)N(R$^O$)$_2$, —O-lower alkylene-C(O)OR$^O$, —O-lower alkylene-C(O)N(R$^O$)$_2$, —OR$^O$, —O-halogeno lower alkyl, —N(R$^O$)$_2$, —NR$^O$—C(O)R$^O$, —C(O)R$^O$, —C(O)OR$^O$, —C(O)N(R$^O$)$_2$, —C(O)NR$^O$-lower alkylene-C(O)OR$^O$, —C(O)NR$^O$-lower alkylene-C(O)N(R$^O$)$_2$, —C(O)NR$^O$—S(O)$_2$-lower alkyl, aryl, lower alkylene-aryl, —O-aryl, —S(O)$_2$NH$_2$, —S(O)$_n$-aryl and hetero ring group. However, the aryl and hetero ring group in the group P may be respectively substituted with a group selected from the following group p$^a$.

Group p$^a$: halogen, nitro, cyano, lower alkyl, halogeno lower alkyl, —OR$^O$, —O-halogeno lower alkyl, oxo, —C(O)OR$^O$ and —C(O)N(R$^O$)$_2$.

Preferred as the substituent group of the "cycloalkyl" which may be substituted in the case of R$^1$ is a group selected from the following group Q.

Group Q: lower alkyl, —OR$^O$, —O-halogeno lower alkyl, oxo, —C(O)OR$^O$, —C(O)N(R$^O$)$_2$, —N(R)$_2$, —NR—C(O)R$^O$, —NR$^O$-lower alkylene-C(O)OR$^O$, —NR$^O$— lower alkylene-C(O)N(R)$_2$, aryl and hetero ring group. However, the aryl and hetero ring group in the group Q may be respectively substituted with a group selected from the aforementioned group P$^a$.

Preferred as the substituent group of the "C$_{1-12}$ alkyl" and "lower alkenyl", which may be substituted in the case of R$^1$ is a group selected from the following group G or group G$^a$.

Group G: halogen, oxo, —OR$^O$, halogeno lower alkyl, —N(R$^O$)$_2$, —NR$^O$—C(O)R$^O$, —C(O)R$^O$, —C(O)N(R$^O$)$_2$, —C(O)NR$^8$-lower alkylene(O)OR$^O$, —C(O)NR$^O$-lower alkylene-C(O)N(R$^O$)$_2$, cycloalkyl, aryl and hetero ring group. However, the cycloalkyl in the group G may be substituted with a group selected from the group Q, and the aryl and hetero ring group may be substituted with a group selected from the group P.

Group G$^a$: —O-aryl, —S(O)$_n$-aryl, —C(O)aryl, —NR$^O$—C(O)aryl, —C(O)NR$^O$-aryl, —C(O)NR$^O$-lower alkylene which may be substituted with —C(O)OR$^O$)-aryl and —C(O)NR$^O$-hetero ring group. However, the aryl and hetero ring group in the group G$^a$ may be respectively substituted with a group selected from the aforementioned group P$^a$.

The substituent group of the "aryl" and "hetero ring group", which may be respectively substituted, in the R$^2$ and R$^3$ is preferably a group selected from the aforementioned group P$^a$.

The substituent group of the "cycloalkyl ring" and "hetero ring group" which are formed by R$^2$ and R$^3$ in combination together with the carbon atom to which they are bonded is preferably a group selected from the aforementioned group p$^a$.

The substituent group of the "aryl" and "hetero ring group", which may be respectively substituted, in the R$^4$ is preferably halogen, nitro, cyano, lower alkyl, halogeno lower alkyl, —OR$^O$, —O-halogeno lower alkyl, oxo, —C(O)OR$^O$, —C(O)N(R$^O$)$_2$ or —O-aryl.

A preferred embodiment of the invention is described in the following.

Preferred as R$^1$ is a lower alkyl, a cycloalkyl, an aryl or a hetero ring group, which is substituted with —CO$_2$H and may be further substituted, or a lower alkylene-(aryl or hetero ring group, which is substituted with —CO$_2$H and may be further substituted). More preferred is lower alkylene-CO$_2$H, cycloalkyl substituted with —CO$_2$H, phenyl is substituted with —CO$_2$H and may be substituted with a group selected from the class consisting of halogen, halogeno lower alkyl and —O-lower alkyl, further preferred is phenyl which is substituted with —CO$_2$H and may be further substituted with a group selected from the class consisting of halogen, halogeno lower alkyl and —O-lower alkyl.

Preferred as X is single bond, —C(O), *—NHC(O)—, or *—OC(O), more preferred is —OC(O)—.

Preferred as A and B are each independently —CH$_2$— or —C(O), more preferably —CH$_2$—.

Preferred as R$^2$ is —H, a lower alkyl or an aryl which may be substituted, more preferably a halogen, a lower alkyl or phenyl which may be substituted with a halogeno lower alkyl, further preferably unsubstituted phenyl.

Preferred as R$^3$ is —H or a lower alkyl, more preferably —H.

Preferred as R$^4$ is an aryl which may be substituted, more preferably an aryl which may be substituted with an —O-lower alkyl, further preferably naphthyl or phenyl substituted with —O-lower alkyl, still further preferably 1-naphthyl or 3-methoxyphenyl.

Preferred as R$^5$ is a lower alkyl, more preferably methyl.

Preferred as R$^6$ is —H.

A compound consisting of a combination of the aforementioned preferred groups is most desirable.

In addition, another preferred embodiment of the compound of the invention represented by the general formula (I) is shown below.

(1) A compound described in (I), wherein R$^6$ is —H.
(2) A compound described in (1), wherein A and B are —CH$_2$—.
(3) A compound described in (2), wherein R$^6$ is —H.
(4) A compound described in (3), wherein R$^3$ is —H.

(5) A compound described in (4), wherein $R^4$ is an aryl which may be substituted with an lower alkyl.

(6) A compound described in (5), wherein $R^2$ is phenyl which may be substituted with a group selected from the class consisting of halogen, lower alkyl and halogeno lower alkyl.

(7) A compound described in (6), wherein $R^1$—X— is HO$_2$C-lower alkylene-OC(O)—; HO$_2$C-lower alkylene-C(O); (cycloalkyl substituted with —CO$_2$H)—OC(O)—; (cycloalkyl substituted with —CO$_2$H)—C(O); phenyl which is substituted with —CO$_2$H and may be further substituted with a group consisting of halogen, halogeno lower alkyl and —O-lower alkyl; (phenyl which is substituted with —CO$_2$H and may be further substituted with a group consisting of halogen, halogeno lower alkyl and —O-lower alkyl)-OC(O)—; or (phenyl which is substituted with —CO$_2$H and may be further substituted with a group consisting of halogen, halogeno lower alkyl and —O-lower alkyl)-NHC(O)—.

(8) A compound described in the formula (I), which is selected from the group consisting of
4-({[(3S,4S)-3-({[(1R)-1-(1-naphthyl)ethyl]amino}methyl)-4-phenylpyrrolidin-1-yl]carbonyl}oxy)benzoic acid,
3-(5-{[(3S,4S)-3-({[(1R)-1-(1-naphthyl)ethyl]amino}methyl)-4-phenylpyrrolidin-1-yl]carbonyl}-2-furyl)thiophene-2-carboxylic acid,
6-{(3S,4S)-3-({[(1R)-1-(1-naphthyl)ethyl]amino}methyl)-4-[3-(trifluoromethyl)phenyl]pyrrolidin-1-yl}-6-oxohexanoic acid,
4-[(3S,4S)-3-({[(1R)-1-(1-naphthyl)ethyl]amino}methyl)-4-phenylpyrrolidin-1-yl]benzoic acid,
3,3-dimethyl-5-[(3S,4S)-3-({[(1R)-1-(1-naphthyl)ethyl]amino}methyl)-4-phenylpyrrolidin-1-yl]-5-oxopentanoic acid,
4-({[(3S,4S)-3-({[(1R)-1-(1-naphthyl)ethyl]amino}methyl)-4-phenylpyrrolidin-1-yl]carbonyl}amino)benzoic acid,
2,2-dimethyl-5-[(3S,4S)-3-({[(1R)-1-(1-naphthyl)ethyl]amino}methyl)-4-phenylpyrrolidin-1-yl]-5-oxopentanoic acid,
4-[({(3S,4S)-3-({[(1R)-1-(1-naphthyl)ethyl]amino}methyl)-4-[3-(trifluoromethyl)phenyl]pyrrolidin-1-yl}carbonyl)oxy]benzoic acid,
4-({[(3S,4S)-3-(3-fluorophenyl)-4-({[(1R)-1-(1-naphthyl)ethyl]amino}methyl)pyrrolidin-1-yl]carbonyl}oxy)benzoic acid,
4-({[(3S,4S)-3-(3-methylphenyl)-4-({[(1R)-1-(1-naphthyl)ethyl]amino}methyl)pyrrolidin-1-yl]carbonyl}oxy)benzoic acid,
4-({[(3S,4S)-3-(2,3-difluorophenyl)-4-({[(1R)-1-(1-naphthyl)ethyl]amino}methyl)pyrrolidin-1-yl]carbonyl}oxy)benzoic acid,
3,5-difluoro-4-[(3S,4S)-3-({[(1R)-1-(1-naphthyl)ethyl]amino}methyl)-4-phenylpyrrolidin-1-yl]benzoic acid,
3-methoxy-4-({[(3S,4S)-3-({[(1R)-1-(1-naphthyl)ethyl]amino}methyl)-4-phenylpyrrolidin-1-yl]carbonyl}amino)benzoic acid,
4-({[(3S,4S)-3-({[(1R)-1-(1-benzothien-3-yl)ethyl]amino}methyl)-4-phenylpyrrolidin-1-yl]carbonyl}oxy)benzoic acid,
5-[(3S,4S)-3-(3-fluorophenyl)-4-({[(1R)-1-(1-naphthyl)ethyl]amino}methyl)pyrrolidin-1-yl]-2,2-dimethyl-5-oxopentanoic acid,
3-methoxy-4-({[(3S,4S)-3-(3-methylphenyl)-4-({[(1R)-1-(1-naphthyl)ethyl]amino}methyl)pyrrolidin-1-yl]carbonyl}amino)benzoic acid,
3,5-difluoro-4-[(3S,4S)-3-(3-methylphenyl)-4-({[(1R)-1-(1-naphthyl)ethyl]amino}methyl)pyrrolidin-1-yl]benzoic acid,
(1R)-1-(1-naphthyl)-N-({(3S,4S)-4-phenyl-1-[4-(1H-tetrazol-5-yl)phenyl]pyrrolidin-3-yl}methyl)ethanamine,
2,2-dimethyl-5-[(3S,4S)-3-({[(1R)-1-(1-naphthyl)ethyl]amino}methyl)-4-phenylpyrrolidin-1-yl]-5-oxohexanoic acid,
3-methyl-4-({[(3S,4S)-3-({[(1R)-1-(1-naphthyl)ethyl]amino}methyl)-4-phenylpyrrolidin-1-yl]carbonyl}amino)benzoic acid,
3-chloro-4-({[(3S,4S)-3-({[(1R)-1-(1-naphthyl)ethyl]amino}methyl)-4-phenylpyrrolidin-1-yl]carbonyl}amino)benzoic acid,
3-fluoro-4-({[(3S,4S)-3-({[(1R)-1-(1-naphthyl)ethyl]amino}methyl)-4-phenylpyrrolidin-1-yl]carbonyl}amino)benzoic acid,
5-[(3S,4S)-3-(2,3-difluorophenyl)-4-({[(1R)-1-(1-naphthyl)ethyl]amino}methyl)pyrrolidin-1-yl]-2,2-dimethyl-5-oxopentanoic acid, and
4-[(3S,4S)-3-(2,3-difluorophenyl)-4-({[(1R)-1-(1-naphthyl)ethyl]amino}methyl)pyrrolidin-1-yl]-3,5-difluorobenzoic acid, or a pharmaceutically acceptable salt thereof.

The compounds of the invention exist in geometrical isomer or tautomer forms in some cases depending on the kind of substituent groups, and separated counterparts of these isomers or mixtures thereof are included in the invention.

Also, since the compounds of the invention have asymmetric carbons, (R) and (S) optical isomers based on this may be present. The invention includes mixtures and separated counterparts of all of these optical isomers.

In addition, pharmacologically acceptable prodrugs are also included in the invention. The pharmacologically acceptable prodrug is a compound of the invention having a group which may be converted into NH$_2$, OH, CO$_2$H or the like by solvolysis or under a physiological condition. Examples of the group capable of forming a prodrug include those which are described in "Progress in Medicine", Life Science Medica, 1985, vol. 5, p. 2157-2161 and "Iyakuhin no Kaihatsu (Development of Medicines) (vol. 7) Bunshi Sekkei (Molecular Design)", Hirokawa Shoten, 1990, p. 163-198.

The compounds of the invention sometimes form acid addition salts or salts with bases depending on the kind of substituent groups. Such salts are pharmacologically acceptable salts, and their illustrative examples include acid addition salts with inorganic acids (e.g., hydrochloric acid, hydrobromic acid, hydroiodic acid, sulfuric acid, nitric acid, phosphoric acid and the like) and with organic acids (e.g., formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, aspartic acid, glutamic acid and the like), salts with inorganic bases (e.g., sodium, potassium, magnesium, calcium, aluminum and the like) and organic bases (e.g., methylamine, ethylamine, ethanolamine, lysine, ornithine and the like), ammonium salts and the like.

In addition, the invention also includes various hydrates and solvates of the compounds (I) and salts thereof and their polymorphic substances.

(Production Methods)

The compounds (I) of the invention and pharmacologically acceptable salts thereof may be produced by applying various known synthetic methods making use of their basic nuclei or their characteristics based on the kind of substituent groups. In that case, depending on the kind of functional group, it is sometimes effective in view of production techniques to protect said functional group with an appropriate protecting group or replace it by a group which may be easily converted into said functional group, during the steps of from starting materials to intermediates. Examples of such a functional group include amino group, hydroxyl group, carboxyl group and the like, and as their protecting groups, the protecting groups described for example in "Protective Groups in Organic Synthesis", edited by T. W. Greene and P. G. M. Wuts, (USA), 3rd edition, John Wiley & Sons, 1999, may be exemplified, which may be optionally selected and used in response to the reaction conditions. By such a method, the desired compound may be obtained by introducing said protecting group to carry out the reaction, and then removing the protecting group or converting it into a desired group as occasion demands. In addition, prodrugs of the compounds (I) of the invention may be produced by introducing a specified group during the steps of from starting materials to intermediates, similar to the aforementioned protecting groups, or by carrying out the reaction using the obtained compounds (I) of the invention. The reaction may be carried out by employing general esterification, amidation, carbamate formation, dehydration and the like methods conventionally known by those skilled in the art.

(Production Method 1)

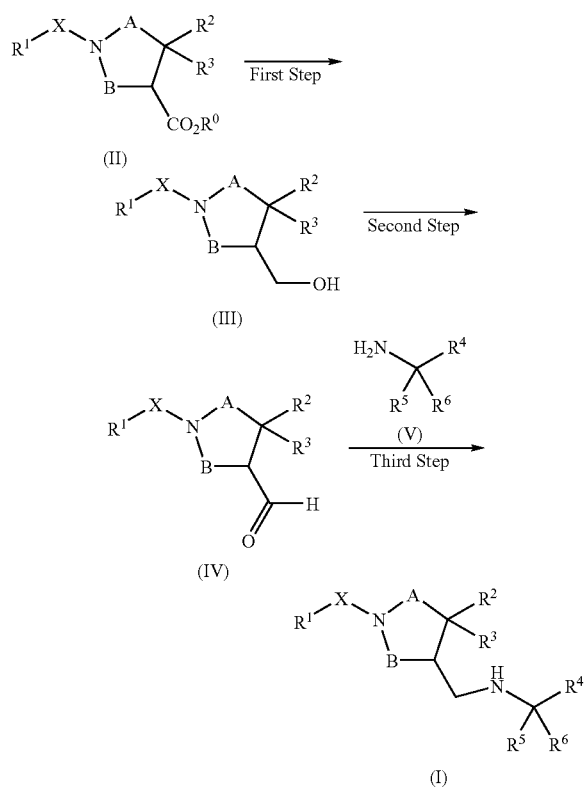

First Step:

This step is a step for obtaining a compound (III) by reducing a compound (II). As the reducing reaction of this step, a reducing reaction generally used by those skilled in the art may be employed. For example, this may be carried out from under cooling to under heat reflux in a solvent inert to the reaction, such as aromatic hydrocarbons (e.g., benzene, toluene, xylene and the like), ethers (e.g., diethyl ether, tetrahydrofuran (THF), dioxane and the like), halogenated hydrocarbons (e.g., dichloromethane, 1,2-dichloroethane, chloroform and the like), N,N-dimethylformamide (DMF), N,N-dimethylacetamide (DMA), N-methylpyrrolidone (NMP), dimethyl sulfoxide (DMSO), acetonitrile, alcohols (e.g., methanol, ethanol and the like), water and the like, using equimolar to excess amount of a reducing agent such as lithium aluminum hydride, sodium borohydride, lithium borohydride or the like.

Second Step:

This step is a step for obtaining a compound (IV) by oxidizing the compound (III). As the oxidation reaction of this step, an oxidation reaction generally used by those skilled in the art may be employed. For example, the methods described in "Jikken Kagaku Koza (Experimental Chemistry Course) (4th edition)", vol. 23 (1992) (Maruzen), edited by The Chemical Society of Japan, and the like may be employed. Preferably, this may be carried out by the Swern oxidation which is a method in which treatments with equimolar to excess amounts of DMSO and oxalyl chloride and subsequent triethylamine are carried out under cooling in a reaction-inert solvent such as the aforementioned ethers, halogenated hydrocarbons and the like.

Third Step:

This step is a step for obtaining the compound (I) of the invention by carrying out reductive alkylation of a compound (V) with the compound (IV). As the reductive alkylation reaction of this step, a reductive alkylation reaction generally used by those skilled in the art may be employed. For example, the methods described in "Jikken Kagaku Koza (Experimental Chemistry Course) (4th edition)", vol. 20 (1992) (Maruzen), edited by The Chemical Society of Japan, and the like may be cited. It is desirable to carry out the reaction under cooling, room temperature or heat reflux without solvent or in a reaction-inert solvent such as the aforementioned halogenated hydrocarbons, aromatic hydrocarbons, esters (e.g., ethyl acetate and the like), ethers, alcohols, acetic acid and the like, using a reducing agent such as sodium borohydride, sodium triacetoxyborohydride or a reducing agent-carrying polystyrene resin, such as MP-triacetoxyborohydride (mfd. by Argonaut Technologies, USA), or the like. Depending on the compound, it is sometimes advantageous to carry out the reaction in the presence of an acid such as a mineral acid (e.g., sulfuric acid, hydrochloric acid, hydrobromic acid or the like) or an organic acid (e.g., formic acid, acetic acid or the line), or titanium(IV) chloride, tetraisopropyl orthotitanate or the like Lewis acid. In addition, the reductive alkylation can also be carried out at room temperature to heat reflux under ordinary pressure or pressurization in an atmosphere of hydrogen, in a reaction-inert solvent such as the aforementioned aromatic hydrocarbons, esters, ethers, halogenated hydrocarbons, DMF, DMA, NMP, acetonitrile, acetic acid and the like, for example using palladium/carbon, Raney nickel, platinum or the like as the catalyst. Depending on the compound, it is sometimes advantageous in advancing the reaction smoothly to carry out the reaction in the presence of an acid (preferably, hydrochloric acid, acetic acid or the like). In some cases, it is desirable to use an isocyanate-carrying polystyrene resin, such as PS-isocyanate (mfd. by Argonaut Technologies, USA) or the like, in order to remove excess amine after completion of the reaction. In addition, depending on the compound, a reduction reaction may be carried out after isolation of the imine as the reaction intermediate.

(Production Method 2)

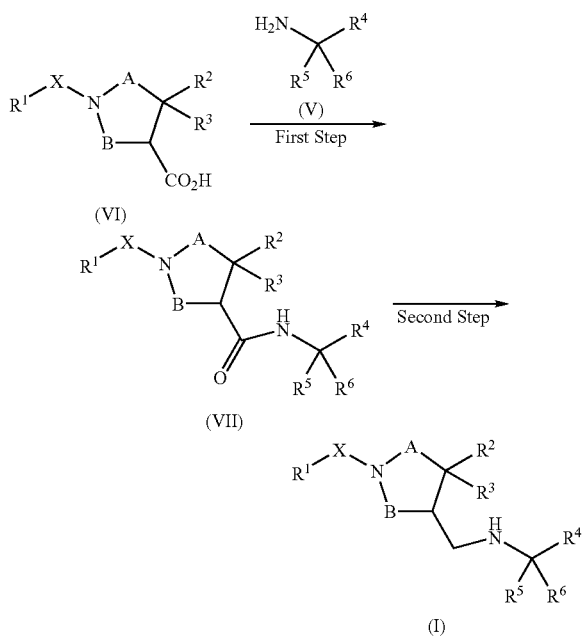

First Step:

This step is a method for obtaining a compound (VII) by an amidation reaction of a compound (VI) with the compound (V). The amidation reaction of this step may be carried out by allowing the carboxylic acid compound (VI) or a reactive derivative thereof to react with the amine compound (V). Examples of said reactive derivative include an acid halide (acid chloride, acid bromide or the like), an acid anhydride (mixed acid anhydride obtained by the reaction with ethyl chlorocarbonate, benzyl chlorocarbonate, phenyl chlorocarbonate, p-toluenesulfonic acid, isovaleric acid or the like, or a symmetric acid anhydride), an active ester (an ester which may be prepared using phenol which may be substituted with electron attractive group (e.g., nitro group, fluorine atom or the like), 1-hydroxybenzotriazole (HOBt), N-hydroxysuccinimide (HONSu) or the like), a reactive derivative which may be prepared using carbonyldiimidazole (CDI), a lower alkyl ester, an acid azide and the like. These reactive derivatives may be produced by standard methods.

The reaction may be carried out using equimolar of the carboxylic acid compound (VI) or a reactive derivative thereof and the amine compound (V), or one of them in excess amount, under cooling to heating in an inert solvent such as aromatic hydrocarbons, halogenated hydrocarbons, ethers, DMF, DMA, NMP, ethyl acetate, acetonitrile or the like. Depending on the kind of reactive derivatives, it is sometimes advantageous in advancing the reaction smoothly to carry out the reaction in the presence of a base (preferably, triethylamine, diisopropylethylamine, N-methylmorpholine, pyridine, 4-(N,N-dimethylamino)pyridine or the like). Pyridine can also serve as the solvent.

When a free carboxylic acid is used, it is desirable to use a condensing agent (N,N'-dicyclohexylcarbodiimide (DCC), 1-[3-(dimethylamino)propyl]-ethylcarbodiimide (WSC), 1,1'-carbonylbisimidazole (CDI), N,N'-disuccinimidyl carbonate, Bop reagent (mfd. by Aldrich, USA), 2-(1H-benzotriazol-1-yl)-1,1,3,3-tetramethyluronium tetrafluoroborate (TBTU), 2-(1H-benzotriazol-1-yl)-1,1,3,3-tetramethyluronium hexafluorophosphate (HBTU), diphenylphosphoric acid azide (DPPA), phosphorus oxychloride, phosphorus trichloride, triphenylphosphine/N-bromosuccinimide or the like, or a condensing agent-carrying polystyrene resin such as PS-carbodiimide (mfd. by Argonaut Technologies, USA) or PL-DCC resin (mfd. by Polymer Laboratories, UK).

Depending on the kind of reaction, it is sometimes advantageous for the acceleration of the reaction to further use an additive agent (e.g., HONSu, HOBt or the like). Also, in some cases, it is desirable to use an isocyanate-carrying polystyrene resin, such as PS-isocyanate (mfd. by Argonaut Technologies, USA) or the like, in order to remove excess amine after completion of the reaction. In addition, it is desirable in some cases to use a quaternary ammonium salt-carrying polystyrene resin, such as MP-carbonate (mfd. by Argonaut Technologies, USA) or the like, in order to remove excess carboxylic acid, the aforementioned additive agent and the like after completion of the reaction.

Second Step:

This step is a step for obtaining the compound (I) of the invention by reducing the compound (VII). As the reduction reaction of this step, an reduction reaction generally used by those skilled in the art may be employed. For example, the methods described in "Jikken Kagaku Koza (Experimental Chemistry Course) (4th edition)", vol. 20, p. 282 (1992) (Maruzen), edited by The Chemical Society of Japan, and the like may be employed. It is desirable to carry out the reaction at from cooling to heat reflux in a solvent inert to the reaction, such as the aforementioned ethers, aromatic hydrocarbons or the like, using equimolar to excess amount of a borane-dimethyl sulfoxide complex or lithium aluminum hydride as the reducing agent.

(Production Method 3)

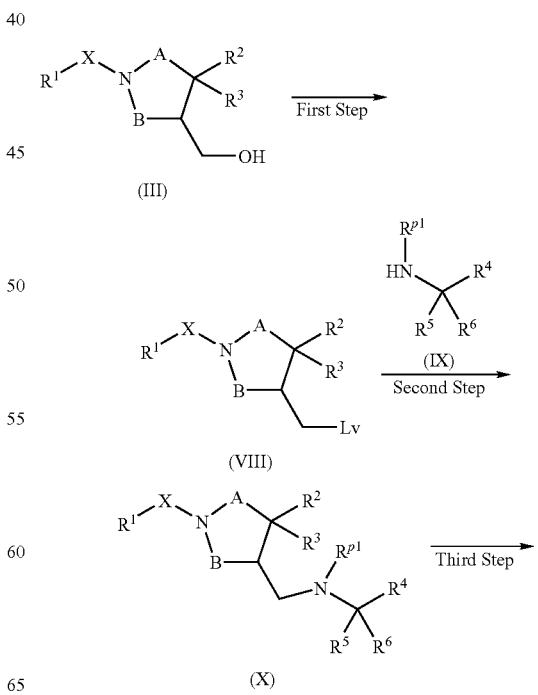

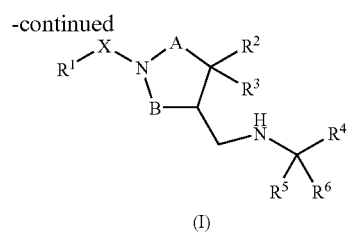

(In the formula, Lv represents a leaving group, and $R^{p1}$ a protecting group, the same shall apply hereinafter.)

First Step:

This step is a step for obtaining a compound (VIII) by converting the compound (III) with a leaving group. The leaving group represented by Lv may be any leaving group which is generally used in the nucleophilic substitution reaction, and halogen (e.g., chloro, bromo or the like); sulfonyloxy (e.g., methanesulfonyloxy, p-toluenesulfonyloxy, trifluoromethanesulfonyloxy or the like); sulfonyl (e.g., lower alkylsulfonyl, arylsulfonyl or the like); and the like may be suitably used.

For example, as the halogenation reaction, a halogenation reaction generally used by those skilled in the art may be employed. For example, the methods described in "Jikken Kagaku Koza (Experimental Chemistry Course) (4th edition)", vol. 19 (1992) (Maruzen), edited by The Chemical Society of Japan, and the like may be employed. For example, N-bromosuccinimide may be used as the halogenation agent in the presence of 2,2'-azobisisobutyronitrile or benzoyl peroxide. The reaction may be carried out at from cooling to heat reflux in a reaction-inert solvent such as the aforementioned aromatic hydrocarbons, esters, ethers, halogenated hydrocarbons, alcohols, DMF, DMA, NMP, DMSO, acetonitrile, pyridine, water or the like.

For example, as the sulfonic acid esterification, the sulfonic acid esterification conditions described in the aforementioned "Protective Groups in Organic Synthesis" may be employed. In addition, this may be obtained by carrying out the reaction under standard conditions for forming trifluoromethane sulfonic acid ester (e.g., at a temperature of from cooling to room temperature, preferably about 0° C., with trifluoromethane sulfonic acid anhydride in a halogenation solvent in the presence of a base such as 2,6-lutidine, N,N-(diisopropyl)ethylamine (DIEA) or the like).

Second Step:

This step is a step for obtaining a compound (X) by alkylating the compound (III) with an amine compound (IX) protected with $R^{p1}$. The protecting group represented by $R^{p1}$ may be any protecting group which is generally used in the nucleophilic substitution reaction, and carbonyl (e.g., trifluoroacetyl or the like); oxycarbonyl (e.g., t-butylcarboxyl, benzylcarboxyl or the like); sulfonyl (e.g., methanesulfonyl, p-toluenesulfonyl, trifluoromethanesulfonyl, p-nitrophenylsulfonyl, 2,4-dinitrosulfonyl or the like) and the like may be suitably used. The protected amine compound (IX) may be produced by the methods generally used by those skilled in the art for protecting amino group. For example, this may be produced by the carboxamidation, carbamation or sulfonamidation method described in the aforementioned "Protective Groups in Organic Synthesis". In addition, the compound (IX) in which $R^{p1}$ is trifluoromethanesulfonyl may be produced under the trifluoromethane sulfonamidation condition generally used by those skilled in the art. For example, this may be produced at a temperature of from cooling to room temperature, preferably about 0° C., using trifluoromethane sulfonic acid anhydride in a halogenation solvent in the presence of a base such as 2,6-lutidine, N,N-(diisopropyl)ethylamine (DIEA) or the like.

As the alkylation reaction of this step, the alkylation generally used by those skilled in the art may be employed. For example, this may be carried out at from room temperature to heat reflux without solvent or in a reaction-inert solvent such as the aforementioned aromatic hydrocarbons, esters, ethers, halogenated hydrocarbons, ketones (e.g., acetone, methyl ethyl ketone and the like), DMF, DMA, NMP, DMSO, acetonitrile or the like, or in a solvent such as alcohols or the like. Depending on the compound, it is sometimes advantageous for smoothly advancing the reaction to carry out the reaction in the presence of an organic base (triethylamine, diisopropylethylamine, N-methylmorpholine, pyridine, 4-(N,N-dimethylamino)pyridine or the like is suitably used) or a metal salt base (potassium carbonate, cesium carbonate, sodium hydroxide, potassium hydroxide, sodium hydroxide, potassium tert-butoxide or the like is suitably used). In addition, the alkylation which uses a compound (IX) in which $R^{p1}$ is sulfonyl may be carried out in accordance, for example, with the method of Fukuyama et al. ("Chemical Communications", 2004, p. 353-359) or the like.

Depending on the compound, the compound (I) of the invention may be directly obtained by using an unprotected amine compound instead of the compound (IX).

Third Step:

This step is a step for obtaining the compound (I) of the invention by deprotecting the compound (X).

The deprotection of this step may be carried out by employing a deprotection condition which is generally used by those skilled in the art. For example, the conditions for decarboxamidation, decarbamation or desulfonamidation described in the aforementioned "Protective Groups in Organic Synthesis" may be employed. In addition, when $R^{p1}$ is p-nitrophenylsulfonyl group or 2,4-dinitrosulfonyl group, deprotection may be carried out in accordance, for example, with the method of Fukuyama et al. ("Chemical Communications", 2004, p. 353-359) or the like.

(Production Method 4)

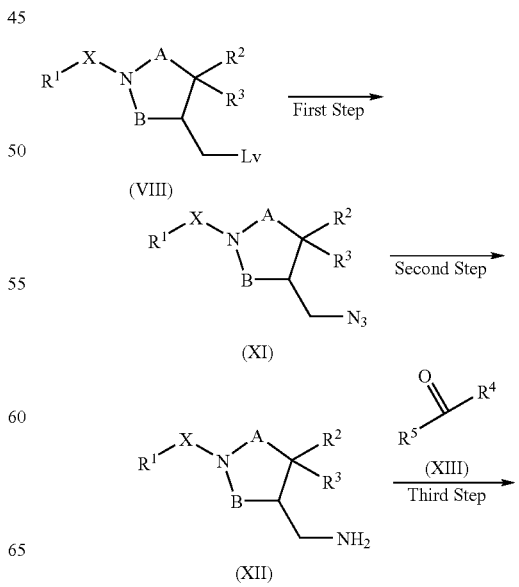

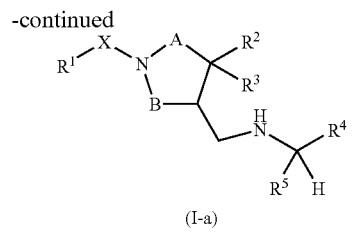

(I-a)

First Step:

This step is a step for obtaining a compound (XI) by carrying out azidation of the compound (VIII). An azidation reaction generally used by those skilled in the art may be used in the azidation reaction. For example, the methods described in "Jikken Kagaku Koza (Experimental Chemistry Course) (4th edition)", vol. 20. p.416 (1992) (Maruzen), edited by The Chemical Society of Japan, and the like may be employed.

Second Step:

This step is a step for obtaining a compound (XII) by reducing the compound (XI). A reduction reaction generally used by those skilled in the art may be used in the reduction reaction. For example, a catalytic reduction which uses palladium catalyst (e.g., Lindlar catalyst or the like), Raney Ni or the like, a reduction by metal hydride (e.g., lithium aluminum hydride or the like), a reduction by triphenylphosphine or the like, and the like may be cited. This may be carried out at from cooling to heat reflux using equimolar to excess amounts of these reducing reagents in a reaction-inert solvent such as the aforementioned aromatic hydrocarbons, esters, ethers, halogenated hydrocarbons, DMF, DMA, NMP, DMSO, acetonitrile, alcohols, water and the like.

Third Step:

This step is a step for obtaining a compound (I-a) of the invention by carrying out reductive alkylation of the compound (XII) with the compound (XIII). The reductive alkylation reaction of this step may be carried out in the same manner as the aforementioned third step of the production method 1.

(Production Method 5)

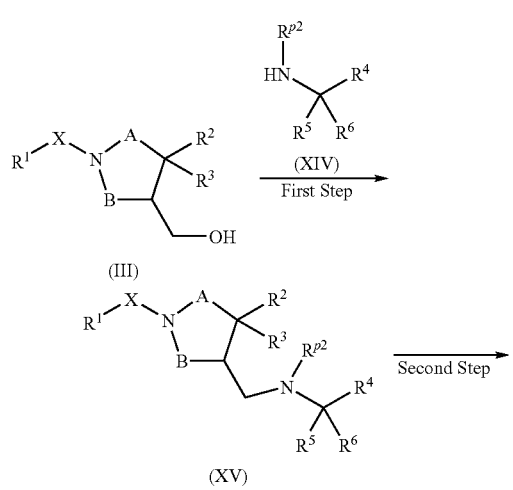

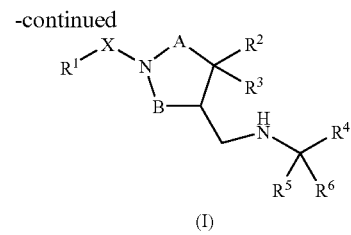

(I)

(In the formula, $R^{p2}$ means a protecting group. The same shall apply hereinafter).

First Step:

This step is a step for obtaining a compound (XV) by converting the alcohol group of the compound (III) by Mitsunobu reaction.

The protecting group represented by $R^{p2}$ may be any protecting group which is generally used in introducing an amine compound into its reactive derivative by Mitsunobu reaction, and a sulfonyl such as methanesulfonyl, p-toluenesulfonyl, trifluoromethanesulfonyl, p-nitrophenylsulfonyl, 2,4-dinitrosulfonyl or the like may be suitably used. Protection of the amine compound may be carried out in the same manner as the aforementioned second step of the production method 3.

As the Mitsunobu reaction, a reduction reaction generally used by those skilled in the art may be employed. For example, the method described in a contributed paper "New Mitsunobu reagent" reported by Tsunoda et al. in the "Kenkyu Happyo (research release)" (published July, 2004) (http://www.tokyokasei.cojp/kikou/bun/123dr.pdf), inserted in a home page of Tokyo Kasei Kogyo (http://www.tokyokasei.cojp/index-j.html), may be employed. In addition, this may be carried out in accordance with the method of Fukuyama et al. ("Chemical Communications", 2004, p. 353-359) or the like. The reaction may be carried out at from cooling to heat reflux using the alcohol compound (III) and a reactive derivative (XIV) of the amine compound in equimolar amounts, or one of them in excess amount, without solvent or in a reaction-inert solvent such as the aforementioned halogenated hydrocarbons, aromatic hydrocarbons, esters, ethers and the like.

Second Step:

This step is a step for obtaining the compound (I) of the invention by deprotecting the compound (XV).

Deprotection of the amine compound may be carried out in the same manner as the aforementioned third step of the production method 3.

(Production Method 6)

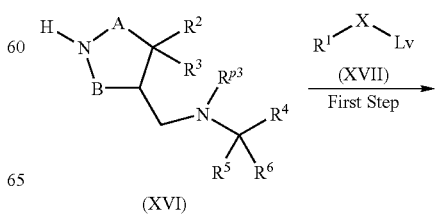

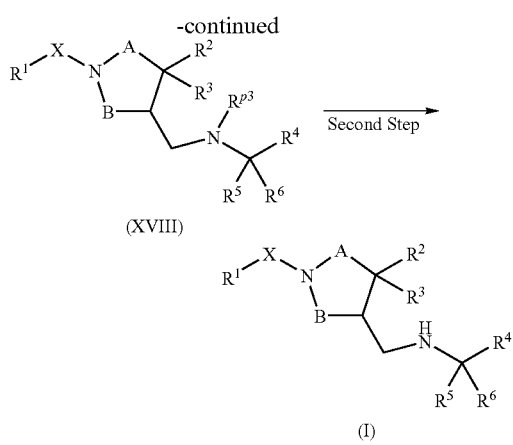

(In the formula, $R^{p3}$ means a protecting group. The same shall apply hereinafter).

The protecting group represented by $R^{p3}$ may be any amino group-protecting group generally used by those skilled in the art, and carbonyl (e.g., trifluoroacetyl or the like); oxycarbonyl (e.g., t-butylcarboxyl, benzylcarboxyl or the like); sulfonyl (e.g., methanesulfonyl, p-toluenesulfonyl, trifluoromethanesulfonyl, p-nitrophenylsulfonyl, 2,4-dinitrosulfonyl or the like) and the like may be suitably used. Protection of the amine compound may be carried out in the same manner as the aforementioned second step of the production method 3.

5-a: A Case in which X is Single Bond

This step is a step for obtaining a compound (XVIII) by alkylating a compound (XVI) and a compound (XVII). The alkylation reaction of this step may be carried out in the same manner as the aforementioned third step of the production method 1 and the aforementioned second step of the production method 3.

5-b: A Case in which X is —C(=O)— or —S(O)$_2$—

This step is a step for obtaining the compound (XVIII) by acylating or sulfonylating the compound (XVI) and the compound (XVII). The acylation and sulfonylation conditions described in the aforementioned "Protective Groups in Organic Synthesis" may be employed.

5-c: A Case in which X is Carbamate Bond

This step is a step for obtaining the compound (XVIII) by allowing the amine compound (XVI) to react with the carbamation agent (XVII), thereby effecting carbamation. For example, the method described in "Jikken Kagaku Koza (Experimental Chemistry Course) (4th edition)", vol. 20, p. 355-365 (1992) (Maruzen), edited by The Chemical Society of Japan, or the like or the carbamation condition described in the aforementioned "Protective Groups in Organic Synthesis" may be employed. The reaction may be carried out at from cooling to heat reflux using the amine compound (XVI) and the carbamation agent (XVII) in equimolar amounts, or one of them in excess amount, in a reaction-inert solvent such as the aforementioned aromatic hydrocarbons, esters, ethers, halogenated hydrocarbons, alcohols, ketones, DMF, DMA, NMP, DMSO, acetonitrile, pyridine, water and the like. Examples of the carbamation agent (XVII) include an acid halide (chloroformate or the like), an acid anhydride (a mixed acid anhydride obtained by the reaction with ethyl chlorocarbonate, benzyl chlorocarbonate, phenyl chlorocarbonate, p-toluenesulfonic acid, isovaleric acid or the like, or a symmetric acid anhydride), an active ester (an ester which may be prepared using phenol which may be substituted with electron attractive group (e.g., nitro group, fluorine atom or the like), CDI, HONSu or the like) and the like. Reactive derivatives thereof may be produced in the standard method. Depending on the compound, it is sometimes advantageous for smoothly advancing the reaction to carry out the reaction in the presence of an organic base (triethylamine, diisopropylethylamine, N-methylmorpholine, pyridine, 4-(N,N-dimethylamino)pyridine or the like is suitably used) or a metal salt base (potassium carbonate, cesium carbonate, sodium hydroxide, potassium hydroxide, sodium hydroxide, potassium tert-butoxide or the like is suitably used). Preparation of the carbamation agent using p-nitrophenol or CDI and the carbamation may be carried out, for example, in accordance with the method of Vatele et al. ("*Tetrahedron*", 2004, vol. 60, p. 4251-4260) or the like. Also, preparation of the carbamation agent using HONSu for example and the carbamation may be carried out in accordance with the method of Ghosh et al. ("*Tetrahedron Letters*", 1992, vol. 33, p. 2781-2784) or the like.

5-d: A Case in which X is Urea Bond

This step is a step for obtaining the compound (XVIII) by allowing the amine compound (XVI) to react with the ureation agent (XVII), thereby effecting ureation. For example, the method described in "Jikken Kagaku Koza (Experimental Chemistry Course) (4th edition)", vol. 20, p. 355-365 (1992) (Maruzen), edited by The Chemical Society of Japan, or the like may be employed. The reaction may be carried out at from cooling to heat reflux using the amine compound (XVI) and the ureation agent (XVII) in equimolar amounts, or one of them in excess amount, in a reaction-inert solvent such as the aforementioned aromatic hydrocarbons, esters, ethers, halogenated hydrocarbons, alcohols, ketones, DMF, DMA, NMP, DMSO, acetonitrile, pyridine, water and the like. Depending on the compound, it is sometimes advantageous for smoothly advancing the reaction to carry out the reaction in the presence of an organic base (triethylamine, diisopropylethylamine, N-methylmorpholine, pyridine, 4-(N,N-dimethylamino)pyridine or the like is suitably used) or a metal salt base (potassium carbonate, cesium carbonate, sodium hydroxide, potassium hydroxide, sodium hydroxide, potassium tert-butoxide or the like is suitably used).

Examples of the ureation agent include an acid halide (e.g., chloroformate or the like), an acid anhydride (e.g., a mixed acid anhydride obtained by the reaction with ethyl chlorocarbonate, benzyl chlorocarbonate, phenyl chlorocarbonate, p-toluenesulfonic acid, isovaleric acid or the like, or a symmetric acid anhydride), an active ester (an ester which may be prepared using phenol which may be substituted with electron attractive group (e.g., nitro group, fluorine atom or the like), CDI, HONSu or the like), an acid azide and the like. These ureation agents may be produced in the standard method.

For example, preparation of the ureation agent using p-nitrophenol and the ureation may be carried out in accordance with the method of Tor et al. ("*Tetrahedron Letters*", 2001, vol. 42, p. 1445-1447) or the like.

For example, preparation of the ureation agent using CDI and the ureation may be carried out in accordance with the method of Batey et al. ("*Tetrahedron Letters*", 1998, vol. 39, p. 6267-6270), the method of Koga et al. ("*Bioorganic & Medicinal Chemistry Letters*", 1998, vol. 8, p. 1471-1476) and the like.

For example, preparation of the ureation agent using HONSu and the ureation may be carried out in accordance with the method of Ogura et al. ("*Tetrahedron Letters*", 1983, vol. 24, p. 4569-4572) or the like.

For example, preparation of the ureation agent using acid azide and the ureation may be carried out in accordance with the method of Carceller et al. ("*Journal of Medicinal Chemistry*", 1996, vol. 39, p. 487-493), the method of Ryng et al. ("*Pharmazie*", 1999, vol. 54, p. 359-361) and the like.

Depending on the kind of compound, the compound (I) of the invention may be directly produced by carrying out similar methods of 5-a to 5-d using unprotected compound instead of the compound (XVI).

Second Step:

This step is a step for obtaining the compound (I) of the invention by deprotecting the compound (XVIII). Deprotection of the amine compound may be carried out in the same manner as the aforementioned third step of the production method 3.

Production Method 6 Other Production Methods

Compounds of the invention having various functional groups such as carboxyl group, amido group, hydroxyl group, alkylamino group and the like may be produced by using corresponding compounds of the invention having ester group, carboxyl group, amino group and the like as the starting materials and employing a method obvious to those skilled in the art, a conventionally known method or a modified method thereof.

6-a: Hydrolysis

A compound having carboxyl group or hydroxyl group may be produced by hydrolyzing a compound having esterified carboxy group. For example, this may be carried out in accordance of the deprotection reaction described in the aforementioned "Protective Groups in Organic Synthesis".

6-b: Amidation

Amidation may be carried out in the same manner as in the aforementioned first step of production method 2.

6-c: Alkylation

Alkylation may be carried out in the same manner as, for example, in the third step of the aforementioned production method 1 or the second step of the aforementioned production method 3. Also, when a secondary amine is produced from a primary amine, a method in which it is once converted into a trifluoroacetylamino compound, and then subjected to alkylation and subsequent hydrolysis ("*Tetrahedron Letters*", 1978, p. 4987, or the like) may be employed.

6-d: Oxidation 1

A compound having aldehyde may be produced by oxidizing hydroxymethyl group. As the oxidation reaction, an oxidation reaction of from hydroxymethyl group to aldehyde group generally used by those skilled in the art may be employed. For example, the same method of the second step of the aforementioned production method 1, the method described in "Jikken Kagaku Koza (Experimental Chemistry Course) (5th edition)", vol. 17 (2004) (Maruzen), edited by The Chemical Society of Japan, or the like may be employed.

6-e: Oxidation 2

A compound having carboxyl group may be produced by oxidizing hydroxymethyl group or aldehyde group. As the oxidation reaction, an oxidation reaction of from hydroxymethyl group or aldehyde group to carboxyl group generally used by those skilled in the art may be employed. For example, the method described in "Jikken Kagaku Koza (Experimental Chemistry Course) (5th edition)", vol. 16, p. 1-10 (2005) (Maruzen), edited by The Chemical Society of Japan, or the like may be employed.

6-f: Oxidation 3

An oxide compound and/or dioxide compound may be produced by oxidizing the nitrogen atom or sulfur atom of a tertiary amine, pyridine or the like heteroaryl having nitrogen atom or a sulfide compound, using various oxidizing agent. The reaction may be carried out under cooling or from room temperature to heating in a solvent such as halogenated hydrocarbons, acetic acid, water or the like, for example, using equimolar to excess amount of m-chloroperbenzoic acid, peracetic acid, hydrogen peroxide or the like as the oxidizing agent.

6-g: Reduction 1

As the reduction of amide, carboxylic acid, ester, aldehyde and ketone, a reduction reaction generally used by those skilled in the art may be employed. For example, the same method of the second step of the aforementioned production method 2, or the method described in "Jikken Kagaku Koza (Experimental Chemistry Course) (3rd edition)", vol. 15 (1977) (Maruzen), edited by The Chemical Society of Japan, or "House Saishin Yuki Gosei Hanno (the Newest House Organic Synthesis Reactions) (2nd. edition)" translated by Toshio Goto (1974) (Hirokawa Shoten), or the like may be employed.

6-h: Reduction 2

A compound having amino group may be produced by reducing a compound having nitro group. Regarding the reduction reaction of nitro group, a reduction reaction of nitro group generally used by those skilled in the art may be used. For example, this may be carried our at from room temperature to heating in an atmosphere of hydrogen under ordinary pressure or pressurization, using palladium-carbon, Raney nickel, platinum or the like as the catalyst, in a reaction-inert solvent such as the aforementioned aromatic hydrocarbons, esters, ethers, halogenated hydrocarbons, DMF, DMA, NMP, acetic acid or the like. Depending on the compound, it is sometimes advantageous in smoothly advancing the reaction to carry out the reaction in the presence of an acid (preferably, hydrochloric acid, acetic acid or the like).

6-g: Tetrazole Formation

A reaction generally used by those skilled in the art may be used as the tetrazole formation. For example, the method described in "Shinpen Hetero Kan Kagobutsu (New Edition Heterocyclic Compounds) Oyohen (Application course)" edited by Masako Nakagawa et al. (2004) p. 98-100 (Kodansha) or the like may be employed.

6-h: 1,2,4-Oxadiazole Formation

A reaction generally used by those skilled in the art may be used as the 1,2,4-oxadiazole formation. For example, the method described in "Shinpen Hetero Kan Kagobutsu (New Edition Heterocyclic Compounds) Oyohen (Application course)" edited by Masako Nakagawa et al. (2004) p. 95-97 (Kodansha) or the like may be employed. In addition, this can also be carried out in accordance with the method of Coote et al. ("*Tetrahedron Letters*", 1995, vol. 36, p. 4471-4474) or the like.

The starting materials to be used in producing the compound (I) of the invention may be produced, for example, by using the following methods, conventionally known methods or modified methods thereof.

(Starting Material Synthesis 1)

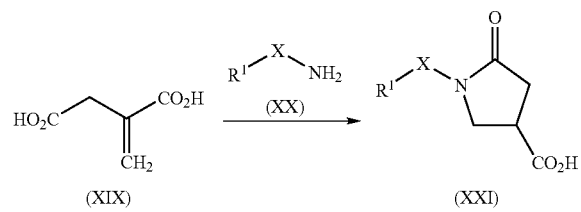

This production method is a production method for obtaining a starting material compound (XXI) by carrying out cyclic condensation of a compound (XIX) and a compound (XX).

For example, this may be carried out in accordance with the method of Paytash et al. ("*Journal of the American Chemical Society*", 1950, vol. 72, p. 1415-1416), the method of Evans et al. ("*Journal of the American Chemical Society*", 1950, vol. 72, p. 2727-2728) or the like.

(Starting Material Synthesis 2)

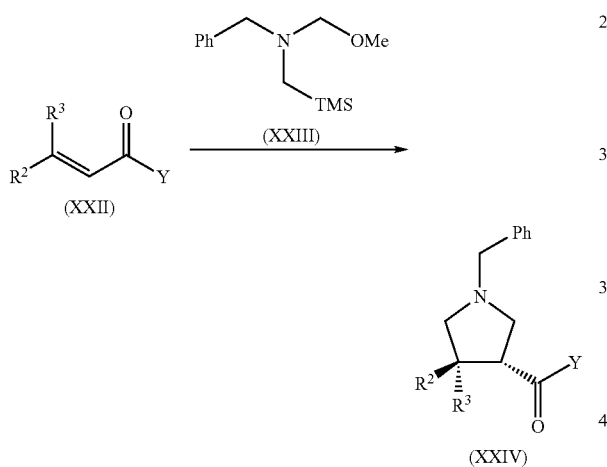

(In the formula, Me, Ph, TMS and Y show the following meanings. Me: methyl, Ph: phenyl, TMS: trimethylsilyl, and Y: an alkyloxy group or a chiral auxiliary group. The same shall apply hereinafter.)

This production method is a method for preferentially obtaining a 3,4-pyrrolidine compound (XXIV) in which $R^2$ and —C(=O)Y are in trans relation, by allowing azomethine ylide formed from an amine compound (XXIII) to react with an α,β-unsaturated carbonyl compound (XXII). For example, this may be carried out in accordance with the method of Achiwa et al. ("*Chemical & Pharmaceutical Bulletin*", 1985, vol. 33, no. 7, p. 2762-2766). For example, 3,4-cis-pyrrolidine is preferentially formed when this procedure is carried out using a cis-cinnamic acid ester as the starting material.

The reaction may be carried out at from room temperature to heating, preferably from −20° C. to 60° C., using the compound (XXII) and the compound (XXIII) in equimolar amounts, or one of them in excess amount, without solvent or in a reaction-inert solvent such as aromatic hydrocarbons, ethers, halogenated hydrocarbons, DMF, DMA, NMP, ethyl acetate, acetonitrile or the like. The reaction temperature may be optionally set in response to the compounds. The reaction for generating azomethine ylide may be carried out treating commercially available N-benzyl-N-methoxymethylamine in the presence of a stoichiometric amount of trifluoroacetic acid (TFA).

In addition, other than TFA, this may be carried out in the coexistence of lithium fluoride and cesium fluoride in accordance with the method of Padwa et al. ("*Journal of Organic Chemistry*", 1987, vol. 52, p. 235-244).

In this connection, when a chiral auxiliary group is used as Y, optically pure pyrrolidine compound (XXIV) may be obtained. For example, this may be carried out in accordance with the method of Zhenkun et al. (US patent US 005618949 specification). As the chiral auxiliary group of Y in this case, (S)-4-benzyl-2-oxazolidinone, (S)-(+)-4-phenyl-2-oxazolidinone, (+)-10,2-camphorsultam, (−)-menthol and the like may for example be cited.

(Starting Material Synthesis 3)

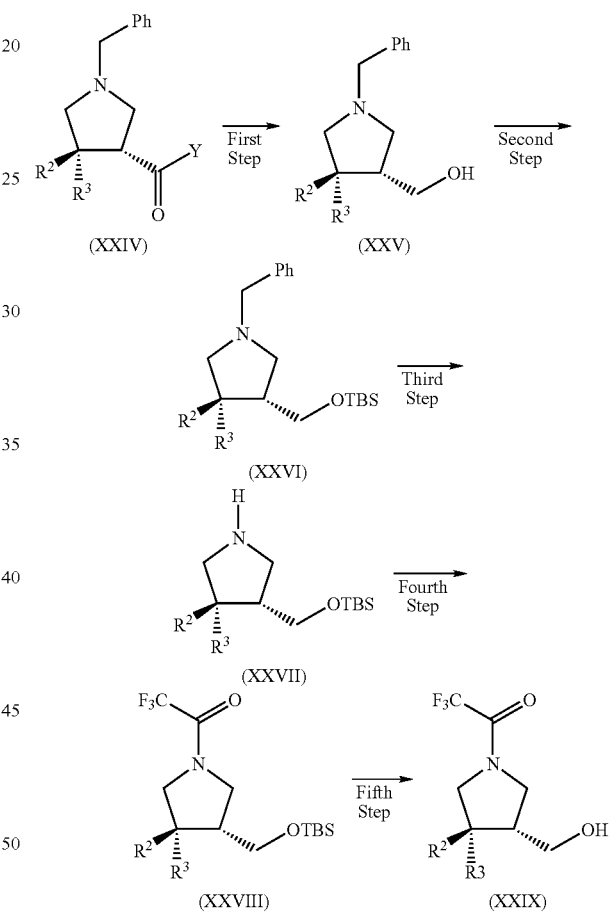

(In the Formula, Tbs Represents Tert-Butyldimethylsilyl.)

The reduction reaction of the first step may be carried out in the same manner as the first step of the aforementioned production method 1. The silylation reaction of the second step, de-benzyl reaction of the third step and de-silylation reaction of the fifth step may be carried out in accordance with the respective silylation reaction, de-benzyl reaction and de-silylation reaction described in the aforementioned "Protective Groups in Organic Synthesis". The amidation reaction of the fourth step may be carried out in the same manner as the first step of the aforementioned production method 2.

The compounds produced in this manner may be isolated and purified as their free forms or, after carrying out a salt formation treatment in the standard method, as their salts or various types of solvates (e.g., hydrates and the like). The isolation and purification are carried out by employing general chemical operations such as extraction, concentration, evaporation, crystallization, filtration, recrystallization, various types of chromatography and the like.

Various types of isomers may be isolated in the standard method making use of the differences in physicochemical properties among isomers. For example, a racemic mixture may be separated into optically pure isomers, for example by a general racemic resolution such as a method in which they are converted into diastereomer salts with a general optically active acid such as tartaric acid or the like and then subjected to optical resolution, or by various types of chromatography or the like. Also, a diastereomer mixture may be separated for example by fractional crystallization or various types of chromatography or the like. In addition, an optically active compound can also be produced by using an appropriate optically active starting material.

A pharmaceutical preparation containing one or two or more of the compounds of the invention or salts thereof is prepared using a carrier, a filler and other additive agents generally used in the preparation of medicines.

Its administration may be in the form of either oral administration by tablets, pills, capsules, granules, powders, solutions or the like or parenteral administration by injections for intravenous injection, intramuscular injection or the like, suppositories, percutaneous preparations, transnasal preparations, inhalations or the like. The dose is optionally decided in response to individual case by taking the symptoms, age and sex of the object and the like into consideration, but is generally from about 0.001 mg/kg to about 100 mg/kg per day per adult in the case of oral administration, and this is administered in one portion or dividing it into 2 to 4 portions. Also, in the case of intravenous administration, this is administered generally within the range of from 0.0001 mg/kg to 10 mg/kg per day per adult, once a day or two or more times a day. Also, in the case of transnasal administration, this is administered generally within the range of from 0.0001 mg/kg to 10 mg/kg per adult, once a day or two or more times a day. In addition, in the case of inhalation, this is administered generally within the range of from 0.0001 mg/kg to 1 mg/kg per adult, once a day or two or more times a day.

Regarding the solid composition of the invention for oral administration, tablets, powders, granules and the like are used. In such a solid composition, one or more of active substances are mixed with at least one inactive filler such as lactose, mannitol, glucose, hydroxypropylcellulose, microcrystalline cellulose, starch, polyvinyl pyrrolidone, aluminum magnesium silicate or the like. In the standard method, the composition may contain inactive additive agents such as lubricants (e.g., magnesium stearate or the like), disintegrators (e.g., carboxymethylstarch sodium or the like), and solubilizing agents. As occasion demands, tablets or pills may be coated with a sugar coating or a gastric or enteric coating agent.

The liquid composition for oral administration includes pharmaceutically acceptable emulsions, solutions, suspensions, syrups, elixirs and the like, and contains a generally used inert solvent such as purified water or ethanol. In addition to the inert solvent, this composition may contain auxiliary agents such as a solubilizing agent, a moistening agent, a suspending agent and the like, sweeteners, correctives, aromatics and antiseptics.

Injections for parenteral administration include sterile aqueous or non-aqueous solutions, suspensions and emulsions. As the aqueous solvent, for example, distilled water for injection and physiological saline are included. As the non-aqueous solvent, for example, there are propylene glycol, polyethylene glycol, plant oils (e.g., olive oil and the like), alcohols (e.g., ethanol and the like), polysorbate 80 (pharmacopeia) and the like. Such a composition may further contain tonicity agents, antiseptics, moistening agents, emulsifying agents, dispersing agents, stabilizing agents and solubilizing agents. These are sterilized, for example, by filtration through bacteria retaining filter, blending of bactericides or irradiation. In addition, these can also be used by producing sterile solid compositions and dissolving or suspending them in sterile water or a sterile solvent for injection prior to their use.

Regarding transmucosal agents such as inhalations and a transnasal agent and the like, those in a solid, liquid or semi-solid state are used, and may be produced in accordance with conventionally known methods. For example, excipients (e.g., lactose, starch and the like) and also pH adjusting agents, antiseptics, surfactants, lubricants, stabilizers, thickeners and the like may be optionally added thereto. For their administration, an appropriate device for inhalation or blowing may be used. For example, a compound may be administered alone or as a powder of formulated mixture, or as a solution or suspension by combining it with a pharmaceutically acceptable carrier, using conventionally known device or sprayer (e.g., a measured administration inhalation device or the like). The dry powder inhaler or the like may be for single or multiple administration use, and a dry powder or a powder-containing capsule may be used. Alternatively, this may be in a form such as a high pressure aerosol spray or the like which uses an appropriate propellant such as suitable gas (e.g., chlorofluoroalkane, hydrofluoroalkane or carbon dioxide or the like).

EXAMPLES

The following illustratively describes the invention based on examples, but the scope of the invention is not restricted thereby. Also, production methods of the starting material compounds are shown in Reference Examples.

The following abbreviations are used in the Reference Examples, Examples and tables which are shown later.

EX: represents Example number, and REx: Reference Example number, No: compound number, Structure: structural formula, DATA: physicochemical data (EI: EI-MS (Pos) ([M]$^+$); EP: ESI-MS (Pos) ([M+H]$^+$ unless otherwise noted); EN: ESI-MS (Neg) ([M–H]$^-$); FP: FAB-MS (Pos) ([M+H]$^+$); FN: FAB-MS (Neg) ([M–H]$^-$); AP: APCI- MS (Pos) ([M+H]$^+$); AN: APCI-MS (Neg) ([M–H]$^-$); NMR 1: δ (ppm) of characteristic peak in DMSO-d$_6$ by $^1$H-NMR; NMR 2: δ (ppm) of characteristic peak in CDCl$_3$ by $^1$H-NMR; NMR 3: δ (ppm) of characteristic peak in CD$_3$OD by $^1$H-NMR; Sal: salt (no description: free form; HCl: hydrochloride; oxalate: oxalate; fumarate: fumarate; numeral shows ratio of acid component, for example, 2HCl means dichloride)), Me: methyl, Et: ethyl, nPr: normal propyl, iPr: isopropyl, cPr: cyclopropyl, tBu: tert-butyl, nBu: normal butyl, iBu: isobutyl, cBu: cyclobutyl, cPen: cyclopentyl, cHex: cyclohexyl, Ph: phenyl, Bn: benzyl, Ac: acetyl, TBAF: tetrabutylammonium fluoride, Boc: tert-butoxycarbonyl, TBS: tert-butyldimethylsilyl and TBDPS: tert-butyldiphenylsilyl, respectively. In addition, the numeral before substituent group shows the substitution position, and two or more numerals indicate two or more substitutions. For example, 3,4-diCl represents 3,4-dichloro. Syn: production method (the numeral shows that it was produced using a corresponding starting material, similar to the case of an Example compound having its number as the Example number. A case in which two or more numerals are shown indicates that it was produced by carrying out corresponding production methods in order starting from the first number.). RSyn: production method (the numeral shows that it was produced using a corresponding starting material, similar to the case of a Reference Example compound having its number as the Reference Example number. A case in which two or more numerals are shown indicates that it was produced by carrying out corresponding production methods in order starting from the first number.).

Reference Example 1

In accordance with the method of "Helvetica Chimica Acta", 2002, vol. 85, no. 11, p. 3616-3623, triethylamine was added under ice-cooling to a mixture of trans-cinnamic acid chloride, (S)-4-benzyl-2-oxazolidinone, lithium chloride and dichloromethane, and then stirred at room temperature for 3Hours. Thereafter, (4S)-4-benzyl-3-[(2E)-3-phenylprop-2-enoyl]-1,3-oxazolidin-2-one was obtained by purifying it in the standard method. FP: 308.

Reference Example 2

In accordance with the technique of Ling et al. ("*Tetrahedron*", 2001, vol. 57,p. 6579-6588) and the method of International Patent Publication WO 2000/59502, a 20 ml dichloromethane solution of 7.3 ml of trifluoroacetic acid anhydride was added under ice-cooling to a mixture of (3R,4S)-3-({[tert-butyl(dimethyl)silyl]oxy}methyl)-4-phenylpyrrolidine synthesized from (4S)-4-benzyl-3-[(2E)-3-phenylprop-2-enoyl]-1,3-oxazolidin-2-one, 21.6 ml of triethylamine and 70 ml of dichloromethane, and stirred at room temperature for 4Hours. The reaction solution was concentrated under a reduced pressure, and the residue was mixed with water, extracted with ethyl acetate and washed with water and saturated brine in that order. The organic layer was dried with anhydrous sodium sulfate and concentrated under a reduced pressure. The thus obtained residue was purified by a silica gel column chromatography (chloroform) to obtain 11.9 g of (3R,4S)-3-({[tert-butyl(dimethyl)silyl]oxy}methyl)-4-phenyl-1-(trifluoroacetyl)pyrrolidine as a yellow amorphous substance. FP: 388.

Reference Example 3

A 11.9 g portion of (3R,4S)-3-({[tert-butyl(dimethyl)silyl]oxy}methyl)-4-phenyl-1-(trifluoroacetyl)pyrrolidine was dissolved in 30 ml of THF, and a THF solution of TBAF (1.0 M, 37 ml) was added thereto at room temperature and stirred for 2Hours. The reaction solution was concentrated under a reduced pressure, and the residue was mixed with water, extracted with diethyl ether and washed with water and saturated brine in that order. The organic layer was dried with anhydrous sodium sulfate and concentrated under a reduced pressure. The thus obtained residue was purified by a silica gel column chromatography (chloroform-ethyl acetate) to obtain 6.28 g of [(3R,4S)-4-phenyl-1-(trifluoroacetyl)pyrrolidin-3-yl]methanol as a yellow amorphous substance. FP: 274.

Reference Example 4

(1) A 7.18 g portion of DMSO was dissolved in 30 ml of dichloromethane, and a 10 ml dichloromethane solution of 4.0 ml oxalyl chloride was added thereto while keeping the internal temperature at −60° C. or less. After stirring for 15 minutes, a 40 ml dichloromethane solution of 6.28 g of [(3R,4S)-4-phenyl-1-(trifluoroacetyl)pyrrolidin-3-yl]methanol was added thereto while keeping the inner temperature at −60° C. and stirred for 15 minutes. A 19.3 ml portion of triethylamine was added to the reaction solution while keeping the internal temperature at −50° C. or less, and then the internal temperature was allowed to warm to −25° C. over 30 minutes or more, and this was further stirred at −25° C. for 20 minutes. Under ice-cooling, the reaction solution was added to saturated ammonium chloride aqueous solution to quench the reaction, and extracted with diethyl ether. The organic layer was washed with water and saturated brine in that order and dried with anhydrous sodium sulfate. By concentrating under a reduced pressure, (3R,4S)-4-phenyl-1-(trifluoroacetyl)pyrrolidine-3-carbaldehyde was obtained as a crude product.

(2) A 7.31 g portion of sodium triacetoxyborohydride was added at room temperature to a mixture of the crude product obtained in (1), 5.00 g of (R)-(+)-1-(1-naphthyl)ethylamine, 4.0 ml of acetic acid and 100 ml of 1,2-dichloroethane, and stirred at room temperature for 10Hours. A 3.65 g portion of sodium triacetoxyborohydride was further added to the reaction solution and stirred at 50° C. for 2Hours. A 1.00 g portion of sodium triacetoxyborohydride was further added to the reaction solution, and this was further stirred at 50° C. for 1Hour and then cooled to room temperature. The reaction solution was washed with saturated sodium bicarbonate aqueous solution until it became neutral, and the combined washing solution was further extracted with chloroform. The combined organic layer was washed with saturated sodium bicarbonate aqueous solution, water and saturated brine in that order. The organic layer was dried with anhydrous sodium sulfate and concentrated under a reduced pressure. By purifying the thus obtained residue by a silica gel column chromatography (chloroform-methanol-aqueous ammonia), (1R)-1-(1-naphthyl)-N-{[(3S,4S)-4-phenyl-1-(trifluoroacetyl)pyrrolidin-3-yl]methyl}ethanamine was obtained as a crude product.

(3) A 7.53 g portion of di-tert-butyl dicarbonate was added at room temperature to a mixture of the crude product obtained in (2) with 3.20 ml of triethylamine and 100 ml of THF, and stirred at 50° C. for 13Hours. By cooling to room temperature, the reaction solution was concentrated under a reduced pressure. The thus obtained residue was purified by a silica gel column chromatography (hexane-ethyl acetate) to obtain 9.28 g of tert-butyl [(1R)-1-(1-naphthyl)ethyl]{[(3R,4S)-4-phenyl-1-(trifluoroacetyl)pyrrolidin-3-yl]methyl}carbamate as a colorless amorphous substance. FP: 527.

Reference Example 5

A 9.27 g portion of tert-butyl [(1R)-1-(1-naphthyl)ethyl]{[(3R,4S)-4-phenyl-1-(trifluoroacetyl)pyrrolidin-3-yl]methyl}carbamate was dissolved in 105 ml of THF-methanol (2:1), mixed with 35 ml of 1 M sodium hydroxide aqueous solution and stirred at room temperature for 1Hour. The reaction solution was concentrated under a reduced pressure, the residue was mixed with water and extracted with chloroform, and the organic layer was dried with anhydrous sodium sulfate. This was concentrated under a reduced pressure, and the thus obtained residue was purified by a silica gel column chromatography (chloroform-methanol-aqueous ammonia) to obtain 6.97 g of tert-butyl [(1R)-1-(1-naphthyl)ethyl]{[(3R,4S)-4-phenylpyrrolidin-3-yl]methyl}carbamate as a colorless oily substance. FP: 431, NMR 1 (80° C.): 1.42 (9H, s), 1.45-1.55 (1H, m), 1.48 (3H, d, J=6.8 Hz), 2.23-2.30 (1H, m), 2.30-2.38 (1H, m), 2.48-2.57 (2H, m), 2.82-2.88 (1H, m), 2.87-2.92 (1H, m), 2.96-3.03 (1H, m), 5.95 (1H, q, J=6.8 Hz), 6.70-6.76 (2H, m), 7.04-7.17 (3H, m), 7.37 (1H, t, J=7.6 Hz), 7.39 (1H, m), 7.47-7.54 (2H, m), 7.81 (1H, m), 7.88-7.94 (1H, m), 8.02-8.09 (1H, m).

Reference Example 6

In accordance with the method of "Organic Synthesis", 1963, vol. 4, p. 731-734, John Wiley & Sons, methyl 3-formylbenzoate (mfd. by Fluka), malonic acid and pyridine were allowed to undergo the reaction in methanol, by heating under reflux, thereby obtaining (2E)-3-[3-(methoxycarbonyl) phenyl]acrylic acid. FP: 207, NMR 1: 3.88 (3H, 3), 6.62 (1H, d, J=16.0 Hz), 7.58 (1H, t, J=7.5 Hz), 7.67 (1H, d, J=16.0 Hz), 7.96-8.06 (2H, m), 8.18-8.21 (1H, m), 12.52 (1H, br.s).

Reference Example 7

In accordance with the method of "Organic Synthesis", 1963, vol. 4, p. 731-734, John Wiley & Sons, 3-cyanobenzaldehyde, malonic acid and pyridine were allowed to undergo the reaction in ethanol, by heating under reflux, thereby obtaining (2E)-3-(3-cyanophenyl)acrylic acid. FN: 172, NMR 1: 6.71 (1H, d, J=16.0 Hz), 7.58-7.66 (2H, m), 7.84-7.90 (1H, m), 8.03-8.05 (1H, m), 8.24 (1H, br.s), 12.6 (1H, br.s).

Reference Example 8

By the same method of Reference Example 7, (2E)-3-(2-fluorophenyl)acrylic acid was produced from 2-fluorobenzaldehyde and malonic acid. FN: 165.

Reference Example 9

Oxalyl chloride was slowly added at room temperature to a mixture of (2E)-3-(3-cyanophenyl)acrylic acid, DMF and dichloromethane and stirred for 30 minutes. The reaction solution was concentrated under a reduced pressure, and the thus obtained residue was dissolved in THF and again concentrated under a reduced pressure. By repeating this operation, excess hydrogen chloride and oxalyl chloride were removed and crude (2E)-3-(3-cyanophenyl)acrylic acid chloride was obtained. The thus obtained crude product and (S)-4-benzyl-2-oxazolidinone were subjected to condensation reaction in the same manner as in Reference Example 1 to obtain 3-{(1E)-3-[(4S)-4-benzyl-2-oxo-1,3-oxazolidin-3-yl]-3-oxoprop-1-en-1-yl}benzonitrile. FP: 333, NMR 1: 3.02 (1H, dd, J=7.0, 13.5 Hz), 3.10 (1H, dd, J=3.5, 13.5 Hz), 4.25 (1H, dd, J=3.0, 8.5 Hz), 4.41 (1H, t, J=8.5 Hz), 4.75-4.85 (1H, m), 7.20-7.37 (5H, m), 7.68 (1H, t, J=8.0 Hz), 7.85 (2H, br.s), 7.90-7.95 (1H, m), 8.01-8.06 (1H, m), 8.20 (1H, br.s).

Reference Example 10

In the same manner as in Reference Example 1, (4S)-4-phenyl-3-{(2E)-3-[3-(trifluoromethyl)phenyl]prop-2-enoyl}-1,3-oxazolidin-2-one was produced from trans-3-(trifluoromethyl)cinnamic acid chloride (mfd. by Aldrich, USA) and (S)-(+)-4-phenyl-2-oxazolidinone.

Reference Example 11

In the same manner as in Reference Example 9, (4S)-3-[(2E)-3-(2-fluorophenyl)prop-2-enoyl]-4-phenyl-1,3-oxazolidin-2-one was produced from (2E)-3-(2-fluorophenyl) acrylic acid and (S)-(+)-4-phenyl-2-oxazolidinone.

Reference Example 12

In accordance with the technique of Ling et al. ("Tetrahedron", 2001, vol. 57, p. 6579-6588) and the method of International Patent Publication WO 2000/59502, the reaction was carried out using 3-{(1E)-3-[(4S)-4-benzyl-2-oxo-1,3-oxazolidin-3-yl]-3-oxoprop-1-en-1-yl}benzonitrile, thereby obtaining 3-((3S,4R)-1-benzyl-4-{[(4S)-4-benzyl-2-oxo-1,3-oxazolidin-3-yl]carbonyl}pyrrolidin-3-yl)benzonitrile (Reference Example 12-1) as a low polarity fraction and 3-((3R,4S)-1-benzyl-4-{[(4S)-4-benzyl-2-oxo-1,3-oxazolidin-3-yl]carbonyl}pyrrolidin-3-yl)benzonitrile (Reference Example 12-2) as a high polarity fraction.

Reference Example 12-1: FP: 466, NMR 2: 2.66-2.74 (1H, m), 2.75-2.84 (1H, m), 2.79 (1H, dd, J=9.0, 13.5 Hz), 3.11-3.20 (1H, m), 3.24 (1H, dd, J=3.0, 13.5 Hz), 3.30-3.39 (1H, m), 3.66 (1H, d, J=13.0 Hz), 3.77 (1H, d, J=13.0 Hz), 4.01-4.24 (4H, m), 4.63-4.73 (1H, m), 7.16-7.63 (14H, m).

Reference Example 12-2: FP: 466, NMR 2: 2.68-2.82 (2H, m), 2.76 (1H, dd, J=9.0, 13.0 Hz), 3.09-3.17 (1H, m), 3.21 (1H, dd, J=3.0, 13.0 Hz), 3.25-3.34 (1H, m), 3.66 (1H, d, J=13.0 Hz).

Reference Example 13

In accordance with the technique of Prashad et al. ("Tetrahedron Letters", 1998, vol. 39, p. 7067-7070), 3-((3S,4R)-1-benzyl-4-{[(4S)-4-benzyl-2-oxo-1,3-oxazolidin-3-yl] methyl}pyrrolidin-3-yl)benzonitrile was allowed to react with sodium borohydride to obtain 3-[(3S,4R)-1-benzyl-4-(hydroxymethyl)pyrrolidin-3-yl]benzonitrile as a colorless amorphous substance. FP: 293, NMR 2: 2.31-2.42 (1H, m), 2.52 (1H, dd, J=7.0, 9.0 Hz), 2.71 (1H, dd, J=4.5, 9.5 Hz), 2.89 (1H, dd, J=7.5, 9.0 Hz), 3.08-3.17 (1H, m), 3.19-3.28 (1H, m), 3.62-3.76 (4H, m), 7.22-7.62 (9H, m).

Reference Example 14

From {(3R,4S)-1-benzyl-4-[3-(trifluoromethyl)phenyl] pyrrolidin-3-yl}methanol obtained using (4S)-4-phenyl-3-{(2E)-3-[3-(trifluoromethyl)phenyl]prop-2-enoyl}-1,3-oxazolidin-2-one and carrying out the reactions in order in the same manner as in Reference Example 12 and Reference Example 23 in accordance with the technique of Ling et al. ("Tetrahedron", 2001, vol. 57, p. 6579-6588), silylation reaction was carried out in accordance with the method of International Patent Publication WO 2000/59502, thereby producing (3R,4S)-1-benzyl-3-({[tert-butyl(dimethyl)silyl] oxy}methyl)-4-[3-(trifluoromethyl)phenyl]pyrrolidine from (4S)-4-phenyl-3-{(2E)-3-[3-(trifluoromethyl)phenyl]prop-2-enoyl}-1,3-oxazolidin-2-one.

Reference Example 15

From (4S)-3-{[(3R,4R)-1-benzyl-4-(2-furyl)pyrrolidin-3-yl]carbonyl}-4-phenyl-1,3-oxazolidin-2-one obtained using (4S)-3-[(2E)-3-(2-furyl)prop-2-enoyl]-4-phenyl-1,3-oxazolidin-2-one and in accordance with the technique of Ling et al. ("Tetrahedron", 2001, vol. 57, p. 6579-6588), (3R,4R)-1-benzyl-3-({[tert-butyl(dimethyl)silyl]oxy}methyl)-4-(2-furyl)pyrrolidine was produced by carrying out reduction with lithium aluminum hydride and silylation reaction in accordance with the method of International Patent Publication WO 2000/59502.

Reference Example 16

At room temperature, 1.0 g of 10% palladium/carbon was added, while suspending in 10 ml of water, to a mixture of 9.69 g of (3R,4S)-1-benzyl-3-({[tert-butyl(dimethyl)silyl]oxy}methyl)-4-[3-(trifluoromethyl)phenyl]pyrrolidine, 5.70 mg of ammonium formate and 100 ml of methanol. This was vigorously stirred at 50° C. for 4 hours and then cooled down to room temperature, and the insoluble matter was removed by filtration through a celite layer. The filtrate was concentrated under a reduced pressure, and the thus obtained residue was purified by a silica gel column chromatography (chloroform-ethyl acetate) to obtain 7.89 g of (3R,4S)-3-({[tert-butyl(dimethyl)silyl]oxy}methyl)-4-[3-(trifluoromethyl)phenyl]pyrrolidine as a pale yellow oily substance.

Reference Example 17

1-Chloroethyl chloride carbonate was added to 4 ml of a 1,2-dichloroethane solution of 390 mg of (3R,4S)-1-benzyl-3-({[tert-butyl(dimethyl)silyl]oxy}methyl)-4-(4-nitrophenyl)pyrrolidine under cooling with ice bath, and this was warmed up to room temperature and stirred for 2Hours. This was again cooled in an ice bath, mixed with saturated sodium carbonate aqueous solution, warmed up to room temperature and stirred for 30 minutes. This was extracted twice with chloroform, and the combined organic layer was washed with saturated brine, dried with anhydrous sodium sulfate and then concentrated under a reduced pressure. The oily residue was dissolved in 4 ml of methanol and heated under reflux for 5Hours. After concentration under a reduced pressure, the residue was purified by a silica gel column chromatography (chloroform-methanol) to obtain 290 mg of (3R,4S)-3-({[tert-butyl(dimethyl)silyl]oxy}methyl)-4-(4-nitrophenyl)pyrrolidine as an orange oily substance.

Reference Example 18

A 309 mg portion of tert-butyl [(1R)-1-(1-naphthyl)ethyl]{[(3R,4S)-4-phenylpyrrolidin-3-yl]methyl}carbamate was dissolved in 7 ml of acetic anhydride and 14 ml of pyridine and stirred at room temperature for 13Hours. The reaction solution was concentrated under a reduced pressure, and the thus obtained residue was purified by a silica gel column chromatography (chloroform-ethyl acetate) to obtain 224 mg of tert-butyl {[(3R,4S)-1-acetyl-4-phenylpyrrolidin-3-yl]methyl}[(1R)-1-(1-naphthyl)ethyl]carbamate as a colorless amorphous substance. FP: 473.

Reference Example 19

At room temperature, 144 mg of WSC hydrochloride, 101 mg of HOBt, 215 mg of tert-butyl [(1R)-1-(1-naphthyl)ethyl]{[(3R,4S)-4-phenylpyrrolidin-3-yl]methyl}carbamate and 0.08 ml of triethylamine were added in that order to a mixture of 80 mg of monomethyl adipate and 5 ml of dichloromethane and stirred for 3 days, and then the reaction was quenched by adding water, and this was extracted with chloroform and washed with saturated brine. The organic layer was dried with anhydrous sodium sulfate and concentrated under a reduced pressure. The thus obtained residue was purified by a silica gel column chromatography (chloroform-methanol) to obtain 270 mg of methyl 6-[(3R,4S)-3-({(tert-butoxycarbonyl)[(1R)-1-(1-naphthyl)ethyl]amino}methyl)-4-phenylpyrrolidin-3-yl]-6-oxohexanoate as a colorless amorphous substance. FP: 573.

Reference Example 20

A 270 mg portion of methyl 6-[(3R,4S)-3-({(tert-butoxycarbonyl)[(1R)-1-(1-naphthyl)ethyl]amino}methyl)-4-phenylpyrrolidin-1-yl]-6-oxohexanoate was dissolved in 3 ml of methanol, mixed with 3 ml of 1 M sodium hydroxide aqueous solution and stirred at room temperature for 4Hours. The reaction solution was concentrated under a reduced pressure, and 1 M hydrochloric acid was added to the residue until it became pH 3.0. After extraction with chloroform and subsequent washing with saturated brine, the organic layer was dried with anhydrous sodium sulfate and concentrated under a reduced pressure. The thus obtained residue was purified by a silica gel column chromatography (chloroform-methanol) to obtain 237 mg of 6-[(3R,4S)-3-({(tert-butoxycarbonyl)[(1R)-1-(1-naphthyl)ethyl]amino}methyl)-4-phenylpyrrolidin-1-yl]-6-oxohexanoic acid as a colorless solid. FP: 559.

Reference Example 21

At room temperature, WSC hydrochloride, HOBt, tert-butyl [(1R)-1-(1-naphthyl)ethyl]{[(3R,4S)-4-phenylpyrrolidin-3-yl]methyl}carbamate and triethylamine were added in that order to a mixture of monomethyl terephthalate and dichloromethane and stirred for 7.5Hours. Monomethyl terephthalate was further added thereto and stirred for 16Hours, and then work-up and purification were carried out in the standard method to obtain methyl 4-{[(3R,4S)-3-({(tert-butoxycarbonyl)[(1R)-1-(1-naphthyl)ethyl]amino}methyl)-4-phenylpyrrolidin-1-yl]carbonyl}benzoate. FP: 593.

Reference Example 22

Methyl 4-{[(3R,4S)-3-({(tert-butoxycarbonyl)[(1R)-1-(1-naphthyl)ethyl]amino}methyl)-4-phenylpyrrolidin-1-yl]carbonylbenzoate was dissolved at room temperature in 4 M hydrogen chloride/1,4-dioxane solution and dioxane and stirred for 2.5Hours. Successively, work-up and purification were carried out in the usual was to obtain methyl 4-{[(3S,4S)-3-({[(1R)-1-(1-naphthyl)ethyl]amino}methyl)-4-phenylpyrrolidin-1-yl]carbonyl}benzoate. FP: 493.

Reference Example 23

(1) A 5.00 g portion of ethyl piperidine-4-carboxylate was dissolved in 100 ml of DMF, and 6.52 g of potassium carbonate and 6.74 g of tert-butyl bromoacetate were added thereto and stirred at 60° C. for 5Hours. After spontaneous cooling, the reaction solution was diluted with diethyl ether, washed with water and saturated brine and dried with anhydrous sodium sulfate. The solvent was evaporated under a reduced pressure, and the thus obtained residue was purified by a silica gel column chromatography (chloroform-methanol) to obtain 7.59 g of ethyl 1-(2-tert-butyl-2-oxoethyl)piperidine-4-carboxylate as a pale yellow oily substance.

(2) At room temperature, 3.0 ml of 4 M hydrogen chloride/1,4-dioxane was added to 8 ml of 1,4-dioxane solution containing 543 mg of ethyl 1-(2-tert-butyl-2-oxoethyl)piperidine-4-carboxylate, and stirred at 60° C. for 8Hours. The thus formed solid was collected by filtration to obtain 300 mg of [4-(ethoxycarbonyl)piperidin-1-yl]acetic acid as a white solid. EP: 216.

Reference Example 24

Ethyl 4-(2-tert-butyl-2-oxoethyl)benzoate obtained by carrying out reaction of ethyl 4-hydroxybenzoate with tert-butyl bromoacetate in the same manner as in Reference Example 23 (1) was dissolved in dichloromethane, mixed with TFA at room temperature and stirred overnight at room temperature. By evaporating the solvent, [4-(ethoxycarbonyl)phenoxy] acetic acid was obtained as a white solid. EN: 223.

Reference Example 25

By carrying out the reaction similar to the case of Reference Example 24, [3-(ethoxycarbonyl)phenoxy]acetic acid was produced using corresponding starting materials. EN: 223.

Reference Example 26

A 780 mg portion of adipic anhydride and 1.06 ml of triethylamine were added in that order under ice-cooling to a mixture of 767 mg of ethyl (benzylamino)acetate and chloroform, stirred at room temperature for 12Hours and then further stirred at 50° C. for 5.5 hours. The reaction solution was washed with 1 M hydrochloric acid and dried with anhydrous sodium sulfate. This was concentrated under a reduced pressure, and the thus obtained residue was purified by a silica gel column chromatography (chloroform-methanol) to obtain 456 mg of 6-[benzyl(2-ethoxy-2-oxyethyl)amino]6-oxohexanoic acid as colorless oily substance. FP: 322.

Reference Example 27

By carrying out the reaction in the same manner as in Reference Example 26, 6-[(2-ethoxy-2-oxoethyl)(methyl) amino]-6-oxohexanoic acid was produced using corresponding starting materials. EP: 246.

Reference Example 28

By hydrolyzing methyl 4-{[(3R,4S)-3-({(tert-butoxycarbonyl)[(1R)-1-(1-naphthyl)ethyl]amino}methyl)-4-phenylpyrrolidin-1-yl]carbonyl}benzoate in the same manner as in Reference Example 20, 4-{[(3R,4S)-3-({(tert-butoxycarbonyl)[(1R)-1-(1-naphthyl)ethyl]amino}methyl)-4-phenylpyrrolidin-1-yl]carbonyl}benzoic acid was obtained. EP: 579.

Reference Example 29

A 76 mg portion of potassium carbonate was added to a 20 ml DMF solution of 214 mg 2,5-dimethylterephthalate and stirred at room temperature for 30 minutes. 0.068 ml of methyl iodide was added to the reaction solution successively and stirred overnight at room temperature. Successively, work-up and purification were carried out in the standard method to obtain 90 mg of 4-methoxycarbonyl-2,5-dimethylbenzoic acid as colorless solid. EN: 207.

Reference Example 30

A 1.00 g portion of 4-(dihydroxyboronyl)benzoic acid, 0.85 ml of methyl 2-bromobenzoate and 0.3 ml of water were added to a 30 ml dioxane suspension of 220 mg palladium(II) chloride diphenylphosphinoferrocene complex, 508 mg diphenylphosphinoferrocene and 5.9 g cesium carbonate, and stirred at 100° C. for 24Hours.

The insoluble matter was removed by filtration, the filtrate was concentrated under a reduced pressure, and the thus obtained residue was purified by a silica gel column chromatography (hexane-ethyl acetate) to obtain 161 mg of 2'-(methoxycarbonyl)biphenyl-4-carboxylic acid as a pale yellow solid. EN: 255.

Reference Example 31

By carrying out the reaction in the same manner as in Reference Example 30, 3'-(ethoxycarbonyl)biphenyl-4-carboxylic acid was produced using corresponding starting materials. EN: 269.

Reference Example 32

(1) A 1.2 g portion of 4-fluorobenzonitrile and 1.0 g of potassium carbonate were added to 25 ml DMF solution of 1.2 g of 3-hydroxybenzaldehyde and stirred overnight with heating at 100° C. The reaction solution was poured into ice water, and then work-up and purification were carried out in the standard method to obtain 1.6 g of 4-(3-formylphenoxy) benzonitrile as an oily substance. EI: 223.

(2) A 15 ml portion of concentrated hydrochloric acid was added to a 15 ml acetic acid solution of 1.5 g of the 4-(3-formylphenoxy)benzonitrile obtained in (1) and heated under reflux overnight. The reaction solution was poured into ice water, and the thus precipitated crystals were collected by filtration and washed with water to obtain 1.5 g of 4-(3-formylphenoxy)benzoic acid. EI: 242.

Reference Example 33

By carrying out the reaction in the same manner as in Reference Example 32, 4-(4-formylphenoxy)benzoic acid was produced using corresponding starting materials. AN: 241.

Reference Example 34

(1) A 4.0 ml portion of DMSO was added at −78° C. to a 40 ml dichloromethane solution of 2.5 ml oxalyl chloride and stirred for 10 minutes, and then a dichloromethane solution of 2.7 g of ethyl 6-hydroxy-2,2-dimethylhexanoate synthesized by the technique described in "Tetrahedron", 2000, vol. 56, p. 9195-9202, was added thereto and stirred at the same temperature for 15 minutes. A 12 ml portion of triethylamine was added to the reaction solution and stirred for 30 minutes, and the reaction was quenched by adding water. Successively, work-up was carried out in the standard method to obtain 2.9 g of ethyl 2,2-dimethyl-6-oxohexanoate as a crude product. EP: 187.

(2) A 30 g portion of potassium dihydrogenphosphate, 30 ml of 2-methyl-2-butene and 13 g of sodium chlorite were added in that order at 0° C. to a 40 ml 2,2-dimethylpropanol-10 ml water solution of the crude ethyl 2,2-dimethyl-6-oxohexanoate obtained in (1) and stirred for 1Hour. Water was added to the reaction solution and the insoluble matter was removed by filtration, and then the organic solvent was evaporated under a reduced pressure. The thus obtained aqueous solution was extracted with chloroform, and the organic layer was dried with anhydrous sodium sulfate. This was concentrated under a reduced pressure to obtain 2.9 g of 6-ethoxy-5,5-dimethyl-6-oxohexanoic acid as a homogenous yellow oily substance. EN: 201.

Reference Example 35

At room temperature, 34 mg of p-toluenesulfonic acid was added to a mixture of 4.33 g of 2,2,6,6-tetramethylpimelic acid (mfd. by Tokyo Kasei (TCI), Japan), 4.24 g of benzyl alcohol and 16 ml of toluene. By equipping with a Dean-Stark type dehydration tube, this was stirred for 60Hours while heating under reflux, and then cooled down to room temperature. The insoluble matter was removed by filtration, the filtrate was concentrated under a reduced pressure, and the thus obtained residue was purified by a silica gel column chromatography (methanol-chloroform) to obtain 2.18 g of 7-(benzyloxy)-2,2,6,6-tetramethyl-7-oxoheptanoic acid as a colorless oily substance. FP: 307.

Reference Example 36

(1) A 0.16 ml portion of concentrated sulfuric acid was added to a 59 ml methanol solution of 5.9 g of 2,2'-(1,4-phenylene)diacetic acid and heated under reflux for 12Hours. The reaction solution was concentrated, and the residue was dissolved in chloroform. This was neutralized with saturated sodium bicarbonate aqueous solution, and the organic layer was dried with anhydrous magnesium sulfate and then concentrated under a reduced pressure to obtain 6.4 g of dimethyl 2,2'-(1,4-phenylene)diacetate.

(2) A 655 mg portion of lithium hydroxide was dissolved in 32 ml of water and added to 32 ml of a mixture of 6.4 g of dimethyl 2,2'-(1,4-phenylene)diacetate, 32 ml of THF and 32 ml of methanol. After 2Hours of stirring at room temperature, the reaction solution was neutralized with 1 M hydrochloric acid and extracted with chloroform. The organic layer was dried with anhydrous sodium sulfate and concentrated under a reduced pressure. The residue was purified by a silica gel column chromatography (chloroform-methanol) to obtain 2.6 g of [4-(2-methoxy-2-oxoethyl)phenyl]acetic acid. EN: 207.

Reference Example 37

Tert-butyl {[(3R,4S)-1-acryloyl-4-phenylpyrrolidin-3-yl]methyl}[(1R)-1-(1-naphthyl)ethyl]carbamate was produced from tert-butyl [(1R)-1-(1-naphthyl)ethyl]{[(3R,4S)-4-phenylpyrrolidin-3-yl]methyl}carbamate and acrylic acid chloride in the same manner as in Example 3 (1) which is described later. EP: 485.

Reference Example 38

A 239 mg portion of tert-butyl {[(3R,4S)-1-(4-cyanobenzoyl)-4-phenylpyrrolidin-3-yl]methyl}[(1R)-1-(1-naphthyl)ethyl]carbamate was obtained as a colorless oily substance from 193 mg of tert-butyl [(1R)-1-(1-naphthyl)ethyl]{[(3R,4S)-4-phenylpyrrolidin-3-yl]methyl}carbamate and 69 mg of 4-cyanobenzoic acid in the same manner as in Reference Example 21. EP: 560.

Reference Example 39

Triethylamine and 4-(chlorosulfonyl)benzoic acid were added in that order to a dichloromethane solution of tert-butyl [(1R)-1-(1-naphthyl)ethyl]{[(3R,4S)-4-phenylpyrrolidin-3-yl]methyl}carbamate and stirred at room temperature for 1Hour.

Successively, work-up and purification were carried out in the standard method to obtain 4-{[(3S,4S)-3-({(tert-butoxycarbonyl)[(1R)-1-(1-naphthyl)ethyl]amino}methyl)-4-phenylpyrrolidin-3-yl]sulfonyl})benzoic acid. FP: 615.

Reference Example 40

Methyl 6-oxohexanoate (mfd. by Sigma, USA) and a catalytically effective amount of acetic acid were added in that order to a dichloroethane solution of tert-butyl [(1R)-1-(1-naphthyl)ethyl]{[(3R,4S)-4-phenylpyrrolidin-3-yl]methyl}carbamate and stirred at room temperature for 20 minutes, and then sodium triacetoxyborohydride was added thereto at room temperature and stirred at room temperature for 13Hours. Thereafter, work-up and purification were carried out in the standard method to obtain methyl 6-{[(3R,4S)-3-({(tert-butoxycarbonyl)[(1R)-1-(1-naphthyl)ethyl]amino}methyl)-4-phenylpyrrolidin-1-yl]hexanoate. FP: 559

Reference Example 41

Ethyl 4-[(3R,4S)-3-({(tert-butoxycarbonyl)[(1R)-1-(1-naphthyl)ethyl]amino}methyl)-4-phenylpyrrolidin-1-yl]cyclohexanecarboxylate was produced from tert-butyl [(1R)-1-(1-naphthyl)ethyl]{[(3R,4S)-4-phenylpyrrolidin-3-yl]methyl}carbamate and 4-(ethoxycarbonyl)cyclohexanone in the same manner as in Reference Example 40. AP: 585.

Reference Example 42

Potassium carbonate and methyl 4-(bromomethyl)benzoate were added in that order to an acetone solution of tert-butyl [(1R)-1-(1-naphthyl)ethyl]{[(3R,4S)-4-phenylpyrrolidin-3-yl]methyl}carbamate and stirred at room temperature for 20Hours. Thereafter, work-up and purification were carried out in the standard method to obtain methyl 4-{[(3R,4S)-3-({(tert-butoxycarbonyl)[(1R)-1-(1-naphthyl)ethyl]amino}methyl)-4-phenylpyrrolidin 1-yl]methyl}benzoate. FP: 579.

Reference Example 43

A 650 mg portion of potassium carbonate and 339 mg of 4-fluorobenzonitrile were added to a mixture of 1.0 g of tert-butyl [(1R)-1-(1-naphthyl)ethyl]{[(3R,4S)-4-phenylpyrrolidin-3-yl]methyl}carbamate and 10 ml of DMSO and stirred overnight at 110° C. After cooling down to room temperature, the reaction solution was mixed with ethyl acetate, washed with water and saturated brine in that order and dried with anhydrous sodium sulfate. The solvent was evaporated under a reduced pressure, and the thus obtained residue was purified by a silica gel column chromatography (hexane-ethyl acetate) to obtain 723 mg of tert-butyl {[(3R,4S)-1-(4-cyanophenyl)-4-phenylpyrrolidin-3-yl]methyl}[(1R)-1-(1-naphthyl)ethyl]carbamate as a colorless amorphous substance. EP: 532.

Reference Example 44

(1) A 0.06 ml portion of pyridine and 103 mg of methyl 4-[(chlorocarbonyl)oxy]benzoate (mfd. by Fluka) were added in that order to a THF (5.0 ml) solution of 173 mg of tert-butyl [(1R)-1-(1-naphthyl)ethyl]{[(3R,4S)-4-phenylpyrrolidin-3-yl]methyl}carbamate and stirred for 1 week. Thereafter, its work-up and purification were carried out in the standard method to obtain 4-(methoxycarbonyl)phenyl (3R,4S)-3-({(tert-butoxycarbonyl) [(1R)-1-(1-naphthyl)ethyl]amino}methyl)-4-phenylpyrrolidine-1-carboxylate as a crude product. FP: 609.

(2) The crude 4-(methoxycarbonyl)phenyl (3R,4S)-3-({(tert-butoxycarbonyl)[(1R)-1-(1-naphthyl)ethyl]amino}methyl)-4-phenylpyrrolidine-1-carboxylate obtained in (1) was dissolved in 2 ml of methanol and 2 ml of THF, mixed with 2 ml of 1 M sodium hydroxide aqueous solution and stirred at room temperature for 7Hours. Thereafter, work-up and purification were carried out in the standard method to obtain 215 mg of 4-({[(3R,4S)-3-({(tert-butoxycarbonyl)[(1R)-1-(1-naphthyl)ethyl]amino}methyl)-4-phenylpyrrolidin-1-yl]carbonyl}oxy)benzoic acid. FP: 595.

Reference Example 45

Under ice-cooling, 1.0 g of 4-nitrophenyl chlorocarbonate was added portionwise to a 10 ml dichloromethane mixture of 1.3 g methyl salicylate and 0.54 ml pyridine, and stirred at room temperature for 3Hours. The reaction solution was diluted with ethyl acetate and washed with saturated sodium bicarbonate aqueous solution and saturated brine in that order, and then the organic layer was dried with anhydrous magnesium sulfate. This was concentrated under a reduced pressure, and the thus obtained residue was mixed with hexane and ethyl acetate and subjected to decantation, thereby obtaining 1.9 g of methyl 2-{[(4-nitrophenoxy)carbonyl]oxy}benzoate as a white solid.

Reference Example 46

Under ice-cooling, 390 mg of N,N'-disuccinimidyl carbonate and 0.42 ml of triethylamine were added to a 5 ml acetonitrile solution of 136 mg of methyl 3-hydroxy-2,2-dimethylpropionate, and stirred at room temperature for 6Hours. The solvent was evaporated under a reduced pressure, and the thus obtained residue was diluted with ethyl acetate and washed with saturated sodium bicarbonate aqueous solution and saturated brine in that order. The organic layer was dried with anhydrous sodium sulfate and concentrated under a reduced pressure to obtain methyl 3-({[(2,5-dioxypyrrolidin-1-yl)oxy]carbonyl}oxy)-2,2-dimethylpropionate.

Reference Example 47

(1) A 2.0 ml portion of morpholine was added at room temperature to 5 ml acetonitrile solution of 1.99 g of 2-fluoro-4-nitrobenzonitrile and stirred overnight at 80° C.
The reaction solution was spontaneously cooled down to room temperature, and the precipitated solid was collected by filtration to obtain 1.11 g of 2-morpholin-4-yl-4-nitrobenzonitrile as orange crystals.
(2) A 6 ml portion of concentrated sulfuric acid was added at room temperature to a 6 ml ethanol solution of 1.11 g of 2-morpholin-4-yl-4-nitrobenzonitrile, and heated under reflux for 8Hours. After spontaneous cooling, the reaction solution was poured onto ice and neutralized with saturated sodium bicarbonate aqueous solution. The organic layer was extracted with chloroform, and the organic layer was dried with anhydrous sodium sulfate. By evaporating the solvent under a reduced pressure, 1.16 g of ethyl 2-morpholin-4-yl-4-nitrobenzoate was obtained as a dark-red oily substance.
(3) A mixture of 1.16 g of ethyl 2-morpholin-4-yl-4-nitrobenzoate, 1.1 g of ammonium chloride, 1.0 g of reduced iron and 14 ml of ethanol-water (5:2) mixed solvent was stirred at 80° C. for 4Hours. The reaction solution was filtered while hot, and the white crystals precipitated after spontaneous cooling were collected by filtration to obtain 493 mg of ethyl 4-amino-2-morpholin-4-ylbenzoate. EP: 251.

Reference Example 48

A 3.5 g portion of 4-nitrophenyl chlorocarbonate was added at 0° C. to a 30 ml dichloromethane suspension of 3 g of methyl 4-amino-3-chlorobenzoate and 4 ml of pyridine and stirred at room temperature for 2Hours. The reaction solution was diluted with chloroform and washed with 1 M hydrochloric acid, water, saturated sodium bicarbonate aqueous solution, water and saturated brine in that order, and the organic layer was dried with anhydrous sodium sulfate. This was concentrated under a reduced pressure, and the thus obtained residue was recrystallized from hexane-ethyl acetate to obtain 4.23 g of methyl 3-chloro-4-{[(4-nitrophenoxy)carbonyl]amino}benzoate as a pale brown powder.

Reference Example 49

3-[(3S,4R)-1-Benzyl-4-(hydroxymethyl)pyrrolidin-3-yl]benzonitrile was dissolved in concentrated hydrochloric acid and allowed to undergo the reaction for 30 minutes by heating under reflux. The reaction solution was concentrated under a reduced pressure, and the thus obtained residue was dissolved in methanol, one drop of concentrated sulfuric acid was added thereto at room temperature, and this was heated under reflux for 8Hours while stirring. The reaction was quenched by adding triethylamine to the reaction solution under ice-cooling, and then work-up and purification were carried out in the standard method to obtain 960 mg of methyl 3-[(3S,4R)-1-benzyl-4-(hydroxymethyl)pyrrolidin-3-yl]benzoate as a colorless oily substance. FP: 326, NMR 2: 2.30-2.54 (2H, m), 2.85-2.97 (2H, m), 3.21-3.37 (2H, m), 3.62-3.80 (5H, m), 3.92 (3H, s), 7.22-7.62 (7H, m), 7.86-7.92 (1H, m), 7.95-7.98 (1H, m).

Reference Example 50

(3R,4S)-3-({[Tert-butyl(dimethyl)silyl]oxy}methyl)-4-[3-(trifluoromethyl)phenyl]pyrrolidine obtained as a crude product from 470 mg of (3R,4S)-1-benzyl-3-({[tert-butyl(dimethyl)silyl]oxy}methyl)-4-[3-trifluoromethylphenyl]pyrrolidine by carrying out the reaction in the same manner as in Reference Example 16 was added at room temperature to a mixture of 247 mg of monobenzyl adipate produced by the technique of English et al. ("Journal of Medicinal Chemistry", (USA), 1990, vol. 33, p. 344-347), 12 mg of HOBt and 5 ml of dichloromethane, to which 300 mg of WSC hydrochloride was added, and stirred for 14Hours. The reaction solution was concentrated under a reduced pressure, and the thus obtained residue was purified by a silica gel column chromatography (chloroform-ethyl acetate) to obtain 521 mg of benzyl 6-{(3R,4S)-3-({[tert-butyl(dimethyl)silyl]oxy}methyl)-4-[3-(trifluoromethyl)phenyl]pyrrolidin-1-yl}-6-oxohexanoate as a colorless amorphous substance.

Reference Example 51

Benzyl 6-{(3R,4S)-3-({[tert-butyl(dimethyl)silyl]oxy}methyl)-4-[3-(trifluoromethyl)phenyl]pyrrolidin-1-yl}-6-oxohexanoate was dissolved in THF, mixed with a THF solution of TBAF at room temperature and stirred for 5Hours. Thereafter, work-up and purification were carried out in the standard method to obtain benzyl 6-{(3R,4S)-3-(hydroxymethyl)-4-[3-(trifluoromethyl)phenyl]pyrrolidin-1-yl}-6-oxohexanoate.

Reference Example 52

A 240 mg portion of [(3R,4S)-4-(3-fluorophenyl)pyrrolidin-3-yl]methanol obtained by eliminating benzyl from (3R,4S)-1-benzyl-3-({[tert-butyl(dimethyl)silyl]oxy}methyl)-4-(3-fluorophenyl)pyrrolidine in the same manner as in Reference Example 17 was dissolved in 2.4 ml of dichloromethane, mixed with 235 mg of monoethyl adipate, 229 mg of WSC and 199 mg of HOBt and stirred at room temperature for 3Hours. The reaction solution was washed with water and dried with anhydrous sodium sulfate, and then the solvent was evaporated under a reduced pressure. By purifying the residue by a silica gel column chromatography (chloroform-methanol), 320 mg of ethyl 6-[(3S,4R)-3-(3-fluorophenyl)-4-(hydroxymethyl)pyrrolidin-1-yl]-6-oxohexanoate was obtained as a pale yellow oily substance.

Reference Example 53

A 0.30 ml portion of DMSO was dissolved in 5 ml of dichloromethane, and 0.18 ml of oxalyl chloride was added thereto while keeping the internal temperature at −60° C. or less. After 30 minutes of stirring, a dichloromethane solution (5 ml) of 323 mg of benzyl 6-{(3R,4S)-3-(hydroxymethyl)-4-[3-(trifluoromethyl)phenyl]pyrrolidin-1-yl}-6-oxohexanoate was added thereto while keeping the internal temperature at −60° C. or less, successively stirring this for 30 minutes. The reaction solution was mixed with 0.87 ml of triethylamine while keeping the internal temperature at −50° C. or less, and then stirred at −78° C. for 4.5 hours. Thereafter, work-up was carried out in the standard method to obtain benzyl 6-{(3R,4S)-3-formyl-4-[3-(trifluoromethyl)phenyl]pyrrolidin-1-yl}-6-oxohexanoate as a crude product. A mixture of the thus obtained crude product, 143 mg of (R)-(+)-1-(1-naphthyl)ethylamine, acetic acid and 5 ml of 1,2-dichloroethane was stirred for 20 minutes, and then mixed with 443 mg of sodium triacetoxyborohydride at room temperature and stirred at room temperature for 17Hours, successively carrying out work-up and purification in the standard method to obtain 312 mg of benzyl 6-{(3S,4S)-3-({[(1R)-1-(naphthyl)ethyl]amino}methyl)-4-[3-(trifluoromethyl)phenyl]pyrrolidin-1-yl}-6-oxohexanoate.

Reference Example 54

A 16.28 g portion of (3R,4S)-3-({[tert-butyl(dimethyl)silyl]oxy}methyl)-4-phenylpyrrolidine and 18 ml of pyridine were dissolved in 100 ml of THF, and 14.6 g of methyl 4-[(chlorocarbonyl)oxy]benzoate (mfd. by Fluka) was added under ice cooling in one portion thereto in an atmosphere of argon. After 1Hour of stirring at room temperature, 2.5 g of methyl 4-[(chlorocarbonyl)oxy]benzoate was further added at room temperature. After 2Hours of further stirring, the reaction solution was concentrated under a reduced pressure. The residue was diluted with water and diisopropyl ether, the thus precipitated insoluble matter was removed by filtration, and then the filtrated was concentrated under a reduced pressure and the resulting residue was extracted with ethyl acetate. The organic layer was washed with water and saturated brine in that order and dried with anhydrous sodium sulfate. This was concentrated under a reduced pressure, and the thus obtained residue was purified by a silica gel column chromatography (chloroform-ethyl acetate) to obtain 23.80 g of 4-(methoxycarbonyl)phenyl (3R,4S)-3-({[tert-butyl(dimethyl)silyl]oxy}methyl)-4-phenylpyrrolidine-1-carboxylate as a colorless oily substance.

Reference Example 55

Using (3R,4S)-1-benzyl-3-({[tert-butyl(dimethyl)silyl]oxy}methyl)-4-(2-methylphenyl)pyrrolidine, de-benzylation and carbamate formation were carried out in that order in the same manner as in Reference Example 15 and Reference Example 54, thereby producing 4-(methoxycarbonyl)phenyl (3R,4S)-3-({[tert-butyl(dimethyl)silyl]oxy}methyl)-4-(2-methylphenyl)pyrrolidine-1-carboxylate.

Reference Example 56

A 350 mg portion of (3R,4R)-3-({[tert-butyl(dimethyl)silyl]oxy}methyl)-4-(2-furyl)pyrrolidine and 470 mg of sodium bicarbonate were suspended in 20 ml of a tetrahydrofuran-water (3:1) mixed solvent, and 320 mg of methyl 4-[(chlorocarbonyl)oxy]benzoate (mfd. by Fluka) was added in one portion thereto at room temperature. After 1Hour of stirring at room temperature, 80 mg of methyl 4-[(chlorocarbonyl)oxy]benzoate was further added thereto at room temperature. After 2 hours of further stirring, the reaction solution was concentrated under a reduced pressure. The residue was separated by diluting it with water and diethyl ether, and then extracted with diethyl ether. The organic layer was washed with water and saturated brine in that order and dried with anhydrous sodium sulfate. This was concentrated under a reduced pressure, and the thus obtained residue was purified by a silica gel column chromatography (chloroform-ethyl acetate) to obtain 571 mg of 4-(methoxycarbonyl)phenyl (3R,4R)-3-({[tert-butyl(dimethyl)silyl]oxy}methyl)-4-(2-furyl)pyrrolidine-1-carboxylate as a colorless oily substance.

Reference Example 57

3-[(3S,4R)-4-({[Tert-butyl(dimethyl)silyl]oxy}methyl)pyrrolidin-3-yl]pyridine and N,N-diisopropylethylamine were dissolved in THF, methyl 4-[(chlorocarbonyl)oxy]benzoate (mfd. by Fluka) was added in one portion thereto at room temperature and stirred for 3 hours, and then the reaction solution was concentrated under a reduced pressure. Work-up and purification of the residue was carried out in the standard method to produce 4-(methoxycarbonyl)phenyl (3R,4S)-3-({[tert-butyl(dimethyl)silyl]oxy}methyl)-4-pyridin-3-ylpyrrolidine-1-carboxylate.

Reference Example 58

A 23.8 g portion of 4-(methoxycarbonyl)phenyl (3R,4S)-3-({[tert-butyl(dimethyl)silyl]oxy}methyl)-4-phenylpyrrolidine-1-carboxylate was dissolved in 80 ml of THF, and a THF solution of TBAF (1.0 M, 76 ml) was added dropwise thereto. After 2 hours of stirring at room temperature, the reaction solution was concentrated under a reduced pressure. The residue was mixed with water and extracted with ethyl acetate, and then the extract was washed with water and saturated brine in that order and dried with anhydrous sodium sulfate. This was concentrated under a reduced pressure, and the thus obtained residue was purified by a silica gel column chromatography (ethyl acetate-chloroform) to obtain 16.6 g of 4-(methoxycarbonyl)phenyl (3R,4S)-3-(hydroxymethyl)-4-phenylpyrrolidine-1-carboxylate as a colorless amorphous substance.

Reference Example 59

By carrying out the reaction in the same manner as in Reference Example 54 using (3R,4S)-3-({[tert-butyl(dimethyl)silyl]oxy}methyl)-4-(4-fluorophenyl)pyrrolidine, 4-(methoxycarbonyl)phenyl (3S,4R)-3-(4-fluorophenyl)-4-(hydroxymethyl)pyrrolidine-1-carboxylate was produced.

Reference Example 60

By carrying out the carbamate formation and de-silylation reactions in the same manner as in Reference Example 54 and Reference Example 58 using (3R,4S)-3-({[tert-butyl(dimethyl)silyl]oxy}methyl)-4-(2-fluorophenyl)pyrrolidine, 4-(methoxycarbonyl)phenyl (3S,4R)-3-(2-fluorophenyl)-4-(hydroxymethyl)pyrrolidine-1-carboxylate was produced.

Reference Example 61

(1) In an atmosphere of argon, 371 mg of DMSO was dissolved in 5.0 ml of dichloromethane, and 301 mg of oxalyl chloride was added thereto while keeping the internal temperature at −60° C. or less. After stirring at −60° C. or less for 15 minutes, a dichloromethane solution (10 ml) of 273 mg of 4-(methoxycarbonyl)phenyl (3R,4R)-3-(2-furyl)-4-(hydroxymethyl)pyrrolidine-1-carboxylate was added thereto and stirred for 30 minutes. A 1.24 ml portion of N,N-diisopropylethylamine was added to the reaction solution while keeping the internal temperature at −60° C. or less. The temperature was allowed to warm to room temperature over about 1Hour, and then this was further stirred at room temperature for 1Hour. The reaction was quenched by pouring the reaction solution into saturated ammonium chloride aqueous solution under ice-cooling, and this was separated by diluting it with diethyl ether. This was further extracted with ethyl acetate, washed with water and saturated brine in that order and dried with anhydrous sodium sulfate. By concentrating under a reduced pressure, crude product of 4-(methoxycarbonyl)phenyl (3R,4R)-3-formyl-4-(2-furyl)pyrrolidine-1-carboxylate was obtained as a yellow oily substance.

(2) A 1,2-dichloroethane solution (10 ml) of the crude 4-(methoxycarbonyl)phenyl (3R,4R)-3-formyl-4-(2-furyl)pyrrolidine-1-carboxylate obtained in (1) was added at room temperature to a mixture of 203 mg of (R)-(+)-1-(1-naphthyl)ethylamine, 302 mg of sodium triacetoxyborohydride 23.8 mg of acetic acid and 5 ml of 1,2-dichloroethane, over 10 minutes or more. After 14Hours of stirring at room temperature, this was neutralized by adding saturated sodium bicarbonate aqueous solution. The reaction solution was extracted with chloroform, dried with sodium sulfate and concentrated under a reduced pressure. The thus obtained residue was purified by a silica gel-column chromatography to obtain 230 mg of 4-(methoxycarbonyl)phenyl (3R,4S)-3-(2-furyl)-4-({[(1R)-1-(1-naphthyl)ethyl]amino}methyl)pyrrolidine-1-carboxylate as a colorless oily substance.

Reference Example 62

A 2.0 ml portion of triethylamine and 1.9 g of orthonitrobenzenesulfonyl chloride were added to a mixed solution of 1.0 g of (1R)-1-(3-methoxyphenyl)ethylamine and 10 ml of dichloromethane under ice-cooling and stirred for 5Hours. Thereafter, work-up and purification were carried out in the standard method to obtain 2.2 g of N-[(1R)-1-(3-methoxyphenyl)ethyl]-2-nitrobenzene sulfonamide as yellow crystals. EN: 335.

Reference Example 63

(1) A 0.45 ml portion of 2.2 M toluene solution of diethyl azodicarboxylate was added to a 3.0 ml toluene solution of 261 mg of 4-(methoxycarbonyl)phenyl (3R,4S)-3-(hydroxymethyl)-4-phenyl-1-pyrrolidinecarboxylate, 313 mg of N-[(1R)-1-(3-methoxyphenyl)ethyl]-2-nitrobenzene sulfonamide and 260 mg of triphenylphosphine, and stirred at room temperature for 4Hours. The reaction solution was concentrated under a reduced pressure, and the thus obtained residue was purified by a silica gel column chromatography (chloroform-methanol) to obtain 542 mg of a crude product of 4-(methoxycarbonyl)phenyl (3R,4S)-3-({[(1R)-1-(3-methoxyphenyl)ethyl][(2-nitrophenyl)sulfonyl]amino}methyl)-4-phenylpyrrolidine-1-carboxylate as a colorless amorphous substance. EP: 674.

(2) A 57 mg portion of lithium hydroxide and 67 μl of thioglycollic acid were added to a 10 ml DMF solution of the crude 4-(methoxycarbonyl)phenyl (3R,4S)-3-({[(1R)-1-(3-methoxyphenyl)ethyl][(2-nitrophenyl)sulfonyl]amino}methyl)-4-phenylpyrrolidine-1-carboxylate obtained in (1), and stirred at room temperature for 3Hours. Thereafter, its work-up and purification were carried out in the standard method to obtain 261 mg of 4-(methoxycarbonyl)phenyl (3S,4S)-3-({[(1R)-1-(3-methoxyphenyl)ethyl][(2-nitrophenyl)sulfonyl]amino}methyl)-4-phenylpyrrolidine-1-carboxylate as a yellow oily substance. EP: 489.

Reference Example 64

(1) A 0.84 ml portion of methanesulfonyl chloride was added dropwise to a 30 ml dichloromethane solution of 3.5 g of 4-(methoxycarbonyl)phenyl (3R,4S)-3-(hydroxymethyl)-4-phenylpyrrolidine-1-carboxylate and 2.75 ml of triethylamine, and stirred at room temperature for 2Hours. Thereafter, its work-up was carried out in the standard method to obtain 4.3 g of 4-(methoxycarbonyl)phenyl (3R,4S)-3-{[(methylsulfonyl)oxy]methyl}-4-phenylpyrrolidine-1-carboxylate as a colorless amorphous substance. EP: 434.

(2) A 972 mg portion of sodium azide was added at room temperature to a 40 ml DMF solution of 4.3 g of the crude 4-(methoxycarbonyl)phenyl (3R,4S)-3-{[(methylsulfonyl)oxy]methyl}-4-phenylpyrrolidine-1-carboxylate obtained in (1) and stirred at 60° C. for 7Hours. Thereafter, its work-up and purification were carried out in the standard method to obtain 3.7 g of 4-(methoxycarbonyl)phenyl (3R,4S)-3-(azidomethyl)-4-phenylpyrrolidine-1-carboxylate as a colorless oily substance. EP: 381.

(3) A 1.5 g portion of sodium borohydride was added portionwise at 0° C. to a 50 ml methanol solution of 3.7 g of the 4-(methoxycarbonyl)phenyl (3R,4S)-3-(azidomethyl)-4-phenylpyrrolidine-1-carboxylate obtained in (2) and 5.6 g of nickel(II) chloride hexahydrate, and stirred for 1Hour. The reaction solution was subjected to celite filtration, and the filtrate was concentrated under a reduced pressure. Thereafter, its work-up and purification were carried out in the standard method to obtain 2.3 g of 4-(methoxycarbonyl)phenyl (3S,4S)-3-(aminomethyl)-4-phenylpyrrolidine-1-carboxylate hydrochloride as a colorless amorphous substance. EP: 355.

Reference Example 65

(1) A 10 ml portion of thionyl chloride was added to 10 ml toluene suspension of 1 g of 2,3-dihydro-1,4-benzodioxin-5-carboxylic acid and 0.75 ml of DMF and stirred at 80° C. for 24Hours. The reaction solution was concentrated under a reduced pressure, and the residue was dissolved in 10 ml of dichloroethane and 5.0 ml of toluene, mixed with 673 mg of N,O-dimethylhydroxylamine hydrochloride and 2.5 ml of triethylamine and stirred at 70° C. for 30Hours. The reaction solution was diluted with water, acidified by adding 1 M hydrochloric acid aqueous solution and then extracted with chloroform, and the organic layer was dried with anhydrous sodium sulfate. This was concentrated under a reduced pressure, and the thus obtained residue was purified by a silica gel column chromatography (chloroform-methanol) to obtain 1 g of N-methoxy-N-methyl-2,3-dihydro-1,4-benzodioxin-5-carboxamide as a colorless solid. EP: 224.

(2) In an atmosphere of argon, a 14 ml THF solution of 1.04 M of methyl lithium was added at 0° C. to a 10 ml THF solution of 1.6 g of the N-methoxy-N-methyl-2,3-dihydro-1,4-benzodioxin-5-carboxamide obtained in (1), and stirred for 1Hour. The reaction solution was mixed with 1 M hydrochloric acid aqueous solution to quench the reaction, and then its work-up and purification were carried out in the standard method to obtain 1.1 g of 1-(2,3-dihydro-1,4-benzodioxin-5-yl)ethanone as a colorless oily substance. EP: 179.

Reference Example 66

A 203 mg portion of sodium hydride (60% oil dispersion) and 734 mg of 1-(2-chloro-1-methyl-1H-indol-3-yl)ethanone synthesized from oxyindole in accordance with the method of "*European Journal of Medicinal Chemistry*", 1991, vol. 26, p. 179-188, were added in that order at room temperature to a mixed solution of 498 mg of phenol and 10 ml of dimethylacetamide and stirred at 90° C. for 2Hours. Thereafter, its work-up and purification were carried out in the standard method to obtain 703 mg of 1-(1-methyl-2-phenoxy-1H-indol-3-yl)ethanone as a colorless solid. EP: 266.

Reference Example 67

1-azulen-1-ylethanone was synthesized from azulene in accordance with the method described in "*Justus Liebigs Annalen der Chemie*", 1959, vol. 625, p. 108-123. EP: 171.

Reference Example 68

In the same manner as in Reference Example 2, (3S,4R)-3-({[tert-butyl(dimethyl)silyl]oxy}methyl)-4-phenyl-1-(trifluoroacetyl)pyrrolidine was produced from (3S,4R)-3-({[tert-butyl(dimethyl)silyl]oxy}methyl)-4-phenylpyrrolidine which had been synthesized from (4S)-4-benzyl-3-[(2E)-3-phenylprop-2-enoyl]-1,3-oxazolidin-2-one, in accordance with the technique of Ling et al. ("*Tetrahedron*", 2001, vol. 57, p. 6579-6588) and the method of International Patent Publication WO 2000/59502. EP: 388.

Reference Example 69

A 1.00 g portion of DMSO was dissolved in 10 ml of dichloromethane, and 0.56 ml of oxalyl chloride was added thereto while keeping the internal temperature at −60° C. or less. After 30 minutes of stirring, a dichloromethane (10 ml) solution of 581 mg of [(3S,4R)-4-phenyl-1-(trifluoroacetyl)pyrrolidin-3-yl]methanol which had been obtained from (3S,4R)-3-({[tert-butyl(dimethyl)silyl]oxy}methyl)-4-phenyl-1-(trifluoroacetyl)pyrrolidine in the same manner as in Reference Example 3 was added thereto while keeping the internal temperature at −60° C. or less and stirred for 45 minutes. A 2.70 ml portion of triethylamine was added to the reaction solution while keeping the internal temperature at −60° C. or less, the internal temperature was allowed to warm to 0° C. over 30 minutes or more, and this was further stirred at 0° C. for 60 minutes. Under ice-cooling, the reaction solution was mixed with water to quench the reaction, extracted with chloroform and dried with anhydrous sodium sulfate. By concentrating under a reduced pressure, (3S,4R)-4-phenyl-1-(trifluoroacetyl)pyrrolidine-3-carboaldehyde was obtained as a crude product. A 1.35 g portion of sodium triacetoxyborohydride was added at room temperature to a mixture of the thus obtained crude product, 365 mg of (R)-(+)-1-(1-naphthyl)ethylamine, a catalytically effective amount of acetic acid and 20 ml of 1,2-dichloroethane, and stirred at room temperature for 14Hours. The reaction solution was washed with saturated sodium bicarbonate aqueous solution until it became neutral, and the combined washing solution was extracted with chloroform. The organic layer was dried with anhydrous sodium sulfate and concentrated under a reduced pressure. The thus obtained residue was purified by a silica gel column chromatography (chloroform-ethyl acetate) to obtain 886 mg of (1R)-1-(1-naphthyl)-N-{[(3R,4R)-4-phenyl-1-(trifluoroacetyl)pyridin-3-yl]methyl}ethanamine as a colorless oily substance. EP: 427.

Reference Example 70

In the same manner as the method of Reference Example 54, 4-(methoxycarbonyl)phenyl (3S,4R)-3-({[tert-butyl(dimethyl)silyl]oxy}methyl)-4-phenylpyrrolidine-1-carboxylate was produced using the corresponding starting material. EP: 470.

Reference Example 71

In the same manner as in Reference Example 2,3-({[tert-butyl(dimethyl)siyl]oxy}methyl)-4-phenyl-1-(trifluoroacetyl)pyrrolidine was produced from 3-({[tert-butyl(dimethyl)silyl]oxy}methyl)-4-phenylpyrrolidine which had been synthesized from methyl trans-cinnamate, in accordance with the technique of Ling et al. ("*Tetrahedron*", (Holland), 2001, vol. 57, p. 6579-6588) and the method of International Patent Publication WO 2000/59502. FP: 388.

Reference Example 72

In the same manner as in Reference Example 69, (1R)-1-(1-naphthyl)-N-{[4-phenyl-1-(trifluoroacetyl)pyridin-3-yl]methyl}ethanamine was produced from [4-phenyl-1-(trifluoroacetyl)pyrrolidin-3-yl]methanol which had been obtained from 3-({[tert-butyl(dimethyl)silyl]oxy}methyl)-4-phenyl-1-(trifluoroacetyl)pyrrolidine in the same manner as in Reference Example 3. FP: 427.

Reference Example 73

A pyridine solution of 3-({[tert-butyl(dimethyl)silyl]oxy}methyl)-4-phenylpyrrolidine which had been synthesized from methyl trans-cinnamate, in accordance with the technique of Ling et al. ("*Tetrahedron*", 2001, vol. 57,p. 6579-6588) and the method of International Patent Publication WO 2000/59502, was mixed with acetic anhydride and stirred at room temperature for 2Hours. After completion of the reaction, this was concentrated under a reduced pressure with toluene azeotropy, and THF and 1 M THF solution of TBAF were added to the thus obtained residue and stirred overnight at room temperature. Thereafter, its work-up and purification were carried out in the standard method to obtain (1-acetyl-4-phenylpyrrolidin-3-yl)methanol. EP: 220.

Reference Example 74

Tert-butyl [(1R)-1-(1-naphthyl)ethyl][(4-phenylpyrrolidin-3-yl)methyl]carbamate was obtained from (1R)-1-(1-naphthyl)-N-{[4-phenyl-1-(trifluoroacetyl)pyrrolidin-3-yl]methyl}ethanamine by respectively carrying out protection with Boc group and hydrolysis in that order in the same manner as in Reference Example 4 (3) and Reference Example 5.
EP: 431, NMR 1: 1.30-1.50 (13H, m), 2.05-2.25 (1H, m), 2.26-2.29 (1H, m), 2.35-2.55 (1H, m), 2.70-2.88 (1H, m), 2.88-3.00 (1H, m), 5.88-6.10 (1H, m), 6.64-6.70 (1H, m), 7.00-7.21 (1H, m), 7.30-7.44 (2H, m), 7.48-7.60 (2H, m), 7.82-7.90 (1H, m), 7.90-8.02 (1H, m), 8.02-8.08 (1H, m).

Reference Example 75

Tert-butyl [(4-benzylpyrrolidin-3-yl)methyl][(1R)-1-(1-naphthyl)ethyl]carbamate was obtained in the same manner as the method of Reference Example 74, using corresponding starting material. FP: 445.

Reference Example 76

Tertbutyl [(1R)-1-(1-naphthyl)ethyl]{[(4-(2-phenylethyl)pyrrolidin-3-yl]methyl}carbamate was obtained in the same manner as the method of Reference Example 74, using corresponding starting materials. FP: 459.

Reference Example 77

1 M sodium hydroxide aqueous solution was added at room temperature to a methanol solution of ethyl 2-oxo-4-phenylpyrrolidine-3-carboxylate (Wako Pure Chemical Industries (Wako), Japan) and stirred for 13Hours. The reaction solution was acidified by adding 1 M hydrochloric acid, and the thus precipitated solid was collected by filtration and dried to obtain 2-oxo-4-phenylpyrrolidine-3-carboxylic acid. FP: 206.

Reference Example 78

HOBt and WSC hydrochloride were added to a DMF solution of 2-oxo-4-phenylpyrrolidine-3-carboxylic acid. After 30 minutes thereof, this was mixed with (1R)-(+)-(1-naphthyl)ethylamine and further stirred overnight. Water and sodium bicarbonate were added in that order to the reaction solution, and the precipitated solid matter was collected by filtration and then dried. The thus obtained solid matter was purified by a silica gel column chromatography (chloroform-methanol) to obtain N-[(1R)-1-(1-naphthyl)ethyl]-2-oxo-4-phenylpyrrolidine-3-carboxamide (Reference Example 78-1) from a low polarity eluate, and its diastereomer (Reference Example 78-2) from a high polarity eluate, respectively.

Reference Example 78-1: FP: 359

Reference Example 78-2: FP: 359

Reference Example 79

Ethyl 1-benzyl-4-methylpyrrolidine-3-carboxylate synthesized in accordance with the method of International Patent Publication WO 2000/15611 was reduced with lithium aluminum hydride in accordance with the method of International Patent Publication WO 2000/59502. Tert-butyldiphenylchlorosilane was added to a THF solution of the thus obtained (1-benzyl-4-methylpyrrolidin-3-yl)methanol, sodium hydride was added thereto under ice-cooling, and the mixture was stirred at room temperature for 2Hours. Thereafter, its work-up and purification were carried out in the standard method to obtain 1-benzyl-3-({[tert-butyl(diphenyl)silyl]oxy}methyl)-4-methylpyrrolidine. AP: 444.

Reference Example 80

1-Benzyl-3-({[tert-butyl(diphenyl)silyl]oxy}methyl)-4-(trifluoromethyl)pyrrolidine was synthesized in the same manner as in Reference Example 79, from ethyl 1-benzyl-4-(trifluoromethyl)pyrrolidine-3-carboxylate which had been synthesized in accordance with the method of "Bioorganic & Medicinal Chemistry Letters", vol. 8, 1998, p. 2833-2838. AP: 498.

Reference Example 81

Ethyl 1-benzyl-4-[3-(trifluoromethyl)phenyl]pyrrolidine-3-carboxylate, which had been synthesized in accordance with the method of "Bioorganic & Medicinal Chemistry Letters", vol. 6, 1996, p. 295-300, was reduced with lithium aluminum hydride in accordance with the method of International Patent Publication WO 2000/59502. By protecting hydroxyl group of the thus obtained {1-benzyl-4-[3-(trifluoromethyl)phenyl]pyrrolidin-3-yl}methanol using tert-butyldimethylsilylchlorosilane and diisopropylethylamine, 1-benzyl-3-({[tert-butyl(dimethyl)silyl]oxy}methyl)-4-[3-(trifluoromethyl)phenyl]pyrrolidine was obtained. FP: 450.

Reference Example 82

Methyl triphenylphosphoranylideneacetate was added to a toluene solution of phenylacetaldehyde and heated under reflux for 17Hours. Thereafter, its work-up and purification were carried out in the standard method to obtain methyl (2E)-4-phenylbute-2-noate. FP: 177.

Reference Example 83

In accordance with the technique of Ling et al. ("*Tetrahedron*", (Holland), 2001, vol. 57,p. 6579-6588) and the method of International Patent Publication WO 2000/59502, methyl 1,4-dibenzylpyrrolidin-3-carboxylate was synthesized using methyl (2E)-4-phenylbute-2-noate. FP: 310.

Reference Example 84

In accordance with the method of International Patent Publication WO 2000/59502, 1,3-dibenzyl-4-({[tert-butyl(dimethyl)silyl]oxy}methyl)pyrrolidine was synthesized using methyl 1,4-dibenzylpyrrolidin-3-carboxylate. FP: 396.

Reference Example 85

Methyl (2E)-5-phenylpente-2-noate was synthesized from 3-phenylpropanal in the same manner as in Reference Example 82. FP: 191.

Reference Example 86

In accordance with the technique of Ling et al. ("*Tetrahedron*", 2001, vol. 57,p. 6579-6588) and the method of International Patent Publication WO 2000/59502, methyl 1-benzyl-4-(2-phenylethyl)pyrrolidine-3-carboxylate was synthesized from methyl (2E)-5-phenylpente-2-noate.

Reference Example 87

In accordance with the method of International Patent Publication WO 2000/59502, 1-benzyl-3-({[tert-butyl(dimethyl)silyl]oxy}methyl)-4-(2-phenylethyl)pyrrolidine was synthesized using methyl 1-benzyl-4-(2-phenylethyl)pyrrolidine-3-carboxylate. FP: 410.

Reference Example 88

In accordance with the method of International Patent Publication WO 2000/59502, 1-benzyl-4-({[tert-butyl(dimethyl)

silyl]oxy}methyl)-3,3-dimethylpyrrolidine was synthesized using ethyl 1-benzyl-4,4-dimethylpyrrolidine-3-carboxylate which had been synthesized in accordance with the method of International Patent Publication WO 2000/15611. AP: 458.

Reference Example 89

In accordance with the technique of "Bioorganic and Medicinal Chemistry Letters", 1991, vol. 1, no. 12, p. 757-760, methyl 1-benzyl-5-oxopyrrolidine-3-carboxylate (mfd. by Aldrich, USA) was added to a THF solution of lithium aluminum hydride in an ice bath, and then stirred at 60° C. for 1.5Hours. Thereafter, its work-up and purification were carried out in the standard method to obtain (1-benzylpyrrolidin-3-yl)methanol. FP: 192.

Reference Example 90

Diisopropylethylamine and tert-butyldimethyl-chlorosilane were added in that order to a chloroform solution of (1-benzylpyrrolidin-3-yl)methanol and stirred at room temperature for 5Hours. Thereafter, its work-up and purification were carried out in the standard method to obtain 1-benzyl-3-({[tert-butyl(dimethyl)silyl]oxy}methyl]pyrrolidine. EP: 306.

Reference Example 91

A methanol solution of 1-benzyl-3-({[tert-butyl(dimethyl)silyl]oxy}methyl]pyrrolidine was mixed with 10% palladium/carbon and ammonium formate and stirred at 50° C. for 3Hours. After celite layer filtration, the solvent of the filtrate was evaporated, and the thus obtained residue was mixed with chloroform, ethyl trifluoroacetate and triethylamine and stirred overnight at room temperature. Thereafter, its work-up and purification were carried out in the standard method to obtain 3-({[tert-butyl(dimethyl)silyl]oxy}methyl)-1-(trifluoroacetyl)pyrrolidine. EP: 312.

Reference Example 92

TBAF was added to a THF solution of 3-({[tert-butyl(dimethyl)silyl]oxy}methyl)-1-(trifluoroacetyl)pyrrolidine and stirred overnight at room temperature. Thereafter, its work-up and purification were carried out in the standard method to obtain [1-(trifluoroacetyl)pyrrolidin-3-yl]methanol. EP: 198.

Reference Example 93

Using [1-(trifluoroacetyl)pyrrolidin-3-yl]methanol, oxidation reaction and reductive alkylation reaction were carried out by the same techniques of Reference Example 4 (1) and Reference Example 4 (2) to synthesize (1R)-1-(1-naphthyl)-N-{[1-(trifluoroacetyl)pyrrolidin-3-yl]methyl}ethanamine. EP: 351.

Reference Example 94

Using (1R)-1-(1-naphthyl)-N-{[1-(trifluoroacetyl)pyrrolidin-3-yl]methyl}ethanamine, the protection of Boc group addition and hydrolysis shown in Reference Example 4 (3) and Reference Example 5 were carried out to obtain tert-butyl [(1R)-1-(1-naphthyl)ethyl](pyrrolidin-3-ylmethyl)carbamate. EP: 355.

Reference Example 95

In accordance with the method of "Journal of the American Chemical Society", vol. 72, 1950, p. 1415, aniline was added to an itaconic acid aqueous solution and heated under reflux for 12Hours. After completion of the reaction, this was ice-cooled and mixed with 70 ml of 1 M hydrochloric acid, and the thus precipitated crystals were collected by filtration to obtain 5-oxo-1-phenylpyrrolidine-3-carboxylic acid. EP: 206.

Reference Example 96

A 10 ml portion of a DMF solution of 500 mg of 5-oxo-1-phenylpyrrolidine-3-carboxylic acid was mixed with 935 mg of WSC hydrochloride, 396 mg of HOBt and 500 mg of(1R)-1-naphthylethylamine and stirred at room temperature for 3 days. After completion of the reaction, 100 ml of saturated sodium bicarbonate aqueous solution was added thereto, and the thus formed solid was collected by filtration to obtain 1.01 g of N-(1R)-1-(1-naphthyl)ethyl]-5-oxo-1-phenylpyrrolidine-3-carboxamide as a colorless solid. EP: 359.

Reference Example 97

A methanol solution of methyl 1-benzyl-5-oxo-3-pyrrolidinecarboxylate was mixed with 1 M sodium hydroxide aqueous solution and stirred at room temperature for 2Hours. After completion of the reaction, this was neutralized with 1 M hydrochloric acid, and methanol was evaporated. The thus formed crystals were collected by filtration to obtain 1-benzyl-5-oxo-3-pyrrolidine-carboxylic acid. FN: 218.

Reference Example 98

4-Methoxybenzylamine was added to an aqueous solution of itaconic acid and heated under reflux for 12Hours. After completion of the reaction, this was cooled in an ice bath and mixed with 1 M hydrochloric acid, and the thus precipitated crystals were collected by filtration to obtain 1-(4-methoxybenzyl)-5-oxopyrrolidine-3-carboxylic acid as colorless crystals. EP: 250.

Reference Example 99

1,1'-Carbonylbisimidazole was added to a THF solution of 5-oxo-1-phenylpyrrolidine-3-carboxylic acid and stirred at room temperature for 1.5Hours. Successively sodium borohydride and 2.0 ml of water were added thereto and stirred at room temperature for 1Hour. Thereafter, its work-up and purification were carried out in the standard method to obtain 4-(hydroxymethyl)-1-phenylpyrrolidin-2-one. EP: 192.

Reference Example 100

Oxalyl chloride was added to a dichloromethane solution of DMSO at −78° C. and stirred for 20 minutes. Successively, this was mixed with a dichloromethane solution of 4-(hydroxymethyl)-1-phenylpyrrolidin-2-one and then with triethylamine 15 minutes thereafter, and stirred for 30 minutes. Thereafter, work-up and purification were carried out to obtain 5-oxo-1-phenylpyrrolidine-3-carboaldehyde. EN: 188.

Reference Example 101

By carrying out the reduction reaction in the same manner as in Reference Example 99, 1-benzyl-4-(hydroxymethyl)pyrrolidin-2-one was obtained from 1-benzyl-5-oxo-3-pyrrolidine-carboxylic acid. FP: 206.

Reference Example 102

Triethylamine and a pyridine-sulfur trioxide complex were added to a DMSO solution of 1-benzyl-4-(hydroxymethyl)pyrrolidin-2-one and stirred at room temperature for 2Hours. Thereafter, its work-up and purification were carried out in the standard method to obtain 1-benzyl-5-oxopyrrolidine-3-carboaldehyde. EI: 203.

Reference Example 103

By carrying out the reduction reaction in the same manner as in Reference Example 99, 1-cyclohexyl-4-(hydroxymethyl)pyrrolidin-2-one was obtained from 1-cyclohexyl-5-oxopyrrolidine-carboxylic acid (mfd. by Matrix, USA). FP: 198.

Reference Example 104

By carrying out the oxidation reaction in the same manner as in Reference Example 100, 1-cyclohexyl-5-oxopyrrolidine-carboaldehyde was obtained from 1-cyclohexyl-4-(hydroxymethyl)pyrrolidin-2-one. FN: 194.

Reference Example 105

Using the (3R,4S)-3-({[tert-butyl(dimethyl)silyl]oxy}methyl)-4-(4-nitrophenyl)pyrrolidine obtained in Reference Example 17, the amidation was carried out in the same manner as in Reference Example 50 to produce benzyl 6-[(3R,4S)-3-({[tert-butyl(dimethyl)silyl]oxy}methyl)-4-(4-nitrophenyl)pyrrolidin-1-yl]-6-oxohexanoate.

Reference Example 106

Using the (3R,4S)-1-benzyl-3-({[tert-butyl(dimethyl)silyl]oxy}methyl)-4-(2-methylphenyl)pyrrolidine obtained in Reference Example 127 which is described later, the elimination of benzyl group and amidation with monoethyl adipate were carried out in that order in the same manner as in Reference Example 16 and Reference Example 50 to produce ethyl 6-[(3R,4S)-3-({[tert-butyl(dimethyl)silyl]oxy}methyl)-4-(2-methylphenyl)pyrrolidin-1-yl]-6-oxohexanoate.

In the same manner as the methods of the aforementioned Reference Examples 1 to 106, compounds of Reference Examples 107 to 204 were produced using respective corresponding starting materials. Structures and physicochemical data of the compounds of Reference Examples are shown in Tables 4 to 21.

Example 1

(1) [(3R,4S)-4-Phenyl-1-(trifluoroacetyl)pyrrolidin-3-yl]methanol was dissolved in 6 ml of dichloromethane and 1.53 ml of triethylamine, 6 ml of a DMSO solution prepared by dissolving 1.71 g of a pyridine-sulfur trioxide complex was added thereto while keeping the internal temperature at −10° C. or less, and this was stirred for 10 minutes. The reaction solution was mixed with ice and then extracted with diethyl ether. The organic layer was washed with water and saturated brine in that order and dried with anhydrous sodium sulfate.

This was concentrated under a reduced pressure to obtain (3R,4S)-4-phenyl-1-(trifluoroacetyl)pyrrolidin-3-carboaldehyde as a crude product.

(2) A 1.46 g portion of sodium triacetoxyborohydride was added at room temperature to a mixture of the thus obtained crude (3R,4S)-4-phenyl-1-(trifluoroacetyl)pyrrolidin-3-carboaldehyde, 376 mg of (R)-(+)-1-(1-naphthyl)ethylamine, a catalytically effective amount of acetic acid and 20 ml of 1,2-dichloroethane, and stirred at room temperature for 13Hours. Saturated sodium bicarbonate aqueous solution was added to the reaction solution until it became neutral, and then this was extracted with chloroform.

The organic layer was dried with anhydrous sodium sulfate and concentrated under a reduced pressure. The thus obtained residue was purified by a silica gel column chromatography (chloroform-ethyl acetate) to obtain 718 mg of (1R)-1-(1-naphthyl)-N-{[(3S,4S)-4-phenyl-1-(trifluoroacetyl)pyrrolidin-3-yl]methyl}ethanamine as a colorless oily substance.

(3) A 389 mg portion of the thus obtained (1R)-1-(1-naphthyl)-N-{[(3S,4S)-4-phenyl-1-(trifluoroacetyl)pyrrolidin-3-yl]methyl}ethanamine was dissolved in 5 ml of ethyl acetate and treated with a 4 M hydrogen chloride/ethyl acetate solution. The reaction solution was diluted with hexane, and the thus precipitated solid was recrystallized from ethyl acetate and hexane to obtain 268 mg of (1R)-1-(1-naphthyl)-N-{[(3S,4S)-4-phenyl-1-(trifluoroacetyl)pyrrolidin-3-yl]methyl}ethanamine hydrochloride as colorless crystals.

Example 2

A 224 mg portion of tert-butyl {[(3R,4S)-1-acetyl-4-phenylpyrrolidin-3-yl]methyl}[(1R)-1-(1-naphthyl)ethyl]carbamate was dissolved in 9.0 ml of 4 M hydrogen chloride/ethyl acetate solution at room temperature and stirred for 12Hours. The precipitate was collected by filtration and recrystallized from methanol-ethyl acetate to obtain 85 mg of (1R)—N-{[(3S,4S)-1-acetyl-4-phenylpyrrolidin-3-yl]methyl-1-(1-naphthyl)ethyl}ethanamine as a colorless solid.

Example 3

(1) A 1.0 ml portion of a dichloromethane solution containing 180 mg of ethyl 6-(chloroformyl)hexanoate was added at room temperature to a mixture of 357 mg of tert-butyl [(1R)-1-(1-naphthyl)ethyl]{[(3R,4S)-4-phenylpyrrolidin-3-yl]methyl}carbamate, 88 mg of triethylamine and 9.0 ml of dichloromethane, and this was stirred overnight. The reaction solution was diluted with ethyl acetate and washed with 1 M hydrochloric acid, water, 1 M sodium hydroxide aqueous solution, water and saturated brine in that order. The organic layer was dried with anhydrous sodium sulfate and concentrated under a reduced pressure.

The thus obtained residue was purified by a silica gel column chromatography (chloroform-methanol) to obtain 556 mg of ethyl 7-[(3R,4S)-3-({(tert-butoxycarbonyl)[(1R)-1-(1-naphthyl)ethyl]amino}methyl)-4-phenylpyrrolidin-1-yl]-7-oxoheptanoate as a pale brown oily substance.

(2) Hydrolysis and Boc-elimination of the thus obtained compound were carried out in that order in the same manner as in Reference Example 20 and Example 5 which is described later, thereby producing 7-[(3S,4S)-3-({[(1R)-1-(1-naphthyl)ethyl]amino}methyl)-4-phenylpyrrolidin-1-yl]-7-oxoheptanoic acid hydrochloride.

Example 4

Elimination of Boc group from the ethyl 7-[(3R,4S)-3-({(tert-butoxycarbonyl)[(1R)-1-(1-naphthyl)ethyl]amino}methyl)-4-phenylpyrrolidin-1-yl]-7-oxoheptanoate produced in Example 3 (1) was carried out in the same manner as in Example 2 to produce ethyl 7-[(3S,4S)-3-({[(1R)-

1-(1-naphthyl)ethyl]amino}methyl)-4-phenylpyrrolidin-1-yl]-7-oxoheptanoate hydrochloride.

Example 5

A 237 mg portion of 6-[(3R,4S)-3-({(tert-butoxycarbonyl)[(1R)-1-(1-naphthyl)ethyl]amino}methyl)-4-phenylpyrrolidin-1-yl]-6-oxohexanoic acid was dissolved in 2.0 ml of 4 M hydrogen chloride/1,4-dioxane solution and 2.0 ml of methanol at room temperature and stirred for 62Hours. The reaction solution was concentrated under a reduced pressure, and the thus obtained residue was purified by a silica gel column chromatography (chloroform-methanol) and then dissolved in 2.0 ml of ethyl acetate, mixed with 1.0 ml of 4 M hydrogen chloride/ethyl acetate solution and concentrated under a reduced pressure. The residue was dissolved in ethanol and mixed with ethyl acetate, and the thus obtained precipitate was collected by filtration and dried under a reduced pressure to obtain 40 mg of 6-[(3S,4S)-3-({[(1R)-1-(1-naphthyl)ethyl]amino}methyl)-4-phenylpyrrolidin-1-yl]-6-oxohexanoic acid hydrochloride as a colorless solid.

Example 6

A 2.0 ml portion of 4 M hydrogen chloride/1,4-dioxane was added to a 5.0 ml ethanol solution of 200 mg of 6-[(3S,4S)-3-({[(1R)-1-(1-naphthyl)ethyl]amino}methyl)-4-phenylpyrrolidin-1-yl]-6-oxohexanoic acid hydrochloride and stirred at room temperature for 1Hour. By evaporating the solvent and crystallizing the residue from ethyl acetate-hexane, 154 mg of ethyl 6-[(3S,4S)-3-({[(1R)-1-(1-naphthyl)ethyl]amino}methyl)-4-phenylpyrrolidin-1-yl]-6-oxohexanoate hydrochloride was obtained as a colorless solid.

Example 7

By carrying out reactions of amidation, hydrolysis and Boc-elimination in that order in the same manner as in Reference Example 19, Reference Example 20 and Example 5, 5-[(3S,4S)-3-({[(1R)-1-(1-naphthyl)ethyl]amino}methyl)-4-phenylpyrrolidin-1-yl]-5-oxohexanoic acid hydrochloride was produced from tert-butyl (1R)-1-(1-naphthyl)ethyl{[(3R,4S)-4-phenylpyrrolidin-3-yl]methyl}carbamate and monoethyl glutarate.

Example 8

By carrying out reactions of amidation and Boc-elimination in that order in the same manner as in Reference Example 19 and Example 2, ethyl 5-[(3S,4S)-3-({[(1R)-1-(1-naphthyl)ethyl]amino}methyl)-4-phenylpyrrolidin-1-yl]-5-oxopentanoate hydrochloride was produced from tert-butyl [(1R)-1-(1-naphthyl)ethyl]{[(3R,4S)-4-phenylpyrrolidin-3-yl]methyl}carbamate and monoethyl glutarate.

Example 9

(1) Succinic anhydride was added to a mixture of 1.0 g of tert-butyl [(1R)-1-(1-naphthyl)ethyl]{[(3R,4S)-4-phenylpyrrolidin-3-yl]methyl}carbamate, 235 mg of triethylamine and 15 ml of THF at room temperature and stirred overnight. The reaction solution was mixed with 1 M hydrochloric acid to quench the reaction and extracted with chloroform. The organic layer was dried with anhydrous sodium sulfate and concentrated under a reduced pressure to obtain 1.72 g of crude 4-[(3R,4S)-3-({(tert-butoxycarbonyl)[(1R)-1-(1-naphthyl)ethyl]amino}methyl)-4-phenylpyrrolidin-1-yl]-4-oxobutanoic acid (compound A) as a colorless amorphous substance. A 1.0 g portion of the thus obtained crude product was purified by a silica gel column chromatography (chloroform-methanol) to obtain 525 mg of 4-[(3R,4S)-3-({(tert-butoxycarbonyl)[(1R)-1-(1-naphthyl)ethyl]amino}methyl)-4-phenylpyrrolidin-1-yl]-4-oxobutanoic acid as a colorless amorphous substance.

(2) The thus obtained 4-[(3R,4S)-3-({(tert-butoxycarbonyl)[(1R)-1-(1-naphthyl)ethyl]amino}methyl)-4-phenylpyrrolidin-1-yl]-4-oxobutanoic acid was subjected to Boc-elimination with 4 M hydrogen chloride/ethyl acetate to obtain 4-[(3S,4S)-3-({[(1R)-1-(1-naphthyl)ethyl]amino}methyl)-4-phenylpyrrolidin-1-yl]-4-oxobutanoic acid hydrochloride.

Example 10

By carrying out amidation and Boc-elimination in that order in the same manner as in Reference Example 19 and Example 5, N,N-dimethyl-4-[(3S,4S)-3-({[(1R)-1-(1-naphthyl)ethyl]amino}methyl)-4-phenylpyrrolidin-1-yl]-4-oxobutanamide hydrochloride was obtained from the crude 4-[(3R,4S)-3-({(tert-butoxycarbonyl)[(1R)-1-(1-naphthyl)ethyl]amino}methyl)-4-phenylpyrrolidin-1-yl]-4-oxobutanoic acid obtained in Example 9 (1) and dimethylamine.

Example 11

A mixture of 350 mg of the crude 4-[(3R,4S)-3-({(tert-butoxycarbonyl)[(1R)-1-(1-naphthyl)ethyl]amino}methyl)-4-phenylpyrrolidin-1-yl]-4-oxobutanoic acid obtained in Example 9 (1), 101 mg of glycine ethyl ester hydrochloride, 45 mg of HOBt, 73 mg of triethylamine and 5 ml of dichloromethane was mixed with 190 mg of WSC hydrochloride and stirred at room temperature for 2 days. The reaction solution was concentrated under a reduced pressure, and the thus obtained residue was purified by a silica gel column chromatography (chloroform-ethyl acetate) to obtain 315 mg of ethyl ({4-[(3R,4S)-3-({(tert-butoxycarbonyl) [(1R)-1-(1-naphthyl)ethyl]amino}methyl)-4-phenylpyrrolidin-1-yl]-4-oxobutanoyl}amino)acetate as a colorless oily substance.

(2) By subjecting the thus obtained ethyl ({4-[(3R,4S)-3-({(tert-butoxycarbonyl)[(1R)-1-(1-naphthyl)amino}methyl)-4-phenylpyrrolidin-1-yl]-4-oxobutanoyl}amino)acetate to hydrolysis and Boc-elimination in that order in the same manner as in Reference Example 20 and Example 5, ({4-[(3S,4S)-3-({[(1R)-1-(1-naphthyl)ethyl]amino}methyl)-4-phenylpyrrolidin-1-yl]-4-oxobutanoyl}amino)acetate hydrochloride was obtained.

Example 12

A 440 mg portion of methyl 4-{[(3S,4S)-3-({[(1R)-1-(naphthyl)ethyl]amino}methyl)-4-phenylpyrrolidin-1-yl]carbonylbenzoate was dissolved in 10 ml of methanol, mixed with 2 ml of 1 M sodium hydroxide aqueous solution at room temperature, stirred for 1Hour, mixed with 3 ml of THF and further stirred for 3.5Hours. The reaction solution was mixed with water and then concentrated, successively adding 1 M hydrochloric acid thereto until its pH became 2.0. The thus precipitated solid was collected by filtration, dried under a reduced pressure, and then dissolved in 2 ml of 1,4-dioxane and 3 ml of THF, mixed with 1.0 ml of 4 M hydrogen chloride/1,4-dioxane solution and then concentrated under a reduced pressure, the residue was dissolved in THF and added dropwise to diethyl ether, the resulting precipitate was collected by filtration, and the filtrate was dried under a reduced pressure to obtain 320 mg of 4-[(3S,4S)-3-({[(1R)-1-(1-naphthyl)

ethyl]amino}methyl)-4-phenylpyrrolidin-1-yl]-carbonylbenzoic acid hydrochloride as a colorless solid.

Example 13

By carrying out salt formation in the same manner as in Example 1 (3), methyl 4-{[(3S,4S)-3-({[(1R)-1-(1-naphthyl)ethyl]amino}methyl)-4-phenylpyrrolidin-1-yl]-carbonylbenzoate hydrochloride was obtained from methyl 4-{[(3S,4S)-3-({[(1R)-1-(naphthyl)ethyl]amino}methyl)-4-phenylpyrrolidin-1-yl]carbonylbenzoate.

Example 14

Using 2,5-chloro-4-(methoxycarbonyl)benzoic acid obtained by carrying out the same reaction of Reference Example 29 and tert-butyl [(1R)-1-(1-naphthyl)ethyl]{[(3SR,4S)-4-phenylpyrrolidin-3-yl]methyl}carbamate, 2,5-dichloro-4-{[(3S,4S)-3-({[(1R)-1-(1-naphthyl)ethyl]amino}methyl)-4-phenylpyrrolidin-1-yl]carbonyl}benzoic acid hydrochloride was produced by the same method of Example 7.

Example 15

Using 2,5-dibromo-4-(methoxycarbonyl)benzoic acid obtained by carrying out the same reaction of Reference Example 29 and tert-butyl [(1R)-1-(1-naphthyl)ethyl]{[(3R,4S)-4-phenylpyrrolidin-3-yl]methyl}carbamate, 2,5-dibromo-4-{[(3S,4S)-3-({[(1R)-1-(1-naphthyl)ethyl]amino}methyl)-4-phenylpyridin-1-yl]carbonyl}benzoic acid hydrochloride was produced by the same method of Example 7.

Example 16

(1) A mixed solution of 198 mg of tert-butyl [(1R)-1-(1-naphthyl)ethyl]{[(3R,4S)-4-phenylpyrrolidin-3-yl]methyl}carbamate, 116 mg of 4-(3-formylphenyl)oxybenzoic acid, 0.2 ml of triethylamine and 5 ml of dichloromethane was mixed with 132 mg of WSC hydrochloride and 18 mg of HOBt and stirred at room temperature for 5Hours. The reaction solution was mixed with 1 M hydrochloric acid aqueous solution to quench the reaction and extracted with chloroform, and the organic layer was washed with saturated brine and dried with anhydrous sodium sulfate. This was concentrated under a reduced pressure, and the thus obtained residue was purified by a silica gel column chromatography (hexane-ethyl acetate) to obtain 286 mg of tert-butyl ({(3R,4S)-1-[4-(4-formylphenoxy)benzoyl]-4-phenylpyrrolidin-3-yl}methyl)[(1R)-1-(1-naphthyl)ethyl]carbamate as a pale yellow oily substance. EP: 655.
(2) A 4 ml 2,2-dimethylpropanol/1 ml water mixed solution of 286 mg of tert-butyl ({(3R,4S)-1-[4-(4-formylphenoxy)benzoyl]-4-phenylpyrrolidin-3-yl}methyl)[(1R)-1-(1-naphthyl)ethyl]carbamate was mixed with 892 mg of potassium dihydrogenphosphate, 1 ml of 2-methyl-2-butene and 394 mg of sodium chlorite and stirred at room temperature for 3 hours. By carrying out its work-up and purification in the standard method, 293 mg of 4-(4-{[(3R,4S)-3-({(tert-butoxycarbonyl)[(1R)-1-(1-naphthyl)ethyl]amino}methyl)-4-phenylpyrrolidin-1-yl]carbonyl}phenoxy)benzoic acid was obtained as a pale yellow oily substance. EP: 671. (3) By carrying out the Boc-elimination reaction in the same manner as in Example 5,4-(4-{[(3S,4S)-3-({[(1R)-1-(1-naphthyl)ethyl]amino}methyl)-4-phenylpyrrolidin-1-yl]carbonyl}phenoxy)benzoic acid hydrochloride was produced from 4-(4-{[(3R,4S)-3-({(tert-butoxycarbonyl)[(1R)-1-(1-naphthyl)ethyl]amino}methyl)-4-phenylpyrrolidin-1-yl]carbonyl}phenoxy)benzoic acid.

Example 17

By carrying out the same reaction of Example 16, 3-(4-{[(3S,4S)-3-({[(1R)-1-(1-naphthyl)ethyl]amino}methyl)-4-phenylpyrrolidin-1-yl]carbonyl}phenoxy)benzoic acid hydrochloride was produced from tert-butyl [(1R)-1-(1-naphthyl)ethyl]{[(3R,4S)-4-phenylpyrrolidin-3-yl]methyl}carbamate and corresponding starting material.

Example 18

A mixture of 750 mg of tert-butyl {[(3R,4S)-1-acryloyl-4-phenylpyrrolidin-3-yl]methyl}[(1R)-1-(1-naphthyl)ethyl]carbamate and 8 ml of an ethanol:chloroform (4:1) mixed solvent was mixed with 487 mg of ethyl isonipecotate and stirred at 60° C. for 6Hours, and the reaction solution was concentrated under a reduced pressure. The thus obtained residue was purified by a silica gel column chromatography (chloroform-methanol) to obtain 700 mg of ethyl 1-{[(3R,4S)-3-({(tert-butoxycarbonyl)[(1R)-1-(1-naphthyl)ethyl]amino}methyl)-4-phenylpyrrolidin-1-yl]-3-oxopropyl}piperidine-4-carboxylate as a pale yellow amorphous substance. By carrying out the Boc-elimination from the thus obtained compound in the same manner as in Example 2, ethyl 1-{3-[(3S,4S)-3-({[(1R)-1-(1-naphthyl)ethyl]amino}methyl)-4-phenylpyrrolidin-1-yl]-3-oxopropyl}pyridine-4-carboxylate dihydrochloride was obtained.

Example 19

By carrying out the hydrolysis and Boc-elimination in that order in the same manner in Reference Example 20 and Example 5, 1-{3-[(3S,4S)-3-({[(1R)-1-(1-naphthyl)ethyl]amino}methyl)-4-phenylpyrrolidin-1-yl]-3-oxopropyl}pyridine-4-carboxylic acid dihydrochloride was produced from ethyl 1-{3-[(3R,4S)-3-({(tert-butoxycarbonyl)[(1R)-1-(1-naphthyl)ethyl]amino}methyl)-4-phenylpyrrolidin-1-yl]-3-oxopropyl}pyridine-4-carboxylate.

Example 20

(1) A 10 ml THF solution of 940 mg of tert-butyl [(1R)-1-(1-naphthyl)ethyl]{[(3R,4S)-4-phenylpyrrolidin-3-yl]methyl}carbamate was mixed with 0.3 ml of triethylamine and 3.54 g of CDI and stirred at room temperature for 2Hours. The reaction solution was concentrated under a reduced pressure and diluted with ethyl acetate. This was washed with 1 M hydrochloric acid and saturated brine, and the organic layer was dried with anhydrous magnesium sulfate. By evaporating the solvent under a reduced pressure, 1.23 g of tert-butyl {[(3R,4S)-1-(1H-imidazol-1-ylcarbonyl)-4-phenylpyrrolidin-3-yl]methyl}[(1R)-1-(1-naphthyl)ethyl]carbamate was obtained as a pale yellow amorphous substance. EP: 525.
(2) A 40 ml acetonitrile solution of 1.234 g of tert-butyl {[(3R,4S)-1-(1H-imidazol-1-ylcarbonyl)-4-phenylpyrrolidin-3-yl]methyl}[(1R)-1-(1-naphthyl)ethyl]carbamate was mixed with 0.60 ml of methyl iodide and stirred overnight at room temperature. By evaporating the reaction solution under a reduced pressure, 1.966 g of 1-{[(3R,4S)-3-({(tert-butoxycarbonyl)[(1R)-1-(1-naphthyl)ethyl]amino}methyl)-4-phenylpyrrolidin-1-yl]carbonyl}-3-methyl-1H-imidazol-3-ium iodide was obtained as a pale yellow solid . . . EP: 539.

(3) A 6.0 ml dichloromethane solution of 250 mg of 1-{[(3R,4S)-3-({(tert-butoxycarbonyl)[(1R)-1-(1-naphthyl)ethyl]amino}methyl)-4-phenylpyrrolidin-1-yl]carbonyl}-3-methyl-1H-imidazol-3-ium iodide and 31 mg of triethylamine was mixed with 48 mg of ethyl 4-piperidinecarboxylate and stirred overnight at room temperature. The reaction solution was mixed with ethyl acetate and washed with water. The solvent was evaporated under a reduced pressure, and the thus obtained residue was purified by a silica gel column chromatography (chloroform-methanol) to obtain 106 mg of ethyl 1-{[(3R,4S)-3-({(tert-butoxycarbonyl)[(1R)-1-(1-naphthyl)ethyl]amino}methyl)-4-phenylpyrrolidin-1-yl]carbonyl}piperidine-4-carboxylate as a white amorphous substance.

(4) A 3.0 ml ethanol solution of 105 mg of ethyl 1-{[(3R,4S)-3-({(tert-butoxycarbonyl)[(1R)-1-(1-naphthyl)ethyl]amino}methyl)-4-phenylpyrrolidin-1-yl]carbonyl}piperidine-4-carboxylate was mixed at room temperature with 1.0 ml of 1 M sodium hydroxide aqueous solution and stirred overnight at room temperature. The reaction solution was concentrated under a reduced pressure, acidified by adding 1 M hydrochloric acid and then extracted with chloroform and dried with anhydrous sodium sulfate. The solvent was evaporated under a reduced pressure, and the thus obtained residue was purified by a silica gel column chromatography to obtain 86 mg of 1-{[(3R,4S)-3-({(tert-butoxycarbonyl)[(1R)-1-(1-naphthyl)ethyl]amino}methyl)-4-phenylpyrrolidin-1-yl]carbonyl}piperidine-4-carboxylic acid as a white amorphous substance. A 2.0 ml 1,4-dioxane solution of 86 mg of 1-{[(3R,4S)-3-({(tert-butoxycarbonyl)[(1R)-1-(1-naphthyl)ethyl]amino}methyl)-4-phenylpyrrolidin-1-yl]carbonyl}piperidine-4-carboxylic acid was mixed at room temperature with 1.0 ml of 4 M hydrogen chloride/1,4-dioxane and stirred overnight at room temperature. The reaction solution was concentrated and crystallized with 1,4-dioxane-diisopropyl ether to obtain 80 mg of 1-{[(3S,4S)-3-({[(1R)-1-(1-naphthyl)ethyl]amino}methyl)-4-phenylpyrrolidin-1-yl]carbonyl}piperidine-4-carboxylic acid hydrochloride as a white solid.

Example 21

(1) A 1.5 ml DMF solution of 72 mg of tert-butyl {[(3R,4S)-1-(4-cyanobenzoyl)-4-phenylpyrrolidin-3-yl]methyl}[(1R)-1-(1-naphthyl)ethyl]carbamate was mixed with 153 mg of sodium azide and 304 mg of triethylamine hydrochloride and stirred at 120° C. for 2Hours. By post-treating and purifying this in the standard method, 68 mg of tert-butyl [(1R)-1-(1-naphthyl)ethyl]({(3R,4S)-4-phenyl-1-[4-(1H-tetrazol-5-yl)benzoyl]pyrrolidin-3-yl}methyl)carbamate was obtained as a yellow amorphous substance. EN: 601

(2) By carrying out the Boc-elimination reaction in the same manner as in Example 5, (1R)-1-(1-naphthyl)-N-({(3S,4S)-4-phenyl-1-[4-(1H-tetrazol-5-yl)benzoyl]pyrrolidin-3-yl}methyl)ethanamine hydrochloride was produced from tert-butyl [(1R)-1-(1-naphthyl)ethyl]({(3R,4S)-4-phenyl-1-[4-(1H-tetrazol-5-yl)benzoyl]pyrrolidin-3-yl}methyl)carbamate.

Example 22

(1) A mixture of 100 mg of tert-butyl [(1R)-1-(1-naphthyl)ethyl]{[(3R,4S)-4-phenylpyrrolidin-3-yl]methyl}carbamate, 53 mg of WSC hydrochloride, 37 mg of HOBt and 1.5 ml of methylene chloride was mixed with 51 mg of 4-(aminosulfonyl)benzoic acid and stirred at room temperature for 3Hours. The reaction solution was washed with water and then concentrated under a reduced pressure. The thus obtained residue was purified by a silica gel column chromatography (chloroform-methanol) to obtain 120 mg of tert-butyl ({(3R,4S)-1-[4-(aminosulfonyl)benzoyl]-4-phenylpyrrolidin-3-yl}methyl)[(1R)-1-(1-naphthyl)ethyl]carbamate as a pale yellow oily substance.

(2) A 1.6 ml 1,4-dioxane solution of 110 mg of tert-butyl ({(3R,4S)-1-[4-(aminosulfonyl)benzoyl]-4-phenylpyrrolidin-3-yl}methyl)[(1R)-1-(1-naphthyl)ethyl]carbamate was mixed with 1.5 ml of 4 M hydrogen chloride/1,4-dioxane and stirred at room temperature for 60Hours. The reaction solution was concentrated under a reduced pressure, mixed with water and neutralized with saturated sodium bicarbonate solution. The organic layer extracted with chloroform was dried with anhydrous sodium sulfate and then concentrated under a reduced pressure. By crystallizing the thus obtained residue from ethyl acetate, 65 mg of 4-{[(3S,4S)-3-({[(1R)-1-(1-naphthyl)ethyl]amino}methyl)-4-phenylpyrrolidin-1-yl]carbonyl}benzene sulfonamide was obtained as colorless crystals.

Example 23

(1) A mixture of 130 mg of tert-butyl {[(3R,4S)-1-(4-cyanobenzoyl)-4-phenylpyrrolidin-3-yl]methyl}[(1R)-1-(1-naphthyl)ethyl]carbamate, 32 mg of hydroxylamine hydrochloride, 65 μl of triethylamine and 1.3 ml of ethanol was heated under reflux for 4Hours. The reaction solution was concentrated under a reduced pressure, and the residue was mixed with water and extracted with ethyl acetate. The organic layer was washed with saturated brine, dried with anhydrous sodium sulfate and then concentrated under a reduced pressure to obtain 135 mg of tert-butyl [((3R,4S)-1-{4-[(Z)-(hydroxyamino)(imino)methyl]benzoyl}-4-phenylpyrrolidin-3-yl)methyl][(1R)-1-(1-naphthyl)ethyl]carbamate as a crude product.

(2) A mixture of 63 mg of the thus obtained crude tert-butyl [((3R,4S)-1-{4-[(Z)-(hydroxyamino)(imino)methyl]benzoyl}-4-phenylpyrrolidin-3-yl)methyl][(1R)-1-(1-naphthyl)ethyl]carbamate, 11 μl of pyridine and DMF was ice-cooled, mixed with 21 μl of 2-ethylhexyl chlorocarbonate and stirred under ice-cooling for 1Hour. The reaction solution was mixed with water and extracted with ethyl acetate. The organic layer was washed with saturated brine, dried with anhydrous sodium sulfate and then concentrated under a reduced pressure. The residue was mixed with 0.6 ml of xylene and heated under reflux for 5Hours. This was concentrated under a reduced pressure, and the residue was purified by a silica gel column chromatography (chloroform-methanol) to obtain 56 mg of tert-butyl [(1R)-1-(1-naphthyl)ethyl]({(3R,4S)-1-[4-(5-oxo-2,5-dihydro-1,2-4-oxadiazol-3-yl)benzoyl]-4-phenylpyrrolidin-3-yl}methyl)carbamate as a pale yellow amorphous.

(3) A 1.6 ml 1,4-dioxane solution of 50 mg of tert-butyl [(1R)-1-(1-naphthyl)ethyl]({(3R,4S)-1-[4-(5-oxo-2,5-dihydro-1,2-4-oxadiazol-3-yl)benzoyl]-4-phenylpyrrolidin-3-yl}methyl)carbamate was mixed with 0.5 ml of 4 M hydrogen chloride/1,4-dioxane and stirred at room temperature for 4Hours. The reaction solution was concentrated under a reduced pressure, and the residue was purified by a silica gel column chromatography (chloroform-methanol) and then crystallized with ethyl acetate to obtain 20 mg of 3-(4-{[(3S,4S)-3-({[(1R)-1-(1-naphthyl)ethyl]amino}methyl)-4-phenylpyrrolidin-1-yl]carbonyl}phenyl)-1,2,4-oxadiazol-5(2H)-one hydrochloride as colorless crystals.

Example 24

(1) A 5 ml acetone solution of 260 mg of tert-butyl {[(3R,4S)-1-(4-hydroxybenzoyl)-4-phenylpyrrolidin-3-yl]methyl}[(1R)-1-(1-naphthyl)ethyl]carbamate obtained from tert-butyl [(1R)-1-(1-naphthyl)ethyl]{[(3R,4S)-4-phenylpyrrolidin-3-yl]methyl}carbamate and 4-hydroxybenzoic acid, by amidation in the same manner as in Reference Example 19, was mixed with 130 mg of potassium carbonate, and then the reaction solution was mixed with 0.1 ml of ethyl bromoacetate and heated under reflux for 3 hours. After cooling down to room temperature, the insoluble matter was removed by filtration, and the filtrate was concentrated under a reduced pressure. The residue was purified by a silica gel column chromatography (hexane-ethyl acetate) to obtain 264 mg of ethyl (4-{[(3R,4S)-3-({(tert-butylcarbonyl)[(1R)-1-(1-naphthyl)ethyl]amino}methyl)-4-phenylpyrrolidin-1-yl]carbonyl}phenoxy)acetate a colorless amorphous substance. FP: 637.

(2) A mixed solution of 264 mg of ethyl (4-{[(3R,4S)-3-({(tert-butylcarbonyl)[(1R)-1-(1-naphthyl)ethyl]amino}methyl)-4-phenylpyrrolidin-1-yl]carbonyl}phenoxy)acetate and 3.0 ml of 1,4-dioxane was mixed with 1.0 ml of 4 M hydrogen chloride/1,4-dioxane and stirred at room temperature for 24Hours. The reaction solution was concentrated under a reduced pressure, and the residue was purified by a silica gel column chromatography (chloroform-methanol) to obtain 174 mg of ethyl (4-{[(3S,4S)-3-({[(1R)-1-(1-naphthyl)ethyl]amino}methyl)-4-phenylpyrrolidin-1-yl]carbonyl}phenoxy)acetate as a colorless amorphous substance. FP: 537.

(3) A mixture of 174 mg of ethyl (4-{[(3S,4S)-3-({[(1R)-1-(1-naphthyl)ethyl]amino}methyl)-4-phenylpyrrolidin-1-yl]carbonyl}phenoxy)acetate and 3.0 ml of a THF-water (2:1) mixed solvent was mixed with 22 mg of lithium hydroxide and stirred at room temperature. After completion of the reaction, this was neutralized by adding 1 M hydrochloric acid. This was extracted with chloroform, dried with anhydrous sodium sulfate and then concentrated under a reduced pressure. The thus obtained residue was purified by a fractional high performance liquid chromatography (acetonitrile-water) and then treated with hydrochloric acid to obtain 31 mg of (4-{[(3S,4S)-3-({[(1R)-1-(1-naphthyl)ethyl]amino}methyl)-4-phenylpyrrolidin-1-yl]carbonyl}phenoxy)acetic acid hydrochloride as a colorless solid.

Example 25

By carrying out amidation, Boc-elimination and hydrolysis reactions in that order in the same manner as in Reference Example 19, Example 24 (2) and Example 24 (3), 4-{2-[(3S,4S)-3-({[(1R)-1-(1-naphthyl)ethyl]amino}methyl)-4-phenylpyrrolidin-1-yl]-2-oxoethyl}benzoic acid hydrochloride was produced from tert-butyl [(1R)-1-(1-naphthyl)ethyl]{[(3R,4S)-4-phenylpyrrolidin-3-yl]methyl}carbamate and [4-(methoxycarbonyl)phenyl]acetic acid.

Example 26

(1) A DMF solution of 140 mg of (4-{[(3R,4S)-3-({(tert-butoxycarbonyl)[(1R)-1-(1-naphthyl)ethyl]amino}methyl)-4-phenylpyrrolidin-1-yl]carbonyl}benzoic acid was mixed with 39 mg of CDI and stirred for 1Hour. A 23 mg portion of methanesulfonamide and 36 μl of DBU were added thereto and stirred for 2Hours. The reaction solution was mixed with water and extracted with ethyl acetate. The organic layer was washed with saturated brine, dried with anhydrous sodium sulfate and then concentrated under a reduced pressure.

The residue was purified by a silica gel column chromatography (chloroform-methanol) to obtain 155 mg of tert-butyl {[(3R,4S)-1-(4-{[(methylsulfonyl)amino]carbonyl}benzoyl)-4-phenylpyrrolidin-3-yl]methyl}[(1R)-1-(1-naphthyl)ethyl]carbamate as a pale yellow oily substance.

(2) A 1.6 ml 1,4-dioxane solution of 160 mg of tert-butyl {[(3R,4S)-1-(4-{[(methylsulfonyl)amino]carbonyl}benzoyl)-4-phenylpyrrolidin-3-yl]methyl}[(1R)-1-(1-naphthyl)ethyl]carbamate was mixed with 1.5 ml of 4 M hydrogen chloride/1,4-dioxane and stirred at room temperature for 4Hours. The reaction solution was concentrated under a reduced pressure and dissolved in water. This was neutralized with saturated sodium bicarbonate solution and extracted with chloroform. The organic layer was dried with anhydrous sodium sulfate and then concentrated under a reduced pressure. The thus obtained residue was crystallized with ethyl acetate to obtain 85 mg of N-(methoxysulfonyl)-4-{[(3S,4S)-3-({[(1R)-1-(1-naphthyl)ethyl]amino}methyl)-4-phenylpyrrolidin-1-yl]carbonyl}benzamide as colorless crystals.

Example 27

A 320 mg portion of 4-{[(3S,4S)-3-({(tert-butoxycarbonyl)[(1R)-1-(1-naphthyl)ethyl]amino}methyl)-4-phenylpyrrolidin-1-yl]sulfonyl}benzoic acid was dissolved at room temperature in 3.0 ml of 4 M hydrogen chloride/1,4-dioxane solution and stirred for 24Hours. The reaction solution was diluted with diethyl ether and then concentrated under a reduced pressure, the thus obtained residue was dissolved in THF and mixed with diisopropyl ether, and the thus precipitated solid was collected by filtration and dried under a reduced pressure to obtain 183 mg of 4-{[(3S,4S)-3-({[(1R)-1-(1-naphthyl)ethyl]amino}methyl)-4-phenylpyrrolidin-1-yl]sulfonyl}benzoic acid hydrochloride as a colorless solid.

Example 28

A 262 mg portion of methyl 6-[(3R,4S)-3-({(tert-butoxycarbonyl)[(1R)-1-(1-naphthyl)ethyl]amino}methyl)-4-phenylpyrrolidin-1-yl]hexanoate was dissolved in 3 ml of methanol and 3 ml of THF, mixed with 2 ml of 1 M sodium hydroxide aqueous solution at room temperature and stirred for 7Hours. The reaction solution was washed with diethyl ether, and 1 M hydrochloric acid was added to the water layer until it became pH 3. After its extraction with diethyl ether, the organic layer was dried with anhydrous sodium sulfate and concentrated under a reduced pressure to obtain 6-[(3R,4S)-3-({(tert-butoxycarbonyl)[(1R)-1-(1-naphthyl)ethyl]amino}methyl)-4-phenylpyrrolidin-1-yl]hexanoic acid as a crude product. The thus obtained crude product was dissolved in 3.0 ml of 4 M hydrogen chloride/1,4-dioxane solution at room temperature, and the reaction solution was concentrated under a reduced pressure. THF and diethyl ether were added to the thus obtained residue, and the resulting precipitate was collected by filtration and dried under a reduced pressure to obtain 123 mg of 6-[(3S,4S)-3-({[(1R)-1-(1-naphthyl)ethyl]amino}methyl)-4-phenylpyrrolidin-1-yl]hexanoic acid dihydrochloride as a white solid.

Example 29

In accordance with the technique in Abstract or Papers, P 1-7 (pp. 48-49), 2004, Summer Symposium of The Japanese Society for Process Chemistry (JSPC), ethyl 4-[(3R,4S)-3-({(tert-butoxycarbonyl)[(1R)-1-(1-naphthyl)ethyl]amino}methyl)-4-phenylpyrrolidin-1-yl]cyclohexane carboxylate was treated in THF with potassium tert-butoxide and water, and then elimination of Boc group was carried out in the same manner as in Example 5, thereby producing 4-[(3S,4S)-3-({[(1R)-1-(1-naphthyl)ethyl]amino}methyl)-4-phenylpyrrolidin-1-yl]cyclohexane carboxylate dihydrochloride.

Example 30

A 170 mg portion of methyl 4-{[(3R,4S)-3-({(tert-butoxycarbonyl)[(1R)-1-(1-naphthyl)ethyl]amino}methyl)-4-phenylpyrrolidin-1-yl]methyl}benzoate was dissolved in 4 ml of methanol, mixed with 2 ml of 1 M sodium hydroxide aqueous solution at room temperature and stirred for 41Hours. The reaction solution was concentrated under a reduced pressure, and 1 M hydrochloric acid was added to the residue until its pH became 3. This was extracted with chloroform and washed with saturated brine, and then the organic layer was dried with anhydrous sodium sulfate and concentrated under a reduced pressure to obtain 4-{[(3R,4S)-3-({(tert-butoxycarbonyl)[(1R)-1-(1-naphthyl)ethyl]amino}methyl)-4-phenylpyrrolidin-1-yl]methyl}benzoic acid as a crude product. The thus obtained crude product was dissolved in 3.0 ml of 4 M hydrogen chloride/1,4-dioxane solution and 30 ml of dioxane at room temperature and stirred for 1Hour. The thus obtained residue was purified by a silica gel column chromatography (chloroform-methanol), and then dissolved in 2.0 ml of dioxane, mixed with 2.0 ml of 4 M hydrogen chloride/1,4-dioxane solution and concentrated under a reduced pressure. The residue was dissolved in chloroform and mixed with diisopropyl ether, and the resulting precipitate was collected by filtration and dried under a reduced pressure to obtain 76 mg of 4-{[(3S,4S)-3-({[(1R)-1-(1-naphthyl)ethyl]amino}methyl)-4-phenylpyrrolidin-1-yl]methyl}benzoic acid dihydrochloride as a colorless solid.

Example 31

(1) A 10 ml DMSO solution of tert-butyl [(1R)-1-(1-naphthyl)ethyl]{[(3R,4S)-4-phenylpyrrolidin-3-yl]methyl}carbamate was mixed with 1.3 g of potassium carbonate and 1.0 g of methyl 3,4,5-trifluorobenzoate and stirred overnight at 110° C. Thr reaction solution was mixed with ethyl acetate, washed with water and dried with anhydrous sodium sulfate. This was concentrated under a reduced pressure, and the thus obtained residue was purified by a silica gel column chromatography (hexane-ethyl acetate) to obtain 2.1 g of methyl 4-[(3R,4S)-3-({(tert-butoxycarbonyl)[(1R)-1-(1-naphthyl)ethyl]amino}methyl)-4-phenylpyrrolidin-1-yl]-3,5-difluorobenzoate as a colorless amorphous substance.

(2) A 60 ml portion of a methanol-THF (1:1) mixed solution of 2.09 g of methyl 4-[(3R,4S)-3-({(tert-butoxycarbonyl)[(1R)-1-(1-naphthyl)ethyl]amino}methyl)-4-phenylpyrrolidin-1-yl]-3,5-difluorobenzoate was mixed with 7.5 ml of 1 M sodium hydroxide aqueous solution at room temperature and stirred overnight at 80° C. The reaction solution was concentrated under a reduced pressure, 1 M hydrochloric acid was added to the thus obtained residue, and the precipitated solid was collected by filtration to obtain 2.02 g of 4-[(3R,4S)-3-({(tert-butoxycarbonyl)[(1R)-1-(1-naphthyl)ethyl]amino}methyl)-4-phenylpyrrolidin-1-yl]-3,5-difluorobenzoic acid.

(3) A 20 ml 1,4-dioxane solution of 2.01 g of 4-[(3R,4S)-3-({(tert-butoxycarbonyl)[(1R)-1-(1-naphthyl)ethyl]amino}methyl)-4-phenylpyrrolidin-1-yl]-3,5-difluorobenzoic acid was mixed with 2.0 ml of 4 M hydrogen chloride/1,4-dioxane and stirred overnight at room temperature. The reaction solution was concentrated under a reduced pressure, and the thus obtained residue was purified by a silica gel column chromatography (chloroform-methanol). The purified product was dissolved in 1,4-dioxane-diethyl ether, 4 M hydrogen chloride/1,4-dioxane was added thereto, and the thus precipitated crystals were collected by filtration and then recrystallized from 1,4-dioxane-water, thereby obtaining 484 mg of 3,5-difluoro-4-[(3S,4S)-3-({[(1R)-1-(1-naphthyl)ethyl]amino}methyl)-4-phenylpyrrolidin-1-yl]benzoic acid hydrochloride.

Example 32

(1) A mixture of 223 mg of tert-butyl [(1R)-1-(1-naphthyl)ethyl]{[(3R,4S)-4-phenylpyrrolidin-3-yl]methyl}carbamate, 78.6 mg of triethylamine and 4.5 ml of MeCN was mixed, under ice-cooling, with 215 mg of methyl 2-{[(4-nitrophenoxy)carbonyl]oxy}benzoate and stirred at room temperature for 4Hours. The reaction solution was mixed with ethyl acetate, washed with saturated sodium bicarbonate aqueous solution and saturated brine in that order and dried with anhydrous magnesium sulfate. The solvent was evaporated under a reduced pressure, and the thus obtained residue was purified by a silica gel column chromatography (hexane-ethyl acetate) to obtain 189 mg of 2-(methoxycarbonyl)phenyl (3R,4S)-3-({(tert-butoxycarbonyl)[(1R)-1-(1-naphthyl)ethyl]amino}methyl)-4-phenylpyrrolidine-1-carbamate as a white amorphous substance.

(2) A mixture of 151 mg of 2-(methoxycarbonyl)phenyl (3R,4S)-3-({(tert-butoxycarbonyl)[(1R)-1-(1-naphthyl)ethyl]amino}methyl)-4-phenylpyrrolidine-1-carbamate and 20 ml of a THF-methanol (1:1) mixed solvent was mixed with 1.0 ml of 1 M sodium hydroxide aqueous solution at room temperature and stirred overnight at room temperature. The reaction solution was mixed with 1 ml of 1 M hydrochloric acid and then extracted with chloroform and dried with anhydrous sodium sulfate. The solvent was evaporated under a reduced pressure, and the thus obtained residue was purified by a silica gel column chromatography (chloroform-methanol) to obtain 145 mg of 2-({[(3R,4S)-3-({(tert-butoxycarbonyl)[(1R)-1-(1-naphthyl)ethyl]amino}methyl)-4-phenylpyrrolidin-1-yl]carbonyl}oxy)benzoic acid as a colorless amorphous substance.

(3) A 2.0 ml 1,4-dioxane solution of 145 mg of 2-({[(3R,4S)-3-({(tert-butoxycarbonyl)[(1R)-1-(1-naphthyl)ethyl]amino}methyl)-4-phenylpyrrolidin 1-yl]carbonyl}oxy)benzoic acid was mixed with 1.0 ml of 4 M hydrogen chloride/1,4-dioxane at room temperature and stirred overnight at room temperature. The reaction solution was concentrated under a reduced pressure, and the thus obtained residue was purified by a silica gel column chromatography (chloroform-methanol) to obtain 39 mg of 2-({[(3S,4S)-3-({[(1R)-1-(1-naphthyl)ethyl]amino}methyl)-4-phenylpyrrolidin-1-yl]carbonyl}oxy)benzoic acid as a colorless amorphous substance.

Example 33

A 1.05 g portion of 4-({[(3R,4S)-3-({(tert-butoxycarbonyl)[(1R)-1-(1-naphthyl)ethyl]amino}methyl)-4-phenylpyrrolidin-1-yl]carbonyl}oxy)benzoic acid was dissolved in 10 ml of 4 M hydrogen chloride/1,4-dioxane solution and stirred at room temperature for 1Hour, and then the reaction solution was concentrated under a reduced pressure. In order to remove excess hydrogen chloride, the residue was dissolved in chloroform and again concentrated under a reduced pressure. By suspending the thus obtained residue in THF-toluene, 784 mg of 4-({[(3S,4S)-3-({[(1R)-1-(1-naphthyl)ethyl]amino}methyl)-4-phenylpyrrolidin-1-yl]carbonyl}oxy)benzoic acid hydrochloride was obtained as a crude product. A 235 mg portion of the thus obtained crude product was suspended in THF-toluene and heated under reflux for 50 minutes, and then the resulting precipitate was collected by filtration to obtain 217 mg of 4-({[(3S,4S)-3-({[(1R)-1-(1-naphthyl)ethyl]amino}methyl)-4-phenylpyrrolidin-1-yl]carbonyl}oxy)benzoic acid hydrochloride as a white solid.

Example 34

A 2.0 ml 1,4-dioxane solution of 40 mg of the 2-(methoxycarbonyl)phenyl (3R,4S)-3-({(tert-butoxycarbonyl)[(1R)-1-(1-naphthyl)ethyl]amino}methyl)-4-phenylpyrrolidine 1-carbamate obtained in the step (1) of Example 32 was mixed with 1.0 ml of 4 M hydrogen chloride/1,4-dioxane and stirred overnight at room temperature. The reaction solution was concentrated under a reduced pressure, the residue was purified by a silica gel column chromatography (chloroform-methanol), 1.0 ml of 4 M hydrogen chloride/1,4-dioxane was added to the thus obtained purified product, and the solvent was evaporated under a reduced pressure to obtain 30 mg of 2-(methoxycarbonyl)phenyl (3S,4S)-3-({[(1R)-1-(1-naphthyl)ethyl]amino}methyl)-4-phenylpyrrolidine-1-carbamate hydrochloride as a colorless amorphous substance.

Example 35

Using the 4-(methoxycarbonyl)phenyl (3R,4S)-3-({(tert-butoxycarbonyl)[(1R)-1-(1-naphthyl)ethyl]amino}methyl)-4-phenylpyrrolidine-1-carboxylate obtained during the synthesis in Reference Example 44, and carrying out the reaction in the same manner as the method of Example 34, 4-(methoxycarbonyl)phenyl (3S,4S)-3-({[(1R)-1-(1-naphthyl)ethyl]amino}methyl)-4-phenylpyrrolidine-1-carbamate hydrochloride was produced using the corresponding starting material.

Example 36

By carrying out the reactions in the same manner as in Example 32 and Example 1 (3), 3-methoxy-4-({[(3S,4S)-3-({[(1R)-1-(1-naphthyl)ethyl]amino}methyl)-4-phenylpyrrolidin-1-yl]carbonyl}oxy)benzoic acid hydrochloride was produced from tert-butyl [(1R)-1-(1-naphthyl)ethyl]{[(3R,4S)-4-phenylpyrrolidin-3-yl]methyl}carbamate and a corresponding starting material.

Example 37

By carrying out carbamate formation, elimination of Boc group, hydrolysis and salt formation in the same manner as in Example 32 (1), Example 34 and Example 2 4 (3), 5-({[(3S,4S)-3-({[(1R)-1-(1-naphthyl)ethyl]amino}methyl)-4-phenylpyrrolidin-1-yl]carbonyl}oxy)isophthalic acid hydrochloride was produced from tert-butyl [(1R)-1-(1-naphthyl)ethyl]{[(3R,4S)-4-phenylpyrrolidin-3-yl]methyl}carbamate and a corresponding starting material.

Example 38

(1) A 2 ml dichloromethane solution of methyl 3-({[(2,5-dioxopyrrolidin-1-yl)oxy]carbonyl}oxy)-2,2-dimethylpropionate prepared from 136 mg of methyl 3-hydroxy-2,2-dimethylpropionate in the same manner as in Reference Example 46 was added to 5 ml dichloromethane solution of 235 mg of tert-butyl [(1R)-1-(1-naphthyl)ethyl]{[(3R,4S)-4-phenylpyrrolidin-3-yl]methyl}carbamate and 0.21 ml of triethylamine. After 12Hours of stirring at room temperature, the reaction solution was concentrated under a reduced pressure, and the thus obtained residue was purified by a silica gel column chromatography (hexane-ethyl acetate) to obtain 227 mg of 3-methoxy-2,2-dimethyl-3-oxopropyl (3R,4S)-3-({(tert-butoxycarbonyl)[(1R)-1-(1-naphthyl)ethyl]amino}methyl)-4-phenylpyrrolidine-1-carboxylate as a colorless amorphous substance.

(2) A 2.5 ml toluene solution of 227 mg of 3-methoxy-2,2-dimethyl-3-oxopropyl (3R,4S)-3-({(tert-butoxycarbonyl)[(1R)-1-(1-naphthyl)ethyl]amino}methyl)-4-phenylpyrrolidine-1-carboxylate was mixed with 1.5 ml of 4 M hydrogen chloride/1,4-dioxane at room temperature and stirred overnight at room temperature. The reaction solution was concentrated under a reduced pressure, and the thus obtained residue was mixed with toluene, washed with saturated sodium bicarbonate aqueous solution and saturated brine in that order and dried with anhydrous sodium sulfate. This was concentrated under a reduced pressure, and the thus obtained residue was purified by a silica gel column chromatography (toluene-methanol) to obtain 3-methoxy-2,2-dimethyl-3-oxopropyl (3S,4S)-3-({[(1R)-1-(1-naphthyl)ethyl]amino}methyl)-4-phenylpyrrolidine-1-carboxylate as a crude product.

(3) A mixture of the crude 3-methoxy-2,2-dimethyl-3-oxopropyl (3S,4S)-3-({[(1R)-1-(1-naphthyl)ethyl]amino}methyl)-4-phenylpyrrolidine-1-carboxylate obtained in (2) and 3.0 ml of a methanol-THF (2:1) mixed solvent was mixed with 0.5 ml of 1 M sodium hydroxide aqueous solution at room temperature and stirred for 24Hours. The reaction solution was neutralized by adding 0.5 ml of 1 M hydrochloric acid and then extracted with chloroform. The organic layer was washed with water and dried with anhydrous sodium sulfate. This was concentrated under a reduced pressure, and the thus obtained residue was mixed with 4 M hydrogen chloride/1,4-dioxane and then concentrated under a reduced pressure. By recrystallizing the residue from water-THF-diisopropyl ether, 48 mg of 2,2-dimethyl-3-({[(3S,4S)-3-({[(1R)-1-(1-naphthyl)ethyl]amino}methyl)-4-phenylpyrrolidin-1-yl]carbonyl}oxy)propionic acid hydrochloride was obtained as a colorless solid.

Example 39

By carrying out carbamate formation, hydrolysis and elimination of Boc group in the same manner as in Example 38 (1), Example 32 (2) and Example 32 (3), 4-[2-({[(3S,4S)-3-({[(1R)-1-(1-naphthyl)ethyl]amino}methyl)-4-phenylpyrrolidin-1-yl]carbonyl}oxy)ethyl]benzoic acid hydrochloride was produced from tert-butyl [(1R)-1-(1-naphthyl)ethyl]

{[(3R,4S)-4-phenylpyrrolidin-3-yl]methyl}carbamate and a corresponding starting material.

Example 40

By using ethyl ({[2,5-dioxypyrrolidin-1-yl]oxy}carbonyl)oxy)acetate obtained in the same manner as in Reference Example 46 and tert-butyl [(1R)-1-(1-naphthyl)ethyl]{[(3R,4S)-4-phenylpyrrolidin-3-yl]methyl}carbamate, and carrying out the reaction in the same manner as the method of Example 39, ({[(3S,4S)-3-({[(1R)-1-(1-naphthyl)ethyl]amino}methyl)-4-phenylpyrrolidin-1-yl]carbonyl}oxy)acetic acid was produced using a corresponding starting material.

Example 41

(1) A mixture of 262 mg of tert-butyl [(1R)-1-(1-naphthyl)ethyl]{[(3R,4S)-4-phenylpyrrolidin-3-yl]methyl}carbamate and 10 ml of toluene was mixed with 0.085 ml of triethylamine and 120 mg of ethyl 4-isocyanate benzoate at room temperature and stirred overnight at 90° C. The reaction solution was mixed with ethyl acetate, washed with 1 M hydrochloric acid and saturated brine in that order and dried with anhydrous magnesium sulfate. The solvent was evaporated under a reduced pressure, and the thus obtained residue was purified by a silica gel column chromatography (chloroform-methanol) to obtain 365 mg of ethyl 4-{[(3R,4S)-3-({(tert-butoxycarbonyl)[(1R)-1-(1-naphthyl)ethyl]amino}methyl)-4-phenylpyrrolidin-1-yl]carbonyl}amino)benzoate as a pale yellow amorphous substance.

(2) A 214 mg portion of ethyl 4-{[(3R,4S)-3-({(tert-butoxycarbonyl)[(1R)-1-(1-naphthyl)ethyl]amino}methyl)-4-phenylpyrrolidin-1-yl]carbonyl}amino)benzoate was dissolved in 5.0 ml of ethanol, mixed with 1.0 ml of 1 M sodium hydroxide aqueous solution and stirred overnight at room temperature. The reaction solution was poured into 1 M hydrochloric acid, and the thus formed precipitate was collected by filtration. The thus obtained solid matter was purified by a silica gel column chromatography (chloroform-methanol) to obtain 131 mg of 4-{[(3R,4S)-3-({(tert-butoxycarbonyl)[(1R)-1-(1-naphthyl)ethyl]amino}methyl)-4-phenylpyrrolidin-1-yl]carbonyl}amino)benzoic acid as a colorless amorphous substance.

(3) A 3.0 ml 1,4-dioxane solution of 130 mg of 4-{[(3R,4S)-3-({(tert-butoxycarbonyl)[(1R)-1-(1-naphthyl)ethyl]amino}methyl)-4-phenylpyrrolidin-1-yl]carbonyl}amino)benzoic acid was mixed with 0.8 ml of 4 M hydrogen chloride/1,4-dioxane and stirred overnight at room temperature. The reaction solution was concentrated under a reduced pressure and mixed with ethyl acetate, and the thus formed solid was collected by filtration to obtain 96 mg of 4-({[(3S,4S)-3-({[(1R)-1-(1-naphthyl)ethyl]amino}methyl)-4-phenylpyrrolidin-1-yl]carbonyl}amino)benzoic acid hydrochloride as a pale brown solid.

Example 42

A 124 mg portion of the ethyl 4-({[(3R,4S)-3-({(tert-butoxycarbonyl)[(1R)-1-(1-naphthyl)ethyl]amino}methyl)-4-phenylpyrrolidin-1-yl]carbonyl}amino)benzoate obtained in Example 41 (1) was dissolved in 3.0 ml of ethyl acetate, and 1.0 ml of 4 M hydrogen chloride/ethyl acetate was added thereto and stirred overnight at room temperature. The reaction solution was concentrated under a reduced pressure, and the thus obtained residue was purified by a silica gel column chromatography (chloroform-methanol) to obtain 83 mg of ethyl 4-({[(3S,4S)-3-({[(1R)-1-(1-naphthyl)ethyl]amino}methyl)-4-phenylpyrrolidin-1-yl]carbonyl}amino)benzoate as a pale brown amorphous substance.

Example 43

(1) A 162 ml portion of 0.1 M potassium hydroxide aqueous solution was added to a 50 ml methanol solution of 3.01 g of dimethylpyridine-3,5-dicarboxylate and stirred at room temperature for 3Hours. The reaction solution was washed with diethyl ether, and the aqueous layer was concentrated under a reduced pressure. The residue was mixed with ethanol and stirred at 50° C. for 15Hours. The insoluble matter was removed by filtration, and then the filtrate was concentrated under a reduced pressure to obtain 2.51 g of potassium 5-(methoxycarbonyl)nicotinate as white crystals.

(2) A 3.29 ml portion of DPPA was added under ice-cooling to 24 ml of a THF-DMF (1:1) mixed solution of 3.04 g of potassium 5-(methoxycarbonyl)nicotinate and 2.32 ml of triethylamine and stirred at room temperature for 3Hours. The reaction solution was mixed with ethyl acetate, washed with water, saturated sodium bicarbonate aqueous solution and saturated brine in that order and dried with anhydrous magnesium sulfate. By concentrating this under a reduced pressure, methyl 5-(azidocarbonyl)nicotinate was obtained as a pale yellow solid.

(3) A 2 ml toluene solution of 115 mg of methyl 5-(azidocarbonyl)nicotinate was stirred with heating at 90° C. for 1Hour, and then the reaction solution was cooled down to room temperature. A mixture of 215 mg of tert-butyl [(1R)-1-(1-naphthyl)ethyl]{[(3R,4S)-4-phenylpyrrolidin-3-yl]methyl}carbamate, 0.07 ml of triethylamine and 2.0 ml of toluene/DMF (1:1) mixed solvent was added dropwise thereto and stirred at room temperature for 4Hours. The reaction solution was mixed with ethyl acetate, washed with water and saturated brine in that order and then dried with anhydrous sodium sulfate. This was concentrated under a reduced pressure, and the thus obtained residue was purified by a silica gel column chromatography (chloroform-methanol) to obtain 88 mg of methyl 5-({[(3R,4S)-3-({(tert-butoxycarbonyl)[(1R)-1-(1-naphthyl)ethyl]amino}methyl)-4-phenylpyrrolidin-1-yl]carbonyl}amino)nicotinate as a brown oily substance.

(4) The thus obtained oily substance was subjected to hydrolysis and elimination of Boc group in the same manner as in Example 41 (2) and supplementary Example 41 (3) to produce 5-({[(3S,4S)-3-({[(1R)-1-(1-naphthyl)ethyl]amino}methyl)-4-phenylpyrrolidin-1-yl]carbonyl}amino)nicotinic acid dihydrochloride.

Example 44

(1) A mixture of 144 mg of trans-1,4-cyclohexanedicarboxylic acid monomethyl ester, 213 mg of DPPA and 6 ml of toluene was mixed with 157 mg of triethylamine at room temperature and stirred at 80° C. for 3Hours. The reaction solution was spontaneously cooled down to room temperature, and a 2 ml toluene solution of 332 mg of tert-butyl [(1R)-1-(1-naphthyl)ethyl]{[(3R,4S)-4-phenylpyrrolidin-3-yl]methyl}carbamate was added thereto and stirred overnight at room temperature. The reaction solution was washed with 1 M hydrochloric acid, water and 1 M sodium hydroxide aqueous solution in that order and dried with anhydrous sodium sulfate. The solvent was evaporated under a reduced pressure, and the residue was purified by a silica gel column chromatography (chloroform-methanol) to obtain 336 mg of methyl trans-4-({[(3R,4S)-3-({(tert-butoxycarbonyl)[(1R)-

1-(1-naphthyl)ethyl]amino}methyl)-4-phenylpyrrolidin-1-yl]carbonyl}amino)cyclohexane-carboxylate as a colorless amorphous substance.

(2) A 8.0 ml methanol solution of 330 mg of methyl trans-4-({[(3R,4S)-3-({(tert-butoxycarbonyl) [(1R)-1-(1-naphthyl)ethyl]amino}methyl)-4-phenylpyrrolidin-1-yl]carbonyl}amino)cyclohexane-carboxylate was mixed with 1.5 ml of 1 M sodium hydroxide aqueous solution at room temperature and stirred overnight at room temperature. The solvent was evaporated under a reduced pressure, and the residue was mixed with 1 M hydrochloric acid, extracted with chloroform and dried with anhydrous sodium sulfate. The solvent was evaporated under a reduced pressure, and the thus obtained residue was purified by a silica gel column chromatography (chloroform-methanol) to obtain 176 mg of trans-4-({[(3R,4S)-3-({(tert-butoxycarbonyl)[(1R)-1-(1-naphthyl)ethyl]amino}methyl)-4-phenylpyrrolidin-1-yl]carbonyl}amino)cyclohexane carboxylic acid as a colorless amorphous substance.

(3) A 6.0 ml 1,4-dioxane solution of 175 mg of trans-4-({[(3R,4S)-3-({(tert-butoxycarbonyl)[(1R)-1-(1-naphthyl)ethyl]amino}methyl)-4-phenylpyrrolidin-1-yl]carbonyl}amino)cyclohexane carboxylic acid was mixed with 1.0 ml of 4 M hydrogen chloride/1,4-dioxane at room temperature and stirred overnight at room temperature. The reaction solution was concentrated under a reduced pressure, and the thus obtained residue was purified by a silica gel column chromatography (chloroform-methanol), and the thus obtained solid was recrystallized from chloroform-diethyl ether to obtain 36 mg of trans-4-({[(3S,4S)-3-({[(1R)-1-(1-naphthyl)ethyl]amino}methyl)-4-phenylpyrrolidin-1-yl]carbonyl}amino)cyclohexane carboxylic acid as a white solid.

Example 45

(1) A 1,4-dioxane solution of 250 mg of tert-butyl [(1R)-1-(1-naphthyl)ethyl]{[(3R,4S)-4-phenylpyrrolidin-3-yl]methyl}carbamate was mixed, under ice-cooling, with 0.13 ml of triethylamine and 250 mg of methyl 3-methoxy-4-{[(4-nitrophenoxy)carbonyl]amino}benzoate and stirred overnight at 80° C. The solvent was evaporated under a reduced pressure, and the residue was purified by a silica gel column chromatography (chloroform-methanol) to obtain 245 mg of methyl 4-({[(3R,4S)-3-({(tert-butoxycarbonyl)[(1R)-1-(1-naphthyl)ethyl]amino}methyl)-4-phenylpyrrolidin-1-yl]carbonyl}amino)-3-methoxybenzoate as a colorless amorphous substance.

(2) A mixture of 243 mg of methyl 4-({[(3R,4S)-3-({(tert-butoxycarbonyl)[(1R)-1-(1-naphthyl)ethyl]amino}methyl)-4-phenylpyrrolidin-1-yl]carbonyl}amino)-3-methoxybenzoate and 6.0 ml of a THF-methanol (2:1) mixed solvent was mixed with 1.0 ml of 1 M sodium hydroxide aqueous solution at room temperature and stirred overnight at room temperature. The reaction solution was concentrated under a reduced pressure, and the residue was mixed with 1 M hydrochloric acid, extracted with chloroform and dried with anhydrous sodium sulfate. The solvent was evaporated under a reduced pressure, and the thus obtained residue was purified by a silica gel column chromatography (chloroform-methanol) to obtain 227 mg of 4-({[(3R,4S)-3-({(tert-butoxycarbonyl)[(1R)-1-(1-naphthyl)ethyl]amino}methyl)-4-phenylpyrrolidin-1-yl]carbonyl}amino)-3-methoxybenzoic acid as a pale brown oily substance.

(3) An 8.0 ml 1,4-dioxane solution of 226 mg of 4-({[(3R,4S)-3-({(tert-butoxycarbonyl)[(1R)-1-(1-naphthyl)ethyl]amino}methyl)-4-phenylpyrrolidin 1-yl]carbonyl}amino)-3-methoxybenzoic acid was mixed with 2.0 ml of 4 M hydrogen chloride/1,4-dioxane at room temperature and stirred overnight at room temperature. The solvent was evaporated under a reduced pressure, and the residue was crystallized with 1,4-dioxane-diisopropyl ether to obtain 180 mg of 3-methoxy-4-({[(3S,4S)-3-({[(1R)-1-(1-naphthyl)ethyl]amino}methyl)-4-phenylpyrrolidin-1-yl]carbonyl}amino)benzoic acid hydrochloride as a beige solid.

Example 46

(1) A 0.43 ml portion of DMSO was dissolved in 6 ml of dichloromethane, and a 3 ml dichloromethane solution of 0.26 ml of oxalyl chloride was added thereto while keeping the internal temperature at −60° C. or less. After 30 minutes of stirring, a 10 ml dichloromethane solution of 270 mg of [(3R,4S)-1-benzyl-4-phenylpyrrolidin-3-yl]methanol which had been synthesized in accordance with the technique of Ling et al. ("Tetrahedron", 2001, vol. 57, p. 6579-6588) and the method of International Patent Publication WO 2000/59502 was added thereto while keeping the internal temperature at −60° C. or less and stirred for 30 minutes. A 1.27 ml portion of triethylamine was added to the reaction solution while keeping the internal temperature at −50° C. or less, and then the internal temperature was allowed to warm to 0° C. over 30 minutes or more, and this was stirred at 0° C. for 30 minutes. The reaction solution was mixed with water to quench the reaction and extracted with chloroform. The organic layer was washed with saturated brine and dried with anhydrous sodium sulfate. This was concentrated under a reduced pressure to obtain (3R,4S)-1-benzyl-4-phenylpyrrolidine-3-carboaldehyde as a crude product.

(2) A mixture of 173 mg of the thus obtained crude product, 5 drops of acetic acid and 10 ml of dichloroethane was stirred for 30 minutes, and then mixed with 642 mg of sodium triacetoxyborohydride at room temperature and stirred at room temperature for 1.5 hours. The reaction solution was mixed with water to quench the reaction and extracted with chloroform. The organic layer was washed with saturated brine, dried with anhydrous sodium sulfate and then concentrated under a reduced pressure. The thus obtained residue was purified by a silica gel column chromatography (methanol-chloroform) and an NH silica gel chromatography (hexane-ethyl acetate) to obtain 221 mg of (1R)—N-{[(3S,4S)-1-benzyl-4-phenylpyrrolidin-3-yl]methyl}-1-(1-naphthyl)ethanamine. A 221 mg portion of the thus obtained compound was dissolved in 5 ml of ethyl acetate, mixed with 1 ml of 4 M hydrogen chloride/ethyl acetate and concentrated. Concentration under a reduced pressure with toluene azeotropy was further repeated 3 times. The residue was mixed with chloroform-diisopropyl ether, and the resulting precipitate was collected by filtration and dried under a reduced pressure to obtain 240 mg of (1R)—N-{[(3S,4S)-1-benzyl-4-phenylpyrrolidin-3-yl]methyl}-1-(1-naphthyl)ethanamine dihydrochloride.

Example 47

A 215 mg portion of methyl 3-[(3S,4R)-1-benzyl-4-({(tert-butoxycarbonyl)[(1R)-1-(1-naphthyl)ethyl]amino}methyl)pyrrolidin-3-yl]benzoate, which had been produced by oxidizing methyl 3-[(3S,4R)-1-benzyl-4-(hydroxymethyl)pyrrolidin-3-yl]benzoate and condensing with (R)-(+)-1-(1-naphthyl)ethylamine in the same manner as in Reference Example 46(1) and carrying out the protection of Boc group in the same manner as in Reference Example 4(3), was dissolved in 4 ml of methanol, mixed with 3 ml of 1 M sodium hydroxide aqueous solution and stirred at room temperature for 18 hours. This was mixed with 3 ml of THF and further stirred at room temperature for 5 days, and then the reaction solution was concentrated under a reduced pressure, and the residue was mixed with water and washed with diethyl ether, and then 1 M hydrochloric acid was added thereto until its pH became 2. After extraction with chloroform, the organic layer was dried with anhydrous sodium sulfate and then concentrated under a reduced pressure to obtain 3-[(3S,4R)-1-benzyl-4-({(tert-butoxycarbonyl)[(1R)-1-(1-naphthyl)ethyl]amino}methyl)pyrrolidin-3-yl]benzoic acid as a crude product. The thus obtained crude product was dissolved in 1 ml of 1,4-dioxane, mixed with 1.0 ml of 4 M hydrogen chloride/1,4-dioxane solution and then concentrated under a reduced pressure, the residue was dissolved in THF and added dropwise to diethyl ether, the resulting precipitate was collected by filtration, and the filtered product was dried under a reduced pressure to obtain 135 mg of 3-[(3S,4S)-1-benzyl-4-({[(1R)-1-(1-naphthyl)ethyl] amino}methyl)pyrrolidin-3-yl]benzoic acid dihydrochloride.

Example 48

A 310 mg portion of benzyl 6-{(3S,4S)-3-({[(1R)-1-(1-naphthyl)ethyl]amino}methyl)-4-[3-(trifluoromethyl)phenyl]pyrrolidin-1-yl}-6-oxohexanoate was dissolved in 2 ml of methanol and 2 ml of THF, mixed with 2 ml of 1 M sodium hydroxide aqueous solution at room temperature and stirred for 16 hours. The reaction solution was washed with diethyl ether, 1 M hydrochloric acid was added to the water layer until its pH became 2.0, and then this was extracted with chloroform. After washing this with saturated brine, the organic layer was dried with anhydrous sodium sulfate and concentrated under a reduced pressure. By purifying the thus obtained residue by a silica gel column chromatography (chloroform-methanol), 6-{(3S,4S)-3-({[(1R)-1-(1-naphthyl)ethyl]amino}methyl)-4-[3-(trifluoromethyl)phenyl] pyrrolidin-1-yl}-6-oxohexanoic acid was obtained. The thus obtained compound was dissolved in 2 ml of 4 M hydrogen chloride/1,4-dioxane solution and then concentrated under a reduced pressure. THF and diethyl ether were added to the residue, the thus obtained precipitate was collected by filtration, and the filtered product was dried under a reduced pressure to obtain 200 mg of 6-{(3S,4S)-3-({[(1R)-1-(1-naphthyl)ethyl]amino}methyl)-4-[3-(trifluoromethyl)phenyl] pyrrolidin-1-yl}-6-oxohexanoic acid hydrochloride as a colorless solid.

Example 49

By carrying out successive reactions of carbamate formation, hydrolysis and elimination of Boc group in the same manner as the methods of Reference Example 44 and Example 33, 4-[({(3S,4S)-3-({[(1R)-1-(1-naphthyl)ethyl] amino}methyl)-4-[3-(trifluoromethyl)phenyl]pyrrolidin-1-yl}carbonyl)oxy]benzoic acid hydrochloride was produced using a corresponding starting material.

Example 50

By carrying out hydrolysis in the same manner as the method of Example 38(3), 4-({[(3S,4S)-3-(4-fluorophenyl)-4-({[(1R)-1-(1-naphthyl)ethyl]amino}methyl)pyrrolidin-1-yl]carbonyl}oxy)benzoic acid was produced using respectively corresponding starting materials.

Example 51

By successively carrying out the reactions in the same manner as the methods of Reference Example 53 and Example 38(3), 4-({[(3S,4S)-3-({[(1S)-1-(1-naphthyl)ethyl] amino}methyl)-4-phenylpyrrolidin-1-yl]carbonyl}oxy)benzoic acid was produced using respectively corresponding starting materials.

Example 52

A 2.0 ml THF, 1.0 ml water and 0.5 ml methanol mixed solution of 261 mg of 4-(methoxycarbonyl)phenyl(3S,4S)-3-({[(1R)-1-(3-methoxyphenyl)ethyl]amino}methyl)-4-phenylpyrrolidine-1-carboxylate was mixed with 45 mg of lithium hydroxide and stirred at room temperature for 20 hours. The reaction solution was acidified by adding 1 M hydrochloric acid and post-treated and purified in the standard method to obtain 136 ml of 4-({[(3S,4S)-3-({[(1R)-1-(3-methoxyphenyl)ethyl]amino}methyl)-4-phenylpyrrolidin-1-yl]carbonyl}oxy)benzoic acid as a colorless amorphous substance.

Example 53

(1) A 1.0 ml dichloroethane solution of 119 mg of 4-(methoxycarbonyl)phenyl(3S,4S)-3-(aminomethyl)-4-phenylpyrrolidine-1-carboxylate and 62 mg of 3-acetylbenzothiophene was mixed with 0.12 ml of tetraisopropoxy titanium and stirred for 2 hours. The reaction solution was diluted with 1.0 ml of methanol, mixed with 38 mg of sodium borohydride, further stirred for 1 hour and then concentrated under a reduced pressure, and the thus obtained was purified by a silica gel chromatography (chloroform-methanol) to obtain 95 mg of 4-(methoxycarbonyl)phenyl(3S,4S)-3-({[1-(1-benzothien-3-yl)ethyl]amino}methyl)-4-phenylpyrrolidine-1-carboxylate as a yellow amorphous substance. EP: 515.

(2) By successively carrying out hydrolysis and salt formation of 4-(methoxycarbonyl)phenyl(3S,4S)-3-({[1-(1-benzothien-3-yl)ethyl]amino}methyl)-4-phenylpyrrolidine-1-carboxylate in the same manner as the methods of Example 52 and Example 1(3), 4-({[(3S,4S)-3-({[1-(1-benzothien-3-yl)ethyl]amino}methyl)-4-phenylpyrrolidin-1-yl] carbonyl}oxy)benzoic acid hydrochloride was produced.

Example 54

(1) A 2.0 ml THF solution of 253 mg of 4-(methoxycarbonyl)phenyl(3S,4S)-3-(aminomethyl)-4-phenylpyrrolidine-1-carboxylate and 144 mg of 5-acetylbenzodioxane was mixed with 0.12 ml of a boron trifluoride diethyl ether complex at 0° C. and stirred overnight at room temperature. The reaction solution was concentrated under a reduced pressure, and the thus obtained residue was purified by a silica gel chromatography (chloroform-methanol) to obtain 146 mg of 4-(methoxycarbonyl)phenyl(3S,4S)-3-({[1-(2,3-dihydro-1,4-benzodioxin-5-yl)ethyl]amino}methyl)-4-phenylpyrrolidine-1-carboxylate as a colorless amorphous substance. EP: 517.

(2) 4-({[(3S,4S)-3-({[1-(2,3-Dihydro-1,4-benzodioxin-5-yl)ethyl]amino}methyl)-4-phenylpyrrolidin-1-yl] carbonyl}oxy)benzoic acid hydrochloride was produced by carrying out the reaction of 4-(methoxycarbonyl)phenyl(3S, 4S)-3-({[1-(2,3-dihydro-1,4-benzodioxin-5-yl)ethyl]

amino}methyl)-4-phenylpyrrolidine-1-carboxylate in the same manner as the method of Example 53(2).

Example 55

By successively carrying out reductive amination and hydrolysis in the same manner as the methods of Example 53(1) and Example 38(3), 4-{[(3S,4S)-3-{[(1-azulen-1-yl-ethyl)amino]methyl}-4-phenylpyrrolidin-1-yl)carbonyl]oxy}benzoic acid was produced using a corresponding starting material.

Example 56

By carrying out the reaction in the same manner as the method of Example 55, 4-({[(3S,4S)-3-({[1-(1-methyl-2-phenoxy-1H-indol-3-yl)ethyl]amino}methyl)-4-phenylpyrrolidin-1-yl]carbonyl}oxy)benzoic acid was produced using a corresponding starting material.

Example 57

A 470 mg portion of (1R)-1-(1-naphthyl)-N-{[(3R,4R)-4-phenyl-1-(trifluoroacetyl)pyrrolidin-3-yl]methyl}ethanamine was dissolved in 8 ml of ethyl acetate and treated with 4 M hydrogen chloride/ethyl acetate solution. Diethyl ether was added to the reaction solution, and the thus precipitated crystals were recrystallized from ethyl acetate and diethyl ether to obtain 258 mg of (1R)-1-(1-naphthyl)-N-{[(3R,4R)-4-phenyl-1-(trifluoroacetyl)pyrrolidin-3-yl]methyl}ethanamine hydrochloride as colorless crystals.

Example 58

By successively carrying out protection of Boc group, hydrolysis, acetylation and Boc elimination in the same manner as in Reference Example 4(3), Reference Example 5, Reference Example 18 and Example 2 respectively, (1R)—N-{[(3R,4R)-1-acetyl-4-phenylpyrrolidin-3-yl]methyl}-1-(1-naphthyl)ethanamine hydrochloride was produced from (1R)-1-(1-naphthyl)-N-{[(3S,4R)-4-phenyl-1-(trifluoroacetyl)pyrrolidin-3-yl]methyl}ethanamine.

Example 59

By successively carrying out the reactions in the same manner as the methods of Reference Example 58, Reference Example 53 and Example 38(3), 4-({[(3R,4R)-3-({[(1S)-1-(1-naphthyl)ethyl]amino}methyl)-4-phenylpyrrolidin-1-yl]carbonyl}oxy)benzoic acid was produced from 4-(methoxycarbonyl)phenyl(3S,4R)-3-({[tert-butyl(dimethyl)silyl]oxy}methyl)-4-phenylpyrrolidine-1-carboxylate using respectively corresponding starting materials.

Example 60

By carrying out salt formation in the same manner as in Example 57, (1R)-1-(1-naphthyl)-N-{[4-phenyl-1-(trifluoroacetyl)pyrrolidin-3-yl]methyl}ethanamine hydrochloride was produced from (1R)-1-(1-naphthyl)-N-{[4-phenyl-1-(trifluoroacetyl)pyrrolidin-3-yl]methyl}ethanamine.

Example 61

At −78° C., 1.4 ml of oxalyl chloride was added dropwise to a 25 ml dichloromethane solution of 2.35 ml of DMSO and stirred for 20 minutes. A 10 ml dichloromethane solution of 1.21 g of (1-acetyl-4-phenylpyrrolidin-3-yl)methanol was added thereto and stirred for 30 minutes, and 7.0 ml of triethylamine was added thereto and stirred for 20 minutes. The reaction solution was poured into 100 ml of ice water, extracted with chloroform and dried with anhydrous magnesium sulfate. The solvent was evaporated, and the thus obtained residue was mixed with 22 ml of dichloroethane, 0.71 g of (1R)-(+)-1-naphthylethylamine, 2.63 g of sodium triacetoxyborohydride and 0.24 ml of acetic acid and stirred at room temperature for 3 days. After completion of the reaction, this was mixed with 50 ml of water and 50 ml of saturated sodium bicarbonate aqueous solution and extracted with chloroform. The organic layer was concentrated, and the thus obtained residue was purified by a silica gel column chromatography (chloroform-methanol) to obtain 726 mg of (1R)—N-[(1-acetyl-4-phenylpyrrolidin-3-yl)methyl]-1-(1-naphthyl)ethanamine as a colorless oily substance. This was mixed with 10 ml of ethyl acetate and 0.5 ml of 4 M hydrogen chloride/ethyl acetate, and the resulting solution was concentrated. By its crystallization (ethyl acetate-hexane), 574 mg of (1R)—N-[(1-acetyl-4-phenylpyrrolidin-3-yl)methyl]-1-(1-naphthyl)ethanamine hydrochloride was obtained as a colorless solid.

Example 62

A 6 ml THF solution of 300 mg of tert-butyl [(1R)-1-(1-naphthyl)ethyl]{[4-phenylpyrrolidin-3-yl]methyl}carbamate was mixed with 0.29 ml of triethylamine and 0.13 ml of pivaloyl chloride and stirred at room temperature for 3 hours. After completion of the reaction, 20 ml of water was added thereto and THF was evaporated. This was extracted with ethyl acetate, washed with saturated brine and dried with magnesium sulfate, and then the organic layer was concentrated. The thus obtained residue was mixed with 10 ml of 4 M hydrogen chloride/ethyl acetate and stirred at 50° C. for 4 hours. After completion of the reaction, the solvent was evaporated, and the thus obtained residue was purified by a silica gel column chromatography (chloroform-methanol) and crystallized (diethyl ether-ethyl acetate) to obtain 92 mg of (1R)—N-{[1-(2,2-dimethylpropanoyl)-4-phenylpyrrolidin-3-yl]methyl}-1-(1-naphthyl)ethanamine hydrochloride as colorless crystals.

Example 63

In the same manner as in Example 62, (1R)-1-(1-naphthyl)-N-[(4-phenyl-1-propionylpyrrolidin-3-yl)methyl]ethanamine hydrochloride was produced from tert-butyl [(1R)-1-(1-naphthyl)ethyl]{[4-phenylpyrrolidin-3-yl]methyl}carbamate and a corresponding starting material.

Example 64

An 8 ml acetonitrile solution of 192 mg of 2-hydroxy-2-methylpropanoic acid was mixed with 392 mg of WSC hydrochloride, 62 mg of HOBt and 400 mg of tert-butyl [(1R)-1-(1-naphthyl)ethyl]{[4-phenylpyrrolidin-3-yl]methyl}carbamate and stirred at 60° C. for 12 hours. After completion of the reaction, 30 ml of water was added thereto, and acetonitrile was evaporated. This was extracted with ethylamine, the organic layer was concentrated, and then the thus obtained residue was purified by a silica gel column chromatography (chloroform-ethyl acetate). This was further mixed with 2 ml of ethyl acetate and 0.5 ml of 4 M hydrogen chloride/ethyl acetate and stirred at 60° C. for 4 hours. After completion of the reaction, this was neutralized with saturated sodium bicarbonate aqueous solution, extracted with ethyl acetate and concentrated, and then the thus obtained residue was again purified by a silica gel column chromatography (chloroform-ethyl acetate), treated with 4 M hydrogen chloride/ethyl acetate and crystallized (ethyl acetate-hexane) to obtain 43 mg of 2-methyl-1-[3-({[(1R)-1-(1-naphthyl) ethyl]amino}methyl)-4-phenylpyrrolidin-1-yl]-1-oxopropan-2-ol hydrochloride as a colorless solid

Example 65

A 10 ml THF solution of 500 mg of tert-butyl [(1R)-1-(1-naphthyl)ethyl][(4-phenylpyrrolidin-3-yl)methyl]carbamate was mixed with 0.34 ml of ethyl chloroformate and stirred at 50° C. A 0.24 ml portion of triethylamine and 20 ml of water were added thereto, and the solvent was evaporated. This was extracted with ethyl acetate, washed with saturated brine and dried with magnesium sulfate, and the solvent was evaporated. The thus obtained residue was treated with 4 M hydrogen chloride/ethyl acetate solution and recrystallized from ethyl acetate-hexane to obtain 312 mg of ethyl 3-({[(1R)-1-(1-naphthyl)ethyl]amino}methyl)-4-phenylpyrrolidine-1-carboxylate as colorless crystals.

Example 66

A mixture of 215 mg of tert-butyl [(1R)-1-(1-naphthyl) ethyl][(4-phenylpyrrolidin-3-yl)methyl]carbamate and 5 ml of dichloromethane was mixed with 119 mg of phenyl isocyanate and stirred at room temperature for 4 hours. The reaction solution was diluted with ethyl acetate and washed with water and 1 M hydrochloric acid. The organic layer was dried with anhydrous sodium sulfate and concentrated under a reduced pressure. The thus obtained residue was purified by a silica gel column chromatography (chloroform-methanol)to obtain 270 mg of crude tert-butyl {[1-(anilinocarbonyl)-4-phenylpyrrolidin-3-yl]methyl}[(1R)-1-(1-naphthyl)ethyl] carbamate as a colorless solid. The thus obtained compound was dissolved in 5 ml of ethyl acetate, mixed with 1 ml of 4 M hydrogen chloride/ethyl acetate and stirred overnight at room temperature. The resulting precipitate was collected by filtration to obtain 56 mg of 3-({[(1R)-1-(1-naphthyl)ethyl] amino}methyl)-N,4-diphenylpyrrolidine-1-carboxamide hydrochloride as a white solid.

Example 67

An 8.0 ml ethyl acetate solution of 318 mg of 1-acetylpiperidine-4-carboxylic acid was mixed with 0.18 ml of ethyl chloroformate, 0.52 ml of triethylamine and 400 mg of tert-butyl [(1R)-1-(1-naphthyl)ethyl][(4-phenylpyrrolidin-3-yl) methyl]carbamate in that order and stirred at room temperature for 30 minutes. This was mixed with 10 ml of water and extracted with ethyl acetate. The solvent was evaporated, and the thus obtained residue was purified by a silica gel column chromatography (chloroform-methanol). This was treated with 4 M hydrogen chloride/ethyl acetate and concentrated to dryness to obtain 75 mg of (1R)—N-({1-[(1-acetylpiperidin-4-yl)carbonyl]-4-phenylpyrrolidin-3-yl}methyl)-1-(1-naphthyl)ethanamine hydrochloride as a pale pink solid.

Example 68

A 5 ml THF solution of 100 mg of the N-[(1R)-1-(1-naphthyl)ethyl]-2-oxo-4-phenylpyrrolidine-3-carboxamide obtained from a high polarity eluate in Reference Example 78 was mixed with 0.84 ml of a borane-THF complex (1 M THF solution) and heated overnight under reflux. The reaction solution was cooled down to room temperature, acidified by adding hydrochloric acid to the reaction solution and heated under reflux for 30 minutes. The reaction solution was again cooled down to room temperature, alkalified by adding 1 M sodium hydroxide aqueous solution to the reaction solution and extracted with chloroform. The organic layer was dried with anhydrous sodium sulfate and concentrated under a reduced pressure. The thus obtained residue was purified by a silica gel column chromatography (chloroform-methanol-aqueous ammonia). This was made into fumaric acid salt in the standard method and then crystallized from ethanol-ethyl acetate to obtain 58 mg of (1R)-1-(1-naphthyl)-N-[(4-phenylpyrrolidin-3-yl)methyl]ethanamine difumarate as a colorless solid.

Example 69

In accordance with the techniques of "Journal of Organic Chemistry", 2001, vol. 66, p. 1403-1412, a mixture of 215 mg of tert-butyl [(1R)-1-(1-naphthyl)ethyl][(4-phenylpyrrolidin-3-yl)methyl]carbamate, 113 mg of chlorobenzene and 3 ml of toluene was mixed with 231 mg of potassium tert-butoxide and heated at 135° C. for 36 hours in a sealed tube. The organic layer was washed with 1 M hydrochloric acid, and the organic layer was dried with anhydrous sodium sulfate and concentrated under a reduced pressure. The thus obtained residue was purified by a silica gel column chromatography (chloroform-methanol) to obtain 85 mg of tert-butyl [(1,4-diphenylpyrrolidin-3-yl)methyl][(1R)-1-(1-naphthyl) ethyl]carbamate as a colorless oily substance. The thus obtained compound was dissolved in 2 ml of ethyl acetate, mixed with 1 ml of 4 M hydrogen chloride/ethyl acetate and stirred at room temperature for 6 hours. The reaction solution was concentrated under a reduced pressure, and the thus precipitated solid was collected by filtration to obtain 30 mg of (1R)—N-[(1,4-diphenylpyrrolidin-3-yl)methyl]-1-(1-naphthyl)ethanamine dichloride as a purple solid.

Example 70

A 10 ml THF solution of 500 mg of tert-butyl [(1R)-1-(1-naphthyl)ethyl][(4-phenylpyrrolidin-3-yl)methyl]carbamate was mixed with 0.26 ml of methanesulfonyl chloride and stirred at 50° C. A 0.24 ml portion of triethylamine and 20 ml of water were added thereto, and the solvent was evaporated. This was extracted with ethyl acetate, washed with saturated brine and dried with magnesium sulfate, and the solvent was evaporated. The thus obtained residue was treated with 4 M hydrogen chloride/ethyl acetate solution and recrystallized from ethyl acetate-hexane to obtain 294 mg of (1R)—N-{[(methylsulfonyl)-4-phenylpyrrolidin-3-yl]methyl}-1-(1-naphthyl)ethanamine hydrochloride as colorless crystals.

Example 71

In the same manner as in Example 61, (1R)—N-[(1-acetyl-4-phenylpyrrolidin-3-yl)methyl]-1-(3-methoxyphenyl)ethanamine hydrochloride was produced using corresponding (1R)-1-(3-methoxyphenyl)ethanamine instead of (1R)-(+)-(1-naphthyl)ethylamine.

Example 72

A mixture of 10.8 mg of tert-butyl [(1R)—-(1-naphthyl) ethyl]{[4-phenylpyrrolidin-3-yl]methyl}carbamate, 2.6 mg of butyric acid, 3.4 mg of HOBt, 3.5 μl of triethylamine, 60 μl of 1-methylpyrrolidin-2-one and 0.8 ml of DMF was mixed with 100 mg of PS-Carbodiimide (mfd. by Argonaut Technologies, USA) at room temperature and stirred for 15 hours. At room temperature, the reaction solution was mixed with 50 mg of MP-Carbonate (mfd. by Argonaut Technologies, USA) and 50 mg of PS-Isocyanate (mfd. by Argonaut Technologies) and stirred for 4 hours. The reaction solution was filtered. The filtrate was concentrated under a reduced pressure to obtain tert-butyl [(1-butyryl-4-phenylpyrrolidin-3-yl)methyl][1-(1-naphthyl)ethyl]carbamate as a crude product. A 0.5 ml methanol solution of the thus obtained crude product was mixed with 0.5 ml of 4 M hydrogen chloride/ethyl acetate solution at room temperature and stirred for 15 hours. By concentrating the reaction solution under a reduced pressure, 9.6 mg of (1R)—N-[(1-butyryl-4-phenylpyrrolidin-3-yl)methyl]-1-(1-naphthyl)ethanamine hydrochloride was obtained.

Example 73

A mixture of 12.9 mg of tert-butyl [(1R)-1-(1-naphthyl)ethyl]{[4-phenylpyrrolidin-3-yl]methyl}carbamate, 6.3 mg of 3-methoxycarbonylbenzoic acid, 4.1 mg of HOBt and 1 ml of DMF was mixed at room temperature with 75 mg of PL-DCC Resin (mfd. by Polymer Laboratories, UK) and stirred for 15 hours. At room temperature, the reaction solution was mixed with 50 mg of MP-Carbonate (mfd. by Argonaut Technologies, USA) and 50 mg of PS-Isocyanate (mfd. by Argonaut Technologies, USA) and stirred for 4 hours, and the reaction solution was filtered. The filtrate was concentrated under a reduced pressure to obtain methyl 3-{[3-({(tert-butoxycarbonyl)[(1R)-(1-naphthyl)ethyl]amino}methyl)-4-phenylpyrrolidin-1-yl]carbonyl}benzoate as a crude product. A 0.5 ml methanol solution of the thus obtained crude product was mixed with 0.5 ml of 4 M hydrogen chloride/ethyl acetate solution at room temperature and stirred for 15 hours. By concentrating the reaction solution under a reduced pressure, methyl 3-{[3-({[(1R)-(1-naphthyl)ethyl]amino}methyl)-4-phenylpyrrolidin-1-yl]carbonyl}benzoate was obtained as a crude product. A 0.5 ml THF solution of the thus obtained crude product was mixed with 0.5 ml of methanol and 0.5 ml of 2 M sodium hydroxide aqueous solution at room temperature and stirred at 50° C. for 15 hours. The reaction solution was mixed with 1.1 ml of 1 M hydrochloric acid and concentrated under a reduced pressure. The thus obtained residue was purified by a fractional high performance liquid chromatography (methanol-0.1% formic acid aqueous solution) to obtain 5.2 mg of 3-{[3-({[(1R)-(1-naphthyl)ethyl]amino}methyl)-4-phenylpyrrolidin-1-yl]carbonyl}benzoic acid.

Example 74

A mixture of 9.9 mg of tert-butyl [(1R)-1-(1-naphthyl)ethyl]{[4-phenylpyrrolidin-3-yl]methyl}carbamate, 4.9 mg of 2-chlorobenzaldehyde, 50 μl of acetic acid and 0.5 ml of DMF was mixed at room temperature with 75 mg of MP-Triacetoxyborohydride (mfd. by Argonaut Technologies, USA) and stirred for 15 hours. At room temperature, the reaction solution was mixed with 50 mg of PS-Isocyanate (mfd. by Argonaut Technologies, USA) and stirred for 4 hours, and the reaction solution was filtered. The filtrate was concentrated under a reduced pressure to obtain tert-butyl {[1-(2-chlorobenzoyl)-4-phenylpyrrolidin-3-yl]methyl}[1-(1-naphthyl)ethyl]carbamate as a crude product. A 0.5 ml methanol solution of the thus obtained crude product was mixed with 0.5 ml of 4 M hydrogen chloride/ethyl acetate solution at room temperature and stirred for 4 hours. The reaction solution was concentrated under a reduced pressure, and the thus obtained residue was purified by a fractional high performance liquid chromatography (methanol-0.1% formic acid aqueous solution) to obtain 3.3 mg of N-{[1-(2-chlorobenzoyl)-4-phenylpyrrolidin-3-yl]methyl}-1-(1-naphthyl)ethanamine.

Example 75

By carrying out benzyl elimination reaction in the same manner as in Reference Example 16, and then successively carrying out the reactions of trifluoro-acetylation, TBDPS elimination, oxidation, reductive alkylation and salt formation in the same manner as in Reference Example 2, Reference Example 3 and Example 1, (1R)—N-{[4-methyl-1-(trifluoroacetyl)pyrrolidin-3-yl]methyl}-1-(1-naphthyl)ethanamine oxalate was synthesized from 1-benzyl-3-({[tert-butyl(diphenyl)silyl]oxy}methyl)-4-methylpyrrolidine.

Example 76

By carrying out benzyl elimination reaction from respective corresponding starting materials in the same manner as in Reference Example 16, and then successively carrying out the reactions of trifluoro-acetylation, TBS elimination, oxidation, reductive alkylation and salt formation in the same manner as in Reference Example 2, Reference Example 3, Reference Example 69 and Example 57, (1R)-1-(1-naphthyl)-N-({1-(trifluoroacetyl)-4-[3-(trifluoromethyl)phenyl]pyrrolidin-3-yl}methyl)ethanamine hydrochloride was synthesized from 1-benzyl-3-({[tert-butyl(diphenyl)silyl]oxy}methyl)-4-[3-(trifluoromethyl)phenyl]pyrrolidine.

Example 77

By successively carrying out protection of Boc group, hydrolysis, acetylation and Boc elimination in the same manner as in Reference Example 4(3), Reference Example 5, Reference Example 18 and Example 2, (1R)—N-({1-acetyl-4-[3-(trifluoromethyl)phenyl]pyrrolidin-3-yl}methyl)-1-(1-naphthyl)ethanamine hydrochloride was produced from (1R)-1-(1-naphthyl)-N-({1-(trifluoroacetyl)-4-[3-(trifluoromethyl)phenyl]pyrrolidin-3-yl}methyl)ethanamine.

Example 78

By successively carrying out amidation, hydrolysis and Boc elimination in the same manner as in Reference Example 19, Reference Example 20 and Example 5, 6-[3-benzyl-4-({[(1R)-1-(1-naphthyl)ethyl]amino}methyl)pyrrolidin-1-yl]-6-oxohexanoic acid hydrochloride was produced from monoethyl adipate and tert-butyl [(4-benzylpyrrolidin-3-yl)methyl][1-(1-naphthyl)ethyl]carbamate.

Example 79

Using the (1R)—N-{[4-methyl-1-(trifluoroacetyl)pyrrolidin-3-yl]methyl}-1-(1-naphthyl)ethanamine obtained during the production process of Example 75, 6-[3-methyl-4-({[(1R)-1-(1-naphthyl)ethyl]amino}methyl)pyrrolidin-1-yl]-6-oxohexanoic acid was produced by successively carrying out protection of Boc group and hydrolysis in the same manner as in Reference Example 4(3) and Reference Example 5, and then carrying out the reaction of the same procedure of Example 9 except that succinic anhydride was changed to adipic anhydride.

Example 80

Using 1-benzyl-4-({[tert-butyl(diphenyl)silyl]oxy}methyl)-3,3-dimethylpyrrolidine, the benzyl elimination reaction shown in Reference Example 16 was carried out and then the reactions were successively carried out in the same manner as in Reference Example 2, Reference Example 3 and Example 1, thereby producing (1R)—N-{[4,4-dimethyl-1-(trifluoroacetyl)pyrrolidin-3-yl]methyl}-1-(1-naphthyl)ethanamine oxalate.

Example 81

A 8.0 ml THF solution of 124 mg of tert-butyl [(1R)-1-(1-naphthyl)ethyl](pyrrolidin-3-ylmethyl)carbamate was mixed with 45 μl of benzoyl chloride and stirred overnight at room temperature. A 20 ml portion of saturated sodium bicarbonate aqueous solution was added thereto, and the solvent was evaporated. This was extracted with ethyl acetate, washed with saturated brine and dried with magnesium sulfate, and the solvent was evaporated. The thus obtained residue was treated with 4 M hydrogen chloride/ethyl acetate and recrystallized from isopropanol-diethyl ether to obtain 100 mg of (1R)—N-[(1-benzoylpyrrolidin-3-yl)methyl]-1-(1-naphthyl)ethanamine hydrochloride as colorless crystals.

Example 82

By successively carrying out amidation and Boc elimination in the same manner as in Example 64, methyl 4-{[3-({[1-(1-naphthyl)ethyl]amino}methyl)pyrrolidin-1-yl]carbonyl}benzoate was produced from tert-butyl [(1R)-1-(1-naphthyl)ethyl](pyrrolidin-3-ylmethyl)carbamate and a corresponding starting material.

Example 83

Using methyl 4-{[3-({(tert-butoxycarbonyl)[(1R)-1-(1-naphthyl)ethyl]amino}methyl)pyrrolidin-1-yl]carbonyl}benzoate obtained during the production process of Example 82, hydrolysis and Boc elimination were successively carried out in the same manner as in Reference Example 20 and Example 5 to produce 4-{[3-({[(1R)-1-(1-naphthyl)ethyl]amino}methyl)pyrrolidin-1-yl]carbonyl}benzoic acid hydrochloride.

Example 84

A 6.0 ml THF solution of 300 mg of N-[(1R)-1-(1-naphthyl)ethyl]-5-oxo-1-phenylpyrrolidine-3-carboxamide was mixed with 0.34 ml of a borane-dimethyl sulfide complex and stirred at 60° C. for 1 hour. Successively this was mixed with 7 ml of 1 M hydrochloric acid and stirred for 1.5 hors. After completion of the reaction, the solvent was evaporated, the residue was mixed with 20 ml of 1 M hydrochloric acid and washed with ethyl acetate, and then the water layer was neutralized with 1 M sodium hydroxide and extracted with ethyl acetate. The solvent in the organic layer was evaporated, and the thus obtained residue was purified by a silica gel column chromatography (chloroform-methanol) to obtain 125 mg of (1R)-1-(1-naphthyl)-N-[(1-phenylpyrrolidin-3-yl)methyl]ethanamine fumarate as a colorless solid.

Example 85

(1R)-1-(3-Methoxyphenyl)-N-[(1-phenylpyrrolidin-3-yl)methyl]ethanamine fumarate was produced by using corresponding (1R)-1-(3-Methoxyphenyl)ethanamine instead of (1R)-(+)-(1-naphthyl)ethylamine and carrying out successive reactions with 5-oxo-1-phenylpyrrolidine-3-carboxylic acid in the same manner as in Reference Example 96 and Example 84.

Example 86 and Example 87

A 20 ml DMF solution of 1.16 g of 1-benzyl-5-oxopyrrolidine-3-carboxylic acid was mixed with 2.0 g of WSC hydrochloride and 859 mg of HOBt and stirred at room temperature for 30 minutes. 1.1 g of (1R)-1-naphthylethylamine was added thereto successively and stirred at 60° C. After completion of the reaction, this was mixed with 100 ml of water, extracted with ethyl acetate and washed with 1 M hydrochloric acid. The organic layer was concentrated, and the thus obtained residue was purified by a silica gel column chromatography (chloroform-methanol) and then recrystallized from ethyl acetate-hexane to obtain 856 mg and 831 mg of (3R)-1-benzyl-N-[(1R)-1-(1-naphthyl)ethyl]5-oxopyrrolidine-3-carboxamide and (3S)-1-benzyl-N-[(1R)-1-(1-naphthyl)ethyl]5-oxopyrrolidine-3-carboxamide (stereoisomers un-verified). Both of the thus obtained compounds were respectively subjected to reduction in the same manner as in Example 84, made into salt with fumaric acid and recrystallized from ethanol-ethyl acetate to obtain (1R)—N-{[(3S)-1-benzylpyrrolidin-3-yl]methyl}-1-(1-naphthyl)ethanamine fumarate and (1R)—N-{[(3R)-1-benzylpyrrolidin-3-yl]methyl}-1-(1-naphthyl)ethanamine fumarate.

Example 88

A 10 ml dichloroethane solution of 0.53 g of 5-oxo-1-phenylpyrrolidine-3-carboaldehyde was mixed with 508 mg of (1R)-1-(3-methoxyphenyl)ethanamine and 0.1 ml of acetic acid and stirred at room temperature for 1 hour. Successively this was mixed with 1.8 g of sodium triacetoxyborohydride and stirred overnight at room temperature. This was mixed with 40 ml of water and extracted with chloroform. The organic layer was concentrated, and the thus obtained residue was purified by a silica gel column chromatography (chloroform-methanol), treated with 4 M hydrogen chloride/ethyl acetate and concentrated to dryness to obtain 161 mg of 4-({[(1R)-1-(3-methoxyphenyl)ethyl]amino}methyl)-1-phenylpyrrolidin-2-one hydrochloride as a colorless solid.

Example 89

In the same manner as in Example 88, 1-benzyl-4-({[(1R)-1-(1-naphthyl)ethyl]amino}methyl)pyrrolidin-2-one hydrochloride was obtained from 1-benzyl-5-oxopyrrolidine-3-carboaldehyde and (1R)-1-naphthylethylamine.

Example 90

In the same manner as in Example 88, 1-cyclohexyl-4-({[(1R)-1-(1-naphthyl)ethyl]amino}methyl)pyrrolidin-2-one hydrochloride was obtained from 1-cyclohexyl-5-oxopyrrolidine-3-carboaldehyde and (1R)-1-naphthylethylamine.

Example 91

By carrying out elimination of Boc group from tert-butyl [(1R)-1-(1-naphthyl)ethyl]{[(3R,4S)-4-phenylpyrrolidin-3-yl]methyl}carbamate in the same manner as in Example 2, (1R)-1-(1-naphthyl)-N-{[(3R,4S)-4-phenylpyrrolidin-3-yl]methyl}ethanamine dihydrochloride was produced.

In the same manner as the aforementioned methods of Examples 1 to 91, Example compounds 92 to 363 were produced using respective corresponding starting materials. Structures and physicochemical data of the Example compounds are shown in Tables 22 to 78.

In addition, structures of other compounds of the compounds of the invention are shown in Tables 79 to 99. These may be easily synthesized by using the methods described in the aforementioned production methods and Examples, methods which are obvious to those skilled in the art, or modified methods thereof.

TABLE 4

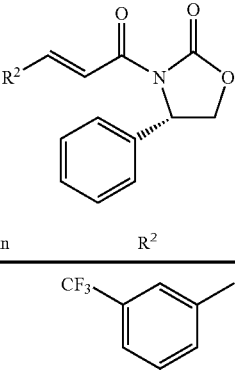

| REx | RSyn | R² | DATA |
|---|---|---|---|
| 10 | 10 | 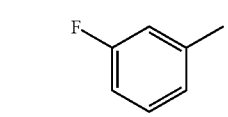 | FP: 362 |
| 107 | 11 | 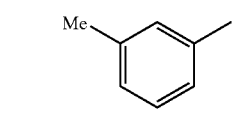 | EP: 312 |
| 108 | 11 | 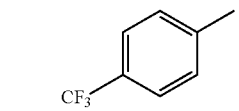 | EP: 330 (M + Na) |
| 109 | 11 | 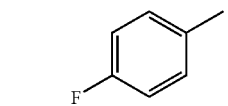 | EP: 362 |
| 110 | 11 | 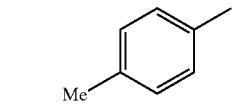 | EP: 312 |
| 111 | 11 | 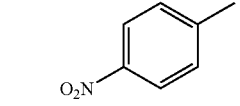 | EP: 330 (M + Na) |
| 112 | 11 | 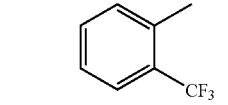 | EP: 361 (M + Na) |
| 113 | 11 | 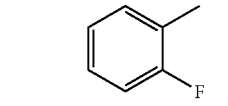 | EP: 384 (M + Na) |
| 11 | 11 | 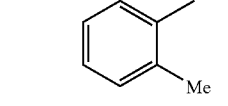 | FP: 312 |
| 114 | 11 | 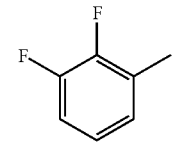 | EP: 308 |

TABLE 5

| 115 | 11 | 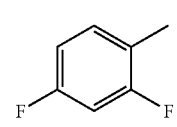 | EP: 330 |
| 116 | 11 | 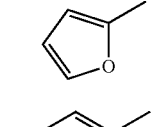 | EP: 330 |
| 117 | 11 | 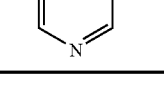 | FP: 284 |
| 118 | 11 | 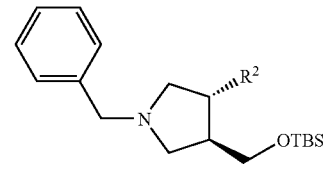 | FP: 295 |

TABLE 6

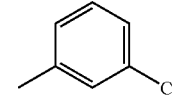

| REx | RSyn | R² | DATA |
|---|---|---|---|
| 14 | 14 | 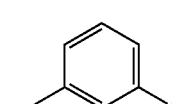 | FP: 450 |
| 119 | 14 | 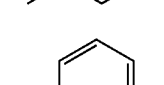 | EP: 400 |
| 120 | 14 | 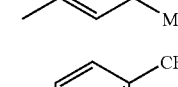 | EP: 396 |
| 121 | 14 | 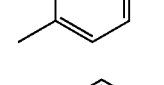 | EP: 450 |
| 122 | 14 | 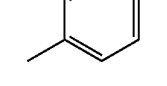 | EP: 400 |
| 123 | 14 | Me | EP: 396 |
| 124 | 14 | NO₂ | EP: 427 |

TABLE 6-continued
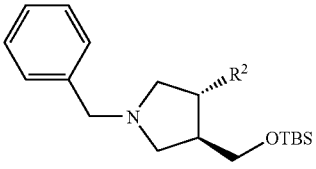
| REx | RSyn | R² | DATA |
|---|---|---|---|
| 125 | 14 | 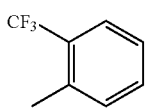 (o-CF₃-phenyl) | EP: 450 |
| 126 | 14 | 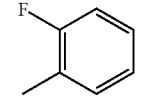 (o-F-phenyl) | FP: 400 |
| 127 | 14 | 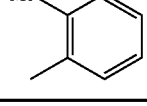 (o-Me-phenyl) | EP: 396 |
TABLE 7
| 128 | 14 | 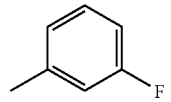 (2,3-diF-phenyl) | EP: 418 |
| 129 | 14 | 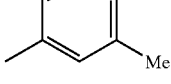 (2,4-diF-phenyl) | EP: 418 |
| 15 | 15 | 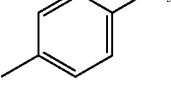 (furyl) | FP: 372 |
| 130 | 15 | 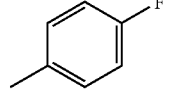 (pyridyl) | FP: 383 |
TABLE 8
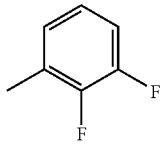
| REx | RSyn | R² | DATA |
|---|---|---|---|
| 16 | 16 | 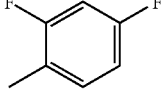 (m-CF₃-phenyl) | EP: 360 |
TABLE 8-continued
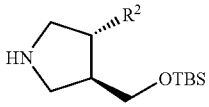
| REx | RSyn | R² | DATA |
|---|---|---|---|
| 131 | 16 | 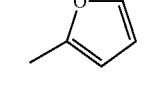 (m-F-phenyl) | EP: 310 |
| 132 | 16 | 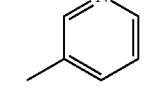 (m-Me-phenyl) | EP: 306 |
| 133 | 16 | 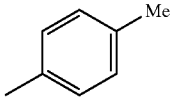 (p-CF₃-phenyl) | EP: 360 |
| 134 | 17 | 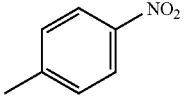 (p-F-phenyl) | EP: 310 |
| 135 | 16 | 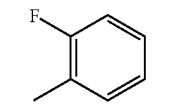 (p-Me-phenyl) | EP: 306 |
| 17 | 17 | 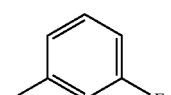 (p-NO₂-phenyl) | EP: 337 |
| 136 | 16 | 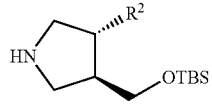 (o-F-phenyl) | EP: 310 |
| 137 | 16 | 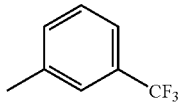 (2,3-diF-phenyl) | EP: 328 |
| 138 | 16 | 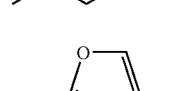 (2,4-diF-phenyl) | EP: 328 |
| 139 | 16 | 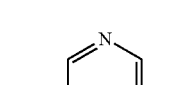 (furyl) | FP: 282 |
| 140 | 16 | (pyridyl) | FP: 293 |

TABLE 9

| REx | RSyn | R² | DATA |
|---|---|---|---|
| 141 | 2 | 3-CF₃-phenyl | FP: 456 |
| 142 | 2 | 3-F-phenyl | EP: 406 |
| 143 | 2 | 3-Me-phenyl | EP: 402 |
| 144 | 2 | 2,3-diF-phenyl | FP: 424 |

TABLE 10

| REx | RSyn | R² | DATA |
|---|---|---|---|
| 145 | 3, 4 | 3-CF₃-phenyl | EP: 595 |
| 146 | 3, 4 | 3-F-phenyl | EP: 545 |
| 147 | 3, 4 | 3-Me-phenyl | EP: 541 |
| 148 | 3, 4 | 2,3-diF-phenyl | FP: 563 |

TABLE 11

| REx | RSyn | R² | DATA |
|---|---|---|---|
| 149 | 5 | 3-CF₃-phenyl | EP: 499 |
| 150 | 5 | 3-F-phenyl | EP: 449 |
| 151 | 5 | 3-Me-phenyl | EP: 445 |
| 152 | 5 | 2,3-diF-phenyl | FP: 467 |

TABLE 12

| REx | RSyn | R¹ | DATA |
|---|---|---|---|
| 45 | 45 | 2-CO₂Me-phenyl | FP: 318 |
| 153 | 45 | 3-CO₂Me-phenyl | FP: 318 |
| 154 | 45 | 3-OMe-4-CO₂Et-phenyl | FP: 362 |
| 155 | 45 | 3,5-bis(CO₂Me)-phenyl | FP: 376 |

TABLE 12-continued
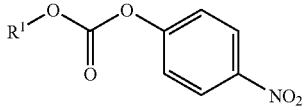
| REx | RSyn | R¹ | DATA |
|---|---|---|---|
| 156 | 45 | 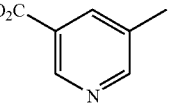 MeO₂C— (5-methylpyridin-3-yl) | EP: 319 |
TABLE 13
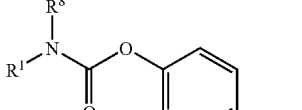
| REx | RSyn | R¹ | DATA |
|---|---|---|---|
| 46 | 46 | 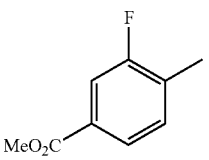 | FP: 274 |
| 157 | 46 | 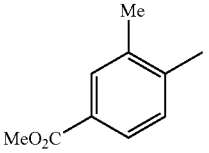 | FP: 308 |
| 158 | 46 | 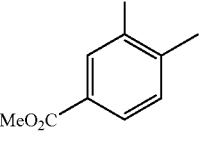 | FP: 322 |
| 159 | 46 | 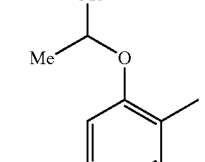 | FP: 336 |
| 160 | 46 | 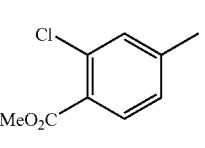 | FP: 314 |
TABLE 14
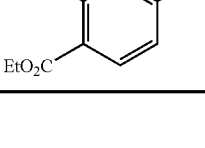
| REx | RSyn | R¹ | R⁸ | DATA |
|---|---|---|---|---|
| 48 | 48 | 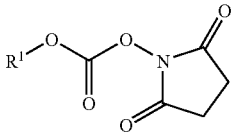 | H | FP: 351 |
TABLE 14-continued
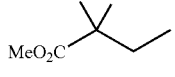
| REx | RSyn | R¹ | R⁸ | DATA |
|---|---|---|---|---|
| 161 | 48 | 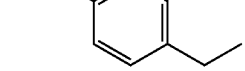 | H | FP: 335 |
| 162 | 48 | 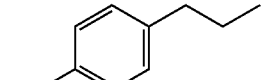 | H | FP: 331 |
| 163 | 48 | 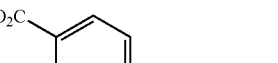 | H | FP: 347 |
| 164 | 48 | 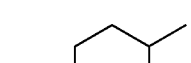 | H | EP: 375 |
| 165 | 48 | 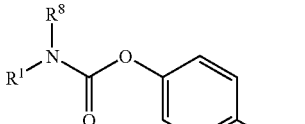 | H | EP: 351 |
| 166 | 48 | 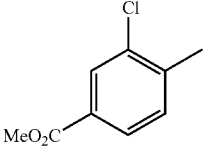 | H | EP: 349 |
TABLE 15
| 167 | 48 | 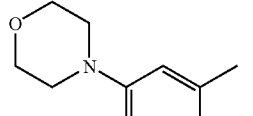 | H | EP: 416 |
|---|---|---|---|---|
| 168 | 48 | 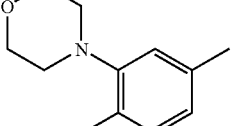 | Me | EP: 331 |
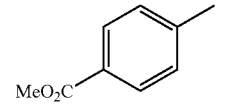

TABLE 15-continued
| 169 | 48 | 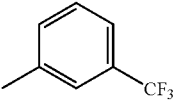 MeO₂C- | Bn | EP: 407 |
TABLE 16
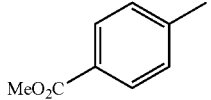
| REx | RSyn | R | R² | DATA |
|---|---|---|---|---|
| 50 | 50 | Bn | 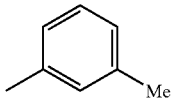 CF₃ | FP: 578 |
| 170 | 50 | Bn | 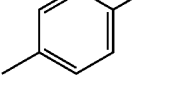 Me | EP: 524 |
| 171 | 50 | Et | 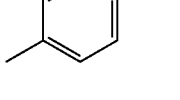 CF₃ | EP: 516 |
| 172 | 50 | Bn | 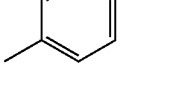 Me | EP: 524 |
| 105 | 105 | Bn | 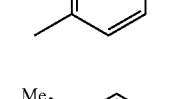 NO₂ | EP: 555 |
| 173 | 50 | Bn | 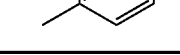 F | EP: 528 |
| 106 | 106 | Et | 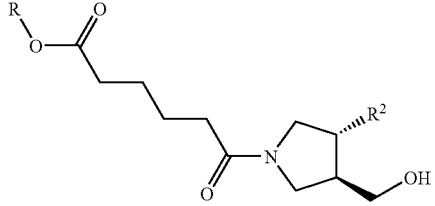 Me | EP: 462 |
TABLE 17
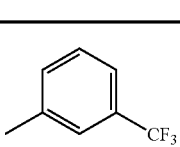
| REx | RSyn | R | R² | DATA |
|---|---|---|---|---|
| 51 | 51 | Bn | 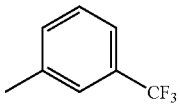 CF₃ | FP: 464 |
| 52 | 52 | Et | 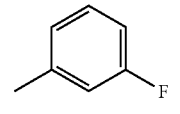 F | EP: 352 |
| 174 | 51 | Bn | 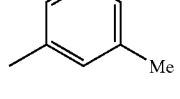 Me | EP: 410 |
| 175 | 51 | Et | 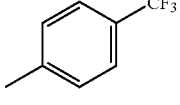 CF₃ | EP: 402 |
| 176 | 51 | Bn | 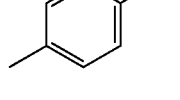 Me | EP: 410 |
| 177 | 51 | Bn | 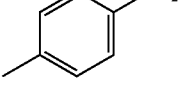 NO₂ | EP: 441 |
| 178 | 52 | Et | 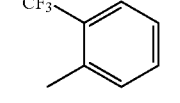 CF₃ | EP: 402 |
| 179 | 51 | Bn | 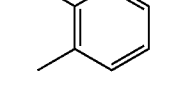 F | FP: 414 |
| 180 | 51 | Et | 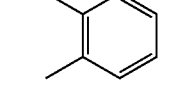 Me | EP: 348 |

TABLE 18
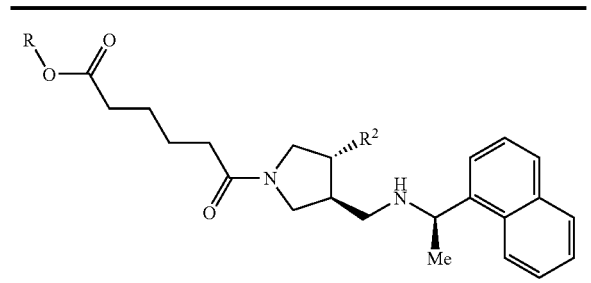
| REx | RSyn | R | R² | DATA |
|---|---|---|---|---|
| 53 | 53 | Bn | 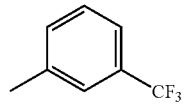 | FP: 617 |
| 181 | 53 | Et | 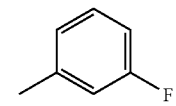 | EP: 505 |
| 182 | 53 | Bn | 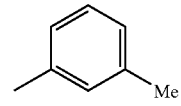 | EP: 563 |
| 183 | 53 | Et | 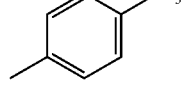 | EP: 555 |
| 184 | 53 | Bn | 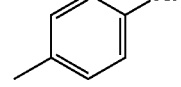 | EP: 563 |
| 185 | 53 | Bn | 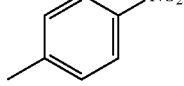 | EP: 594 |
| 186 | 53 | Et | 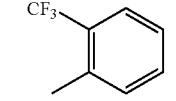 | EP: 555 |
| 187 | 53 | Bn | 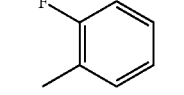 | FP: 567 |
| 188 | 53 | Et | 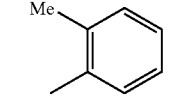 | EP: 501 |
TABLE 19
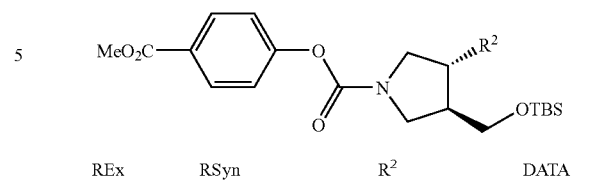
| REx | RSyn | R² | DATA |
|---|---|---|---|
| 54 | 54 | Ph | FP: 470 |
| 189 | 54 | 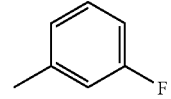 | EP: 488 |
| 55 | 55 | 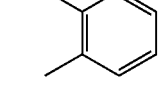 | EP: 484 |
| 190 | 54 | 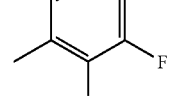 | EP: 506 |
| 191 | 54 | 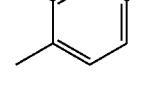 | EP: 506 |
| 56 | 56 | 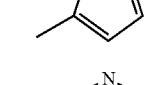 | FP: 460 |
| 57 | 57 | 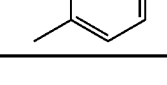 | FP: 471 |
TABLE 20
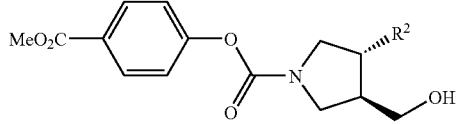
| REx | RSyn | R² | DATA |
|---|---|---|---|
| 58 | 58 | Ph | FP: 356 |
| 192 | 58 | 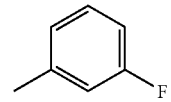 | EP: 374 |
| 59 | 59 | 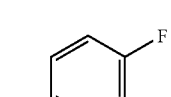 | EP: 374 |
| 60 | 60 | 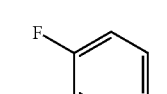 | EP: 374 |

TABLE 20-continued

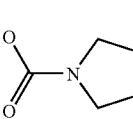

| REx | RSyn | R² | DATA |
|---|---|---|---|
| 193 | 58 | 2-Me-phenyl | EP: 370 |
| 194 | 58 | 2,3-diF-phenyl | EP: 392 |
| 195 | 58 | 2,4-diF-phenyl | EP: 392 |
| 196 | 58 | 2-furyl | FP: 346 |
| 197 | 58 | 3-pyridyl | FP: 357 |

TABLE 21

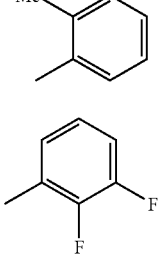

| REx | RSyn | R² | DATA |
|---|---|---|---|
| 198 | 53 | 3-F-phenyl | EP: 527 |
| 199 | 53 | 4-F-phenyl | EP: 527 |
| 200 | 53 | 2-F-phenyl | EP: 527 |
| 201 | 53 | 2-Me-phenyl | EP: 523 |

TABLE 21-continued

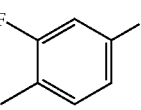

| REx | RSyn | R² | DATA |
|---|---|---|---|
| 202 | 53 | 2,3-diF-phenyl | EP: 545 |
| 203 | 53 | 2,4-diF-phenyl | EP: 545 |
| 61 | 61 | 2-furyl | FP: 499 |
| 204 | 61 | 3-pyridyl | FP: 510 |

TABLE 22

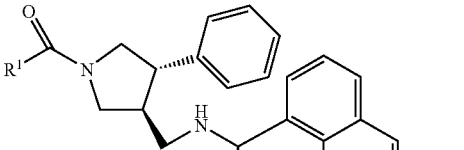

| EX | Syn | R¹ | DATA |
|---|---|---|---|
| 1 | 1 | CF₃— | FP: 427; NMR1: 1.63 (3H, d, J = 6.1), 2.76-2.99 (3H, brm), 3.10 (0.5H, dd, J = 9.8, 18.6 Hz,), 3.24-3.50 (2.0H, m), 3.56 (0.5H, t, J = 10.6 Hz), 3.90 (0.5H, dd, J = 8.2, 11.9 Hz), 4.01 (0.5H, t, J = 8.6 Hz), 4.20-4.27 (0.5H, m), 4.39-4.47 (0.5H, m), 5.26-5.38 (1H, m), 7.13-7.24 (5H, m), 7.56-7.64 (3H, m), 7.93-8.03 (3H, m), 8.15-8.20 (1H, m), 9.35-9.52 (1H, brm), 10.07 (1H, brs); Sal: HCl |
| 2 | 2 | Me | FP: 373; NMR1: 1.60-1.69 (3H, m), 1.92 (1.5H, s), 1.97 (1.5H, s), 2.70-2.85 (3H, brm), 3.05-3.16 (2H, m), 3.34-3.42 (1H, m), 3.72 (0.5H, dd, J = 7.3, 11.2 Hz), 3.81 (0.5H, dd, J = 8.3, 9.8 Hz) 4.17-4.07 (1H, brm), 5.28-5.38 (1H, brm), 7.02-7.23 (5H, m), 7.55-7.65 (3H, m), 7.92-8.05 (3H, m), 8.17-8.24 (1H, m), 9.27 (0.5H, brs), 9.56 (0.5H, brs), 10.11 (1H, brs); Sal: HCl |
| 3 | 3 | HO₂C—(CH₂)₅— | FP: 473; NMR1: 1.24-1.35 (2H, m), 1.45-1.60 (4H, m), 1.63 (1.5H, d, J = 5.2 Hz), 1.66 (1.5H, d, J = 6.4 Hz), 2.16-2.32 (4H, m), 2.70-2.86 (3H, m), 3.02-3.15 (2H, m), 3.29-3.41 (1H, m), 3.74 (0.5H, dd, J = 8.0, 12.0 Hz), 3.82 (0.5H, dd, J = 7.6, 9.6 Hz), 4.09-4.16 (1H, m), 5.26-5.40 |

TABLE 22-continued

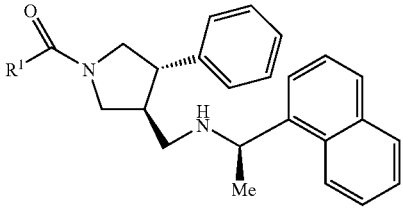

| EX | Syn | R¹ | DATA |
|---|---|---|---|
| | | | (1H, brm), 7.04-7.20 (5H, m), 7.56-7.62 (3H, m), 7.94-8.09 (3H, m), 8.19-8.22 (1H, m), 9.20-9.34 (0.5H, brm), 9.46-9.58 (0.5H, brm), 10.00-10.16 (1H, brm); Sal: HCl |

TABLE 23

| | | | |
|---|---|---|---|
| 4 | 4 | EtO₂C—(CH₂)₅— | FP: 501; NMR1: 1.16(1.5 H, t, J = 6.8 Hz), 1.18 (1.5H, t, J = 6.8 Hz), 1.24-1.31 (2H, m), 1.45-1.59 (4H, m), 1.62 (1.5H, d, J = 6.8 Hz), 1.65 (1.5H, d, J = 6.8 Hz), 2.18-2.31 (4H, m), 2.64-2.86 (3H, m), 2.99-3.16 (2H, m), 3.28-3.89 (1H, m), 3.74 (0.5H, dd, J = 8.4, 11.6 Hz), 3.82 (0.5H, dd, J = 7.6, 10.4 Hz), 4.00-4.11 (3H, m), 5.26-5.40 (1H, brm), 7.04-7.21 (5H, m), 7.56-7.62 (3H, m), 7.90-8.09 (3H, m), 8.18-8.22 (1H, m), 9.10-9.24 (0.5H, brm), 9.34-9.50 (0.5 H, bm), 9.84-10.02 (1H, bm) ; Sal: HCl |
| 5 | 5 | HO₂C—(CH₂)₄— | FP: 459 ; NMR1: 1.45-1.59 (4H, m), 1.60-1.70 (3H, m), 2.14-2.34 (4H, m), 2.66-2.87 (3H, m), 3.00-3.18 (2H, m), 3.30-3.40 (1H, m), 3.70-3.86 (1H, m), 4.04-4.18 (1H, m), 5.26-5.40 (1H, m), 7.02-7.08 (1H, m), 7.08-7.14 (1H, m), 7.14-7.24 (3H, m), 7.54-7.66 (3H, m), 7.90-8.04 (3H, m), 8.16-8.24 (1H, m), 9.14-9.28 (0.6H, m), 9.38-9.54 (0.4H, m), 9.94-10.04 (1H, m); Sal: HCl |
| 6 | 6 | EtO₂C—(CH₂)₄— | FP: 487 ; NMR1: 1.10-1.28 (4H, m), 1.43-1.70 (6H, m), 2.16-2.37 (4H, m), 2.65-2.87 (3H, m), 2.97-3.19 (2H, m), 3.68-3.87 (1H, m), 3.97-4.18 (3H, m), 5.34 (1H, m), 7.00-7.24 (5H, m), 7.52-7.67 (3H, m), 7.88-8.06 (3H, m), 8.15-8.26 (1H, m); Sal: HCl |
| 7 | 7 | HO₂C—(CH₂)₃— | FP: 445; NMR1: 1.64 (3H, app.t, J = 6.8 Hz), 1.66-1.83 (2H, m), 2.24 (2H, t, J = 7.2 Hz), 2.29 (2H, t, J = 7.2 Hz), 2.70-2.86 (3H, m), 3.00-3.16 (2H, m), 3.28-3.36 (1H, m), 3.72-3.82 (1H, m), 4.10-4.14 (1H, m), 5.33 (1H, brs), 7.03-7.20 (5H, m), 7.56-7.64 (3H, m), 7.95 (1.5H, d, J = 8.8 Hz), 7.99-8.02 (1.5H, m), 8.19-8.22 (1H, brt), 9.22-9.34 (0.5H, brm), 9.42-9.5 8 (0.5H, brm), 10.00-10.18 (1H, brm); Sal: HCl |

TABLE 24

| 8 | 8 | EtO₂C—(CH₂)₃— | FP: 473; NMR1: 1.16 (3H, app. quintet, J = 7.2 Hz), 1.63 (3H, app. t, J = 6.8 Hz), 1.71-1.82 (2H, m), 2.23-2.38 (4H, m), 2.66-2.84 (3H, m), 3.02-3.17 (2H, m), 3.72-3.82 (1H, m), 4.01-4.12 (3H, m), 5.30-5.40 (1H, brm), 7.00-7.21 (5H, m), 7.56-7.61 (3H, m), 7.90-8.02 (3H, m), 8.15-8.25 (1H, m), 9.10-9.24 (0.5H, brm), 9.34-9.48 (0.5H, brm), 9.84-10.02 (1H, brm); Sal: HCl |
|---|---|---|---|
| 9 | 9 | HO₂C—(CH₂)₂— | FP: 431; NMR1: 1.63 (1.5H, d, J = 6.4 Hz), 1.66 (1.5H, d, J = 6.4 Hz), 2.44-2.48 (2H, brm), 2.73-2.89 (3H, m), 3.32-3.64 (3H, m), 3.74 (0.5H, dd, J = 7.2, 11.2 Hz), 3.83 (0.5H, dd, J = 8.4, 9.6 Hz), 4.10-4.20 (1H, m), 5.26-5.40 (1H, brm), 7.02-7.22 (5H, m), 7.54-7.65 (3H, m), 7.95 (1.5H, d, J = 7.6 Hz), 7.98-8.04 (1.5H, m), 8.16-8.24 (1H, brt), 9.22-9.34 (0.5H, brm), 9.46-9.58 (0.5H, brm), 10.00-10.16 (1H, brm); Sal: HCl |
| 10 | 10 | H₂NOC—(CH₂)₂— | FP: 458; NMR1: 1.64 (1.5H, d, J = 6.4 Hz), 1.67 (1.5H, d, J = 6.4 Hz), 2.41-2.47 (1H, m), 2.52-2.58 (1H, m), 2.73-2.89 (6H, m), 2.98 (1.5H, s), 2.99 (1.5H, s), 3.00-3.18 (2H, m), 3.35-3.47 (1H, m), 3.73 (0.5H, dd, J = 8.0, 11.2 Hz), 3.89 (0.5H, dd, J = 7.6, 9.6 Hz), 4.09-4.40 (3H, m), 5.26-5.40 (1H, brm), 7.03-7.06 (1H, m), 7.12-7.20 (4H, m), 7.56-7.62 (3H, m), 7.94-8.08 (3H, m), 8.18-8.24 (1H, m), 9.22-9.40 (0.5H, brm), 9.50-9.68 (0.5H, brm), 10.12-10.28 (1H, brm); Sal: HCl |
| 11 | 11 | HO₂C—CH₂—NH—C(O)—CH₂CH₂— | FP: 488; NMR1: 1.62-1.66 (3H, brt), 2.33-2.45 (3H, m), 2.66-2.89 (3H, m), 2.99-3.17 (2H, m), 3.32-3.41 (1H, m), 3.65-3.90 (4H, m), 4.08-4.18 (1H, m), 5.28-5.40 (1H, brm), 7.03-7.24 (5H, m), 7.56-7.64 (3H, m), 7.92-8.02 (3H, m), 8.15-8.24 (2H, m), 9.20-9.30 (0.5H, brm), 9.38-9.47 (0.5H, brm), 9.92-10.06 (1H, brm); Sal: HCl |

TABLE 25

| | | | |
|---|---|---|---|
| 12 | 12 | HO₂C—⟨C₆H₄⟩— | FP: 479; NMR1: 1.55 (1.5H, d, J = 6.8 Hz), 1.65 (1.5H, d, J = 6.8 Hz), 2.67-2.90 (3H, m), 3.07-3.15 (1H, m), 3.36-3.46 (1H, m), 3.51 (1H, app. t, J = 10.4 Hz), 3.60 (0.5H, dd, J = 10.4, 17.6 Hz), 3.90 (0.5H, dd, J = 8.4, 12.4 Hz), 3.96-4.02 (0.5H, m), 4.20-4.25 (0.5H, m), 5.25-5.35 (1H, m), 7.09-7.20 (5H, m), 7.52 (app. t, 0.5H, J = 8.0 Hz), 7.58-7.62 (2H, m), 7.66 (2H, dd, J = 8.4, 13.6 Hz), 7.84 (0.5H, d, J = 7.2 Hz), 7.91-8.06 (4H, m), 8.14-8.23 (2H, m), 9.28 (1H, brs), 9.84-10.05 (1H, brm); Sal: HCl |
| 13 | 13 | MeO₂C—⟨C₆H₄⟩— | FP: 493; NMR1: 1.50-1.70 (3H), 2.73-3.00 (3H, m), 3.06-3.18 (1H, m), 3.36-3.64 (2H, m), 3.82-4.24 (4H, m), 4.22 (0.5H, m), 4.20-4.25 (0.5H, m), 5.25-5.39 (1H, m), 7.09-7.20 (5H, m), 7.50-7.63 (4H, m), 7.69 (1H, dd, J = 8.4, 10.8 Hz), 7.81-8.23 (6H, m), 9.19-9.26 (1H, brm), 9.77 (0.5H, brs), 9.96 (0.5H, brs); Sal: HCl |
| 92 | 7 | HO₂C—(CH₂)₆— | FP: 487; NMR1: 1.24-1.31 (4H, m), 1.47-1.65 (9H, m), 2.16-2.33 (4H, m), 2.65-2.78 (3H, m), 2.98-3.17 (2H, m), 3.72-3.85 (1H, m), 5.30-5.38 (1H, m), 7.06-7.25 (5H, m), 7.57-7.61 (3H, m), 7.88 (1H, d, J = 7.2 Hz), 7.96 (1H, d, J = 8.0 Hz), 8.01 (1H, d, J = 7.6 Hz), 8.19-8.22 (1H, m), 9.15 (1H, brs), 9.36 (0.6H, brs), 9.83 (0.4H, brs), 11.89 (1H, brs); Sal: HCl |
| 93 | 8 | MeO₂C—(CH₂)₆— | FP: 501; NMR1: 1.25-1.31 (4H, m), 1.48-1.53 (4H, m), 1.58-1.70 (3H), 2.18-2.33 (4H, m), 2.67-2.80 (3H, m), 2.99-3.17 (2H, m), 3.34-3.39 (1H, m), 3.52-3.62 (3H), 3.72-3.85 (1H, m), 4.08-4.12 (1H, m), 5.33-5.38 (1H, m), 7.06-7.21 (5H, m), 7.56-7.62 (3H, m), 7.87-8.02 (3H, m), 8.18-8.22 (1H, m), 9.04-9.96 (2H, brm); Sal: HCl |

TABLE 26

| | | | |
|---|---|---|---|
| 94 | 8 | HO-C(CF₃)₂-⟨C₆H₄⟩— | FP: 601; NMR1: 1.50-1.72 (3H), 2.73-2.89 (3H, m), 3.07-3.19 (1H, m), 3.30-3.70 (2.5H, m), 3.89 (0.5H, dd, J = 8.4, 12.4 Hz), 4.04-4.08 (0.5H, m), 4.24 (0.5H, dd, J = 7.2, 12.4 Hz), 5.28-5.36 (1H, m), 7.08-7.20 (5H, m), 7.49-8.03 (10H, m), 8.15-8.24 (1H, m), 9.31 (1H, brs), 9.82 (0.5H, brs), 10.07 (0.5H, brm); Sal: HCl |
| 95 | 8 | MeO₂C—⟨C₆H₄⟩—CH=CH— | FP: 519; NMR1: 1.62-1.67 (3H, m), 2.76-2.91 (3H, m), 3.12-3.26 (2H, m), 3.44-3.71 (1H, m), 3.82-3.94 (3H), 4.17-4.50 (2H, m), 5.35-5.40 (1H, m), 7.00-7.23 (6H, m), 7.52-7.63 (5H, m), 7.89-8.03 (5H, m), 8.20-8.23 (2H, m), 9.06-9.90 (2H, brs); Sal: HCl |
| 96 | 7 | HO₂C—⟨C₆H₄⟩—CH=CH— | FP: 505; NMR1: 1.62-1.66 (3H, m), 3.11-3.73 (6H, m), 4.17-4.27 (1.67H, m), 4.38-4.43 (0.33H, m), 5.36-5.42 (1H, m), 6.98-7.23 (6H, m), 7.52 (1H, dd, J = 7.6, 15.6 Hz), 7.58-7.63 (4H, m), 7.87-8.03 (5H, m), 8.20-8.23 (2H, m), 9.15 (0.67H, brs), 9.33 (0.33H, brs), 9.75 (1H, brs), 13.15 (1H brs); Sal: HCl |
| 97 | 7 | HO₂C—⟨N-Me-pyrrole⟩—CH=CH— | FP: 508; NMR1: 1.57-1.72 (3H), 2.73-2.89 (3H, m), 3.12-3.32 (3H, m), 3.50 (0.5H, t, J = 10.4 Hz), 3.78-3.87 (3H), 4.06 (0.5H, dd, J = 8.0, 10.4 Hz), 4.19-4.23 (0.5H, dd, J = 6.8, 12.0 Hz), 4.32 (0.5H, m), 5.32-5.37 (1H, m), 6.53-6.68 (1H, m), 7.05-7.43 (8H, m), 7.56-7.64 (3H, m), 7.90-8.03 (3H, m), 8.20-8.24 (1H, m), 9.18 (0.5H, brs), 9.42 (0.5H, brs), 9.88 (brs, 1H), 12.41 (brs, 1H); Sal: HCl |

TABLE 26-continued

| 98 | 7 | (thiophene-furan structure with HO₂C) | FP: 551; NMR1: 1.69 (3H, d, J = 6.4 Hz), 2.67-2.84 (2H, m), 3.00 (1H, dd, J = 10.8, 18.4 Hz), 3.27 (1H, t, J = 10.8 Hz), 3.57-3.63 (1H, m), 3.95-4.04 (2H, m), 4.87-4.92 (1H, m), 5.26-5.34 (1H, m), 6.90-7.24 (7H, m), 7.34-7.69 (5H, m), 7.79-8.07 (3H, m), 8.24-8.26 (1H, m) |

TABLE 27

| 99 | 8 | EtO₂C—C₆H₄—O—CH₂— (para) | FP: 537 |
| 100 | 8 | EtO₂C—C₆H₄—O—CH₂— (meta) | FP: 537; Sal: HCl |
| 101 | 7 | HO₂C—C₆H₄—O—CH₂— (para) | FP: 509; Sal: HCl |
| 102 | 7 | HO₂C—C₆H₄—O—CH₂— (meta) | FP: 509; Sal: HCl |
| 103 | 7 | HO₂C—C₆H₄—CH₂— (meta) | FP: 479; NMR1: 1.54 (1.5H, d, J = 6.5 Hz), 1.65 (1.5H, d, J = 6.5 Hz), 2.78-2.84 (2.5H, m), 3.07-3.17 (1H, m), 3.38-3.47 (1H, m), 3.53 (0.5H, t, J = 10.1 Hz), 3.59-3.67 (1.5H, m), 3.89 (0.5H, dd, J = 11.8, 8.1 Hz), 4.01-4.04 (0.5H, m), 4.22 (0.5H, dd, J = 12.3, 7.2 Hz), 5.27 (0.5H, br.s), 5.36 (0.5H, br.s), 7.10-7.20 (7H, m), 7.53 (0.5H, q, J = 8.1 Hz), 7.58-7.67 (2.5H, m), 7.78-7.83 (1.5H, m), 7.91-8.09 (3.5H, m), 8.13-8.16 (0.5H, m), 8.22 (0.5H, d, J = 7.9 Hz), 9.22 (0.5H, brs), 9.29 (0.5H, brs), 9.81 (0.5H, brs), 10.02 (0.5H, brs), 13.17 (1H, brs), 13.17 (1H, brs); Sal: HCl |
| 104 | 8 | MeO₂C—C₆H₄—CH₂— (meta) | FP: 493; NMR1: 1.24 (1.5H, d, J = 6.5 Hz), 1.33 (1.5H, d, J = 6.6 Hz), 2.17-2.33 (1.5H, m), 2.49-2.51 (1H, m), 2.64-2.67 (0.5H, m), 2.95-3.08 (1H, m), 3.28-3.63 (3H, m), 3.67-3.71 (0.5H, m), 3.76-3.80 (0.5H, m), 3.85 (1.5H, s), 3.87-3.90 (0.5H, m), 3.93 (1.5H, s), 4.02-4.07 (0.5H, m), 4.35-4.36 (0.5H, m), 4.45-4.47 (0.5H, m), 7.16-7.29 (5H, m), 7.35-7.40 (1H, m), 7.43-7.52 (2H, m), 7.56 (1H, t, J = 7.8 Hz), 7.66-7.77 (2H, m), 7.83 (1H, t, J = 7.8 Hz), 7.87-7.92 (1H, m), 8.00 (0.5H, d, J = 7.9 Hz), 8.06-8.12 (1.5H, m), 8.19-8.26 (1H, m); Sal: HCl |

TABLE 28

| 105 | 7 | HO₂C—CH₂—N(Me)C(O)—(CH₂)₄— | EP: 530; NMR1: 1.39-1.73 (8H, m), 2.11-2.43 (4H, m), 2.64-2.91 (4H, m), 2.94-3.22 (4H, m), 3.27-4.26 (4H, m), 5.23-5.46 (1H, m), 6.96-7.27 (5H, m), 7.51-7.69 (3H, m), 7.88-8.04 (3H, m), 8.14-8.27 (1H, m); Sal: HCl |

TABLE 28-continued

| | | | |
|---|---|---|---|
| 106 | 7 | HO$_2$C—CH$_2$—N(Bn)C(O)—(CH$_2$)$_4$— | EP: 606; Sal: HCl |
| 107 | 8 | [structure: ethyl 1-ethylpiperidine-4-carboxylate, EtO$_2$C-piperidine-N-Et] | FP: 528; Sal: HCl |
| 108 | 7 | [structure: 1-ethylpiperidine-4-carboxylic acid, HO$_2$C-piperidine-N-Et] | FP: 500; Sal: 2HCl |
| 109 | 9 | HO$_2$C—CH$_2$C(Me)$_2$CH$_2$— | FP: 473; NMR1: 1.05 (d, J = 3.4 Hz), 1.10 (d, J = 3.6 Hz, total 6 H), 1.61-1.65 (3H, app. t), 2.27-2.45 (4H, m), 2.69-2.79 (3H, m), 3.01-3.18 (1H, m), 3.74-3.79 (m), 3.83-3.88 (m, total 1 H), 4.10-4.15 (1H, m), 5.34 (1H, brs), 7.07-7.12 (2H, m), 7.17-7.21 (2H, m), 7.57-7.63 (3H, m), 7.88-7.90 (1H, d, J = 8.2 Hz), 8.00-8.22 (1H, m), 8.19-8.21 (1H, m), 9.19 (brs), 9.38 (brs, total 1 H), 9.87 (1H, brs), 10.03 (1H, brs); Sal: HCl |
| 110 | 7 | [structure: trans-4-carboxycyclohexyl, HO$_2$C-cyclohexyl] | FP: 485; Sal: HCl |
| 111 | 9 | [structure: 2-methylbenzoic acid linker, o-Me-C$_6$H$_4$-CO$_2$H] | FP: 479; NMR1: 1.24 (1.5H, d, J = 6.5 Hz), 1.35 (1.5H, d, J = 6.5 Hz), 2.12-2.17 (0.5H, m), 2.26-2.33 (0.5H, m), 2.43-2.54 (2H, m), 2.97-2.64 (6H, m), 3.74-3.94 (0.5H, m), 4.06-4.11 (0.5H, m), 4.38-4.40 (0.5H, m), 4.51-4.52(0.5H, m), 7.12-7.39 (7H, m), 7.44-7.53 (3H, m), 7.56-7.61 (1H, m), 7.68-7.79 (2H, m), 7.85-7.93 (1.5H, m ), 7.99 (0.5H, d, J = 7.8 Hz), 8.16 (0.5H, d, J = 8.8 Hz), 8.23-8.25 (0.5H, m) |

TABLE 29

| | | | |
|---|---|---|---|
| 112 | 7 | [structure: 2,4,5-trimethylbenzoic acid, HO$_2$C-C$_6$H$_2$(Me)$_3$] | FP: 507; NMR1: 1.25 (1.5H, d, J = 6.6 Hz), 1.35 (1.5H, d, J = 6.6 Hz), 2.11-2.16 (0.5H, m), 2.21 (1.5H, s), 2.23 (1.5H, s), 2.25-2.30 (0.5H, m), 2.42-2.62 (1H, m), 2.44 (1.5H, s), 2.54 (1.5H, s), 2.96-3.05 (1.5H, m), 3.15 (0.5H, t, J = 10.1 Hz), 3.31-3.44 (2.5H, m), 3.51 (0.5H, dd, J = 10.6, 7.5 Hz), 3.94 (0.5H, dd, J = 11.9, 8.1 Hz), 4.08 (0.5H, dd, J = 12.2, 7.9 Hz), 4.35 (0.5H, q, J = 6.4 Hz), 4.49 (0.5H, q, J = 6.5 Hz), 7.13-7.38 (7.5H, m), 7.43-7.52 (2.5H, m), 7.66-7.77 (2H, m), 7.87-7.92 (1H, m), 8.19 (0.5H, d, J = 8.6 Hz), 8.24-8.26 (0.5H, m); Sal: HCl |
| 113 | 7 | [structure: 6-methylpyridine-3-carboxylic acid, HO$_2$C-pyridyl-Me] | FP: 480; NMR1: 1.59 (1.5H, d, J = 6.8 Hz), 1.67 (1.5H, d, J = 6.7 Hz), 2.83-2.85 (2H, m), 3.11-3.18 (1H, m), 3.39-4.01 (5H, m), 4.20-4.23 (0.5H, m), 4.31-4.36 (0.5H, m), 5.27-5.38 (1H, m), 7.06-7.20 (5H, m), 7.51-7.65 (3H, m), 7.87-8.03 (4H, m), 8.15-8.17 (0.5H, m), 8.22-8.24 (0.5H, m), 8.36-8.38 (0.5H, m), 8.42-8.45 (0.5H, m), 9.01 (0.5H, m), 9.13 (0.5H, m), 9.33 (0.5H, brs), 9.45 (0.5H, brs), 10.02 (0.5H, brs) 10.17 (0.5H, brs); Sal: HCl |
| 114 | 7 | HO$_2$C—C(Me)$_2$—(CH$_2$)$_3$—C(Me)$_2$— | FP: 529; NMR1: 1.06 (6H, s), 1.13-1.15 (6H, m), 1.39-1.50 (4H, m), 1.63 (3H, d, J = 6.5 Hz), 2.47-2.80 (5H, m), 3.17-3.47 (5H, m), 5.35-5.36 (1H, m), 7.11-7.22 (5H, m), 7.57-7.64 (3H, m), 7.90 (1H, brs), 7.96 (1H, d, J = 8.2 Hz), 8.00-8.03 (1H, m), 8.18-8.20 (1H, m), 9.24 (1H, brs), 9.76 (1H, brs), 12.03 (1H, brs); Sal: HCl |

TABLE 29-continued

| | | | |
|---|---|---|---|
| 115 | 7 | HO$_2$C—C(Me)$_2$—(CH$_2$)$_3$— | FP: 487; NMR1: 1.07 (3H, s), 1.10 (3H, s), 1.43-1.48 (3H, m), 1.62-1.67 (4H, m), 2.19-2.25 (2H, m), 2.79 (3H, brm), 3.04-3.16 (2H, m), 3.71-3.82 (1H, m), 4.08-4.13 (1H, m), 5.33 (1H, brs), 7.05-7.20 (6H, m), 7.56-7.63 (3H, m), 7.93-8.02 (3H, m), 8.18-8.22 (1H, m), 9.24 (0.5H, brs), 9.52 (0.5H, brs), 10.04 (1H, brs), 12.04 (1H, brs); Sal: HCl |

TABLE 30

| | | | |
|---|---|---|---|
| 116 | 9 | HO$_2$C—C(Me)$_2$—(CH$_2$)$_2$— | FP: 473; NMR1: 1.07 (3H, s), 1.13 (3H, s), 1.61-1.77 (5H, m), 2.13-2.27 (2H, m), 2.78 (2H, m), 2.98-3.15 (2H, m), 3.27-3.60 (2H, m), 3.67-3.84 (1H, m), 4.09-4.13 (1H, m), 5.33 (1H, brs), 7.02-7.04 (1H, m), 7.11-7.21 (4H, m), 7.55-7.64 (3H, m), 7.91-8.02 (3H, m), 8.18-8.22 (1H, m), 9.21 (0.5H, brs), 9.43 (0.5H, brs), 9.95 (1H, brs), 12.13 (1H, brs); Sal: HCl |
| 117 | 9 | HO$_2$C—C(Me)$_2$CH$_2$— | FP: 459; NMR1: 1.03 (3H, s), 1.04 (3H, s), 1.61-1.65 (3H, m), 2.43-2.59 (1H, m), 2.67-2.92 (3H, m), 2.99-3.16 (2H, m), 3.28-3.39 (1H, m), 3.56-3.65 (1H, m), 3.71-3.76 (0.5H, m), 3.81-3.85 (0.5H, m), 4.08-4.12 (1H, m), 5.34 (1H, brs), 7.04-7.06 (1H, m), 7.10-7.14 (1H, m), 7.16-7.20 (3H, m), 7.57-7.65 (3H, m), 7.90 (1H, d, J = 7.2 Hz), 7.96 (1H, d, J = 7.7 Hz), 8.00-8.05 (1H, m), 8.16-8.22 (1H, m), 9.21 (0.5H, brs), 9.39 (0.5H, brs), 9.90 (1H, brs), 11.88 (1H, brs); Sal: HCl |
| 118 | 8 | biphenyl-CO$_2$Me (2-position) | FP: 569; NMR 1: 1.56 (1.5H, d, J = 6.5 Hz), 1.65 (1.5H, d, J = 6.5 Hz), 2.73-2.89 (2H, m), 3.11-3.23 (1H, m), 3.28-3.70 (6.5H, m), 3.87-3.92 (0.5H, m), 4.12-4.14 (0.5H, m), 4.20-4.23 (0.5H, m), 5.31 (0.5H, brs), 5.38 (0.5H, brs), 7.11-7.21 (5H, m), 7.32 (1H, d, J = 8.1 Hz), 7.41-7.69 (10H, m), 7.75-7.83 (1H, m), 7.93-8.04 (2H, m), 8.15-8.17 (0.5H, m), 8.23 (0.5H, d, J = 8.0 Hz), 9.24 (1H, brs), 9.75 (0.5H, brs), 9.91 (0.5H, brs); Sal: HCl |

TABLE 31

| | | | |
|---|---|---|---|
| 119 | 7 | biphenyl-CO$_2$H (2-position) | FP: 555; NMR1: 1.57 (1.5H, d, J = 6.4 Hz), 1.67 (1.5H, d, J = 6.4 Hz), 2.85-2.92 (3H, m), 3.09-3.18 (1H, m), 3.35-3.61 (2H, m), 3.66-3.70 (0.5H, m), 3.86-3.91 (0.5H, m), 4.12-4.13 (0.5H, m), 4.21-4.26 (0.5H, m), 5.30 (0.5H, brs), 5.37 (0.5H, brs), 7.11-7.27 (6H, m), 7.34-7.69 (10H, m), 7.73-7.80 (1H, m), 7.87-8.03 (3H, m), 8.16-8.18 (0.5H, m), 8.23 (0.5H, d, J = 7.8 Hz), 9.34 (0.5H, brs), 9.89 (0.5H, brs), 10.10 (0.5H, brs), 12.81 (0.5H, brs); Sal: HCl |
| 120 | 8 | biphenyl-CO$_2$Et (3-position) | FP: 583; NMR1: 1.31-1.37 (3H, m), 1.54 (1.5H, d, J = 6.2 Hz), 1.65 (1.5H, d, J = 6.0 Hz), 2.73-2.87 (3H, m), 3.12-3.74 (3.5H, m), 3.88-3.93 (0.5H, m), 4.08 (0.5H, m), 4.21-4.23 (0.5H, m), 4.32-4.40 (2H, m), 5.29 (0.5H, brs), 5.40 (0.5H, brs), 7.11-7.21 (5H, m), 7.52-8.02 (13H, m), 8.14-8.23 (2H, m), 9.08 (0.5H, brs), 9.19 (0.5H, brs), 9.59 (0.5H, brs), 9.80 (0.5H, brs); Sal: HCl |

TABLE 31-continued

| 121 | 7 | 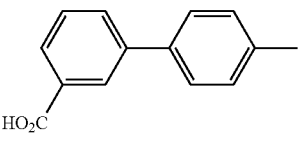 | FP: 555; NMR1: 1.54 (1.5H, d, J = 6.5 Hz), 1.65 (1.5H, d, J = 6.5 Hz), 2.73-2.86 (3H, m), 3.12-3.75 (3.5H, m), 3.88-3.92 (0.5H, m), 4.06-4.10 (0.5H, m), 4.21-4.22 (0.5H, m), 5.29 (0.5H, brs), 5.39 (0.5H, brs), 7.10-7.21 (5H, m), 7.52-7.78 (7H, m), 7.84 (1H, d, J = 8.2 Hz), 7.89-8.04 (5H, m), 8.14-8.23 (2H, m), 9.08 (0.5H, brs), 9.19 (0.5H, brs), 9.60 (0.5H, brs), 9.79 (0.5H, brs), 13.10 (1H, brs); Sal: HCl |
| 122 | 7 | 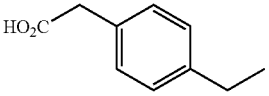 | FP: 507 |
| 123 | 8 | 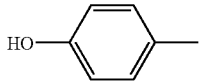 | FP: 451; NMR1: 1.52-1.61 (3H, m), 2.33-4.12 (9H, m), 5.30-5.41 (1H, m), 6.72-7.84 (2H, m), 7.09-7.20 (5H, m), 7.42-7.93 (6H, m), 7.97-8.21 (3H, m), 8.85-8.98 (1H, m), 9.88-9.99 (1H, m); Sal: HCl |
| 124 | 10 | EtO$_2$C—CH$_2$—NHC(O)—(CH$_2$)$_4$— | FP: 544; Sal: HCl |

TABLE 32

| 125 | 11 | 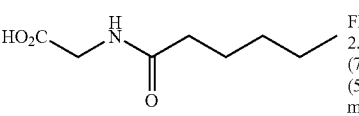 | FP: 516; NMR1: 1.43-1.69 (9H, m), 2.06-2.46 (2H, m), 2.73-2.85 (2H, m), 2.80-4.00 (7H, m), 4.11 (1H, m), 5.34 (1H, m), 7.00-7.24 (5H, m), 7.54-7.67 (3H, m), 7.84-8.26 (4H, m); Sal: 1.5 HCl |
| 126 | 11 | 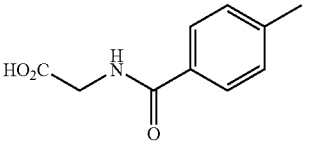 | FP: 536; NMR1: 1.55 (1.5H, d, J = 6.4 Hz), 1.66 (1.5 Hz, d, J = 6.4 Hz), 2.66-2.97 (3H, m), 3.03-3.20 (1H, m), 3.36-4.07 (4H, m), 4.16-4.28 (0.5H, m), 4.28-4.45 (0.5H, m), 5.27 (0.5H, m), 5.36 (0.5H, m), 7.02-7.26 (5H, m), 7.48-7.71 (5H, m), 7.81-8.07 (5H, m), 8.10-8.19 (0.5H, m), 8.19-8.27 (0.5H, m), 8.86-8.96 (0.5H, m), 8.96-9.08 (0.5H, m); Sal: HCl |
| 14 | 14 | 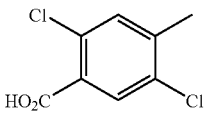 | FP: 547; NMR1: 1.44 (3H, d, J = 6.3 Hz), 2.46-2.67 (2H, m), 3.03-3.12 (1H, m), 3.20-3.44 (5.3H, m), 3.75-3.79 (0.7H, m), 3.93 (0.7H, dd, J = 11.9, 8.3 Hz), 4.12 (0.3H, dd, J = 12.2, 7.7 Hz), 4.78 (0.3H, br.s), 4.88 (0.7H, br.s), 7.12-7.27 (5H, m), 7.43-7.55 (4H, m), 7.65-7.73 (2H, m), 7.83 (1H, d, J = 8.2 Hz), 7.93-7.95 (1H, m), 8.18 (0.7H, d, J = 8.3 Hz), 8.24 (0.3H, d, J = 9.1 Hz), Sal: HCl |
| 15 | 15 | 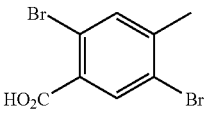 | FP: 637; NMR1: 1.55 (1.5H, d, J = 6.6 Hz), 1.65 (1.5H, d, J = 6.6 Hz), 2.81-2.85 (3H, m), 3.13-3.71 (6H, m), 3.95 (0.5H, dd, J = 11.9, 8.1 Hz), 4.24-4.29 (0.5H, m), 5.24-5.26 (0.5H, m), 5.34-5.36 (0.5H, m), 7.11-7.26 (5H, m), 7.52 (0.5H, t, J = 7.8 Hz), 7.58-7.63 (2.5H, m), 7.77-7.83 (1.5H, m), 7.93-8.04 (3.5H, m), 8.12-8.14 (0.5H, m ), 8.20-8.24 (0.5H, m); Sal: HCl |
| 16 | 16 | 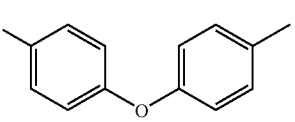 | FP: 571; NMR1: 1.58 (1.5H, d, J = 6.2 hz), 1.65 (1.5H, d, J = 6.2 Hz), 2.80-2.84 (3H, brm), 3.09-3.74 (4.5H, m), 3.84-3.89 (0.5H, m), 4.10 (0.5H, m), 4.17-4.20 (0.5H, m), 5.29 (0.5H, brs), 5.37 (0.5H, brs), 7.07-7.19 (9H, m), 7.52-7.72 (5H, m), 7.85-8.01 (5H, m), 8.15-8.23 (1H, m), 9.26 (1H, brs), 9.79 (0.5H, brs), 9.94 (0.5H, brs); Sal: HCl |

TABLE 33

| | | Structure | Data |
|---|---|---|---|
| 17 | 17 | 3-(4-substituted-phenoxy)benzoic acid (HO2C-C6H4-O-C6H4-) | FP: 571; NMR1: 1.30 (1.5H, d, J = 6.5 Hz), 1.37 (1.5H, d, J = 6.4 Hz), 2.26-2.34 (0.5H, m), 2.46-2.51 (1H, m), 2.64 (0.5H, m), 2.97-3.89 (7.5H, m), 4.00-4.05 (0.5H, m), 4.49 (0.5H, m), 4.56 (0.5H, m), 7.03 (1H, d, J = 8.6 Hz), 7.09-7.32 (7H, m), 7.39-7.79 (10H, m), 7.88-7.93 (1H, m), 8.23 (1H, m) |
| 18 | 18 | EtO2C-(1-propylpiperidin-4-yl) | FP: 542; NMR1: 1.17-1.24 (3H, m), 1.49-1.79 (6H, m), 2.54-3.46 (16H, m), 3.77 (0.4H, dd, J = 8.0, 11.2 Hz), 3.86 (0.6H, brt), 4.01-4.19 (3H, m), 5.22-5.40 (1H, brm), 7.03-7.26 (5H, m), 7.56-7.64 (3H, m), 7.92-8.10 (3H, m), 8.18-9.22 (1H, brt), 9.30-9.42 (0.6H, brs), 9.60-9.72 (0.4H, brs), 10.14-10.30 (1H, nrs), 10.58-10.82 (1H, brm); Sal: 2 HCl |
| 19 | 19 | HO2C-(1-propylpiperidin-4-yl) | FP: 514; NMR1: 1.62-1.68 (3H, m), 1.81-2.06 (4H, m), 2.73-3.88 (16H, m), 4.15-4.19 (1H, m), 5.24-5.38 (1H, brm), 7.06-7.22 (5H, m), 7.56-7.62 (3H, m), 7.94-8.22 (4H, m), 9.32-9.48 (0.6H, brm), 9.62-9.78 (0.4J, brm), 10.20-10.40 (1H, brm), 10.60-10.85 (1H, brm), 12.53 (0.6H, brs); Sal: 2 HCl |
| 127 | 18 | 1-propylpiperidine | FP: 470; NMR1: 1.36-1.45 (1H, m), 1.64-1.79 (9H, m), 2.73-2.93 (6H, m), 3.06-3.45 (5H, m), 3.57-3.66 (2H, m), 3.77 (0.4H, dd, J = 7.6, 11.2 Hz), 3.84-3.88 (0.6H, m), 4.18 (1H, dd, J = 6.4, 11.2 Hz), 5.24-5.38 (1H, m), 7.03-7.22 (5H, m), 7.52-7.64 (3H, m), 7.90-8.22 (4H, m), 9.32-9.48 (0.6H, brm), 9.62-9.76 (0.4H, brm), 10.20-10.60 (2H, brm); Sal: 2 HCl |
| 128 | 18 | 4-propylmorpholine | FP: 472; NMR1: 1.64 (d, J = 6.8 Hz), 1.67 (d, J = 6.8 Hz, total 3H), 2.67-3.22 (7H, m), 3.26-3.44 (8H, m), 3.75-4.02 (4H, m), 4.15-4.19 (1H, m), 5.26-5.38 (1H, m), 5.26-5.38 (1H, m), 7.07-7.22 (5H, m), 7.52-7.64 (3H, m), 7.90-8.26 (4H, m), 9.30-9.42 (0.6H, brm), 9.60-9.76 (0.4H, brm), 10.16-10.30 (1H, brm), 11.06-11.28 (1H, brm); Sal: 2 HCl |

TABLE 34

| | | Structure | Data |
|---|---|---|---|
| 20 | 20 | 1-methylpiperidine-4-carboxylic acid | FP: 486; Sal: HCl |
| 21 | 21 | 5-(4-substituted-phenyl)-1H-tetrazole | FP: 503; NMR1: 1.54 (1.5H, d, J = 6.6 Hz), 1.65 (1.5H, d, J = 6.7 Hz), 2.75-2.86 (3H, m), 3.14-3.73 (5.5H, m), 3.89-3.94 (0.5H, m), 4.05-4.07 (0.5H, m), 4.21-4.24 (0.5H, m), 5.28-5.29 (0.5H, m), 5.37-5.39 (0.5H, m), 7.10-7.20 (5H, m), 7.51-7.66 (3H, m), 7.75-7.86 (2.5H, m), 7.92-8.24 (5.5H, m), 9.21 (1H, brs); Sal: HCl |
| 22 | 22 | benzenesulfonamide (H2N-SO2-C6H5) | FP: 514 |
| 23 | 23 | 3-(4-substituted-phenyl)-1,2,4-oxadiazol-5(4H)-one | FP: 519; Sal: HCl |

TABLE 34-continued

| | | | |
|---|---|---|---|
| 24 | 24 | [HO₂C-CH₂-O-C₆H₄-CH₃ structure] | EP: 509; NMR1: 1.55 (1.5H, d, J = 6.4 Hz), 1.64 (1.5H, d, J = 5.9 Hz), 2.67-2.84 (3H, m), 3.10-3.17 (1H, m), 3.55-3.71 (2.5H, m), 3.80-3.85 (0.5H, m), 4.08-4.16 (1H, m), 4.70 (1H, s), 4.77 (1H, s), 5.30 (0.5H, brs), 5.37 (0.5H, brs), 6.91 (1H, d, J = 8.4 Hz), 7.00 (1H, d, J = 8.4 Hz), 7.09-7.18 (5H, m), 7.51-7.61 (5H, m), 7.80 (0.5H, d, J = 7.0 Hz), 7.90-8.01 (2.5H, m), 8.16-8.23 (1H, m), 9.19 (1H, brs), 9.65 (0.5H, brs), 9.85 (0.5H, brs), 13.08 (1H, brs); Sal: HCl |
| 25 | 25 | [HO₂C-C₆H₄-CH₂CH₃ structure] | EP: 493; Sal: HCl |
| 26 | 26 | [MeSO₂-NH-CO-C₆H₄-CH₃ structure] | EP: 556 |

TABLE 35

[Structure: R¹-X-N-pyrrolidine-phenyl with CH₂-NH-CH(Me)-naphthyl substituent]

| EX | Syn | R¹—X— | DATA |
|---|---|---|---|
| 91 | 91 | H | EP: 331; Sal: 2HCl |
| 27 | 27 | [HO₂C-C₆H₄-SO₂- structure] | FP: 515; NMR1: 1.58 (2.5H, d, J = 6.4 Hz), 1.62 (0.5H, d, J = 6.4 Hz), 2.65-2.85 (2H, m), 2.95-3.11 (3H, m), 3.54-3.66 (1H, m), 3.86-4.00 (1H, m), 4.20-4.25 (0.5H, m), 5.20-5.26 (1H, m), 6.84-6.93 (2H, m), 7.07-7.26 (4H, m), 7.53-7.60 (3H, m), 7.89-8.13 (5H, m), 7.96 (2H, d, J = 7.6), 8.18 (2H, d, J = 8.0 Hz), 9.64 (1H, brs); Sal: HCl |

TABLE 36

[Structure: R¹-N-pyrrolidine-phenyl with CH₂-NH-CH(Me)-naphthyl substituent]

| EX | Syn | R¹ | DATA |
|---|---|---|---|
| 28 | 28 | HO₂C—(CH₂)₅— | FP: 445; NMR1: 1.32-1.38 (2H, m), 1.49-1.56 (2H, m), 1.63-1.70 (6H, m), 2.24 (2H, t, J = 7.6 Hz), 2.85-3.76 (8.5H, m), 4.15-4.23 (0.5H, m), 5.28-5.34 (1H, m), 7.15- |

TABLE 36-continued

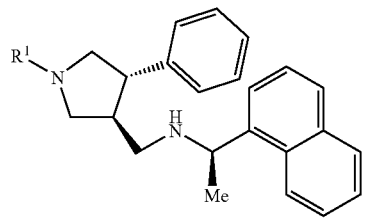

| EX | Syn | R¹ | DATA |
|---|---|---|---|
| | | | 7.28 (5H, m), 7.57-7.61 (3H, m), 7.95-8.02 (3H, m), 8.17 (1H, d, J = 8.8 Hz), 9.65 (1H, brs), 9.96-10.06 (1H, brm), 11.13 (0.5H, brs), 11.65 (0.5H, brs), 11.98 (1H, brs); Sal: 2 HCl |
| 29 | 29 | HO₂C-cyclohexyl- | FP: 457; NMR1: 1.29-1.65 (6H, m), 1.83-2.33 (5H, m), 2.67-3.48 (8H, m), 3.53-3.77 (1.5H, m), 4.20-4.32 (0.5H, brm), 5.22-5.38 (1H, brm), 7.14-7.29 (5H, m), 7.56-7.62 (3H, m), 7.94-8.18 (4H, m), 9.72-10.32 (2H, brm), 11.40-11.60 (0.5H, brm), 11.90-12.40 (1H, brm); Sal: 2 HCl |
| 30 | 30 | 4-(HO₂C)C₆H₄CH₂- | FP: 465; NMR3: 1.69 (3H, d, J = 6.8 Hz), 2.86-3.04 (3H, m), 3.09-3.18 (2H, m), 3.25-3.31 (1H, m), 3.48-3.60 (1H, m), 3.67 (1H, dd, J = 7.6, 11.2 Hz), 4.33 (2H, s), 5.29 (1H, q, J = 6.8 Hz), 7.18-7.25 (5H, m), 7.50-7.69 (6H, m), 7.88-7.96 (2H, m), 8.05-8.10 (3H, m); Sal: HCl |
| 129 | 2 | 4-NC-C₆H₄-CH₂- | FP: 432; Sal: HCl |
| 130 | 21 | 4-(1H-tetrazol-5-yl)C₆H₄- | FP: 475; NMR 1: 1.68 (3H, d, J = 6.7 Hz), 2.89-2.95 (3H, m), 3.22-3.34 (3H, m), 3.73 (1H, t, J = 6.8 Hz), 4.02-4.04 (1H, m), 5.35-5.45 (1H, m), 6.69 (2H, d, J = 9.0 Hz), 7.13-7.15 (2H, m), 7.20-7.22 (3H, m), 7.59-7.64 (3H, m), 7.90 (2H, d, J = 8.9 Hz), 7.98 (1H, d, J = 8.3 Hz), 8.01-8.04 (2H, m), 8.26-8.24 (1H, m), 9.42-9.56 (1H, brm), 9.98-10.10 (1H, brm); Sal: HCl |

TABLE 37

| 31 | 31 | 3,5-difluoro-4-methyl-HO₂C-phenyl | FP: 487; NMR1: 1.64 (3H, d, J = 6.6 Hz), 2.57-2.87 (3H, m), 3.13 (1H, m), 3.57-3.69 (2H, m), 3.82-3.86 (1H, m), 4.10-4.17 (1H, m), 5.36 (1H, brs), 7.11-7.14 (2H, m), 7.18-7.25 (3H, m), 7.38-7.50 (2H, m), 7.57-7.65 (3H, m), 7.93-7.97 (2H, m), 8.01-8.03 (1H, m), 8.21-8.23 (1H, m), 9.33 (1H, brs), 9.92 (1H, brs), 12.93 (1H, brs); Sal: HCl |
|---|---|---|---|
| 131 | 31 | 3-CF₃-4-methyl-HO₂C-phenyl | FP: 519; Sal: HCl |
| 132 | 31 | 3-NO₂-4-methyl-HO₂C-phenyl | FP: 496; Sal: HCl |
| 133 | 31 | 4-(HO₂C)-biphenyl | FP: 451; NMR1: 1.65 (3H, d, J = 6.4 Hz), 2.80-3.00 (3H, m), 3.22-3.32 (3H, m), 3.73 (1H, brt), 3.95-4.05 (1H, m), 5.45-5.50 (1H, m), 6.56 (2H, d, J = 8.8 Hz), 7.12-7.25 (5H, m), 7.58-7.64 (3H, m), 7.79-7.98 (2H, m), 8.02 (1H, d, J = 2.4 Hz), 8.23 (1H, d, J = 1.2 Hz), 9.25-9.50 (1H, brm), 9.80-10.00 (1H, brm), 12.10 (1H, brs); Sal: HCl |
| 134 | 31 | 6-methyl-5-(HO₂C)pyridin-2-yl | EP: 452; Sal: 2 HCl |

TABLE 38

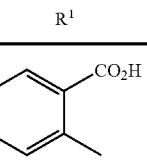

| EX | Syn | R¹ | DATA |
|---|---|---|---|
| 32 | 32 | 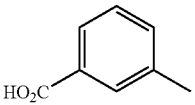 | FP: 495; NMR 1: 1.35-1.37 (3H, app. t), 2.32-2.56 (3H, m), 3.02-4.14 (5H, m), 4.58 (1H, brs), 6.58-6.63 (1H, m), 7.12-7.28 (7H, m), 7.31-7.36 (1H, brq), 7.46-7.51 (3H, m), 7.56-7.63 (1H, brq), 7.66-7.70 (1H, brt), 7.78 (1H, d, J = 8.1 Hz), 7.87-7.93 (2H, m), 8.22-8.24 (1H, m) |
| 135 | 32 | 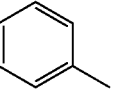 | FP: 495; NMR 1: 1.33 (3H, d, J = 6.5 Hz), 2.26-2.36 (1H, m), 2.51-2.70 (1H, m), 3.04-3.12 (1H, m), 3.49-3.54 (0.5H, m), 3.74-3.79 (0.5H, m), 3.94 (0.5H, dd, J = 8.2, 18.7 Hz), 4.10 (0.5H, dd, J = 7.9, 10.7 Hz), 4.48 (1H, q, J = 6.6 Hz), 7.20-7.26 (5H, m), 7.37-7.56 (5H, m), 7.65 (1H, d, J = 6.9 Hz), 7.68-7.71 (1H, brd), 7.75-7.82 (2H, m), 7.90-7.91 (1H, m), 8.24-8.26 (1H, m) |
| 33 | 33 | 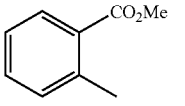 | FP: 495; NMR 1: 1.65 (3H, d, J = 6.5 Hz), 2.72-3.00 (3H, m), 3.10-3.48 (2H, m), 3.48-3.55 (1H, m), 3.77 (0.5H, dd, J = 8.0, 10.5 Hz), 3.95 (0.5H, dd, J = 8.0, 10.5 Hz), 4.14 (0.5H, dd, J = 6.5, 11.5 Hz), 4.30 (0.5H, dd, J = 7.0, 11.0 Hz), 5.25-5.44 (1H, m), 7.10-7.18 (2H, m), 7.17-7.25 (3H, m), 7.28 (2H, t, J = 8.5 Hz), 7.53-7.67 (3H, m), 7.90-8.07 (5H, m), 8.17-8.27 (1H, m), 9.40 (1H, brs), 10.12 (1H, brs), 12.97 (1H, brs); Sal: HCl |
| 34 | 34 | 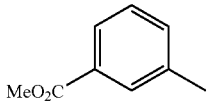 | FP: 509; Sal: HCl |
| 136 | 34 | 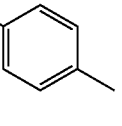 | FP: 509; Sal: HCl |

TABLE 39

| 35 | 35 | 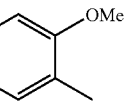 | FP: 509; NMR1: 1.64 (3H, d, J = 6 Hz), 2.76-2.92 (3H, m), 3.10-3.52 (3H, m), 3.77 (0.5H, dd, J = 8 Hz, 11 Hz), 3.86 (3H, d, J = 4 Hz), 3.95 (0.5H, dd, J = 8 Hz, 11 Hz), 4.13 (0.5H, dd, J = 6 Hz, 11 Hz), 4.29 (0.5H, dd, J = 6 Hz, 11 Hz), 5.31-5.41 (1H, m), 7.09-7.25 (5H, m), 7.26-7.36 (2H, m), 7.54-7.66 (3H, m), 7.90-8.05 (5H, m), 8.22 (1H, d, J = 7 Hz), 9.22-9.41 (1H, br), 9.97 (1H, br.s); Sal: HCl |
| 36 | 36 | 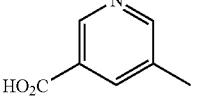 | EP: 525; Sal: HCl |
| 137 | 36 |  | FP: 496; Sal: 2 HCl |

TABLE 39-continued

| | | | |
|---|---|---|---|
| 37 | 37 | 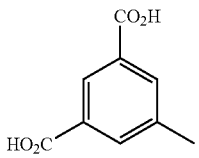 3,5-bis(CO2H)-phenyl-methyl | EP: 539; NMR1: 1.62-1.63 (3H, brm), 2.85 (3H, brs), 3.15-3.56 (4H, m), 3.76-3.81 (0.5H, m), 3.96-4.01 (0.5H, m), 4.10-4.15 (0.5H, m), 4.26-4.31 (0.5H, m), 5.37 (1H, brs), 7.14-7.23 (5H, m), 7.58-7.66 (3H, m), 7.88 (1H, d, J = 6.5 Hz), 7.91-7.93 (2H, m), 7.97 (1H, d, J = 8.2 Hz), 8.02 (1H, d, J = 8.2 Hz), 8.22 (1H, d, J = 8.2 Hz), 8.33 (1H, d, J = 8.3 Hz), 9.19 (1H, brs), 9.77 (1H, brs), 13.47 (1H, brs); Sal: HCl |
| 38 | 38 | HO$_2$C—C(Me)$_2$CH$_2$— | FP: 475; NMR1: 1.09(3H, s), 1.18 (3H, s), 1.62 (3H, d, J = 6.3 Hz), 2.78 (3H, brs), 3.05-3.23 (3H, m), 3.57-3.69 (1H, m), 3.97-4.05 (3H, m), 5.33 (1H, brs), 7.10 (2H, brm), 7.18 (3H, brm), 7.57-7.63 (3H, m), 7.91 (1H, d, J = 7.1 Hz), 7.95 (1H, d, J = 8.2 Hz), 8.00-8.02 (1H, m), 8.19 (1H, brm), 9.23-9.30 (1H, brm), 9.89 (1H, brs), 12.34 (1H, brs); Sal: HCl |
| 138 | 38 | 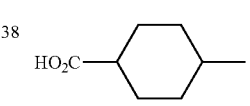 HO2C-cyclohexyl | FP: 501; NMR1: 1.34-1.47 (2H, m), 1.60-1.78 (6H, m), 1.92-1.95 (2H, m), 2.25-2.37 (1H, m), 2.78 (3H, brs), 3.06-3.25 (3H, m), 3.56-3.72 (2H, m), 4.01 (1H, brm), 4.48-4.50 (0.5H, m), 4.74 (0.5H, brs), 5.34 (1H, brs), 7.10-7.19 (5H, m), 7.57-7.64 (3H, m), 7.89 (1H, d, J = 6.9 Hz), 7.96 (1H, d, J = 8.2 Hz), 8.00-8.02 (1H, m), 8.19-8.21 (1H, brm), 9.18 (1H, brm), 9.81 (1H, brs), 12.07 (1H, brs); Sal: HCl |

TABLE 40

| | | | |
|---|---|---|---|
| 139 | 38 | 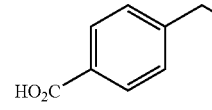 4-(HO2C)phenyl-propyl | FP: 537; NMR1: 1.62 (3H, d, J = 5.8 Hz), 1.86-1.95 (2H, m), 2.68-2.77 (5H, m), 3.03-3.21 (3H, m), 3.62-3.71 (1H, m), 4.00-4.04 (3H, m), 5.33 (1H, brs), 7.07-7.10 (2H, m), 7.18-7.19 (3H, m), 7.31 (1H, d, J = 8.1 Hz), 7.38 (1H, d, J = 8.0 Hz), 7.55-7.63 (3H, m), 7.83-8.02 (5H, m), 8.19-8.21 (1H, m), 9.22-9.31 (1H, brm), 9.89 (1H, brs), 12.75 (1H, brs); Sal: HCl |
| 39 | 39 | 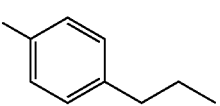 4-(HO2C)phenyl-propyl | EP: 523; Sal: HCl |
| 140 | 39 | 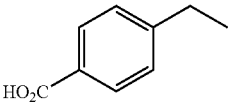 4-(HO2C)phenyl-ethyl | EP: 509; Sal: HCl |
| 40 | 40 | HO$_2$C—CH$_2$— | FP: 433 |

TABLE 41

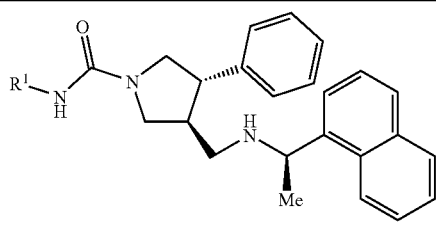

| EX | Syn | R$^1$ | DATA |
|---|---|---|---|
| 41 | 41 | 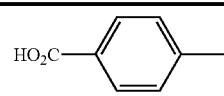 | FP: 494; NMR1: 1.66 (3H, d, J = 6.6 Hz), 2.83 (3H, brs), 3.19-3.30 (2H, m), 3.37-3.42 (1H, brt), 3.84-3.89 (1H, brt), 4.14-4.17 (1H, m), 5.35 (1H, brs), 7.14-7.16 (2H, m), 7.18-7.25 (3H, m), 7.58-7.71 (5H, m), 7.81-7.85 (2H, m), 7.95-8.03 (3H, m), 8.21-8.22 (1H, m), 8.56 (1H, s), 9.35 (1H, brs), 10.12 (1H, brs), 12.52 (1H, brs); Sal: HCl |

TABLE 41-continued

| EX | Syn | R¹ | DATA |
|---|---|---|---|
| 141 | 41 | 3-HO₂C-C₆H₄- | FP: 494; NMR1: 1.64 (3H, d, J = 6.6 Hz), 2.73-2.89 (3H, m), 3.19-3.25 (2H, m), 3.42 (1H, t, J = 9.8 Hz), 3.82-3.87 (1H, brt), 4.13 (1H, dd, J = 6.8, 11.0 Hz), 5.30-5.40 (1H, m), 7.15-7.17 (2H, m), 7.20-7.24 (3H, m), 7.34 (1H, t, J = 8.0 Hz), 7.50-7.52 (1H, brd), 7.58-7.64 (3H, m), 7.78-7.80 (1H, m), 7.93-8.03 (3H, m), 8.12-8.13 (1H, m), 8.20-8.22 (1H, brs), 8.40 (1H, s), 9.25 (1H, brs), 9.93 (1H, brs), 10.82 (1H, brs); Sal: HCl |
| 142 | 41 | 2-HO₂C-C₆H₄- | FP: 494; NMR1: 1.64 (3H, d, J = 6.7 Hz), 2.85 (3H, brs), 3.24-3.42 (3H, m), 3.82 (1H, dd, J = 8.6, 9.0 Hz), 4.16-4.20 (1H, m), 5.34-5.35 (1H, m), 6.99-7.03 (1H, m), 7.16-7.26 (5H, m), 7.52-7.58 (1H, m), 7.59-7.64 (3H, m), 7.94-7.97 (3H, m), 8.19-8.22 (1H, m), 8.49 (1H, d, J = 8.2 Hz), 9.31 (1H, brs), 10.03 (1H, brs), 10.67 (1H, s), 13.46 (1H, brs); Sal: HCl |
| 42 | 42 | 4-EtO₂C-C₆H₄- | FP: 522 |
| 143 | 42 | 3-MeO₂C-C₆H₄- | FP: 508 |
| 144 | 42 | 2-EtO₂C-C₆H₄- | FP: 522 |

TABLE 42

| EX | Syn | R¹ | DATA |
|---|---|---|---|
| 145 | 41 | HO₂C—CH₂— | FP: 432; Sal: HCl |
| 43 | 43 | 5-(HO₂C)-pyridin-3-yl | FP: 495; Sal: 2 HCl |
| 44 | 44 | trans-4-(HO₂C)-cyclohexyl | FP: 500 |
| 45 | 45 | 4-HO₂C-2-OMe-C₆H₃- | FP: 524; NMR1: 1.66 (3H, d, J = 6.5 Hz), 2.73-2.89 (3H, m), 3.17-3.39 (3H, m), 3.83 (1H, t, J = 8.4 Hz), 3.90 (3H, s), 4.17-4.19 (1H, m), 5.35 (1H, brs), 7.10-7.11 (2H, m), 7.18-7.19 (3H, m), 7.41 (1H, s), 7.49 (1H, d, J = 1.8 Hz), 7.54-7.64 (4H, m), 7.95 (1H, d, J = 8.2 Hz), 8.00-8.02 (2H, m), 8.14 (1H, d, J = 8.4 Hz), 8.21-8.24 (1H, m), 9.52 (1H, brs), 10.16 (1H, brs), 12.64 (1H, brs); Sal: HCl |

TABLE 42-continued

| | | | | |
|---|---|---|---|---|
| 146 | 45 | HO₂C-phenyl(Me)(O-CH(Me)₂) | | FP: 552; NMR1: 1.32 (6H, d, J = 5.6 Hz), 1.65 (3H, d, J = 6.7 Hz), 2.82 (3H, brs), 3.20-3.30 (2H, m), 3.38-3.45 (1H, m), 3.82 (1H, t, J = 8.7 Hz), 4.17-4.23 (1H, m), 4.65-4.75 (1H, m), 5.30-5.40 (1H, m), 7.14-7.15 (2H, m), 7.21-7.22 (3H, m), 7.34 (1H, s), 7.49-7.64 (5H, m), 7.95-8.03 (3H, m), 8.16 (1H, d, J = 8.4 Hz), 8.21-8.23 (1H, m), 9.43 (1H, brs), 10.06 (1H, brs), 12.69 (1H, brs); Sal: HCl |
| 147 | 45 | HO₂C-phenyl(Me)(Me) | | EP: 508; NMR1: 1.67 (3H, d, J = 6.5 Hz), 2.27 (3H, s), 2.82 (3H, brs), 3.20-3.27 (2H, m), 3.35-3.42 (2H, m), 3.86 (1H, t, J = 8.8 Hz), 4.16-4.18 (1H, m), 5.34 (1H, brs), 7.12-7.22 (5H, m), 7.57-7.76 (6H, m), 7.95 (1H, d, J = 8.2 Hz), 8.00-8.03 (2H, m), 8.21-8.24 (1H, m), 9.46 (1H, brs), 10.23 (1H, brs), 12.63 (1H, brs); Sal: HCl |
| 148 | 45 | HO₂C-phenyl(Cl)(Me) | | EP: 528; NMR1: 1.65 (3H, d, J = 6.7 Hz), 2.83 (3H, brs), 3.20-3.43 (3H, m), 3.88 (1H, t, J = 8.8 Hz), 4.19-4.20 (1H, m), 5.36 (1H, brs), 7.12-7.21 (5H, m), 7.57-7.64 (3H, m), 7.75 (1H, brs), 7.84-7.87 (1H, m), 7.93-8.08 (5H, m), 8.21-8.24 (1H, m), 9.44 (1H, brs), 10.12 (1H, brs), 13.04 (1H, brs); Sal: HCl |

TABLE 43

| | | | | |
|---|---|---|---|---|
| 149 | 45 | HO₂C-phenyl(F)(Me) | | FP: 512; NMR1: 1.63 (3H, d, J = 6.4 Hz), 2.81 (3H, brs), 3.19-3.41 (3H, m), 3.84 (1H, t, J = 8.9 Hz), 4.13-4.14 (1H, m), 5.33 (1H, brs), 7.14-7.22 (5H, m), 7.29-7.34 (1H, m), 7.57-7.64 (3H, m), 7.67-7.71 (1H, m), 7.95-7.97 (2H, m), 8.00-8.02 (1H, m), 8.08 (1H, brs), 8.19-8.23 (2H, m), 9.34 (1H, brs), 10.06 (1H, brs); Sal: HCl |
| 150 | 45 | HO₂C-phenyl(Cl)(Me) | | FP: 528; Sal: HCl |
| 151 | 45 | HO₂C-phenyl(F)(Me) | | EP: 512; Sal: HCl |
| 152 | 45 | HO₂C-phenyl(morpholino)(Me) | | EP: 579; Sal: 2 HCl |

TABLE 44

[Structure: HO₂C-phenyl-N(R⁸)-C(=O)-pyrrolidine-CH₂-NH-CH(Me)-naphthyl]

| EX | Syn | R⁸ | DATA |
|---|---|---|---|
| 153 | 45 | Me | EP: 508; Sal: HCl |
| 154 | 45 | Bn | FP: 584; Sal: HCl |

TABLE 45

[Structure: Bn-N-pyrrolidine(R²)-CH₂-NH-CH(Me)-naphthyl]

| EX | Syn | R² | DATA |
|---|---|---|---|
| 46 | 46 | Ph | FP: 421; NMR1: 1.57-1.62 (3H, m), 2.75-2.92 (2H, m), 3.06-3.18 (2H, m), 3.25-3.42 (4H, m), 4.33-4.51 (2H, m), 5.23-5.30 (1H, m), 7.18-7.30 (5H, m), 7.43-7.68 (8H, m), |

TABLE 45-continued

| | | | |
|---|---|---|---|
| | | | 7.93-8.02 (3H, m), 8.12-8.16 (1H, m), 9.52 (1H, brs), 9.91 (0.5H, brs), 10.13 (0.5H, brs), 11.68 (0.5H, brs), 12.14 (0.5H, brs); Sal: 2HCl |
| 47 | 47 |  | FP: 465; NMR1: 1.57-1.59 (3H, m), 2.75-3.76 (8H, m), 3.93-4.00 (0.5H, m), 4.32-4.50 (1.5H, m), 5.23-5.30 (1H, m), 7.37-7.66 (10H, m), 7.81-7.97 (5H, m), 8.05-8.14 (1H, m), 9.51 (1H, brs), 9.89 (1H, brs), 11.55 (0.5H, brs), 11.94 (0.5H, brs), 12.99 (1H, brs); Sal: 2HCl |

TABLE 46

| EX | Syn | R² | DATA |
|---|---|---|---|
| 48 | 48 | 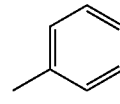 | FP: 527; NMR3: 1.63-1.70 (4H, m), 1.72-1.76 (3H, m), 2.29-2.40 (4H, m), 2.68-2.76 (1H, m), 2.90-2.95 (2H, m), 3.05-3.22 (1H, m), 3.33-3.39 (1H, m), 3.53-3.58 (1H, m), 3.88-3.97 (1H, m), 4.13-4.20 (1H, m), 5.35-5.42 (1H, m), 7.28-7.41 (2H, m), 7.48-7.71 (6H, m), 7.94-7.99 (2H, m), 8.08-8.12 (1H, m); Sal: HCl |
| 155 | 48 | 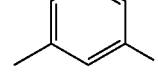 | FP: 477; Sal: HCl |
| 156 | 48 | 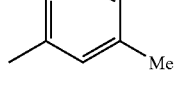 | EP: 473; Sal: HCl |
| 157 | 48 | 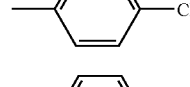 | FP: 527 |
| 158 | 48 |  | FP: 473; Sal: HCl |
| 159 | 48 | 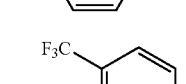 | EN: 502; Sal: HCl |
| 160 | 48 | 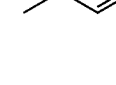 | FP: 527; Sal: HCl |

TABLE 46-continued

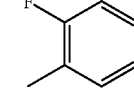

| EX | Syn | R² | DATA |
|---|---|---|---|
| 161 | 48 | 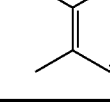 | FP: 477; NMR3: 1.63-1.70 (4H, m), 1.73-1.77 (3H, m), 2.29-2.40 (4H, m), 2.70-2.98 (3H, m), 3.13-3.20 (1H, m), 3.34-3.39 (1H, m), 3.55-3.60 (1H, m), 3.82-3.92 (1H, m), 4.11-4.16 (1H, m), 5.38-5.44 (1H, m), 6.97-7.07 (3H, m), 7.21-7.25 (1H, m), 7.56-7.67 (4H, m), 7.94-7.99 (2H, m), 8.08-8.12 (1H, m); Sal: HCl |
| 162 | 48 | 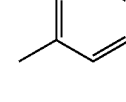 | FP: 473; Sal: HCl |

TABLE 47

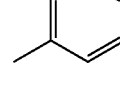

| EX | Syn | R² | DATA |
|---|---|---|---|
| 163 | 9 | 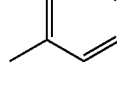 | EP: 491; NMR1: 1.08 (3H, s), 1.15 (3H, s), 1.32 (3H, t, J = 6 Hz), 1.67-1.78 (2H, m), 2.11-2.25 (2H, m), 2.39-2.58 (2H, m), 2.92-3.96 (6H, m), 4.44 (1H, q, J = 6 Hz), 6.97-7.16 (3H, m), 7.27 (1H, q, J = 6 Hz), 7.41-7.52 (3H, m), 7.63 (1H, dd, J = 3 Hz, 6 hz), 7.75 (1H, dd, J = 3 Hz, 6 hz), 8.20-8.29 (1H, m) |
| 164 | 9 | | FP: 487; Sal: HCl |
| 165 | 9 | | FP: 541; Sal: HCl |

TABLE 47-continued

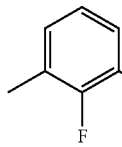

| EX | Syn | R² | DATA |
|---|---|---|---|
| 166 | 9 | 3-Me, 4-F phenyl | FP: 509; NMR1: 1.02-1.07 (4H, m), 1.08-1.12 (2H, m), 1.64 (3H, t, J = 6.5 Hz), 2.26-2.47 (4H, m), 2.75-2.84 (3H, m), 3.05-3.25 (1H, m), 3.25-3.50 (2H, m), 3.72-3.94 (1H, m), 4.10-4.24 (1H, m), 5.30-5.40 (1H, m), 6.95-7.18 (2H, m), 7.22-7.33 (1H, m), 7.53-7.64 (3H, m), 7.90-8.04 (3H, m), 8.16-8.23 (1H, m), 9.27 (0.5H, brs), 9.46 (0.5H, brs), 10.03 (1H, brs), 12.01 (1H, brs); Sal: HCl |

TABLE 48

| EX | Syn | R² | DATA |
|---|---|---|---|
| 167 | 9 | 3-F phenyl | FP: 491 |
| 168 | 9 | 3-Me phenyl | FP: 487; Sal: HCl |
| 169 | 9 | 3-CF₃ phenyl | FP: 541; Sal: HCl |
| 362 | 9 | 3-Me, 4-F phenyl | FP: 509; NMR1: 1.07 (3H, s), 1.13 (3H, s), 1.62 (3H, t, J = 6.0 Hz), 1.65-1.78 (2H, m), 2.10-2.30 (1H, m), 2.70-3.00 (3H, m), 3.02-3.25 (1H, m), 3.25-3.65 (3H, m), 3.72-3.85 (1H, m), 4.05-4.15 (1H, m), 5.30-5.42 (1H, m), 6.92-7.12 (2H, m), 7.22-7.34 (1H, m), 7.53-7.67 (3H, m), 7.85 (1H, dd, J = 7.0, 15.0 Hz), 7.96 (1H, d, J = 8.0 Hz), 7.98-8.05 (1H, m), 8.15-8.25 (1H, m), 9.09 (0.5H, brs), 9.25 (0.5H, brs), 9.71 (1H, brs), 12.12 (1H, brs); Sal: HCl |

TABLE 49

| EX | Syn | R² | DATA |
|---|---|---|---|
| 170 | 31 | 3-F phenyl | FP: 505; Sal: HCl |
| 171 | 31 | 3-Me phenyl | FP: 501; NMR1: 1.64 (3H, d, J = 6.6 Hz), 2.21 (3H, s), 2.80-2.87 (3H, m), 3.05-3.11 (1H, m), 3.65 (2H, m), 3.79-3.84 (1H, m), 4.14 (1H, m), 5.35 (1H, brs), 6.90 (1H, d, J = 7.6 Hz), 6.99-7.02 (2H, m), 7.09 (1H, t, J = 7.5 Hz), 7.39-7.49 (2H, m), 7.57-7.64 (3H, m), 7.95-8.03 (3H, m), 8.20-8.23 (1H, m), 9.41 (1H, brs), 10.05 (1H, brs), 12.92 (1H, brs); Sal: HCl |
| 172 | 31 | 3-CF₃ phenyl | FP: 555; Sal: HCl |
| 173 | 31 | 3-Me, 4-F phenyl | FP: 523; NMR1: 1.63 (3H, d, J = 6.5 Hz), 2.77-2.90 (1H, m), 2.90-3.30 (2H, m), 3.43 (1H, m), 3.60 (1H, dd, J = 9.0, 17.5 Hz), 3.60-3.76 (2H, m), 3.81-3.90 (1H, m), 4.06-4.18 (1H, m), 5.32-5.44 (1H, m), 7.00-7.10 (2H, m), 7.25-7.35 (1H, m), 7.42 (1H, dd, J = 3.0, 12 Hz), 7.47 (1H, dd, J = 3.0, 12 Hz), 7.55-7.65 (3H, m), 7.87 (1H, d, J = 7.0 Hz), 7.97 (1H, d, J = 8.0 Hz), 7.99-8.05 (1H, m), 8.17-8.24 (1H, m), 9.23 (1H, brs), 9.75 (1H, brs), 12.6 (1H, brs); Sal: HCl |

TABLE 50

| EX | Syn | R² | DATA |
|---|---|---|---|
| 49 | 49 | 3-CF₃ phenyl | FP: 563; NMR1: 1.63 (3H, d, J = 6.4 Hz), 2.80-3.00 (3H, m), 3.22-3.45 (2H, m), 3.56-3.63 (1H, m), 3.79-3.83 (0.5H, m), 3.96-4.01 (0.5H, m), 4.12-4.17 (0.5H, m), 4.27-4.32 (0.5H, m), 5.34 (1H, brs), 7.28 (2H, t, J = 8.3 Hz), 7.44-7.53 (2H, m), 7.59-7.66 (5H, m), 7.92-8.01 (5H, m), 8.17-8.19 (1H, m), 9.26 (1H, brs), 9.96 (1H, brs), 12.94 (1H, brs); Sal: HCl |

TABLE 50-continued

[Structure: HO2C-phenyl-O-C(=O)-N-pyrrolidine with R2 substituent and CH2-NH-CH(Me)-naphthyl group]

| EX | Syn | R² | DATA |
|---|---|---|---|
| 174 | 49 | 3-fluorophenyl-methyl | FP: 513; NMR1: 1.65 (3H, d, J = 6 hz), 2.79-2.95 (3H, m), 3.17-3.55 (3H, m), 3.78 (0.5H, dd, J = 8 Hz, 11 Hz), 3.96 (0.5H, dd, J = 8 Hz, 11 Hz), 4.15 (0.5H, dd, J = 7 Hz, 11 Hz), 4.30 (0.5H, dd, J = 7 Hz, 11 Hz), 5.35 (1H, br.s), 6.96-7.15 (3H, m), 7.21-7.32 (3H, m), 7.55-7.64 (3H, m), 7.92-8.04 (5H, m), 8.20 (1H, d, J = 7 Hz), 9.37 (1H, br.s), 10.13 (1H, br.s), 12.97 (1H, br.s); Sal: HCl |
| 175 | 49 | 3-methylphenyl-methyl | FP: 509; NMR1: 1.62 (3H, d, J = 6.5 Hz), 2.22 (3H, s), 2.84 (3H, brs), 3.09-3.52 (3H, m), 3.73-3.78 (0.5H, m), 3.91-3.95 (0.5H, m), 4.11-4.14 (0.5H, m), 4.27 (0.5H, m), 5.37 (1H, brs), 3.93 (1H, t, J = 7.3 Hz), 7.00-7.04 (2H, m), 7.11 (1H, t, J = 7.8 Hz), 7.28 (2H, t, J = 8.3 Hz), 7.58-7.64 (3H, m), 7.88-7.90 (1H, m), 7.96-8.03 (4H, m), 8.19-8.21 (1H, m), 9.19 (1H, brs), 9.78 (1H, brs), 12.95 (1H, brs); Sal: HCl |
| 50 | 50 | 4-fluorophenyl-methyl | FP: 513; NMR1: 1.33 (3H, d, J = 6 Hz), 2.22-2.30 (1H, m), 2.43-2.49 (1H, m), 2.52-2.65 (1H, m), 3.03-3.14 (1H, m), 3.21-3.51 (2H, m), 3.73-4.11 (2H, m), 4.48 (1H, q, J = 6 Hz), 7.02-7.11 (2H, m), 7.24-7.33 (4H, m), 7.43-7.53 (3H, m), 7.65 (1H, d, J = 7 Hz), 7.76 (1H, d, J = 7 Hz), 7.87-7.93 (1H, m), 7.94-8.02 (2H, m), 8.21-8.28 (1H, m) |

TABLE 51

| EX | Syn | R² | DATA |
|---|---|---|---|
| 176 | 38(3) | 2-fluorophenyl-methyl | FP: 513; NMR1: 1.33 (3H, d, J = 6 Hz), 2.26-2.36 (1H, m), 2.61-2.79 (1H, br), 3.22-4.14 (6H, m), 4.50 (1H, q, J = 6 Hz), 7.04-7.18 (2H, m), 7.23-7.41 (4H, m), 7.41-7.53 (3H, m), 7.64 (1H, d, J = 7 Hz), 7.76 (1H, d, J = 7 Hz), 7.87-7.93 (1H, m), 7.94-8.03 (2H, m), 8.20-8.28 (1H, m) |
| 177 | 38(3) | 2-methylphenyl-methyl | FP: 509 |
| 178 | 38(3) | 2,5-difluorophenyl-methyl | FP: 531 |
| 179 | 38(3) | 2-fluoro-3-methylphenyl-methyl | FP: 531; NMR1: 1.34 (3H, d, J = 6 Hz), 2.28-2.38 (1H, m), 2.62-2.76 (1H, br), 3.24-4.13 (4H, ,m), 4.50 (1H, q, J = 6 Hz), 7.05-7.14 (1H, m), 7.15-7.23 (1H, m), 7.23-7.33 (3H, m), 7.40-7.52 (3H, m), 7.63 (1H, d, J = 7 Hz), 7.76 (1H, d, J = 7Hz), 7.87-7.93 (1H, m), 7.94-8.02 (2H, m), 8.20-8.26 (1H, m) |
| 180 | 38(3) | 5-methylfuran-2-yl-methyl | EP: 485; NMR1: 1.36 (3H, d, J = 6.5 Hz), 2.30-2.40 (1H, m), 2.50-2.62 (1H, m), 2.65 (1H, dd, J = 4.0, 11.5 Hz), 3.15-3.45 (4H, m), 3.53-3.65 (1H, m), 3.68-4.03 (2H, m), 4.54 (1H, dd, J = 6.5, 13 Hz), 6.17-6.19 (1H, m), 6.33-6.36 (1H, m), 7.27 (2H, t, J = 8.5 Hz), 7.45-7.53 (3H, m), 7.52-7.55 (1H, m), 7.68 (1H, d, J = 7.0 Hz), 7.78 (1H, d, J = 8.0 Hz), 7.89-7.94 (1H, m), 7.97 (2H, t, J = 8.5 Hz), 8.25-8.30 (1H, m) |
| 181 | 39(3) | 5-methylpyridin-3-yl | EP: 496; NMR1: 1.30 (3H, d, J = 6.5 Hz), 2.42-2.48 (2H, m), 2.53-2.69 (1H, m), 3.15-3.58 (5H, m), 3.78-3.86 (1H, m), 3.99 (1H, dd, J = 8.0, 10.5 Hz), 4.43-4.51 (1H, m), 7.24-7.29 (2H, m), 7.33 (1H, d, J = 4.5, 8.0 Hz), 7.43 (1H, t, J = 7.5 Hz), 7.44-7.53 (2H, m), 7.57 (1H, d, J = 7.5 Hz), 7.72-7.78 (2H, m), 7.87-7.92 (1H, m), 7.93-8.00 (2H, m), 8.15-8.21 (1H, m), 8.42-8.46 (1H, m), 8.50-8.65 (1H, m) |

TABLE 52

[Structure: HO2C-phenyl(OMe)-NH-C(=O)-N-pyrrolidine with R2 substituent and CH2-NH-CH(Me)-naphthyl group]

| EX | Syn | R² | DATA |
|---|---|---|---|
| 182 | 45 | 3-fluorophenyl-methyl | FP: 542 |
| 183 | 45 | 3-methylphenyl-methyl | FP: 538; NMR1: 1.65 (3H, d, J = 6.5 Hz), 2.21 (3H, s), 2.81 (3H, brs), 3.12-3.14 (1H, m), 3.27-3.40 (1H, m), 3.82 (1H, t, J = 8.8 Hz), 3.89 (3H, s), 4.15-4.20 (1H, brm), 5.36 (1H, brm), 6.89 (1H, d, J = 7.5 Hz), 6.98-7.02 (2H, m), 7.08 (1H, t, J = 7.5 Hz), 7.40 (1H, s), 7.48-7.64 (6H, m), 7.95-8.03 (3H, m), 8.13 (1H, d, J = 8.5 Hz), 8.20-8.23 (1H, m), 9.40 (1H, brs), 9.99 (1H, brs), 12.69 (1H, brs); Sal: HCl |

TABLE 52-continued

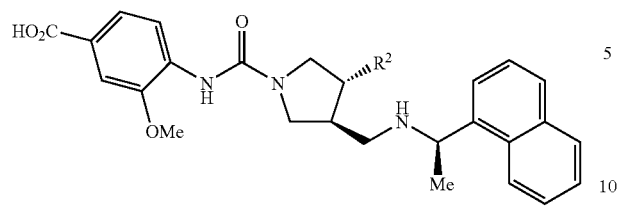

| EX | Syn | R² | DATA |
|---|---|---|---|
| 184 | 45 | 3-methylphenyl-CF₃ | FP: 592; Sal: HCl |
| 363 | 45 | 3-methyl-difluorophenyl | FP: 560; NMR1: 1.65 (3H, d, J = 6.5 Hz), 2.80-2.95 (3H, m), 3.24-3.39 (2H, m), 3.39-3.55 (2H, m), 3.90 (3H, s), 4.15-4.25 (1H, m), 5.32-5.44 (1H, m), 6.99-7.09 (2H, m), 7.24-7.33 (1H, m), 7.42 (1H, s), 7.49 (1H, d, J = 2.0 Hz), 7.54 (1H, dd, J = 1.5, 8.5 Hz), 7.56-7.65 (3H, m), 7.92-7.98 (2H, m), 7.98-8.04 (1H, m), 8.11 (1H, d, J = 8.5 Hz), 8.18-8.24 (1H, m), 9.39 (1H, brs), 9.98 (1H, brs), 12.7 (1H, brs); Sal: HCl |

TABLE 53

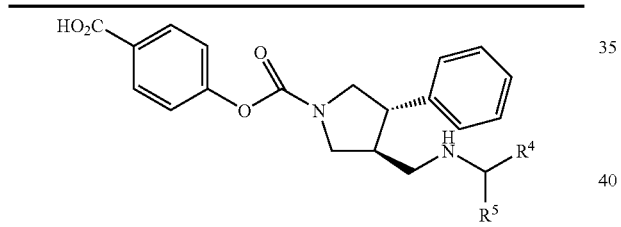

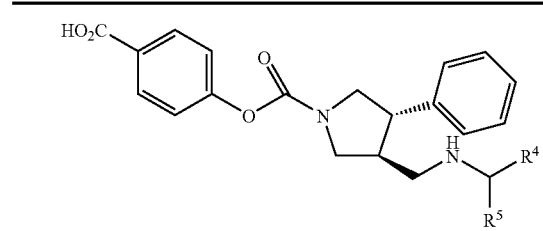

| EX | Syn | R⁴/R⁵ | DATA |
|---|---|---|---|
| 51 | 51 | 1-(1-naphthyl)ethyl | EP: 495; NMR1: 1.31 (3H, d, J = 6 Hz), 2.39-2.48 (1H, m), 2.52-2.65 (1H, m), 3.11-4.01 (6H, m), 4.49 (1H, q, J = 5 Hz), 7.18-7.33 (7H, m), 7.40-7.53 (3H, m), 7.59 (1H, d, J = 7 Hz), 7.75 (1H, d, J = 7 Hz), 7.89 (1H, d, J = 7 Hz), 7.93-8.01 (2H, m), 8.18 (1H, d, J = 7 Hz) |
| 185 | 51 | 1-(2-naphthyl)ethyl | FP: 495 |

TABLE 53-continued

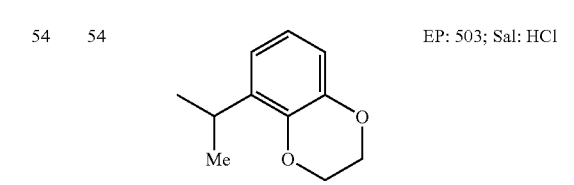

| EX | Syn | R⁴/R⁵ | DATA |
|---|---|---|---|
| 52 | 52 | 1-(3-methoxyphenyl)ethyl | EP: 475; Sal: HCl |
| 53 | 53 | 1-(benzothiophen-3-yl)ethyl | EP: 501; NMR1: 1.59 (3H, brs), 2.67 (3H, brs), 3.07-3.42 (2H, m), 3.50-3.86 (2H, m), 3.94-4.18 (2H, m), 4.91-7.96 (1H, brm), 7.22-7.44 (9H, m), 7.95-8.04 (5H, m), 9.11 (1.5H, brs), 9.35 (0.5H, brs); Sal: HCl |
| 54 | 54 | 1-(2,3-dihydrobenzo[1,4]dioxin-5-yl)ethyl | EP: 503; Sal: HCl |
| 55 | 55 | 1-(azulen-1-yl)ethyl | FN: 493; NMR1: 1.35-1.44 (3H, m), 2.15-2.24 (0.5H, m), 2.42-2.70 (2H, m), 2.77-2.83 (0.5H, m), 2.97-4.11 (6H, m), 4.40-4.42 (0.5H, m), 4.49-4.51 (0.5H, m), 6.91 (1H, d, J = 8.4 Hz), 7.10-7.40 (8.5H, m), 7.59-7.65 (0.5H, m), 7.89-8.00 (5H, m), 8.29-8.33 (1H, m), 8.44-8.54 (1H, m) |
| 56 | 56 | 1-(2-phenoxy-1-methylindol-3-yl)ethyl | FN: 588 |

TABLE 54

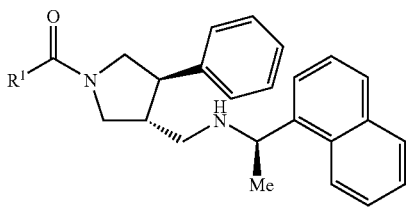

| EX | Syn | R¹ | DATA |
|---|---|---|---|
| 57 | 57 | CF₃— | FP: 427; NMR1: 1.60-1.66 (3H, m), 2.69-3.20 (2H, m), 3.11-3.52 (3H, m), 3.60 (1H, t, J = 10.6 Hz), 3.91-3.96 (0.5H, m), 4.04-4.09 (0.5H, m), 4.20 (0.5H, dd, J = 7.8, 12.7 Hz), 4.39-4.43 (0.5H, m), 5.20-5.30 (1H, m), 7.24-7.32 (5H, m), 7.53-7.61 (3H, m), 7.92-7.94 (3H, m), 8.14-8.17 (1H, m), 9.38-9.55 (1H, brm), 9.80 (0.5H, brs), 10.00 (0.5H, brs); Sal: HCl |
| 58 | 58 | Me | FP: 373; NMR1: 1.59-1.66 (3H, m), 1.94-1.96 (3H, m), 2.70-2.89 (2H, m), 3.09-3.21 (2H, m), 3.36-3.45 (2H, m), 3.77 (0.5H, dd, J = 7.8, 11.3 Hz), 3.87 (0.5H, dd, J = 8.0, 10.8 Hz), 4.00-4.09 (1H, m), 5.20-5.30 (1H, m), 7.20-7.32 (5H, m), 7.52-7.63 (3H, m), 7.88-8.02 (3H, m), 8.17 (1H, t, J = 7.3 Hz), 9.46 (1H, brs), 9.54 (0.5H, brs), 9.93 (0.5H, brs); Sal: HCl |

TABLE 55

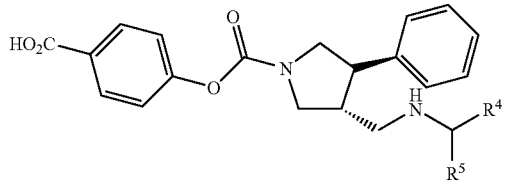

| EX | Syn | | DATA |
|---|---|---|---|
| 59 | 59 | 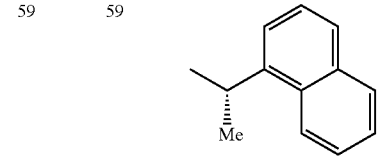 | FP: 495 |
| 186 | 59 | 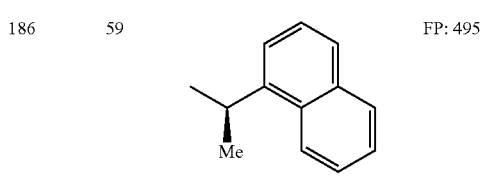 | FP: 495 |

TABLE 56

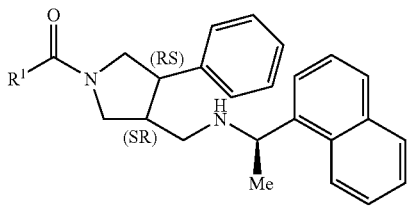

| EX | Syn | R¹ | DATA |
|---|---|---|---|
| 60 | 60 | CF₃— | FP: 427; NMR1: 1.58-1.66 (3H, m), 2.70-3.00 (2.5H, m), 3.10-3.70 (3.5H, m), 3.84-4.11 (1H, m), 4.14-4.28 (0.5H, m), 4.35-4.47 (0.5H, m), 5.18-5.38 (1H, m), 7.12-7.36 (5H, m), 7.50-7.65 (3H, m), 7.89-8.04 (3H, m), 8.12-8.22 (1H, m), 9.30-9.60 (1H, bm), 9.70-10.20 (1H, bm); Sal: HCl |
| 61 | 61 | Me | EP: 373; NMR1: 1.56-1.72 (3H, m), 1.90-2.00 (3H, m), 2.60-3.25 (5H, m), 3.30-3.50 (1H, m), 3.70-3.90 (1H, m), 4.00-4.30 (1H, m), 5.20-5.50 (1H, m), 7.00-7.32 (5H, m), 7.50-7.80 (3H, m), 7.90-8.26 (4H, m), 8.50-10.50 (2H, m); Sal: HCl |
| 62 | 62 | tBu | FP: 415; NMR1: 1.12-1.21 (9H, m), 1.34 (3H, m), 2.20-4.70 (9H, brm), 7,12-7.32 (4H, m), 7.38-7.54 (3H, m), 7.55-7.70 (1H, m), 7.70-7.82 (1H, m), 7.85-8.00 (1H, m), 8.16-8.34 (1H, m); Sal: HCl |
| 63 | 63 | Et | EP: 387; NMR1: 0.92-1.10 (3H, m), 1.56-1.69 (3H, m), 2.27-2.32 (2H, m), 2.60-2.85 (2H, bm), 2.90-3.50 (4H, m), 3.70-3.79 (1H, m), 4.00-4.02 (1H, m), 5.30-5.50 (1H, m), 7.00-7.30 (4H, m), 7.50-7.70 (3H, m), 7.80-8.10 (3H, m), 8.10-8.30 (1H, m); Sal: HCl |
| 64 | 64 | HO-C(Me)(Me)- | EP: 417; NMR1: 1.45-1.70 (9H, m), 2.60-4.10 (7.5H, m), 5.30 (1.5H, m), 7.00-7.35 (5H, m), 7.40-7.67 (3H, m), 7.70-8.30 (4H, m), 9.20-10.10 (2H, brm); Sal: HCl |

TABLE 57

| | | | |
|---|---|---|---|
| 187 | 62 | Ph | EP: 435; NMR1: 1.54 (1.5H, app.t, J = 6.3 Hz), 1.64 (1.5H, dd, J = 3.4, 6.3 Hz), 2.60-3.00 (2H, m), 3.00-3.70 (4.5H, m), 3.82-4.26 (1.5H, m), 5.15-5.50 (1H, m), 7.00-7.66 (13H, m), 7.78-8.26 (4H, m), 9.20-10.20 (2H, m); Sal: HCl |
| 188 | 62 | 2-CF₃-C₆H₄- | EP: 503; NMR1: 1.54 (1.5H, d, J = 6.8 Hz), 1.65 (1.5H, d, J = 6.4 Hz), 2.60-3.50 (6.5H, m), 3.70 (0.5H, m), 3.94 (0.5H, m), 4.29 (0.5H, m), 5.24 (0.5H, m), 5.37 (0.5H, m), 7.00-7.30 (5H, m), 7.40-8.30 (11H, m); Sal: HCl |

TABLE 57-continued

| | | | |
|---|---|---|---|
| 189 | 62 | 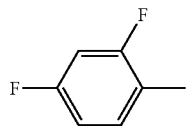 | EP: 471; NMR1: 1.54 (1.5H, d, J = 6.4 Hz), 1.64 (1.5H, d, J = 6.6 Hz), 2.60-3.70 (7.5H, m), 3.84 (0.5H, dd, J = 7.0, 10.6 Hz), 3.95 (0.5H, dd, J = 8.2, 11.5 Hz), 4.18 (0.5H, dd, dd, J = 7.9, 12.6 Hz), 5.20-5.40 (1H, m), 7.00-7.60 (11H, m), 7.80-8.30 (4H, m); Sal: HCl |
| 190 | 64 | 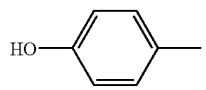 | EP: 451; NMR1: 1.45-1.70 (3H, brd), 2.60-4.10 (8H, br), 5.30 (1H, br), 6.70-6.80 (1H, m), 7.00-7.35 (5H, m), 7.40-7.67 (4H, m), 7.70-8.30 (4H, m), 9.20-10.10 (2H, brm); Sal: HCl |
| 191 | 64 | 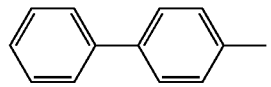 | FP: 511; NMR1: 1.44-1.74 (3H, m), 2.60-4.25 (8H, m), 5.12-5.48 (1H, m), 7.05-8.30 (21H, m), 9.10-10.16 (2H, m); Sal: HCl |
| 192 | 64 | 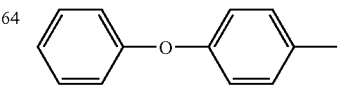 | FP: 527; NMR1: 1.50-1.72 (3H, m), 2.64-3.30 (3H, m), 3.60-4.60 (5H, m), 5.14-5.44 (1H, m), 6.90-7.34 (10H, m), 7.38-7.68 (7H, m), 7.84-8.28 (4H, m), 9.24-10.20 (2H, m); Sal: HCl |
| 193 | 64 | 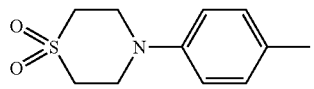 | EP: 568; NMR1: 1.50-1.70 (3H, m), 2.64-3.00 (2H, m), 3.00-3.90 (13H, m), 4.00-4.30 (1H, m), 5.10-5.46 (1H, m), 6.90-7.34 (7H, m), 7.40-7.75 (5H, m), 7.70-8.06 (3H, m), 8.10-8.28 (1H, m), 9.10-10.05 (2H, m); Sal: HCl |
| 67 | 67 | 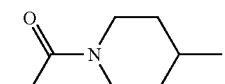 | FP: 484; NMR1: 1.20-1.82 (6.5H, m), 1.86-2.06 (4H, m), 2.30-2.90 (2.5H, m), 2.95-3.30 (3.5H, m), 3.34-3.56 (1H, m), 3.65-4.50 (4.5H, m), 5.16-5.42 (1H, m), 6.98-7.24 (5H, m), 7.46-7.68 (3H, m), 7.84-8.26 (4H, m), 9.20-10.40 (2H, m); Sal: HCl |

TABLE 58

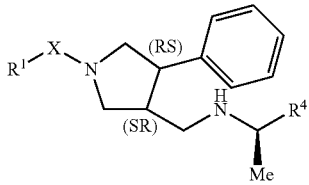

| EX | Syn | R¹—X— | R⁴ | DATA |
|---|---|---|---|---|
| 68 | 68 | H | 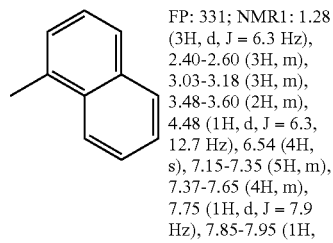 | FP: 331; NMR1: 1.28 (3H, d, J = 6.3 Hz), 2.40-2.60 (3H, m), 3.03-3.18 (3H, m), 3.48-3.60 (2H, m), 4.48 (1H, d, J = 6.3, 12.7 Hz), 6.54 (4H, s), 7.15-7.35 (5H, m), 7.37-7.65 (4H, m), 7.75 (1H, d, J = 7.9 Hz), 7.85-7.95 (1H, m), 8.08-8.22 (1H, m); Sal: 2fumarate |
| 69 | 69 | Ph | 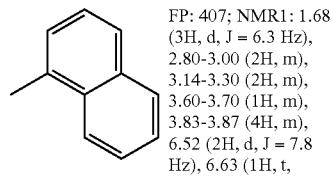 | FP: 407; NMR1: 1.68 (3H, d, J = 6.3 Hz), 2.80-3.00 (2H, m), 3.14-3.30 (2H, m), 3.60-3.70 (1H, m), 3.83-3.87 (4H, m), 6.52 (2H, d, J = 7.8 Hz), 6.63 (1H, t, J = 7.3 Hz), 7.11-7.35 (7H, m), 7.54-7.63 (3H, m), 7.94-8.09 (3H, m), 8.20 (1H, d, J = 7.8 Hz), 9.50-9.60 (1H, brm), 10.00-10.12 (1H, brm); Sal: 2HCl |
| 70 | 70 | 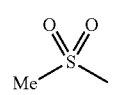 | 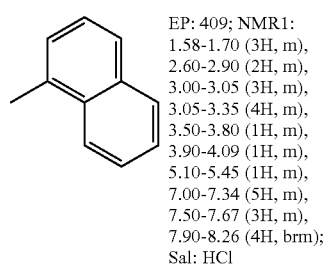 | EP: 409; NMR1: 1.58-1.70 (3H, m), 2.60-2.90 (2H, m), 3.00-3.05 (3H, m), 3.05-3.35 (4H, m), 3.50-3.80 (1H, m), 3.90-4.09 (1H, m), 5.10-5.45 (1H, m), 7.00-7.34 (5H, m), 7.50-7.67 (3H, m), 7.90-8.26 (4H, brm); Sal: HCl |
| 65 | 65 | EtO₂C— | 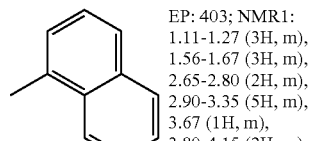 | EP: 403; NMR1: 1.11-1.27 (3H, m), 1.56-1.67 (3H, m), 2.65-2.80 (2H, m), 2.90-3.35 (5H, m), 3.67 (1H, m), 3.80-4.15 (2H, m), 5.20-5.40 (1H, brm), 7.05-7.33 (5H, m), 7.50-7.65 (3H, m), 7.80-8.04 (3H, m), 8.18 (1H, m); Sal: HCl |

TABLE 59
| | | | | |
|---|---|---|---|---|
| 66 | 66 | PhNHC(O)— | 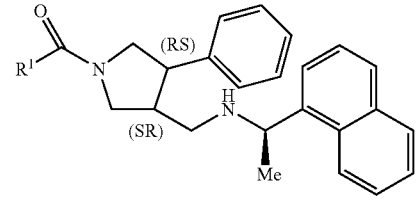 | FP: 450; NMR1: 1.60-1.70 (3H, brt), 2.75-2.90 (3H, m), 3.19-3.43 (3H, m), 3.80-3.86 (1H, brt), 4.10-4.18 (1H, brm), 6.92 (1H, t, J = 7.3 Hz), 7.14-7.33 (7H, m), 7.45-7.64 (5H, m), 7.93-8.03 (3H, m), 8.17-8.28 (2H, m), 9.33 (1H, brs), 10.11 (1H, brs); Sal: HCl |
| 71 | 71 | 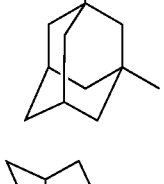 | 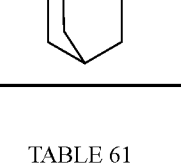 | EP: 353; NMR1: 1.42-1.63 (3H, brm), 1.90-2.00 (3H, m), 2.50-3.50 (4H, m), 3.72-4.40 (3H, m), 3.75 (3H, m), 6.85-7.10 (2H, m), 7.15-7.40 (7H, m); Sal: HCl |
TABLE 60
| EX | Syn | R¹ | DATA (EP) |
|---|---|---|---|
| 72 | 72 | nPr | 401 |
| 194 | 72 | iPr | 401 |
| 195 | 72 | Me—CH(Me)—(CH₂)₂— | 429 |
| 196 | 72 | F₃C—CH₂— | 441 |
| 197 | 72 | HO—CH₂— | 389 |
| 198 | 72 | HO—(CH₂)₂— | 403 |
| 199 | 72 |  | 403 |
| 200 | 72 | HO—CH₂—C(Me)₂— | 431 |
| 201 | 72 | Me—CH(Me)—CH(OH)— | 431 |
| 202 | 72 | HO—C(Me)₂—CH₂— | 431 |
| 203 | 72 | Me—C(—CH₂OH)₂— | 447 |
| 204 | 72 | MeO—CH₂— | 403 |
| 205 | 72 | Me₂N—CH₂— | 416 |
| 206 | 72 | Me₂N—(CH₂)₂— | 430 |
| 207 | 72 | Me₂N—C(O)—(CH₂)₂— | 458 |
| 208 | 72 | cPr | 399 |
| 209 | 72 | cBu | 413 |
| 210 | 72 | cPen | 427 |
| 211 | 72 | dHex | 441 |
| 212 | 72 | cPen-CH₂— | 441 |
| 213 | 72 | cHex-CH₂— | 455 |
| 214 | 72 | dHex-(CH₂)₂— | 469 |
| 215 | 72 |  | 493 |
TABLE 60-continued
| EX | Syn | R¹ | DATA (EP) |
|---|---|---|---|
| 216 | 72 |  | 509 |
| 217 | 72 |  | 507 |
TABLE 61
| 218 | 72 | H₂NOC  | 442 |
|---|---|---|---|
| 219 | 72 | Ph  | 475 |
| 220 | 72 | Ph⫽⫽⫽ | 475 |
| 221 | 72 | Ph | 503 |
| 222 | 72 | | 424 |
| 223 | 72 | Me | 438 |
| 224 | 72 | | 425 |
| 225 | 72 | | 425 |

TABLE 61-continued
| | | | |
|---|---|---|---|
| 226 | 72 | 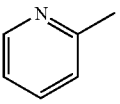 | 436 |
| 227 | 72 | 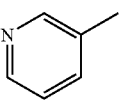 | 436 |
| 228 | 72 | 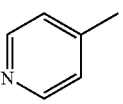 | 436 |
| 229 | 72 | 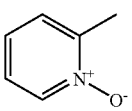 | 452 |
| 230 | 72 | 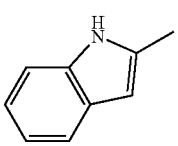 | 474 |
| 231 | 72 | 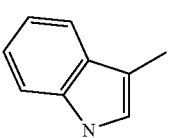 | 474 |
TABLE 62
| | | | |
|---|---|---|---|
| 232 | 72 | 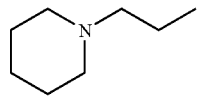 | 488 |
| 233 | 72 | 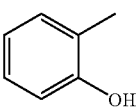 | 488 |
| 234 | 72 | 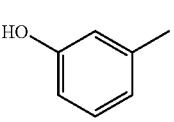 | 450 |
| 235 | 72 | 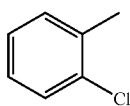 | 488 |
| 236 | 72 | 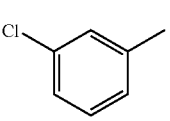 | 582 |
TABLE 62-continued
| | | | |
|---|---|---|---|
| 237 | 72 | 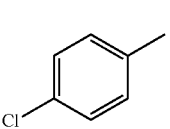 | 470 |
| 238 | 72 | 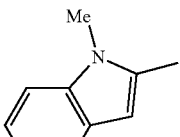 | 451 |
| 239 | 72 | 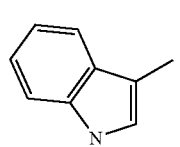 | 451 |
| 240 | 72 | 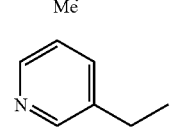 | 469 |
| 241 | 72 | 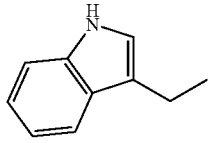 | 469 |
| 242 | 72 | 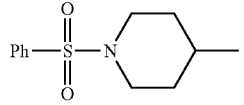 | 469 |
| 243 | 72 | 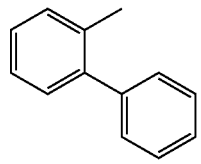 | 503 |
| 244 | 72 | 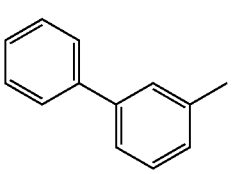 | 503 |
TABLE 63
| | | | |
|---|---|---|---|
| 245 | 72 | 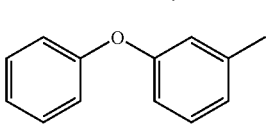 | 511 |
| 246 | 72 |  | 511 |
| 247 | 72 |  | 527 |

TABLE 63-continued

| # | | Structure | Value |
|---|---|---|---|
| 248 | 72 | 2-methylphenyl-N-thiomorpholine-1,1-dioxide | 568 |
| 249 | 72 | 1-methylnaphthalene | 485 |
| 250 | 72 | 2-methylnaphthalene | 485 |
| 251 | 72 | Ph—(CH₂)₂— | 463 |
| 252 | 72 | Ph—(CH₂)₃— | 477 |
| 253 | 72 | Ph—(CH₂)₅— | 505 |
| 254 | 72 | 2-Cl, ethyl phenyl | 483 |
| 255 | 72 | 3-Cl, ethyl phenyl | 483 |
| 256 | 72 | 4-Cl, ethyl phenyl | 483 |
| 257 | 72 | 2-CF₃, ethyl phenyl | 517 |
| 258 | 72 | 3-CF₃, ethyl phenyl | 517 |
| 259 | 72 | 4-CF₃, ethyl phenyl | 517 |
| 260 | 72 | Ph—CH(Ph)— | 525 |

TABLE 64

| # | | Structure | Value |
|---|---|---|---|
| 261 | 72 | PhO—CH₂— | 465 |
| 262 | 72 | PhO—(CH₂)₂— | 479 |
| 263 | 72 | Ph—C(O)—(CH₂)₂— | 491 |
| 264 | 72 | PhS—CH₂— | 481 |
| 265 | 72 | PhS(O)₂—(CH₂)₂— | 527 |
| 266 | 72 | Ph-CH₂-CH(NMe₂)- | 506 |

TABLE 64-continued

| # | | Structure | Value |
|---|---|---|---|
| 267 | 72 | 2-Cl-propenylbenzene | 495 |
| 268 | 72 | 3-Cl-propenylbenzene | 495 |
| 269 | 72 | 4-Cl-propenylbenzene | 495 |
| 73 | 73 | 3-methylbenzoic acid | 479 |
| 270 | 73 | 4-methylbenzoic acid | 479 |
| 271 | 73 | 2-nitro-4-methylbenzoic acid | 524 |
| 272 | 73 | 2-methylphenylacetic acid | 493 |
| 273 | 73 | 2'-methyl-biphenyl-2-carboxylic acid | 555 |
| 274 | 73 | 3-(5-methylfuran-2-yl)thiophene-2-carboxylic acid | 551 |
| 275 | 73 | 1-methyl-4-propenyl-pyrrole-2-carboxylic acid | 508 |

TABLE 65

| | | | |
|---|---|---|---|
| 276 | 73 | HO2C-thiophene with Et, Me, NHC(O)Pr | 598 |
| 277 | 73 | HO2C-CH=CH-C6H4-Et | 519 |
| 278 | 73 | cis-2-methylcyclopentanecarboxylic acid | 471 |
| 279 | 73 | trans-3-methylcyclopentanecarboxylic acid | 471 |
| 280 | 73 | 3-methylcyclohexanecarboxylic acid | 485 |
| 281 | 73 | trans-4-methylcyclohexanecarboxylic acid | 485 |
| 282 | 73 | cis-4-methylcyclohexanecarboxylic acid | 485 |
| 283 | 73 | cis-2-methylcyclohexanecarboxylic acid | 485 |
| 284 | 73 | 3-methylbicyclo[2.2.1]hept-5-ene-2-carboxylic acid | 495 |
| 285 | 73 | 1,2-dimethyl-2-propyl-4-oxocyclopentanecarboxylic acid | 541 |
| 286 | 73 | 3-methylpyridine-4-carboxylic acid | 480 |
| 287 | 73 | HO2C—(CH2)2— | 431 |
| 288 | 73 | HO2C—(CH2)3— | 445 |
| 289 | 73 | HO2C—(CH2)4— | 459 |
| 290 | 73 | HO2C—(CH2)6— | 487 |
| 291 | 73 | HO2C—(CH2)7— | 501 |
| 292 | 73 | HO2C—(CH2)8— | 515 |
| 293 | 73 | HO2C—(CH2)10— | 543 |

TABLE 66

| | | | |
|---|---|---|---|
| 294 | 73 | HO2C-CH2-C(=CH2)-Me | 443 |
| 295 | 73 | (S)-HO2C-CH2-CH(Me)- | 445 |
| 296 | 73 | HO2C-CH2-CH(Ph)-Me | 507 |
| 297 | 73 | (R)-HO2C-CH2-CH2-CH(Me)- | 459 |
| 298 | 73 | HO2C-CH2-CH(Me)-Et | 473 |
| 299 | 73 | HO2C-CH(Et)-CH(Me)2 | 473 |
| 300 | 73 | HO2C-CH(Et)-CH(Me)2 | 473 |
| 301 | 73 | (R)-HO2C-CH(Et)-cyclohexyl | 513 |
| 302 | 73 | (S)-HO2C-CH(Et)-cyclohexyl | 513 |
| 303 | 73 | HO2C-CH(Et)-CH2-CH(Me)2 | 487 |
| 304 | 73 | HO2C-CH(Et)-CH2-CH(Me)2 | 487 |

TABLE 66-continued

| | | | |
|---|---|---|---|
| 305 | 73 | (cyclohexylmethyl, ethyl)-CH-CO₂H | 527 |

TABLE 67

| | | | |
|---|---|---|---|
| 306 | 73 | (cyclohexylmethyl)-CH(ethyl)-CO₂H | 527 |
| 307 | 73 | Ph-CH₂-CH(ethyl)-CO₂H | 521 |
| 308 | 73 | Ph-CH₂-CH(ethyl)-CO₂H | 521 |
| 309 | 73 | Me-(CH₂)₃-CH(ethyl)-CO₂H | 487 |
| 310 | 73 | Me-C(O)-NH-CH(ethyl)-CO₂H | 488 |
| 311 | 73 | HO₂C-CH(NH-C(O)-Me)-propyl | 502 |
| 312 | 73 | Ph-C(O)-NH-CH(ethyl)-CO₂H | 550 |
| 313 | 73 | HO₂C-CH(NH-C(O)-propyl)-CH₂Ph | 578 |
| 314 | 73 | 1-benzyl-4-methyl-pyrrolidine-3-CO₂H | 562 |

TABLE 68

Structure: R-substituted benzyl-pyrrolidine with (RS)/(SR) stereochemistry, phenyl, NH-CH(Me)-naphthyl

| EX | Syn | R | DATA (EP) |
|---|---|---|---|
| 74 | 74 | 2-Cl | 455 |
| 315 | 74 | 3-Cl | 455 |
| 316 | 74 | 4-Cl | 455 |
| 317 | 74 | 2-F | 439 |
| 318 | 74 | 3-F | 439 |
| 319 | 74 | 4-F | 439 |
| 320 | 74 | 2-OMe | 451 |
| 321 | 74 | 3-OMe | 451 |
| 322 | 74 | 4-OMe | 451 |
| 323 | 74 | 2-OH | 437 |
| 324 | 74 | 3-OH | 437 |
| 325 | 74 | 4-OH | 437 |
| 326 | 74 | 2-CF$_3$ | 489 |
| 327 | 74 | 3-CF$_3$ | 489 |
| 328 | 74 | 4-CF$_3$ | 489 |
| 329 | 74 | 2-CO$_2$H | 465 |
| 330 | 74 | 4-CO$_2$H | 465 |
| 331 | 74 | 4-NMe$_2$ | 464 |
| 332 | 74 | 4-NHAc | 478 |

TABLE 69

Structure: R¹-N-pyrrolidine with (RS)/(SR) stereochemistry, phenyl, NH-CH(Me)-naphthyl

| EX | Syn | R¹ | DATA (EP) |
|---|---|---|---|
| 333 | 74 | 4-phenyl-benzyl (biphenyl-CH₂) | 497 |
| 334 | 74 | 1-naphthylmethyl | 471 |
| 335 | 74 | 2-naphthylmethyl | 471 |
| 336 | 74 | 2-furylmethyl | 411 |

TABLE 69-continued

[Structure: R¹-N pyrrolidine (RS)-phenyl, (SR)-CH2-NH-CH(Me)-naphthyl]

| EX | Syn | R¹ | DATA (EP) |
|---|---|---|---|
| 337 | 74 | 3-ethylfuran | 411 |
| 338 | 74 | HO2C-furan-ethyl | 455 |
| 339 | 74 | 2-ethylthiophene | 427 |
| 340 | 74 | 3-ethylthiophene | 427 |
| 341 | 74 | HO2C-thiophene-ethyl | 471 |

TABLE 69-continued

[Structure: R¹-N pyrrolidine (RS)-phenyl, (SR)-CH2-NH-CH(Me)-naphthyl]

| EX | Syn | R¹ | DATA (EP) |
|---|---|---|---|
| 342 | 74 | 2-ethylthiazole | 428 |
| 343 | 74 | 3-ethylpyridine | 422 |

TABLE 70

| EX | Syn | R¹ | DATA |
|---|---|---|---|
| 344 | 74 | 4-ethylpyridine | 422 |
| 345 | 74 | nPr | 373 |
| 346 | 74 | Me—CH(Me)—CH2— | 387 |
| 347 | 74 | Me—C(Me)2—CH2— | 401 |
| 348 | 74 | MeO—(CH2)2— | 389 |
| 349 | 74 | HO2C—CH2— | 389 |
| 350 | 74 | Ph—(CH2)3— | 449 |
| 351 | 74 | Ph—CH=CH—CH2— (cinnamyl) | 447 |

TABLE 71

[Structure: CF3-C(O)-N pyrrolidine (RS)-R², (SR)-CH2-NH-CH(Me)-naphthyl]

| EX | Syn | R² | DATA |
|---|---|---|---|
| 75 | 75 | Me | FP: 365; NMR1: 0.89-1.02 (3H, m), 1.64 (3H, d, J = 6.8 Hz), 1.83-2.33 (2H, m), 2.67-2.78 (1H, m), 2.96-3.55 (3H, m), 3.65-4.13 (2H, m), 5.23-5.26 (1H, brm), 7.57-7.66 (3H, m), 7.83-7.89 (1H, m), 7.96 (1H, d, J = 8.4 Hz), 8.10 (1H, d, J = 8.0 Hz), 8.24 (1H, d, J = 8.4 Hz); Sal: oxalate |
| 352 | 75 | —CF3 | FP: 419; NMR1: 1.56-1.62 (3H, brt), 2.67-4.04 (8H, m), 5.11-5.16 (1H, m), 7.56-7.62 (3H, m), 7.79 (1H, t, J = 6.8 Hz), 7.92-8.01 (2H, m), 8.24 (1H, brd, J = 7.6 Hz); Sal: oxalate |
| 76 | 76 | 3-CF3-phenyl | FP: 495; NMR1: 1.59-1.65 (3H, m), 2.67-3.01 (3H, m), 3.26-3.71 (3H, m), 3.95 (0.5H, ddd, J = 4.4, 8.3, 12.2 Hz), 4.04-4.11 (0.5H, m), 4.21-4.26 (0.5H, m), 4.40-4.48 (0.5H, m), 5.22-5.34 (1H, m), 7.43-7.69 (7H, m), 7.88-8.01 (3H, m), 8.12-8.17 (1H, m), 9.30-9.46 (1H, brm), 9.71-10.08 (1H, brm); Sal: HCl |
| 353 | 76 | —CH2—Ph | FP: 441; NMR1: 1.68-1.70 (3H, m), 2.32-2.67 (3H, m), 2.77-2.89 (2H, m), 3.26-3.63 (4H, m), 3.89-4.00 (0.5H, m), 4.10-4.20 |

TABLE 71-continued

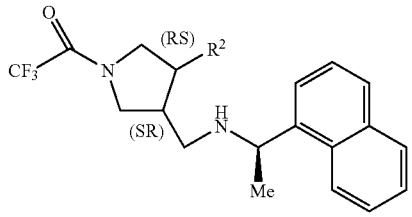

| EX | Syn | R² | DATA |
|---|---|---|---|
| | | | (0.5H, m), 5.28-5.37 (1H, m), 7.14-7.26 (5H, m), 7.60-7.68 (3H, m), 7.96 (1H, app.t, J = 7.3 Hz), 8.00-8.05 (2H, m), 8.18-8.24 (1H, m), 9.16-9.23 (1H, brm), 9.49-9.65 (brm, 0.5H), 9.85 (brs, 0.5H); Sal: HCl |
| 354 | 76 | —(CH₂)₂—Ph | FP: 455; NMR2: 1.30-1.42 (2H, m), 1.68-1.72 (3H, m), 1.77-1.85 (1H, m), 2.30-2.53 (3H, m), 2.80-3.38 (3H, m), 3.50-3.81 (2H, m), 4.28-4.57 (1H, m), 5.20-5.37 (1H, m), 6.83-7.01 (2H, m), 7.13-7.23 (3H, m), 7.51-7.66 (3H, m), 7.87-8.08 (3H, m), 8.18-8.27 (1H, m); Sal: HCl |

TABLE 72

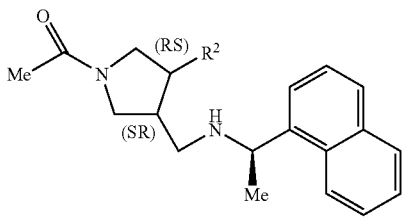

| EX | Syn | R² | DATA |
|---|---|---|---|
| 77 | 77 | (3-methylphenyl with CF₃) | FP; 441; NMR1: 1.61 (1.5H, d, J = 6.8 Hz), 1.94 (1.5H, d, J = 6.4 Hz), 1.98 (1.5H, s), 1.99 (1.5H, s), 2.70-2.85 (2H, m), 3.00-3.55 (4H, m), 3.75-3.94 (1H, m), 4.02-4.10 (1H, m), 5.24-5.36 (1H, m), 7.42-7.65 (7H, m), 7.80-8.01 (3H, m), 8.14-8.18 (1H, m), 9.00-9.34 (1.5H, brm), 9.60-9.75 (0.5H, brm); Sal: HCl |
| 355 | 77 | —CH₂—Ph | FP: 387; NMR1: 1.67-1.70 (1.5H, m), 1.82-1.86 (1.5H, m), 1.90-1.92 (3H, m), 2.29-2.46 (3H, m), 2.67-3.41 (6H, m), 3.79-3.86 (1H, m), 5.27-5.38 (1H, m), 7.11-7.26 (5H, m), 7.60-7.68 (3H, m), 7.90 (0.5H, d, J = 6.8 Hz), 7.96 (0.5H, d, J = 7.4 Hz), 8.00-8.05 (2H, m), 8.19-8.25 (1H, m), 9.00 (brs, 0.5H), 9.17 (brs, 1H), 9.69 (brs, 1H); Sal: HCl |
| 356 | 77 | —(CH₂)₂—Ph | FP: 401; NMR1: 1.32-1.48 (1H, m), 1.67-1.72 (3H, m), 1.91-1.93 (3H, m), 2.16-2.75 (3H, m), 2.86-3.29 (6H, m), 3.52-3.89 (2H, m), 5.30-5.39 (1H, m), 7.09-7.27 (5H, m), 7.57-7.66 (3H, m), 7.93-8.05 (3H, m), 8.23-8.26 (1H, m), 9.01-9.42 (brm, 1.5H), 9.76-9.98 (0.5H, m); Sal: HCl |

TABLE 73

| EX | Syn | R² | DATA |
|---|---|---|---|
| 79 | 79 | Me | FP: 397; NMR1: 0.88-0.95 (3H, m), 1.38 (3H, app. t, J = 6.4 Hz), 1.44-1.56 (4H, brm), 1.74-1.97 (2H, m), 2.16-2.22 (4H, m), 2.36-2.55 (1H, m), 2.58-2.77 (1H, m), 2.90-3.03 (1H, m), 3.10- |

TABLE 73-continued

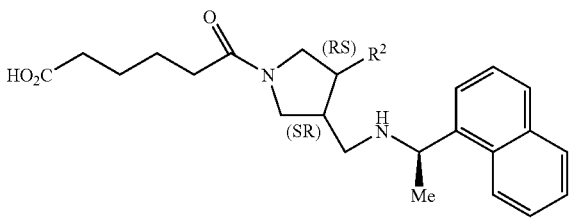

| EX | Syn | R² | DATA |
|---|---|---|---|
|  |  |  | 3.72 (4H, m), 4.50-4.58 (1H, m), 7.47-7.54 (3H, m), 7.68 (1H, d, J = 6.8 Hz), 7.78 (1H, d, J = 8.4 Hz), 7.92 (1H, d, J = 7.2 Hz), 8.26 (1H, d, J = 7.2 Hz) |
| 78 | 78 | —CH₂—Ph | EP: 473; NMR1: 1.34-1.59 (4H, m), 1.63-1.86 (3H, m), 2.01-2.45 (4H, m), 2.63-4.00 (11H, m), 5.15-5.45 (1H, m), 6.94-7.37 (5H, m), 7.51-7.79 (3H, m), 7.90-8.38 (4H, m); Sal: HCl |
| 357 | 78 | —(CH₂)₂—Ph | EP: 487; NMR1: 1.40-1.57 (4H, m), 1.59-1.82 (4H, m), 2.10-2.32 (4H, m), 2.31-4.02 (11H, m), 5.25-5.46 (1H, m), 7.03-7.31 (5H, m), 7.53-7.71 (3H, m), 7.91-8.12 (3H, m), 8.19-8.30 (1H, m); Sal: HCl |

TABLE 74

| EX | Syn | Structure | DATA |
|---|---|---|---|
| 80 | 80 | 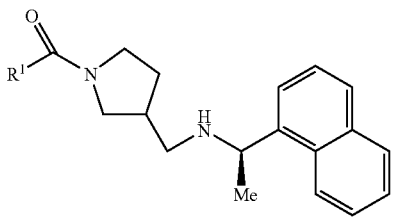 | FP: 379; NMR1: 0.76 (1.5H, d, J = 2.4 Hz), 0.82 (1.5H, d, J = 8.0 Hz), 0.97 (1.5H, d, J = 4.4 Hz), 1.00 (1.5H, s), 1.66 (3H, d, J = 6.0 Hz), 2.22-2.37 (1H, m), 2.74-3.55 (5H, m), 3.90-4.21 (1H, m), 5.25-5.35 (1H, m), 7.60-7.65 (3H, m), 7.84 (1H, dd, J = 4.4, 7.6 Hz), 7.97-8.03 (2H, m), 8.24 (1H, d, J = 8.4 Hz); Sal: oxalate |

TABLE 75

![structure]

| EX | Syn | R¹ | DATA |
|---|---|---|---|
| 81 | 81 | Ph | FP: 359; NMR1: 1.52-1.80 (4H, m), 1.92-2.18 (1H, m), 2.52-2.98 (2H, m), 3.30-3.85 (5H, m), 5.20-5.42 (1H, m), 7.36-7.53 (5H, m), 7.54-7.72 (3H, m), 7.90-8.14 (3H, m), 8.15-8.30 (1H, m), 9.08-9.52 (1H, m), 9.68-10.20 (1H, m); Sal: HCl |
| 358 | 64 | 2-amino-3-methylpyridin-yl | FP: 375; NMR1: 1.58-1.80 (3.5H, m), 2.00-2.18 (0.5H, m), 2.60-2.90 (2H, m), 2.95-3.82 (6H, m), 5.16-5.40 (1H, m), 6.92 (1H, dd, J = 6.5, 6.5), 7.52-7.70 (3H, m), 7.88-8.30 (8H, m), 9.14-9.68 (1H, m), 9.98-10.42 (1H, m); Sal: 2HCl |
| 359 | 64 | biphenyl-4-yl | FP: 435; NMR1: 1.56-1.78 (4H, m), 2.10 (1H, m), 2.58-2.98 (2H, m), 3.00-3.36 (2H, m), 3.40-3.62 (2H, m), 3.62-3.84 (1H, m), 5.20-5.42 (1H, m), 7.36-7.44 (1H, m), 7.45-7.53 (2H, m), 7.54-7.76 (9H, m), 7.90-8.10 (3H, m), 8.14-8.32 (1H, m), 9.04-9.52 (1H, m), 9.62-9.86 (0.5H, m), 10.01 (0.5H, m); Sal: HCl |

TABLE 75-continued

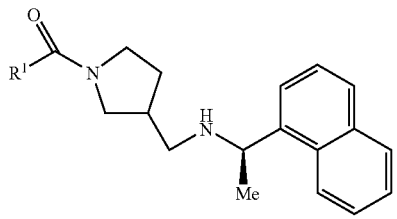

| EX | Syn | R¹ | DATA |
|---|---|---|---|
| 82 | 82 | MeO₂C—C₆H₄— | FP: 417; NMR1: 1.56-1.82 (4H, m), 1.86-2.18 (1H, m), 2.60-3.80 (7H, m), 3.80-3.90 (3H, m), 5.28-5.42 (1H, m), 7.50-7.75 (5H, m), 7.90-8.30 (6H, m), 9.00-10.20 (2H, m); Sal: HCl |
| 83 | 83 | HO₂C—C₆H₄— | FP: 403; NMR1: 1.60-1.76 (4H, m), 1.96-2.14 (1H, m), 2.60-3.64 (6.5H, m), 3.72-3.82 (0.5H, m), 5.20-5.40 (1H, m), 7.56-8.05 (10H, m), 8.16-8.30 (1H, m), 8.96-10.00 (2H, m), 13.14 (1H. m); Sal: HCl |

TABLE 76

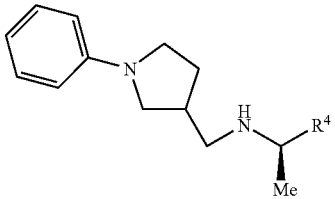

| EX | Syn | R⁴ | DATA |
|---|---|---|---|
| 84 | 84 | 1-naphthyl | EP: 331; NMR1: 1.46 (3H, d, J = 6.4 Hz), 1.67 (1H, m), 2.07 (1H, m), 2.35-2.55 (2H, m), 2.67 (1H, m), 2.94 (1H, m), 3.10-3.27 (2H, m), 3.36 (1H, m), 4.75 (1H, m), 6.42-6.51 (2H, m), 6.52-6.61 (3H, m), 7.07-7.18 (2H, m), 7.45-7.60 (3H, m), 7.75 (1H, m), 7.82 (1H, m), 7.94 (1H, m), 8.28 (1H, m); Sal: fumarate |
| 85 | 85 | 3-MeO-C₆H₄— | EP: 311; NMR1: 1.37 (3H, d, J = 6.6 Hz), 1.67 (1H, m), 2.08 (1H, m), 2.38-2.54 (2H, m), 2.63 (1H, m), 2.92 (1H, m), 3.10-3.28 (2H, m), 3.34 (1H, m), 3.74 (3H), 3.92 (1H, m), 6.47 (2H, d, J = 8.6), 6.52-6.60 (3H, m), 6.84 (1H, m), 6.94-7.06 (2H, m), 7.08-7.18 (2H, m), 7.26 (1H, m); Sal: fumarate |

TABLE 77

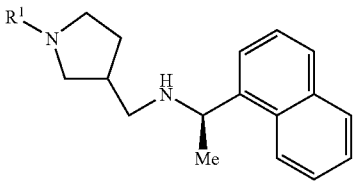

| EX | Syn | R¹ | DATA |
|---|---|---|---|
| 86 | 86 | PhCH₂CH₂— | EP: 345; NMR1: 1.40-1.52 (1H, m), 1.47 (3H, d, J = 6.8), 1.96 (1H, ddd, J = 7.5, 13.6, 13.6 Hz), 2.35-2.55 (3H, m), 2.61-2.75 (3H, m), 2.77-2.88 (1H, m), 3.70-3.81 (2H, m), 4.78-4.87 (1H, m), 6.57 (4H, s), 7.25-7.36 (5H, m), 7.49-7.59 (3H, m), 7.74 (1H, d, J = 6.9 Hz), 7.81 (1H, d, J = 8.3 Hz), 7.93-7.98 (1H, m), 8.23 (1H, d, J = 7.8 Hz); Sal: 2fumarate |

TABLE 77-continued

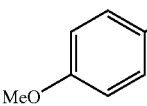

| EX | Syn | R¹ | DATA |
|---|---|---|---|
| 87 | 87 | | FP: 345; NMR1: 1.38-1.51 (4H, m), 1.86-1.98 (1H, m), 2.37-2.52 (3H, m), 2.61-2.74 (3H, brm), 2.78-2.90 (1H, brm), 3.73-3.80 (2H, m), 4.78-4.90 (1H, brm), 6.57 (4H, s), 7.25-7.38 (5H, m), 7.50-7.59 (3H, m), 7.72 (1H, d, J = 7.3 Hz), 7.87 (1H, d, J = 8.3 Hz), 7.92-7.98 (1H, m), 8.23 (1H, d, J = 7.4 Hz); Sal: 2fumarate |
| 360 | 86 | MeO–⟨benzyl⟩– | EP: 375; NMR1: 1.59 (3H, d, J = 6.4 Hz), 1.62 (1H, m), 2.11 (1H, m), 2.54-3.30 (7H, m), 3.76 (3H, s), 4.13 (2H, s), 5.15 (1H, m), 6.95 (2H, d, J = 8.5 Hz), 7.37 (2H, d, J = 8.5 Hz), 7.53-7.66 (3H, m), 7.82 (1H, d, J = 7.0 Hz), 7.92-8.04 (2H, m), 8.21 (1H, d, J = 8.4 Hz); Sal: oxalate |
| 361 | 87 | | EP: 375; NMR1: 1.58 (3H, d, J = 6.6 Hz), 1.65 (1H, m), 2.08 (1H, m), 2.54-3.30 (7H, m), 3.76 (3H, s), 4.11 (2H, s), 5.12 (1H, m), 6.96 (2H, d, J = 8.5 Hz), 7.36 (2H, d, J = 8.5 Hz), 7.53-7.66 (3H, m), 7.79 (1H, d, J = 7.3 Hz), 7.91-8.04 (2H, m), 8.22 (1H, d, J = 7.9 Hz); Sal: oxalate |

TABLE 78

| EX | Syn | R¹ | R⁴ | DATA |
|---|---|---|---|---|
| 88 | 88 | Ph | 3-methoxyphenyl | EP: 325; NMR1: 1.61 (3H, d, J = 6.8 Hz), 2.30-2.60 (2H, m), 2.60-3.20 (3H, m), 3.60-3.76 (1H, m), 3.78-3.79 (3H, m), 3.90-4.01 (1H, m), 4.38 (1H, m), 6.97 (1H, m), 7.08-7.19 (2H, m), 7.27-7.43 (4H, m), 7.52-7.69 (2H, m), 9.30-9.90 (2H, brm); Sal: HCl |
| 89 | 89 | Ph—CH₂— | 1-naphthyl | FP; 359; NMR1 (80° C.): 1.71 (3H, d, J = 6.6 Hz), 2.24 (1H, ddd, J = 7.0, 16.6, 23.4 Hz), 2.46-2.56 (1H, m), 2.76-2.92 (2H, m), 2.98-3.13 (2H, m), 3.38 (1H, ddd, J = 7.8, 9.8, 9.8 Hz), 4.26 (1H, d, J = 14.9 Hz), 4.37 (1H, dd, J = 6.1, 14.9 Hz), 5.16-5.30 (1H, br), 7.14-7.20 (2H, m), 7.21-7.34 (3H, m), 7.54-7.64 (3H, m), 7.92-8.06 (3H, m) 8.18 (1H, d, J = 8.0 Hz), 9.20-9.40 (1H, br), 9.90-10.10 (1H, br); Sal: HCl |
| 90 | 90 | cyclohexyl | 1-naphthyl | FP: 351; NMR1: 0.90-1.20 (1H, m), 1.20-1.80 (12H, m), 2.05-2.17 (1H, m), 2.37-2.47 (1H, m), 2.67-2.90 (2H, m), 3.00-3.15 (2H, m), 3.20-3.50 (1H, m), 3.55-3.71 (1H, m), 5.25-5.37 (1H, m), 7.56-7.67 (3H, m), 7.95-8.11 (3H, m), 8.24 (1H, d, J = 8.3 Hz), 9.30-9.50 (1H, br), 9.96-10.12 (1H, br); Sal: HCl |

TABLE 79

| No | R¹—X— |
|----|-------|
| 1 | HO₂C–C₆H₄– (4-) |
| 2 | 3,5-difluoro-4-methylbenzoic acid |
| 3 | 5-(4-methylphenyl)-1H-tetrazole |
| 4 | 4-(acetyloxy)benzoic acid |
| 5 | 4-(acetylamino)benzoic acid |
| 6 | 4-(acetylamino)-3-methoxybenzoic acid |
| 7 | 2,2-dimethyl-5-oxohexanoic acid |
| 8 | 3,3-dimethyl-6-oxoheptanoic acid |

TABLE 80

| No | R¹—X— |
|----|-------|
| 9 | HO₂C–C₆H₄– (4-) |
| 10 | 3,5-difluoro-4-methylbenzoic acid |
| 11 | 5-(4-methylphenyl)-1H-tetrazole |
| 12 | 4-(acetylamino)benzoic acid |
| 13 | 4-(acetylamino)-3-methoxybenzoic acid |
| 14 | 2,2-dimethyl-5-oxohexanoic acid |
| 15 | 3,3-dimethyl-6-oxoheptanoic acid |
| 414 | 4-(acetyloxy)benzoic acid |

TABLE 81

| No | R¹—X— |
|----|-------|
| 16 | 4-methylbenzoic acid |
| 17 | 3,5-difluoro-4-methylbenzoic acid |
| 18 | 5-(4-methylphenyl)-1H-tetrazole |
| 19 | 4-acetamidobenzoic acid |
| 20 | 4-acetamido-3-methoxybenzoic acid |
| 21 | 2,2-dimethyl-5-oxohexanoic acid |
| 22 | 3,3-dimethyl-5-oxohexanoic acid |
| 415 | 4-acetoxybenzoic acid |

TABLE 82

| No | R¹—X— |
|----|-------|
| 23 | 4-methylbenzoic acid |
| 24 | 3,5-difluoro-4-methylbenzoic acid |
| 25 | 5-(4-methylphenyl)-1H-tetrazole |
| 26 | 4-acetamidobenzoic acid |
| 27 | 4-acetamido-3-methoxybenzoic acid |
| 28 | 2,2-dimethyl-5-oxohexanoic acid |
| 29 | 3,3-dimethyl-5-oxohexanoic acid |
| 416 | 4-acetoxybenzoic acid |

TABLE 83

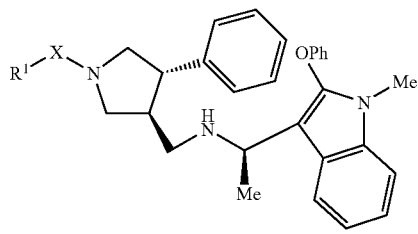

| No | R¹—X— |
|---|---|
| 30 | HO₂C-C₆H₄- (4-carboxyphenyl) |
| 31 | 3,5-diF-4-carboxyphenyl |
| 32 | 5-(4-methylphenyl)-1H-tetrazole |
| 33 | 4-acetamido-benzoic acid |
| 34 | 4-acetamido-3-methoxy-benzoic acid |
| 35 | HO₂C-C(Me)₂-CH₂-CH₂-C(O)-Me |
| 36 | HO₂C-CH₂-C(Me)₂-CH₂-C(O)-Me |
| 417 | 4-acetoxy-benzoic acid |

TABLE 84

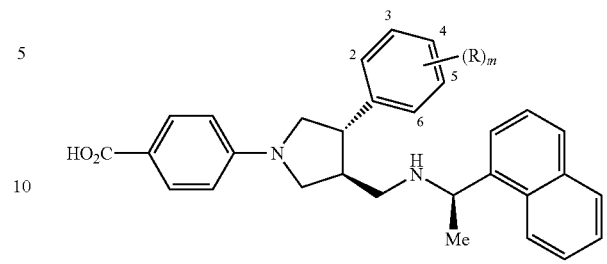

| No | —(R)ₘ |
|---|---|
| 37 | 2-F |
| 38 | 3-F |
| 39 | 4-F |
| 40 | 2-Cl |
| 41 | 3-Cl |
| 42 | 4-Cl |
| 43 | 2-Br |
| 44 | 3-Br |
| 45 | 4-Br |
| 46 | 2-NO$_2$ |
| 47 | 3-NO$_2$ |
| 48 | 4-NO$_2$ |
| 49 | 2-CN |
| 50 | 3-CN |
| 51 | 4-CN |
| 52 | 2-CO$_2$Me |
| 53 | 3-CO$_2$Me |
| 54 | 4-CO$_2$Me |
| 55 | 2-Me |
| 56 | 3-Me |
| 57 | 4-Me |
| 58 | 2-OMe |
| 59 | 3-OMe |
| 60 | 4-OMe |
| 61 | 2-CF$_3$ |
| 62 | 3-CF$_3$ |
| 63 | 4-CF$_3$ |
| 64 | 2,3-diF |
| 65 | 2,4-diF |
| 66 | 2,5-diF |
| 67 | 2,6-diF |
| 68 | 3,4-diF |
| 69 | 3,5-diF |
| 70 | 3,6-diF |
| 71 | 2,3,4-triF |
| 72 | 2,3,5-triF |
| 73 | 2,3,6-triF |

TABLE 85

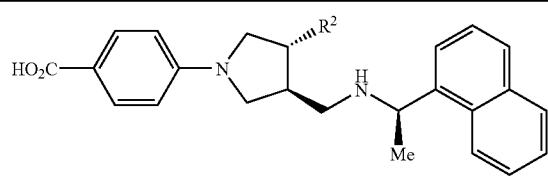

| No | R² |
|---|---|
| 74 | 8-methylnaphthalen-1-yl |

TABLE 85-continued
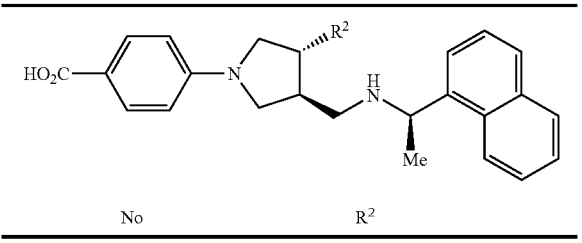
| No | R² |
|---|---|
| 75 | 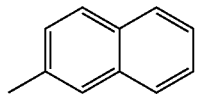 |
| 76 | 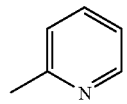 |
| 77 | 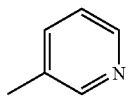 |
| 78 | 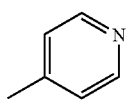 |
| 79 | 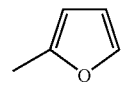 |
| 80 | 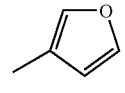 |
| 81 | 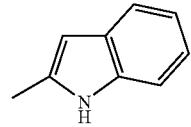 |
| 82 | 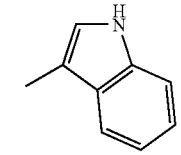 |
| 83 | 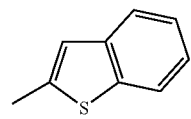 |
| 84 | 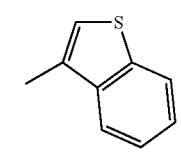 |
| 85 | 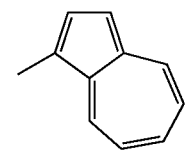 |
TABLE 85-continued
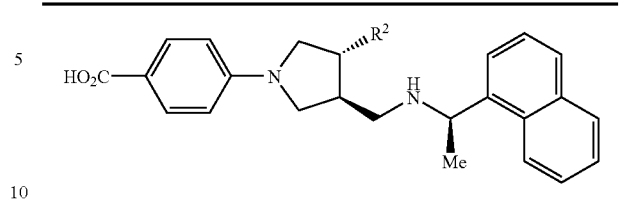
| No | R² |
|---|---|
| 86 | 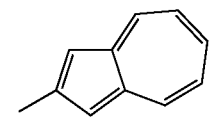 |
| 87 | —CH₂—Ph |
| 88 | —(CH₂)₂—Ph |
| 89 | —(CH₂)₃—Ph |
| 90 | nBu |
| 91 | iBu |
| 92 | —CH₂-cPr |
TABLE 86
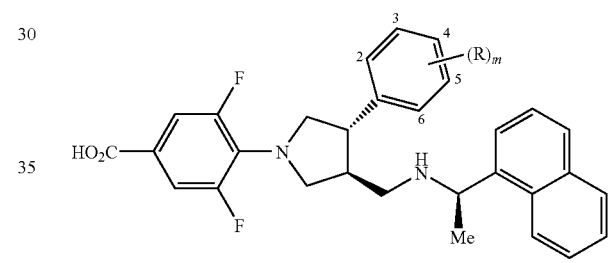
| No | —(R)ₘ |
|---|---|
| 93 | 2-F |
| 94 | 4-F |
| 95 | 2-Cl |
| 96 | 3-Cl |
| 97 | 4-Cl |
| 98 | 2-Br |
| 99 | 3-Br |
| 100 | 4-Br |
| 101 | 2-NO₂ |
| 102 | 3-NO₂ |
| 103 | 4-NO₂ |
| 104 | 2-CN |
| 105 | 3-CN |
| 106 | 4-CN |
| 107 | 2-CO₂Me |
| 108 | 3-CO₂Me |
| 109 | 4-CO₂Me |
| 110 | 2-Me |
| 111 | 4-Me |
| 112 | 2-OMe |
| 113 | 3-OMe |
| 114 | 4-OMe |
| 115 | 2-CF₃ |
| 116 | 4-CF₃ |
| 117 | 2,4-diF |
| 118 | 2,5-diF |
| 119 | 2,6-diF |
| 120 | 3,4-diF |
| 121 | 3,5-diF |
| 122 | 3,6-diF |

TABLE 87
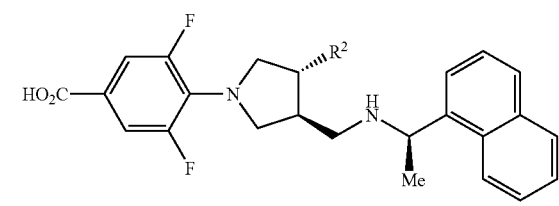
| No | R² |
|---|---|
| 123 | 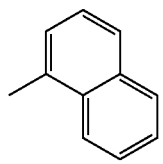 |
| 124 | 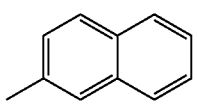 |
| 125 | 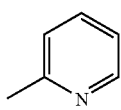 |
| 126 | 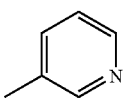 |
| 127 | 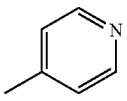 |
| 128 | 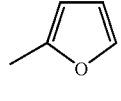 |
| 129 | 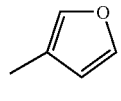 |
| 130 | —(CH₂—Ph |
| 131 | —(CH₂)₂—Ph |
| 132 | —(CH₂)₃—Ph |
| 133 | nBu |
| 134 | iBu |
| 135 | —CH₂-cPr |
TABLE 88
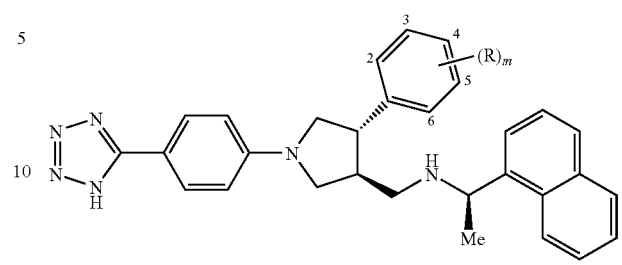
| No | —(R)ₘ |
|---|---|
| 136 | 2-F |
| 137 | 3-F |
| 138 | 4-F |
| 139 | 2-Cl |
| 140 | 3-Cl |
| 141 | 4-Cl |
| 142 | 2-Br |
| 143 | 3-Br |
| 144 | 4-Br |
| 145 | 2-NO₂ |
| 146 | 3-NO₂ |
| 147 | 4-NO₂ |
| 148 | 2-CN |
| 149 | 3-CN |
| 150 | 4-CN |
| 151 | 2-CO₂Me |
| 152 | 3-CO₂Me |
| 153 | 4-CO₂Me |
| 154 | 2-Me |
| 155 | 3-Me |
| 156 | 4-Me |
| 157 | 2-OMe |
| 158 | 3-OMe |
| 159 | 4-OMe |
| 160 | 2-CF₃ |
| 161 | 3-CF₃ |
| 162 | 4-CF₃ |
| 163 | 2,3-diF |
| 164 | 2,4-diF |
| 165 | 2,5-diF |
| 166 | 2,6-diF |
| 167 | 3,4-diF |
| 168 | 3,5-diF |
| 169 | 3,6-diF |
TABLE 89
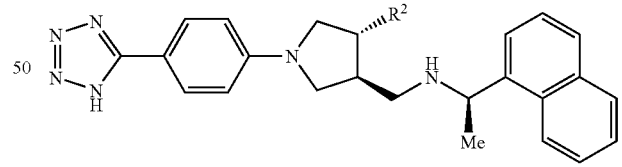
| No | R² |
|---|---|
| 170 | 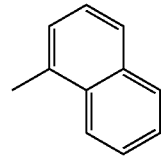 |
| 171 | 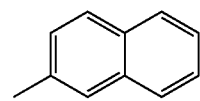 |

TABLE 89-continued
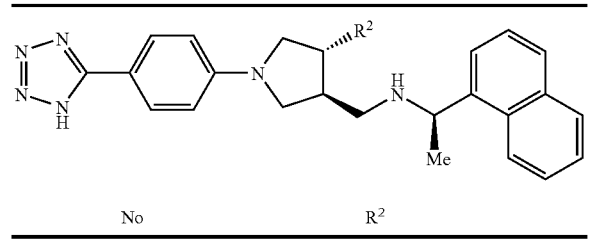
| No | R² |
|---|---|
| 172 | 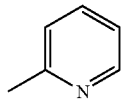 |
| 173 | 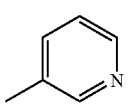 |
| 174 | 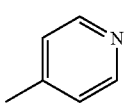 |
| 175 | 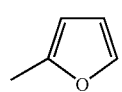 |
| 176 | 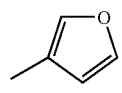 |
| 177 | —CH₂—Ph |
| 178 | —(CH₂)₂—Ph |
| 179 | —(CH₂)₃—Ph |
| 180 | nBu |
| 181 | iBu |
| 182 | —CH₂-cPr |
TABLE 90
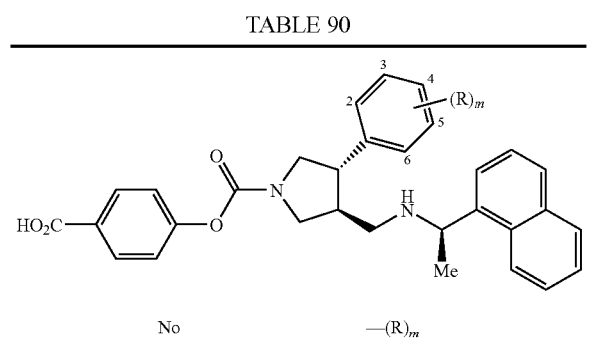
| No | —(R)ₘ |
|---|---|
| 183 | 2-Cl |
| 184 | 3-Cl |
| 185 | 4-Cl |
| 186 | 2-Br |
| 187 | 3-Br |
| 188 | 4-Br |
| 189 | 2-NO₂ |
| 190 | 3-NO₂ |
| 191 | 4-NO₂ |
| 192 | 2-CN |
| 193 | 3-CN |
| 194 | 4-CN |
| 195 | 2-CO₂Me |
| 196 | 3-CO₂Me |
| 197 | 4-CO₂Me |
TABLE 90-continued
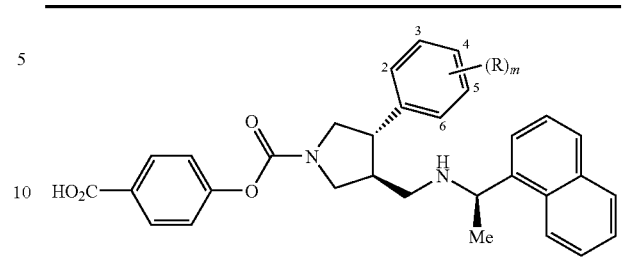
| No | —(R)ₘ |
|---|---|
| 198 | 4-Me |
| 199 | 2-OMe |
| 200 | 3-OMe |
| 201 | 4-OMe |
| 202 | 2-CF₃ |
| 203 | 4-CF₃ |
| 204 | 2,5-diF |
| 205 | 2,6-diF |
| 206 | 3,4-diF |
| 207 | 3,5-diF |
| 208 | 3,6-diF |
| 209 | 2,3,4-triF |
| 210 | 2,3,5-triF |
| 211 | 2,3,6-triF |
TABLE 91
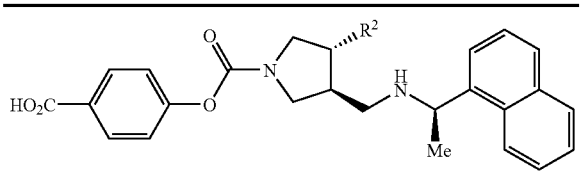
| No | R² |
|---|---|
| 212 | 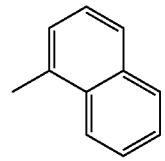 |
| 213 | 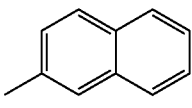 |
| 214 | 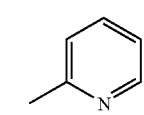 |
| 215 | 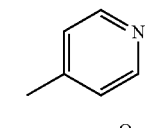 |
| 216 | 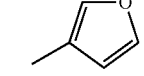 |

TABLE 91-continued
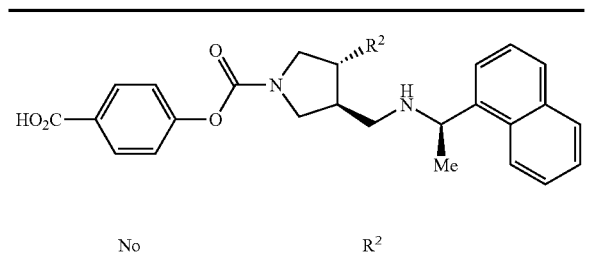
| No | R² |
|---|---|
| 217 | 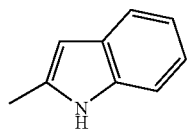 |
| 218 | 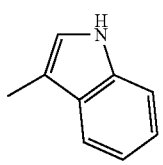 |
| 219 | 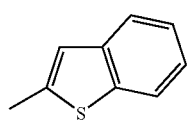 |
| 220 | 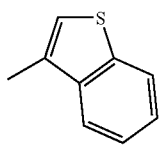 |
| 221 | 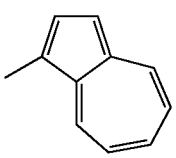 |
| 222 | 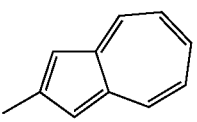 |
| 223 | —CH₂—Ph |
| 224 | —(CH₂)₂—Ph |
| 225 | —(CH₂)₃—Ph |
| 226 | nBu |
| 227 | iBu |
| 228 | —CH₂-cPr |
TABLE 92
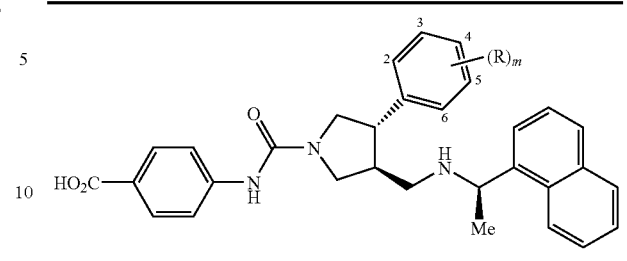
| No | —(R)ₘ |
|---|---|
| 229 | 2-F |
| 230 | 3-F |
| 231 | 4-F |
| 232 | 2-Cl |
| 233 | 3-Cl |
| 234 | 4-Cl |
| 235 | 2-Br |
| 236 | 3-Br |
| 237 | 4-Br |
| 238 | 2-NO₂ |
| 239 | 3-NO₂ |
| 240 | 4-NO₂ |
| 241 | 2-CN |
| 242 | 3-CN |
| 243 | 4-CN |
| 244 | 2-CO₂Me |
| 245 | 3-CO₂Me |
| 246 | 4-CO₂Me |
| 247 | 2-Me |
| 248 | 3-Me |
| 249 | 4-Me |
| 250 | 2-OMe |
| 251 | 3-OMe |
| 252 | 4-OMe |
| 253 | 2-CF₃ |
| 254 | 3-CF₃ |
| 255 | 4-CF₃ |
| 256 | 2,3-diF |
| 257 | 2,4-diF |
| 258 | 2,5-diF |
| 259 | 2,6-diF |
| 260 | 3,4-diF |
| 261 | 3,5-diF |
| 262 | 3,6-diF |
| 263 | 2,3,4-triF |
| 264 | 2,3,5-triF |
| 265 | 2,3,6-triF |
TABLE 93
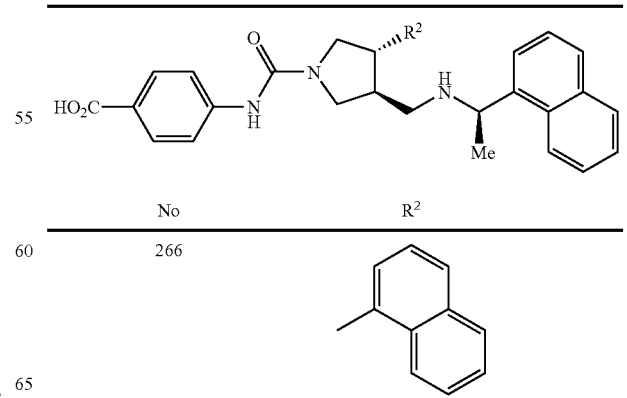
| No | R² |
|---|---|
| 266 | 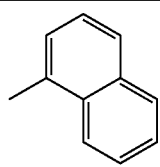 |

TABLE 93-continued
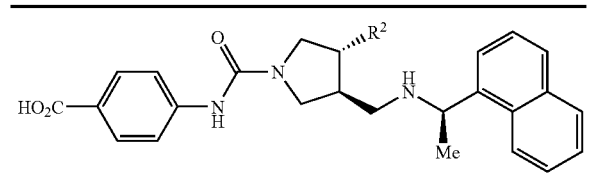
| No | R² |
|---|---|
| 267 | 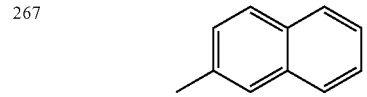 |
| 268 |  |
| 269 |  |
| 270 |  |
| 271 |  |
| 272 |  |
| 273 | 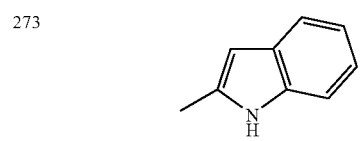 |
| 274 | 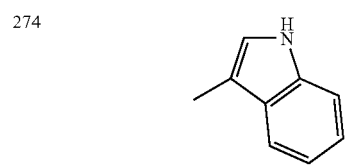 |
| 275 | 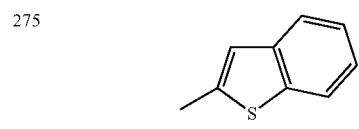 |
| 276 | 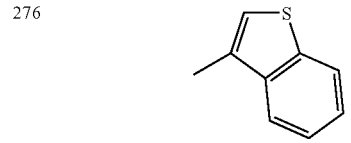 |
| 277 | 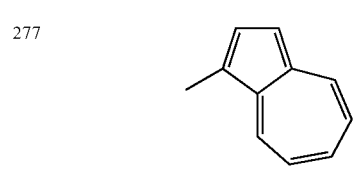 |
TABLE 93-continued
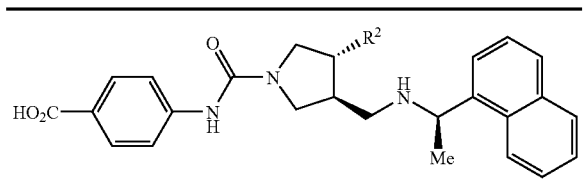
| No | R² |
|---|---|
| 278 | 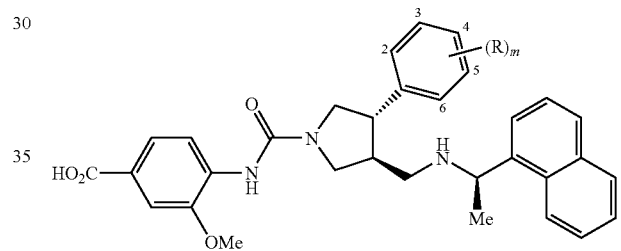 |
| 279 | —CH₂—Ph |
| 280 | —(CH₂)₂—Ph |
| 281 | —(CH₂)₃—Ph |
| 282 | nBu |
| 283 | iBu |
| 284 | —CH₂-cPr |
TABLE 94
| No | —(R)ₘ |
|---|---|
| 285 | 2-F |
| 286 | 4-F |
| 287 | 2-Cl |
| 288 | 3-Cl |
| 289 | 4-Cl |
| 290 | 2-Br |
| 291 | 3-Br |
| 292 | 4-Br |
| 293 | 2-NO₂ |
| 294 | 3-NO₂ |
| 295 | 4-NO₂ |
| 296 | 2-CN |
| 297 | 3-CN |
| 298 | 4-CN |
| 299 | 2-CO₂Me |
| 300 | 3-CO₂Me |
| 301 | 4-CO₂Me |
| 302 | 2-Me |
| 303 | 4-Me |
| 304 | 2-OMe |
| 305 | 3-OMe |
| 306 | 4-OMe |
| 307 | 2-CF₃ |
| 308 | 4-CF₃ |
| 309 | 2,4-diF |
| 310 | 2,5-diF |
| 311 | 2,6-diF |
| 312 | 3,4-diF |
| 313 | 3,5-diF |
| 314 | 3,6-diF |

TABLE 95
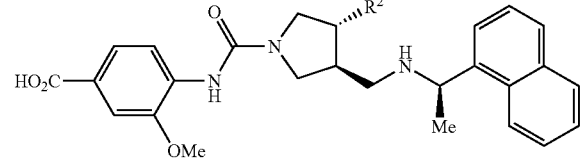
| No | R² |
|---|---|
| 315 | 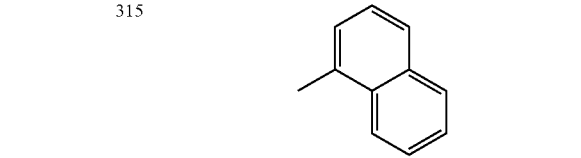 |
| 316 | 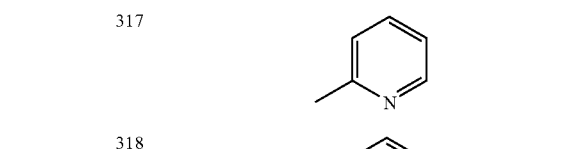 |
| 317 | 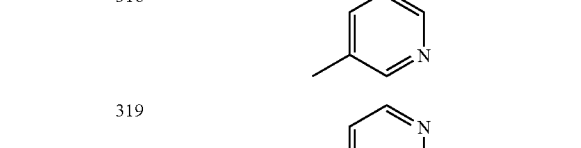 |
| 318 | 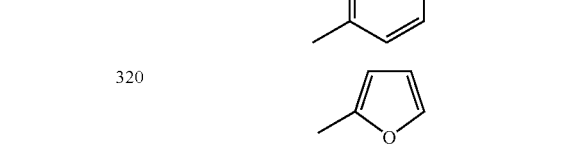 |
| 319 | 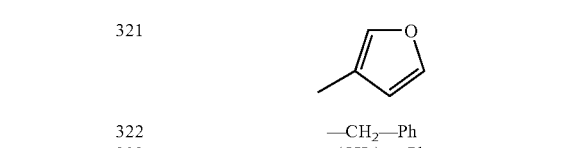 |
| 320 | 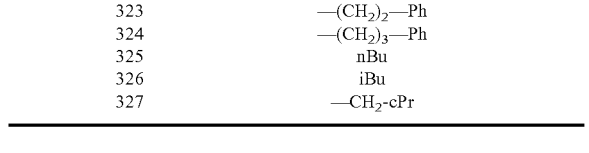 |
| 321 | 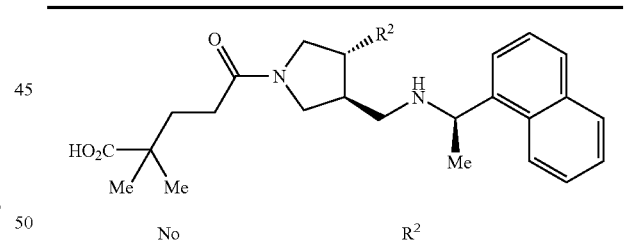 |
| 322 | —CH₂—Ph |
| 323 | —(CH₂)₂—Ph |
| 324 | —(CH₂)₃—Ph |
| 325 | nBu |
| 326 | iBu |
| 327 | —CH₂-cPr |
TABLE 96
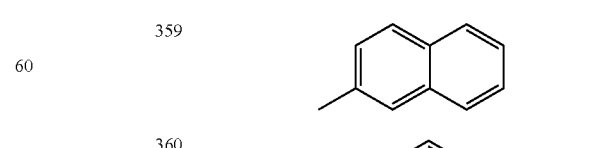
| No | —(R)ₘ |
|---|---|
| 328 | 2-F |
| 329 | 4-F |
TABLE 96-continued
| No | —(R)ₘ |
|---|---|
| 330 | 2-Cl |
| 331 | 3-Cl |
| 332 | 4-Cl |
| 333 | 2-Br |
| 334 | 3-Br |
| 335 | 4-Br |
| 336 | 2-NO₂ |
| 337 | 3-NO₂ |
| 338 | 4-NO₂ |
| 339 | 2-CN |
| 340 | 3-CN |
| 341 | 4-CN |
| 342 | 2-CO₂Me |
| 343 | 3-CO₂Me |
| 344 | 4-CO₂Me |
| 345 | 2-Me |
| 346 | 4-Me |
| 347 | 2-OMe |
| 348 | 3-OMe |
| 349 | 4-OMe |
| 350 | 2-CF₃ |
| 351 | 4-CF₃ |
| 352 | 2,4-diF |
| 353 | 2,5-diF |
| 354 | 2,6-diF |
| 355 | 3,4-diF |
| 356 | 3,5-diF |
| 357 | 3,6-diF |
TABLE 97
| No | R² |
|---|---|
| 358 | 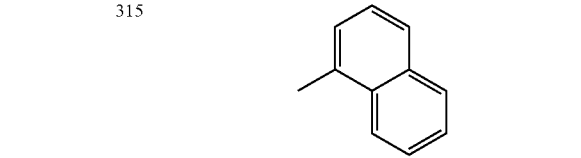 |
| 359 | 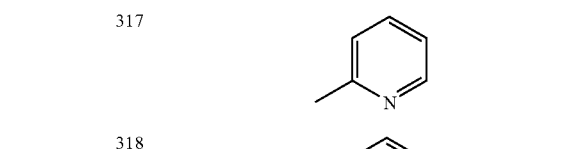 |
| 360 | 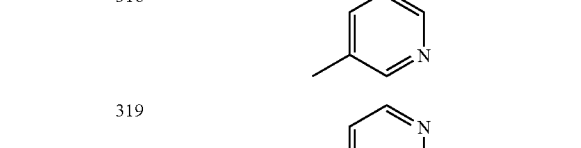 |

TABLE 97-continued
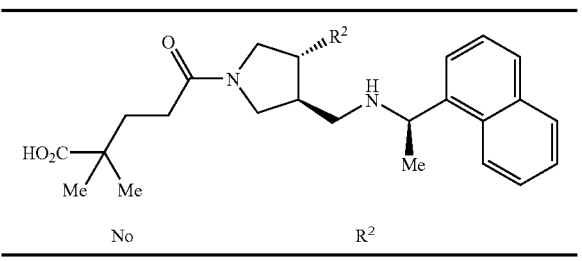
| No | R² |
|---|---|
| 361 | 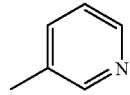 |
| 362 | 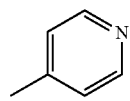 |
| 363 | 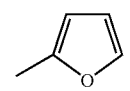 |
| 364 | 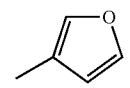 |
| 365 | —CH₂—Ph |
| 366 | —(CH₂)₂—Ph |
| 367 | —(CH₂)₃—Ph |
| 368 | nBu |
| 369 | iBu |
| 370 | —CH₂-cPr |
TABLE 98
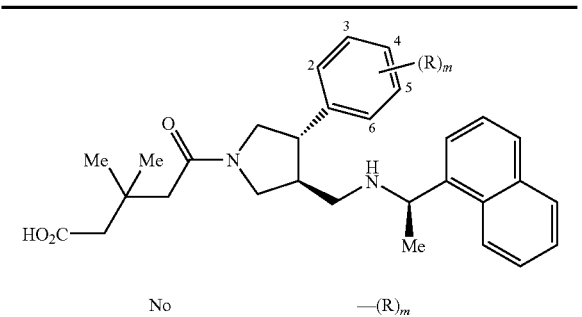
| No | —(R)ₘ |
|---|---|
| 371 | 2-F |
| 372 | 4-F |
| 373 | 2-Cl |
| 374 | 3-Cl |
| 375 | 4-Cl |
| 376 | 2-Br |
| 377 | 3-Br |
| 378 | 4-Br |
| 379 | 2-NO₂ |
| 380 | 3-NO₂ |
| 381 | 4-NO₂ |
| 382 | 2-CN |
| 383 | 3-CN |
| 384 | 4-CN |
| 385 | 2-CO₂Me |
| 386 | 3-CO₂Me |
| 387 | 4-CO₂Me |
| 388 | 2-Me |
| 389 | 4-Me |
| 390 | 2-OMe |
TABLE 98-continued
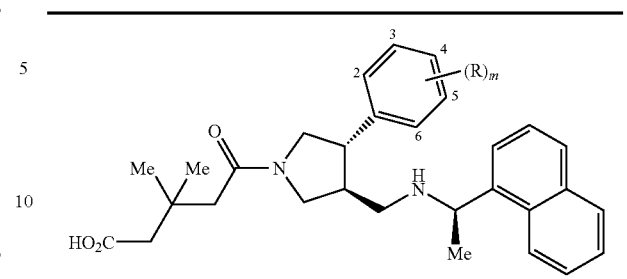
| No | —(R)ₘ |
|---|---|
| 391 | 3-OMe |
| 392 | 4-OMe |
| 393 | 2-CF₃ |
| 394 | 4-CF₃ |
| 395 | 2,4-diF |
| 396 | 2,5-diF |
| 397 | 2,6-diF |
| 398 | 3,4-diF |
| 399 | 3,5-diF |
| 400 | 3,6-diF |
TABLE 99
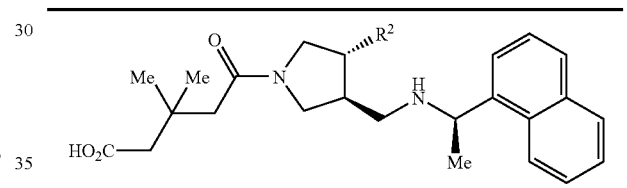
| No | R² |
|---|---|
| 401 | 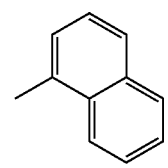 |
| 402 | 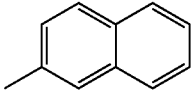 |
| 403 | 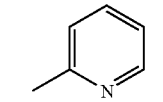 |
| 404 | 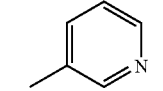 |
| 405 | 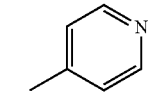 |
| 406 | 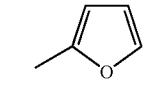 |

TABLE 99-continued

| No | R² |
|----|-----|
| 407 | (3-methylfuran) |
| 408 | —CH₂—Ph |
| 409 | —(CH₂)₂—Ph |
| 410 | —(CH₂)₃—Ph |
| 411 | nBu |
| 412 | iBu |
| 413 | —CH₂-cPr |

INDUSTRIAL APPLICABILITY

Since the compounds of the invention are excellent in the CaSR agonistic regulatory activity and also excellent in the selectivity with CYP2D6 inhibitory activity having a possibility of causing drug interaction, they are useful as therapeutic agents for diseases in which CaSR is concerned (hyperparathyroidism, renal osteodystrophy, hypercalcemia and the like).

The invention claimed is:

1. A pyrrolidine derivative represented by a general formula (I) or a pharmaceutically acceptable salt thereof

[signs in the formula have the following meanings;
A and B: each independently —C($R^7$)($R^{7a}$)— or —C(O)—,
$R^7$ and $R^{7a}$: each independently —H, lower alkyl, aryl or —C(O)OR°,
R°: —H or lower alkyl,
X: single bond, *—C(O)—, *—OC(O)—, *—N($R^8$)C(O)— or *—S(O)$_n$—, wherein * represents bonding to $R^1$,
$R^8$: —H, lower alkyl or lower alkylene-aryl,
n: 0, 1 or 2,
$R^1$: —H, or $C_{1-12}$ alkyl, lower alkenyl, aryl, hetero ring group or cycloalkyl, which may respectively be substituted,
$R^2$ and $R^3$: each independently —H, lower alkyl, halogeno lower alkyl, —OC(O)—R°, cycloalkyl, lower alkylene-cycloalkyl, aryl, lower alkylene-aryl, hetero ring group or lower alkylene-hetero ring group, wherein the aryl and hetero ring group in $R^2$ and $R^3$ may be substituted respectively,
or $R^2$ and $R^3$ in combination may form cycloalkyl ring or hetero ring, which may respectively be substituted, together with the carbon atom to which they are bonded,
$R^4$: aryl or hetero ring group, which may respectively be substituted,
$R^5$: lower alkyl or halogeno lower alkyl, and
$R^6$: —H, lower alkyl or halogeno lower alkyl,
with the proviso that when $R^4$ is unsubstituted phenyl, at least one of $R^2$ and $R^3$ is not —H].

2. The compound described in claim 1, wherein $R^6$ is —H.

3. The compound described in claim 2, wherein $R^5$ is methyl.

4. The compound described in claim 3, wherein A and B are —CH₂—.

5. The compound described in claim 4, wherein $R^3$ is —H.

6. The compound described in claim 5, wherein $R^4$ is aryl which may be substituted with —O-lower alkyl.

7. The compound described in claim 6, wherein $R^2$ is phenyl which may be substituted with a group selected from the class consisting of halogen, lower alkyl and halogeno lower alkyl.

8. The compound described in claim 7, wherein $R^1$—X— is HO₂C-lower alkylene-OC(O)—; HO₂C-lower alkylene-C(O)—; (cycloalkyl substituted with —CO₂H)—OC(O)—; (cycloalkyl substituted with —CO₂H)—C(O)—; phenyl which is substituted with —CO₂H and may be further substituted with a group selected from the class consisting of halogen, halogeno lower alkyl and —O-lower alkyl; (phenyl which is substituted with —CO₂H and may be further substituted with a group selected from the class consisting of halogen, halogeno lower alkyl and —O-lower alkyl)-OC(O)—; or (phenyl which is substituted with —CO₂H and may be further substituted with a group selected from the class consisting of halogen, halogeno lower alkyl and —O-lower alkyl)-NHC(O)—.

9. The compound or a pharmaceutically acceptable salt thereof described in claim 1, which is selected from the group consisting of
4-({[(3S,4S)-3-({[(1R)-1-(1-naphthyl)ethyl]amino}methyl)-4-phenylpyrrolidin-1-yl]carbonyl}oxy)benzoic acid,
3-(5-{(3S,4S)-3-({[(1R)-1-(1-naphthyl)ethyl]amino}methyl)-4-phenylpyrrolidin-1-yl]carbonyl}-2-furyl)thiophene-2-carboxylic acid,
6-{(3S,4S)-3-({[(1R)-1-(1-naphthyl)ethyl]amino}methyl)-4-[3-(trifluoromethyl)phenyl]pyrrolidin-1-yl}-6-oxohexanoic acid,
4-[(3S,4S)-3-({[(1R)-1-(1-naphthyl)ethyl]amino}methyl)-4-phenylpyrrolidin-1-yl]benzoic acid,
3,3-dimethyl-5-[(3S,4S)-3-({[(1R)-1-(1-naphthyl)ethyl]amino}methyl)-4-phenylpyrrolidin-1-yl]-5-oxopentanoic acid,
4-({[(3S,4S)-3-({[(1R)-1-(1-naphthyl)ethyl]amino}methyl)-4-phenylpyrrolidin-1-yl]carbonyl}amino)benzoic acid,
2,2-dimethyl-5-[(3S,4S)-3-({[(1R)-1-(1-naphthyl)ethyl]amino}methyl)-4-phenylpyrrolidin-1-yl]-5-oxopentanoic acid,
4-[({(3S,4S)-3-({[(1R)-1-(1-naphthyl)ethyl]amino}methyl)-4-[3-(trifluoromethyl)phenyl]pyrrolidin-1-yl}carbonyl)oxy]benzoic acid,
4-({[(3S,4S)-3-(3-fluorophenyl)-4-({[(1R)-1-(1-naphthyl)ethyl]amino}methyl)pyrrolidin-1-yl]carbonyl}oxy)benzoic acid,
4-({[(3S,4S)-3-(3-methylphenyl)-4-({[(1R)-1-(1-naphthyl)ethyl]amino}methyl)pyrrolidin-1-yl]carbonyl}oxy)benzoic acid, 4-({[(3S,4S)-3-(2,3-difluorophenyl)-4-({[(1R)-1-(1-naphthyl)ethyl]amino}methyl)pyrrolidin-1-yl]carbonyl}oxy)benzoic acid, 3,5-difluoro-4-[(3S,4S)-3-({[(1R)-1-(1-naphthyl)ethyl]amino}methyl)-4-phenylpyrrolidin-1-yl]benzoic acid, 3-methoxy-4-({[(3S,4S)-3-({[(1R)-1-(1-naphthyl)ethyl]amino}methyl)-4-phenylpyrrolidin-1-yl]carbonyl}amino)benzoic acid, 4-({[(3S,4S)-3-({[(1R)-1-(1-benzothien-3-yl)ethyl]amino}methyl)-4-phenylpyrrolidin-1-yl]carbonyl}oxy)benzoic acid, 5-[(3S,4S)-3-(3-fluorophenyl)-4-({[(1R)-1-(1-naphthyl)ethyl]amino}methyl)pyrrolidin-1-yl]-2,2-dimethyl-5-oxopentanoic acid, 3-methoxy-4-({[(3S,4S)-3-(3-methylphenyl)-4-({[(1R)-1-(1-naphthyl)ethyl]amino}methyl)pyrrolidin-1-yl]carbonyl}amino)benzoic acid, 3,5-difluoro-4-[(3S,4S)-3-(3-methylphenyl)-4-({[(1R)-1-(1-naphthyl)ethyl]amino}methyl)pyrrolidin-1-yl]benzoic acid, (1R)-1-(1-naphthyl)-N-({(3S,4S)-4-phenyl-1-[4-(1H-tetrazol-5-yl)phenyl]pyrrolidin-3-yl}methyl) ethanamine, 2,2-dimethyl-5-[(3S,4S)-3-({[(1R)-1-(1-naphthyl)ethyl]amino}methyl)-4-phenylpyrrolidin-1-yl]-5-oxohexanoic acid, 3-methyl-4-({[(3S,4S)-3-({[(1R)-1-(1-naphthyl)ethyl]amino}methyl)-4-phenylpyrrolidin-1-yl]carbonyl}amino)benzoic acid, 3-Chloro-4-({[(3S,4S)-3-({[(1R)-1-(1-naphthyl)ethyl]amino}methyl)-4-phenylpyrrolidin-1-yl]carbonyl}amino)benzoic acid, 3-fluoro-4-({[(3S,4S)-3-({[(1R)-1-(1-naphthyl)ethyl]amino}methyl)-4-phenylpyrrolidin-1-yl]carbonyl}amino)benzoic acid, 5-[(3S,4S)-3-(2,3-difluorophenyl)-4-({[(1R)-1-(1-naphthyl)ethyl]amino}methyl)pyrrolidin-1-yl]-2,2-dimethyl-5-oxopentanoic acid, and 4-[(3S,4S)-3-(2,3-difluorophenyl)-4-({[(1R)-1-(1-naphthyl)ethyl]amino}methyl)pyrrolidin-1-yl]-3,5-difluorobenzoic acid.

10. A pharmaceutical composition which comprises the compound described in claim 1 or a pharmaceutically acceptable salt thereof and a pharmaceutically acceptable carrier.

11. The pharmaceutical composition described in claim 10, which is a calcium sensing receptor regulator.

12. The pharmaceutical composition described in claim 10, which is a hyperparathyroidism treating agent.

13. The pharmaceutical composition described in claim 10, which is a renal osteodystrophy treating agent.

14. The pharmaceutical composition described in claim 10, which is a hypercalcemia treating agent.

15. A method for treating hyperparathyroidism, renal osteodystrophy or hypercalcemia, which comprises administering a therapeutically effective amount of the compound or a pharmaceutically acceptable salt thereof described in claim 1 to a patient.

* * * * *